(12) United States Patent
Ritter et al.

(10) Patent No.: US 11,608,322 B2
(45) Date of Patent: Mar. 21, 2023

(54) REAGENTS AND PROCESS FOR DIRECT C—H FUNCTIONALIZATION

(71) Applicant: STUDIENGESELLSCHAFT KOHLE MBH, Mülheim (DE)

(72) Inventors: Tobias Ritter, Muelheim (DE); Florian Berger, Leverkusen (DE)

(73) Assignee: STUDIENGESELLSCHAFT KOHLE MBH, Muelheim an der Ruhr (DE)

( * ) Notice: Subject to any disclaimer, the term of this patent is extended or adjusted under 35 U.S.C. 154(b) by 0 days.

(21) Appl. No.: 17/291,113

(22) PCT Filed: Nov. 5, 2019

(86) PCT No.: PCT/EP2019/080301
§ 371 (c)(1),
(2) Date: May 4, 2021

(87) PCT Pub. No.: WO2020/094673
PCT Pub. Date: May 14, 2020

(65) Prior Publication Data
US 2022/0002263 A1   Jan. 6, 2022

(30) Foreign Application Priority Data
Nov. 6, 2018 (EP) .................... 18204755

(51) Int. Cl.
*C07D 339/08* (2006.01)

(52) U.S. Cl.
CPC ................ *C07D 339/08* (2013.01)

(58) Field of Classification Search
CPC .................................................. C07D 339/08
See application file for complete search history.

(56) References Cited

U.S. PATENT DOCUMENTS

| 4,190,609 A | * | 2/1980 | Lin | C07C 17/12 |
| | | | | 570/209 |
| 5,095,157 A | * | 3/1992 | Mais | C07C 201/12 |
| | | | | 568/940 |

FOREIGN PATENT DOCUMENTS

WO   WO-2016201288 A1 * 12/2016  ........... A61K 31/165

OTHER PUBLICATIONS

Xu et al (2016): STN International, CAPLUS database, Columbus (Ohio), accession No. 2016: 1027500.*
Dar et al (2016): STN International, CAPLUS database, Columbus (Ohio), accession No. 2016: 792702.*
Du et al (2010) : STN International, CAPLUS database, Columbus (Ohio), accession No. 2010: 563919.*
Humphries et al (1987): STN International, CAPLUS database, Columbus (Ohio), accession No. 1987: 636879.*

* cited by examiner

*Primary Examiner* — Golam M Shameem
(74) *Attorney, Agent, or Firm* — Norris McLaughlin, P.A.

(57) ABSTRACT

The present invention refers to a process for direct C—H functionalization, the reagents used in the process and the use thereof for the direct C—H functionalization as well as the so-obtained products.

10 Claims, 4 Drawing Sheets

REAGENTS AND PROCESS FOR DIRECT C—H FUNCTIONALIZATION

This application is a 371 of PCT/EP2019/080301, filed Nov. 5, 2019, which claims priority benefit of European Patent Application No. 18204755.5, filed Nov. 6, 2018, the entire contents of which are hereby incorporated herein by reference.

The present invention refers to a process for direct C—H functionalization, the reagents used in the process and the use thereof for the direct C—H functionalization and the so-obtained products. The inventors have found the a highly selective aromatic C—H functionalization reaction that does not require a particular substituent or substitution pattern for selectivity and provides functionalized arenes that can participate in a multitude of transformations to quickly generate structural diversity. The inventors introduce a sulfur-based reagent that can functionalize complex arenes in exquisite selectivity to yield a synthetic linchpin ready to engage in at least two broadly-applicable reactivity manifolds.

Unselective C—H functionalization can give quick access to structural diversity for molecular discovery. When a single isomer is desired, highly selective C—H transformations are preferable because they do not provide other constitutional isomers as waste and therefore facilitate purification.

Synthetically valuable and highly selective aromatic C—H functionalization reactions can be achieved when appropriate directing groups or specific substitution patterns are used to functionalize a particular position selectively or exclusively. In the absence of such substituents, the regioselectivity of a given aromatic C—H functionalization reaction depends on the reaction conditions, and the properties of the particular reagent or catalytic intermediate involved in the selectivity-determining step. Thus, a distinct strategy is required to attain high positional selectivity for each individual C—H functionalization reaction.

An alternative approach to access a large variety of arene derivatives selectively, is to develop one C—H functionalization reaction that proceeds with high positional selectivity and installs a functional group that can serve as a synthetic linchpin for further functionalization.

Some of the most useful linchpin substituents, such as halogens, boronic acid derivatives and silyl groups can already be directly introduced to an aromatic ring by C—H functionalization. However, these reactions give mixtures of constitutional isomers for most substrates. Of the few highly selective aromatic C—H functionalization reactions that do not require particular directing groups or substitution patterns, for example para-selective TEDAylation reaction of the present group (Nature Chemistry 8, 810-815 (2016)), none can introduce synthetic linchpins.

Thus, there is the need for a direct C—H functionalization process avoiding increasing structural and functional molecular complexity and avoiding an aromatic C—H functionalization reaction which undesirably provides more than one isomer.

Here, the inventors have developed a reaction that can do both: exhibit high positional selectivity for a broad range of aromatic substrates, while installing a linchpin functional group that can subsequently participate in diverse transformations.

Thus in a first aspect, the present invention is directed to a thianthrene derivative of the Formula (I):

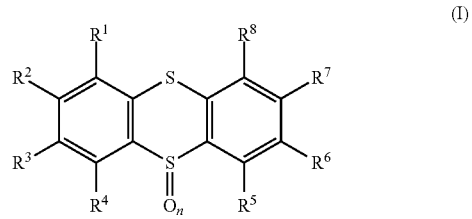

wherein $R^1$ to $R^8$ may be the same or different and are selected from hydrogen, Cl, F, a partially or fully halogenated, preferably fluorinated, $C_1$ to $C_6$ alkyl group, and wherein n is 0 or 1, with the proviso that at least one of $R^1$ to $R^8$ is not hydrogen.

In an embodiment of the thianthrene derivative of the Formula (I), at least two to four of $R^1$ to $R^8$ are Cl, F, a partially or fully fluorinated $C_1$ to $C_6$ alkyl group and the others of $R^1$ to $R^8$ are hydrogen and n is 0 or 1.

In another embodiment of the thianthrene derivative of the Formula (I), four of $R^1$ to $R^8$ are F or $CF_3$ and the others of $R_1$ to $R_8$ are hydrogen and n is 0 or 1.

In still another embodiment of the thianthrene derivative of the Formula (I), $R_2$, $R_3$, $R_6$ and $R_7$ are F or $CF_3$ and the others of $R^1$ to $R^8$ are hydrogen and n is 0 or 1.

In a second aspect, the present invention is directed to a process for preparing an aromatic or heteroaromatic thianthrenium salt of the Formula (III), wherein a monocyclic or polycyclic, aromatic or heteroaromatic hydrocarbon Ar, which may be substituted or unsubstituted, is reacted with an activated thianthrene derivative of the Formula (I) or a mixture of thianthrene derivatives of the Formula (I) in an organic solvent whereby a thianthrenium salt of the Formula (III) is obtained:

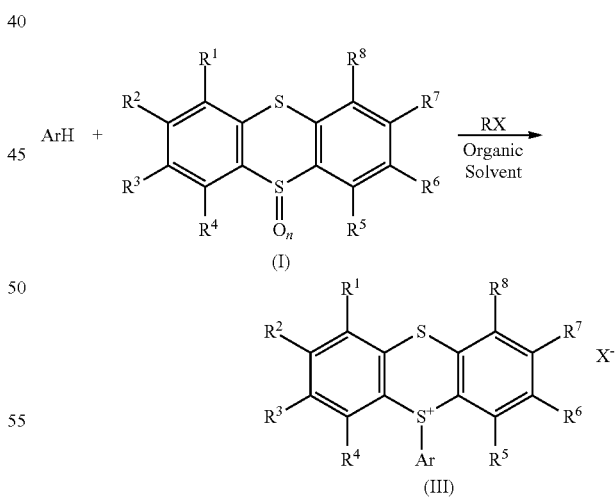

wherein $R^1$ to $R^8$ may be the same or different and are selected from hydrogen, Cl, F, a partially or fully halogenated, preferably fluorinated, $C_1$ to $C_6$ alkyl group, RX is selected from $HBF_4$; $HBF_4.OEt_2$, $BF_3.OEt_2$, trifluoro methane sulfonic acid (triflic acid), triflic acid anhydride, trifluoro acetic acid, trifluoro acetic acid anhydride, trimethylsilyltriflate or a mixture thereof and $X^-$ is an anion derived from RX.

In said process, at least one of $R^1$ to $R^8$ in Formula (I) or (III) may be not hydrogen, and at least two to four of $R^1$ to $R^8$ may each be Cl, F, a partially or fully halogenated, preferably fluorinated, $C_1$ to $C_6$ alkyl group and the others of $R^1$ to $R^8$ are hydrogen and n is 0 or 1. In an embodiment of the process, four of $R^1$ to $R^8$ are F or $CF_3$ and the others of $R_1$ to $R_8$ are hydrogen and n is 0 or 1 and, in another embodiment of the process, most preferred, $R_2$, $R_3$, $R_6$ and $R_7$ are F or $CF_3$ and the others of $R^1$ to $R^8$ are hydrogen and n is 0 or 1.

In the inventive process, Ar may be any monocyclic or polycyclic, aromatic or heteroaromatic hydrocarbon having 5 to 22 carbon atoms, which may be unsubstituted or substituted by one of more substituents selected from saturated or unsaturated, straight chain or branched aliphatic hydrocarbons having 1 to 20 carbon atoms, aromatic or heteroaromatic hydrocarbons having 5 to 22 carbon atoms, heterosubstituents, or which may be part of a cyclic hydrocarbon ring system (carbocyclic) with 5 to 30 carbon atoms and/or heteroatoms. The definition for said aliphatic hydrocarbons may include one or more heteroatoms such O, N, S in the hydrocarbon chain.

In the inventive process, the choice of the activation agent or activation treatment to activate the thianthrene compound of Formula (I) depends on electrodensity of the core of the Ar compound. Depending on the electron density on the arene core, different thianthrenes of Formula (I) or mixtures thereof including unsubstituted thianthrene or thianthrene-S-oxide can be used. According to the invention, the thianthrenation process can proceed on arenes as electron-rich as aniline derivatives to arenes as electron-poor as 1,2-dichlorobenzene. Thus, the skilled man can choose on the basis of the understanding of the reaction partners which thianthrene, substituted or unsubstituted on the arene core, is to be used for the specific reaction. It might be advantageous to use a mixture of a thianthrene of formula (I) with n=1 with up to 10 Mol.-% of a thianthrene of formula (I) with n=0 in the inventive process.

In the inventive process, the choice of the organic solvent is not critical as long as it is an aprotic polar organic solvent selected from acetonitrile, chlorinated hydrocarbons, or mixtures thereof. The reaction conditions are also not critical and the reaction is usually carried out at a temperature between −78° C. and 50° C., preferably 0° C. to 30° C., under ambient pressure and optionally under an inert gas atmosphere.

In an embodiment of the process for preparing a thianthrenium salt compound of the Formula (III), the thianthrene derivative of the Formula (I) may be activated by adding a carboxylic acid anhydride if n=1 in formula (I) as activation agent. Preferably, the reaction may be carried out in the presence of a Brönstedt acid or Lewis acid which may be selected from $HBF_4OEt_2$, triflic acid, trifluoroacetic acid, sulfuric acid, $BF_3OEt_2$, TMSOTf.

In another embodiment of the process for preparing a thianthrenium salt of the Formula (III), the thianthrene derivative of the Formula (I) may be activated by oxidation if n=0 in formula (I).

In the latter embodiment of the process for preparing a thianthrenium salt of the Formula (III), the thianthrene derivative of the Formula (I) may be activated by oxidation with an oxidation agent as activation agent, preferably selected from 1-chloromethyl-4-fluoro-1,4-diazoniabicyclo[2.2.2]octane bis(tetrafluoroborate), dimesylperoxide, potassiumperoxydisulfate, $NOBF_4$ in air.

In said another embodiment of the process for preparing a thianthrenium salt compound of the Formula (III), the thianthrene derivative of the Formula (I) may be activated by electrochemical oxidation as activation treatment.

In one embodiment, the present invention is directed to the process for preparing a thianthrenium salt of the Formula (III) wherein an electron-poor Ar and a thianthrene derivative of the Formula (I) or a mixture of different thianthrene derivatives of the Formula (I), wherein $R_2$, $R_3$, $R_6$ and $R_7$ are F or $CF_3$ and the others of $R^1$ to $R^8$ are hydrogen and wherein n is 0 or 1, are used.

In one embodiment, the present invention is directed to the process for preparing an aromatic or heteroaromatic thianthrenium salt, wherein an electron-rich Ar and a thianthrene derivative of the Formula (I) or a mixture of different thianthrene derivatives of the Formula (I), wherein $R^1$ to $R^8$ are hydrogen and wherein n is 0 or 1, are used.

In the context of the invention, electron-poor Ar is to be understood as an Ar being substituted with at least one electron-withdrawing substituent such as Cl, F, CN, and electron-rich Ar is to be understood as an Ar preferably being substituted with at least one electron-donating substituent such as alkyl, —O-alkyl such as —$OCH_3$.

In a third aspect, the present invention is directed to a thianthrenium salt of the Formula (III):

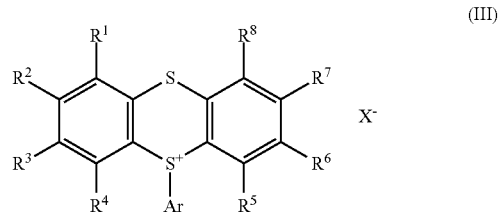

(III)

wherein $R^1$ to $R^8$ may be the same or different and are selected from hydrogen, Cl, F, a partially or fully halogenated, preferably fluorinated, $C_1$ to $C_6$ alkyl group, preferably with the proviso that at least one of $R^1$ to $R^8$ is not hydrogen, and Ar is a monocyclic or polycyclic, aromatic or heteroaromatic hydrocarbon Ar, which may be substituted or unsubstituted as defined before and X is an anion, which does not adversely affect the usability of the thianthrenium salt of Formula (III) in a subsequent reaction, preferably selected from $BF_4^-$; triflate, trifluoro acetate, and $PF_6^-$.

In a fourth aspect, the present invention is directed to the use of a thianthrenium salt of the Formula (III):

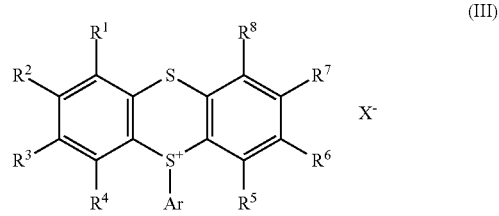

(III)

wherein $R^1$ to $R^8$ may be the same or different and are selected from hydrogen, Cl, F, a partially or fully halogenated, preferably fluorinated, $C_1$ to $C_6$ alkyl group, preferably with the proviso that at least one of $R^1$ to $R^8$ is not hydrogen, and Ar is a monocyclic or polycyclic, aromatic or heteroaromatic hydrocarbon Ar, which may be substituted or unsubstituted as defined before and X is an anion, which does not adversely affect the usability in a subsequent reaction, preferably selected from $BF_4^-$; triflate, trifluoro acetate, and $PF_6^-$, in a photoredox catalysis reaction, a photoredox functionalization reaction as exemplarily illustrated in the Figures or a radical arylation reaction such as Minisci-reaction.

In a fifth aspect, the present invention is directed to the use of a thianthrenium salt of the Formula (III):

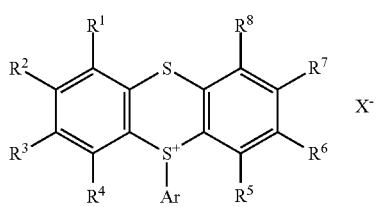
(III)

wherein $R^1$ to $R^8$ may be the same or different and are selected from hydrogen, Cl, F, a partially or fully halogenated, preferably fluorinated, $C_1$ to $C_6$ alkyl group, preferably with the proviso that at least one of $R^1$ to $R^8$ is not hydrogen, and Ar is a monocyclic or polycyclic, aromatic or heteroaromatic hydrocarbon Ar, which may be substituted or unsubstituted as defined before and $X^-$ is an anion, which does not adversely affect the usability in a subsequent reaction, preferably selected from $BF_4^-$; triflate, trifluoro acetate, and $PF_6^-$, in a transition metal catalyzed cross coupling reaction, which is preferably selected from a Heck reaction, a Sonogashira reaction, a Negishi reaction, a Suzuki reaction, and a carbonylation reaction.

In said use, at least one of $R^1$ to $R^8$ in Formula (III) is preferably not hydrogen, more preferably at least two to four of $R^1$ to $R^8$ are Cl, F, a partially or fully fluorinated $C_1$ to $C_6$ alkyl group and the others of $R^1$ to $R^8$ are hydrogen, even more preferably four of $R^1$ to $R^8$ are F or $CF_3$ and the others of $R_1$ to $R_8$ are hydrogen and most preferred, $R_2$, $R_3$, $R_6$ and $R_7$ are F or $CF_3$ and the others of $R^1$ to $R^8$ are hydrogen.

In the context of the aspects of the present invention, the following definitions are more general terms which are used throughout the present application.

When a range of values is listed, it is intended to encompass each value and sub-range within the range. For example "$C_{1-6}$" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$.

The term "aliphatic" includes both saturated and unsaturated, straight chain (i.e., unbranched), branched, acyclic, cyclic, or polycyclic aliphatic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, the term "alkyl" includes straight, branched and acyclic alkyl groups. An analogous convention applies to other generic terms such as "alkenyl", "alkynyl", and the like. Furthermore, the terms "alkyl", "alkenyl", "alkynyl", and the like encompass both substituted and unsubstituted groups. In certain embodiments, "lower alkyl" is used to indicate those alkyl groups (acyclic, substituted, unsubstituted, branched or unbranched) having 1-6 carbon atoms.

As used herein, "alkyl" refers to a radical of a straight-chain or branched saturated hydrocarbon group having from 1 to 20 carbon atoms ("$C_{1-20}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently unsubstituted (an "unsubstituted alkyl") or substituted (a "substituted alkyl") with one or more substituents. In certain embodiments, the alkyl group is an unsubstituted $C_{1-10}$ alkyl (e.g., —$CH_3$). In certain embodiments, the alkyl group is a substituted $C_{1-10}$ alkyl.

As used herein, "haloalkyl" is a substituted alkyl group as defined herein wherein one or more of the hydrogen atoms are independently replaced by a halogen, e.g., fluoro, bromo, chloro, or iodo. "Perhaloalkyl" is a subset of haloalkyl, and refers to an alkyl group wherein all of the hydrogen atoms are independently replaced by a halogen, e.g., fluoro, bromo, chloro, or iodo. In some embodiments, the haloalkyl moiety has 1 to 8 carbon atoms ("$C_{1-8}$ haloalkyl"). In some embodiments, the haloalkyl moiety has 1 to 6 carbon atoms ("$C_{1-6}$ haloalkyl"). In some embodiments, the haloalkyl moiety has 1 to 4 carbon atoms ("$C_{1-4}$ haloalkyl"). In some embodiments, the haloalkyl moiety has 1 to 3 carbon atoms ("$C_{1-3}$ haloalkyl"). In some embodiments, the haloalkyl moiety has 1 to 2 carbon atoms ("$C_{1-2}$ haloalkyl"). In some embodiments, all of the haloalkyl hydrogen atoms are replaced with fluoro to provide a perfluoroalkyl group. In some embodiments, all of the haloalkyl hydrogen atoms are replaced with chloro to provide a "perchloroalkyl" group. Examples of haloalkyl groups include —$CF_3$, —$CF_2CF_3$, —$CF_2CF_2CF_3$, —$CCl_3$, —$CFCl_2$, —$CF_2Cl$, and the like.

"Alkenyl" refers to a radical of a straight-chain or branched hydrocarbon group having from 2 to 20 carbon atoms, and one or more carbon-carbon double bonds ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents. In certain embodiments, the alkenyl group is unsubstituted $C_{2-10}$ alkenyl. In certain embodiments, the alkenyl group is substituted $C_{2-10}$ alkenyl.

"Alkynyl" refers to a radical of a straight-chain or branched hydrocarbon group having from 2 to 20 carbon atoms, and one or more carbon-carbon triple bonds ("$C_{2-20}$ alkynyl"). In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkynyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents. In certain embodiments, the alkynyl group is unsubstituted $C_{2-10}$ alkynyl. In certain embodiments, the alkynyl group is substituted $C_{2-10}$ alkynyl.

"Carbocyclyl" or "carbocyclic" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 7 ring carbon atoms ("$C_{3-7}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclic ring, as defined above, is fused with one or more aryl or heteroaryl groups wherein the point of attachment is on the carbocyclic ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

"Heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, sulfur, boron, phosphorus, and silicon ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged, or spiro ring system, such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclic ring, as defined above, is fused with one or more carbocyclyl groups wherein the point of attachment is either on the carbocyclyl or heterocyclic ring, or ring systems wherein the heterocyclic ring, as defined above, is fused with one or more aryl or heteroaryl groups, wherein the point of attachment is on the heterocyclic ring, and in such instances, the number of ring members continue to designate the number of ring members in the heterocyclic ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-14 membered heterocyclyl. In certain embodiments, the heterocyclyl group is substituted 3-14 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

"Aryl" refers to a radical of a monocyclic or polycyclic (e.g., bicyclic or tricyclic) 4n+2 aromatic ring system (e.g., having 6, 10, or 14 pi electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"Aralkyl" is a subset of alkyl and aryl and refers to an optionally substituted alkyl group substituted by an optionally substituted aryl group. In certain embodiments, the aralkyl is optionally substituted benzyl. In certain embodiments, the aralkyl is benzyl. In certain embodiments, the aralkyl is optionally substituted phenethyl. In certain embodiments, the aralkyl is phenethyl.

"Heteroaryl" refers to a radical of a 5-14 membered monocyclic or bicyclic 4n+2 aromatic ring system (e.g., having 6 or 10 pi electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

"Heteroaralkyl" is a subset of alkyl and heteroaryl and refers to an optionally substituted alkyl group substituted by an optionally substituted heteroaryl group.

"Unsaturated" or "partially unsaturated" refers to a group that includes at least one double or triple bond. A "partially unsaturated" ring system is further intended to encompass rings having multiple sites of unsaturation, but is not intended to include aromatic groups (e.g., aryl or heteroaryl groups) as herein defined. Likewise, "saturated" refers to a group that does not contain a double or triple bond, i.e., contains all single bonds.

Alkyl, alkenyl, alkynyl, carbocyclyl, heterocyclyl, aryl, and heteroaryl groups, which are divalent bridging groups, are further referred to using the suffix -ene, e.g., alkylene, alkenylene, alkynylene, carbocyclylene, heterocyclylene, arylene, and heteroarylene.

An atom, moiety, or group described herein may be unsubstituted or substituted, as valency permits, unless otherwise provided expressly. The term "optionally substituted" refers to substituted or unsubstituted.

Alkyl, alkenyl, alkynyl, carbocyclyl, heterocyclyl, aryl, and heteroaryl groups are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. For purposes of this invention, heteroatoms such as nitrogen may have hydrogen substituents and/or any suitable substituent as described herein which satisfy the valencies of the heteroatoms and results in the formation of a stable moiety. In certain embodiments, the substituent is a carbon atom substituent. In certain embodiments, the substituent is a nitrogen atom substituent. In certain embodiments, the substituent is an oxygen atom substituent. In certain embodiments, the substituent is a sulfur atom substituent.

Exemplary substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, C$_{1-10}$ alkyl, C$_{1-10}$ haloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups; or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ haloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl, C$_{1-10}$ haloalkyl, C$_{2-10}$ alkenyl, C$_{2-10}$ alkynyl, C$_{3-10}$ carbocyclyl, 3-14 membered heterocyclyl, C$_{6-4}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{1-10}$ haloalkyl, C$_{2-10}$ alkenyl, C$_{2-10}$ alkynyl, C$_{3-10}$ carbocyclyl, 3-14 membered heterocyclyl, C$_{6-4}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, C$_{1-6}$ alkyl, C$_{1-6}$ haloalkyl, C$_{2-6}$ alkenyl, C$_{2-6}$ alkynyl, C$_{3-10}$ carbocyclyl, 3-10 membered heterocyclyl, C$_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S;

each instance of R$^{ee}$ is, independently, selected from C$_{1-6}$ alkyl, C$_{1-6}$ haloalkyl, C$_{2-6}$ alkenyl, C$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ haloalkyl, C$_{2-6}$ alkenyl, C$_{2-6}$ alkynyl, C$_{3-10}$ carbocyclyl, 3-10 membered heterocyclyl, $C_{6-10}$ aryl and 5-10 membered heteroaryl, or two $R^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —$NO_2$, —$N_3$, —$SO_2H$, —$SO_3H$, —OH, —$OC_{1-6}$ alkyl, —ON($C_{1-6}$ alkyl)$_2$, —N($C_{1-6}$ alkyl)$_2$, —N($C_{1-6}$ alkyl)$_3^+X^-$, —NH($C_{1-6}$ alkyl)$_2^+X^-$, —$NH_2$($C_{1-6}$ alkyl)$^+$ $X^-$, —$NH_3^+X^-$, —N($OC_{1-6}$ alkyl)($C_{1-6}$ alkyl), —N(OH)($C_{1-6}$ alkyl), —NH(OH), —SH, —$SC_{1-6}$ alkyl, —SS($C_{1-6}$ alkyl), —C(=O)($C_{1-6}$ alkyl), —$CO_2H$, —$CO_2$($C_{1-6}$ alkyl), —OC(=O)($C_{1-6}$ alkyl), —$OCO_2$($C_{1-6}$ alkyl), —C(=O)$NH_2$, —C(=O)N($C_{1-6}$ alkyl)$_2$, —OC(=O)NH($C_{1-6}$ alkyl), —NHC(=O)($C_{1-6}$ alkyl), —N($C_{1-6}$ alkyl)C(=O)($C_{1-6}$ alkyl), —$NHCO_2$($C_{1-6}$ alkyl), —NHC(=O)N($C_{1-6}$ alkyl)$_2$, —NHC(=O)NH($C_{1-6}$ alkyl), —NHC(=O)$NH_2$, —C(=NH)O($C_{1-6}$ alkyl), —OC(=NH)($C_{1-6}$ alkyl), —OC(=NH)$OC_{1-6}$ alkyl, —C(=NH)N($C_{1-6}$ alkyl)$_2$, —C(=NH)NH($C_{1-6}$ alkyl), —C(=NH)$NH_2$, —OC(=NH)N($C_{1-6}$ alkyl)$_2$, —OC(NH)NH($C_{1-6}$ alkyl), —OC(NH)$NH_2$, —NHC(NH)N($C_{1-6}$ alkyl)$_2$, —NHC(=NH)$NH_2$, —$NHSO_2$($C_{1-6}$ alkyl), —$SO_2N$($C_{1-6}$ alkyl)$_2$, —$SO_2NH$ ($C_{1-6}$ alkyl), —$SO_2NH_2$, —$SO_2C_{1-6}$ alkyl, —$SO_2OC_{1-6}$ alkyl, —$OSO_2C_{1-6}$ alkyl, —$SOC_{1-6}$ alkyl, —Si($C_{1-6}$ alkyl)$_3$, —OSi($C_{1-6}$ alkyl)$_3$-C(=S)N($C_{1-6}$ alkyl)$_2$, C(=S)NH($C_{1-6}$ alkyl), C(=S)$NH_2$, —C(=O)S($C_{1-6}$ alkyl), —C(=S)$SC_{1-6}$ alkyl, —SC(=S)$SC_{1-6}$ alkyl, $C_{1-6}$ alkyl, $C_{1-6}$ haloalkyl, $C_{2-6}$ alkenyl, $C_{2-6}$ alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form =O or =S; wherein $X^-$ is an anionic counterion.

"Halo" or "halogen" refers to fluorine (fluoro, —F), chlorine (chloro, —Cl), bromine (bromo, —Br), or iodine (iodo, —I).

"Acyl" refers to a moiety selected from the group consisting of —C(=O)$R^{aa}$, —CHO, —$CO_2R^{aa}$, —C(=O)N($R^{bb}$)$_2$, —C(=$NR^{bb}$)$R^{aa}$, —C(=$NR^{bb}$)$OR^{aa}$, —C(=$NR^{bb}$) N($R^{bb}$)$_2$, —C(=O)$NR^{bb}SO_2R^{aa}$, —C(=S)N($R^{bb}$)$_2$, —C(=O)$SR^{aa}$, or —C(=S)$SR^{aa}$, wherein $R^{aa}$ and $R^{bb}$ are as defined herein.

The term "complex" or "coordination complex" refers to an association of at least one atom or ion (which is referred to as a "central atom," "central ion," or "acceptor," and is usually a metallic cation) and a surrounding array of bound ligands or donors). Ligands are generally bound to a central atom or central ion by a coordinate covalent bond (e.g., ligands may donate electrons from a lone electron pair into an empty orbital of the central atom or central ion) and are referred to as being "coordinated" to the central atom or central ion. There are also organic ligands such as alkenes whose π-bonds can coordinate to empty orbitals of an acceptor. A complex may include one or more donors, which can be the same or different. A complex may also include one or more acceptors, which can be the same or different.

The term "ligand" refers to an ion or molecule that binds to a central atom or ion (e.g., a central metal atom or ion) to form a coordination complex. Ligands are usually electron donors, and the central atom or ion is electron acceptors. The bonding between the central atom or ion and the ligand typically involves formal donation of one or more of the ligand's electron pairs. The nature of such bonding can range from covalent to ionic, and the bond order can range from one to three. One central atom or ion may bind to one or more ligands of the same or different type. A ligand may be capable of binding a central atom or ion through multiple sites, usually because the ligand includes lone pairs on more than one atom of the ligand. Ligands in a complex may affect the reactivity (e.g., ligand substitution rates and redox) of the central atom or ion. Exemplary ligands include charge-neutral ligands ("ligand molecules," e.g., $CH_3CN$, amides (e.g., N,N-dimethylformamide (DMF), N,N-dimethylacetamide (DMA), or N-methyl-2-pyrrolidone (NMP)), dimethyl sulfoxide (DMSO), amines (e.g., ammonia; ethylenediamine (en); pyridine (py); 2,2'-bipyridine (bipy); and 1,10-phenanthroline (phen)), phosphines (e.g., $PPh_3$), ethers (e.g., tetrahydrofuran (THF), 2-methyl-tetrahydrofuran, tetrahydropyran, dioxane, diethyl ether, methyl t-butyl ether (MTBE), dimethoxyethane (DME), and diglyme), ketones (e.g., acetone and butanone), chlorohydrocarbons (e.g., dichloromethane (DCM), chloroform, carbon tetrachloride, and 1,2-dichloroethane (DCE)), esters (e.g., propylene carbonate and ethyl acetate), CO, $N_2$, water, and alkenes) and anionic ligands ("ligand ions," e.g., halides, hydride, alkyls, $S_2^-$, S—$CN^-$, O—$NO_2^-$, N—$N_2^-$, O—$H^-$, [O—C(=O)—C(=O)—O]$_2^-$, O—N—$O^-$, N=C=$S^-$, $CN^-$).

The term "transition metal" refers to elements that are in the d-block and f-block of the Periodic Chart of the Elements, which may exhibit a variety of oxidation states, and which may form numerous complex ions. The term "d-block" refers to those elements that have electrons filling the 3d, 4d, 5d, and 6d orbitals, and the term "f-block" refers to those elements (including lanthanides and the actinides) that have electrons filling the 4f and 5f orbitals. Exemplary transition metals include palladium, nickel, cobalt, copper, platinum, silver, manganese, zinc, iridium, rhodium, iron, and ruthenium. The term "transition metal" also includes alloys, metal/metal composites, metal ceramic composites, and metal polymer composites, as well as other metal composites.

The term "catalysis," "catalyze," or "catalytic" refers to the increase in rate of a reaction due to the participation of a substance called a "catalyst." In certain embodiments, the amount and nature of a catalyst remains essentially unchanged during a reaction. In certain embodiments, a catalyst is regenerated, or the nature of a catalyst is essentially restored after a reaction. A catalyst may participate in multiple chemical transformations. The effect of a catalyst may vary due to the presence of other substances known as inhibitors or poisons (which reduce the catalytic activity) or promoters (which increase the activity). Catalyzed reactions have a lower activation energy (rate-limiting free energy of activation) than the corresponding uncatalyzed reaction, resulting in a higher reaction rate at the same temperature. Catalysts may affect the reaction environment favorably, or bind to the reagents to polarize bonds, or form specific intermediates that are not typically produced by a uncatalyzed reaction, or cause dissociation of reagents to reactive forms.

The invention is not intended to be limited in any manner by the above exemplary listing of substituents.

As stated above, depending on the electron density on the arene core, different thianthrenes or mixtures thereof can be used. According to the invention, the thianthrenation process can proceed on arenes as electron-rich as aniline derivatives to arenes as electron-poor as 1,2-dichlorobenzene. Thus, the skilled man can choose on the basis of the understanding of the reaction partners which thianthrene, substituted or unsubstituted on the arene core, is to be used for the specific reaction. With reference to the Figures, it can be seen that arenes more electron rich than anisole undergo unproductive oxidation with the TFT-reagent 1, presumably through single electron oxidation. Therefore, the inventors used an analogous non-fluorinated thianthrene reagent for all arenes more electron-rich than anisole, such as meclofenamic acid (24) and famoxadone (25), and an halogenated/fluorinated thianthrene reagent for all arenes more electron-poor.

The transformation is highly tolerant of functional groups like amines, amides, alcohols, ethers, esters, carboxylic acids, and heterocycles. Alcohols are trifluoroacetylated under the reaction conditions but the trifluoroacetate esters hydrolyze during the aqueous workup. In the case of sufficiently electro-rich arenes, olefins can be tolerated (e.g. strychnine, 18). Basic functional groups are protonated under the acidic reaction conditions and thus protected from oxidation (e.g. 10, 17, and 18). The $HBF_4OEt_2$ can be replaced by Lewis-acids such as $BF_3OEt_2$ or TMSOTf, which enables successful functionalization of compounds that contain acid-sensitive functionality, such as salicin pentaacetate (5), or compounds that would otherwise be protonated and therefore deactivated for functionalization, such as electron-rich pyridine derivatives (e.g. 15). The reaction is not sensitive to oxygen or traces of water and can thus be carried out under an ambient atmosphere in most cases. The majority of the arylthianthrenium salts are well soluble in organic solvents such as MeCN, DCM, 1,4-dioxane, DMF, and DMSO and can be stored as solids under ambient conditions for at least three months. While the salts can usually be used without purification (vide infra), chromatography on silica gel allows to obtain analytically pure compounds as shown in FIG. 2.

High regioselectivity was observed in all cases, even if compounds contain several reactive positions in different aromatic rings, like in 2-fluorobiphenyl (4), meclofenamic acid (24), famoxadone (25), and bifonazole (6). The only substrate for which the inventors could identify more than one isomer is mizolastine (22), which produced a mixture of two products (ratio: 16:1); the major isomer was obtained in pure form. Thianthrene radical cations have previously been reported to be incompatible with many functional groups like pyridines (11), amines (12), and alcohols (13), and only add to simple, electron-rich arenes like phenol and anisole (14-16), but the fluorine substituents on reagent 1, as well as the synthesis of the thianthrene radical cation via sulfoxides in an acidic reaction medium as reported here prevent side reactions and enabled the substrate scope shown in FIG. 2. Despite the isolated early reports on aryl thianthrenium salts (14-16), their potential as synthetic linchpins documented in the second part of this paper had never been realized.

The thianthrenium salts can behave as electrophiles in both palladium-catalyzed cross coupling chemistry and in photoredox catalysis, both of which provide rich reaction chemistry that render the thianthrenium salts synthetically useful. The inventors have developed an initial set of 12 reactions exemplified by the derivatization of the insecticide pyriproxyfen (13), which functions as a representative example (FIG. 3a).

Selective functionalization in the para position of the phenyl group of pyriproxyfen would be difficult otherwise due to several reactive ortho positions. There are some reports in the state of art that alkylaryl sulfonium salts can function as electrophiles in a few cross coupling reactions. Unlike those alkylaryl sulfonium salts, which are strong alkylating reagents, aryl thianthrenium salts are more resistant to nucleophiles like cyanide, tertiary amines, and organo zinc reagents.

The increased stability of thianthrenium salts makes them useful cross coupling partners in many palladium-catalyzed reactions such as Heck reactions, Sonogashira reactions, Negishi reactions, Suzuki reactions, and carbonylation reactions. Palladium inserts selectively into the desired of the three C—S bonds of the triarylasulfonium group of the thianthrenium salts. The inventors assume that the selectivity is a result of steric hindrance and rigidity of the tricyclic thianthrene structure. In addition, the cleavage of one of the undesired C—S bonds would lead to a seven-membered palladacycle, which may be less favorable.

In addition to palladium-catalyzed cross coupling chemistry, photoredox catalysis enables the coupling of thianthrenium salts with several different nucleophiles at ambient temperature. For example, with nucleophiles like chloride, trifluoromethylthiolate, and triphenylphosphite, various carbon-heteroatom bonds can be accessed.

Photoredox functionalization of thianthrenium salts is complementary to metal-catalyzed cross-coupling chemistry because it tolerates substituents that are not spectators in palladium-catalyzed reactions, such as the aryl iodides in amiodarone (10) shown in FIG. 3b. The inventors assume the thianthrenium salt is cleaved into thianthrene and aryl radicals after single electron reduction by a photosensitizer. The aryl radicals then abstract atoms or groups or react with copper complexes. FIG. 3b also shows that complex molecules like 39, 40, and 41 can be accessed directly in the two step synthetic sequence without purification of the intermediate sulfonium salts.

A current drawback of the presented method might be the use of stoichiometric amounts of the thianthrene reagents with a mass about that of triphenylphosphine (tetrafluorthianthrene TFT: 288 g mol$^{-1}$, thianthrene: 216 g mol$^{-1}$, triphenylphosphine: 262 g mol$^{-1}$). However, TFT can be easily prepared from inexpensive commodity starting materials, purified by recrystallization, and recovered after the reaction; 76% of thianthrene 2 was recovered mostly by precipitation after the two-step reaction sequence to 41 on 25 g scale. Moreover, the use of large stoichiometric groups may be justifiable if the enabled transformation with respect to reactivity and selectivity is not accessible via other reaction chemistry, as exemplified for example by meta selective C—H functionalization reactions (mass of stoichiometric directing group: up to 354 g mol$^{-1}$) (3).

BRIEF DESCRIPTION OF THE DRAWINGS

The present invention is illustrated in more detail by the following Figures. In the attached drawings, the Figures show.

$^a$ nonfluorinated thianthrene-S-oxide and nonfluorinated thianthrene were used instead of 1 and 2, no additional acid was used, reaction was initiated at −78° C., $^b$ $BF_3OEt_2$ was used instead of $HBF_4OEt_2$, $^c$ TfOH was used instead of $HBF_4OEt_2$, $^d$ the amino-group was trifluoroacetylated, $^e$ TMSOTf was used instead of $HBF_4OEt_2$, the reaction was carried out under an inert atmosphere with dry MeCN, $^f$ 0.90 equiv. 1 was used

Figure 1:
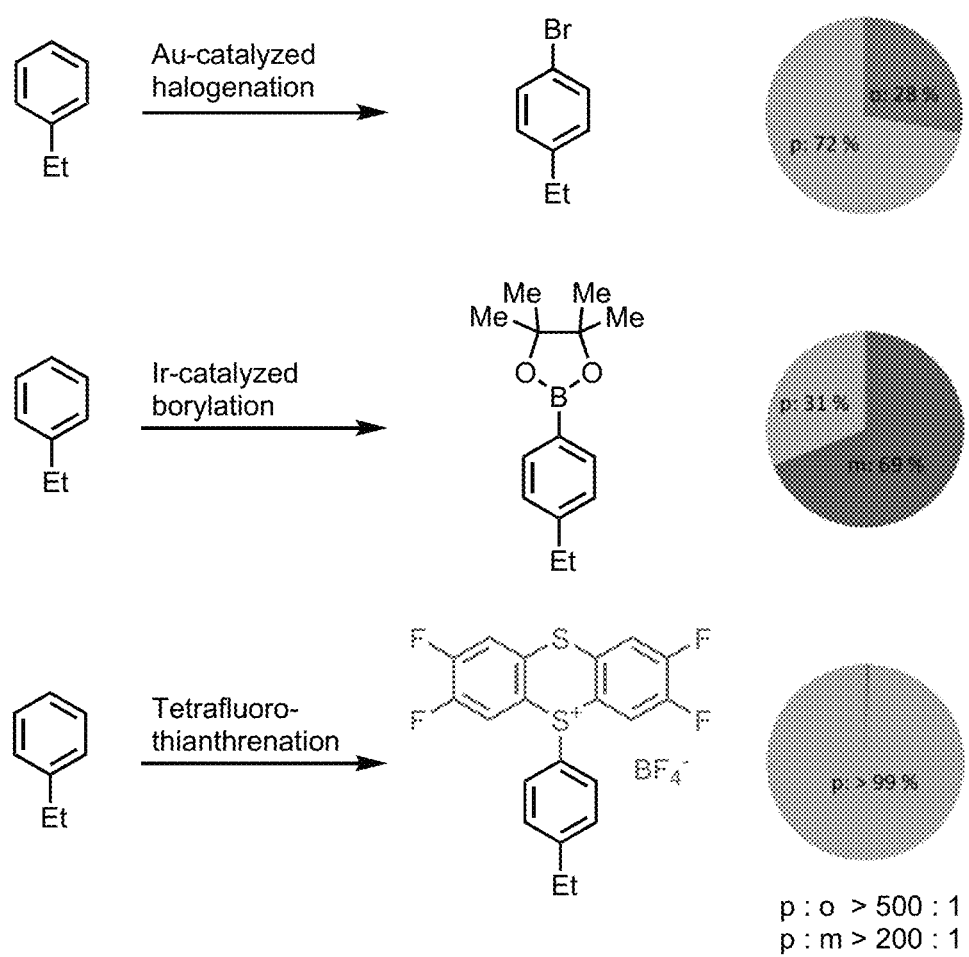
FIG. 1: Comparison of tetrafluorothianthrenation (yield: 92%) with halogenation (*Angew. Chem. Int. Ed.*, 49, 2028-2032 (2010)) and borylation (*J. Am. Chem. Soc.*, 137, 5193-5198 (2015))

a) Functionalization of the pyriproxyfen derived tetrafluorothianthrenium salt 13b.

*a* B$_2$Pin$_2$ (2.5 eq), pyridine (5.0 eq), Ru(bpy)$_3$(PF$_6$)$_2$ (2.0 mol %), MeCN, blue LED, 60 W, 22° C., 18 h,
*b* P(OPh)$_3$ (5.0 eq), pyridine (4.9 eq), NaI (20 mol %), Ru(bpy)$_3$(PF$_6$)$_2$ (3 mol %), MeCN, blue LED, 60 W, 22° C., 3 h,
*c* NBu$_4$CN (2.5 eq), Cu(MeCN)$_4$BF$_4$ (1.2 eq), Ru(bpy)$_3$(PF$_6$)$_2$ (2.0 mol %), MeCN, blue LED, 60 W, 22° C., 5 h,
*d* NMe$_4$SCF$_3$ (1.1 eq), Cu(MeCN)$_4$BF$_4$ (1.0 eq), Ru(bpy)$_3$(PF$_6$)$_2$ (4.0 mol %), MeCN, blue LED, 60 W, 22° C., 6 h,
*e* CuCl (2.0 eq), NBu$_4$Cl (2.5 eq), Ru(bpy)$_3$(PF$_6$)$_2$ (2.0 mol %), MeCN, blue LED, 60 W, 22° C., 3 h,
*f* LiI (10 eq), Cu(MeCN)$_4$BF$_4$ (1.0 eq), Ru(bpy)$_3$(PF$_6$)$_2$ (3.6 mol %), MeCN, DMSO, 3/2, blue LED, 60 W, 22° C., 4 h,
*g* Pd(OAc)$_2$ (9.0 mol %), PPh$_3$ (15 mol %), styrene (2.0 eq), NEt$_3$ (3.0 eq), DMF, 100° C., 24 h,
*h* c-PrZnBr (3.0 eq), Pd(PPh$_3$)$_2$Cl$_2$ (5.0 mol %), KOAc (6.0 eq), THF, 50° C., 36 h,
*i* MeZnCl (3.0 eq), Pd(PPh$_3$)$_2$Cl$_2$ (5.0 mol %), KOAc (6.0 eq), THF, 50° C., 36 h,
*j* 1-hexyne (2.0 eq), CuI (20 mol %), Pd(dppf)Cl$_2$ (3.0 mol %), A/-methylmorpholine (2.0 eq), dioxane, 40° C., 45 h,
*k* cyclohexylvinylboronic acid (2.0 eq), K$_2$CO$_3$ (4.0 eq), Pd(dppf)Cl$_2$ (3.0 mol %), EtOH, 50° C., 20 h,
*l* CO (1.0 bar), N-methylmorpholine (2.0 eq), Pd(dppf)Cl$_2$ (3.0 mol %), EtOH/dioxane, 1/1, 50° C., 16 h,
b) additional complex examples.
*m* Cu(MeCN)$_4$BF$_4$ (1.6 eq), LiCl (4.8 eq), CF$_3$CO$_2$H (1.2 eq), Ru(bpy)$_3$(PF$_6$)$_2$ (4.0 mol %), MeCN, blue LED, 60 W, 22° C., 8 h,
*n* NBu$_4$CN (2.5 eq), Cu(MeCN)$_4$BF$_4$ (1.0 eq), Ru(bpy)$_3$(PF$_6$)$_2$ (3.0 mol %), MeCN, DMSO, 2/1, blue LED, 60 W, 22° C., 7 h.
*o* m-methoxyphenylboronic acid (1.2 eq), K$_3$PO$_4$ (2.0 eq), Pd(dppf)Cl$_2$ (2.0 mol %), i-PrOH/dioxane, 1/1, 50° C., 48 h,
*p* CO (1.0 bar), N-methylmorpholine (2.0 eq), Pd(dppf)Cl$_2$ (3.0 mol %), EtOH, 50° C., 30 h.

Figure 4:
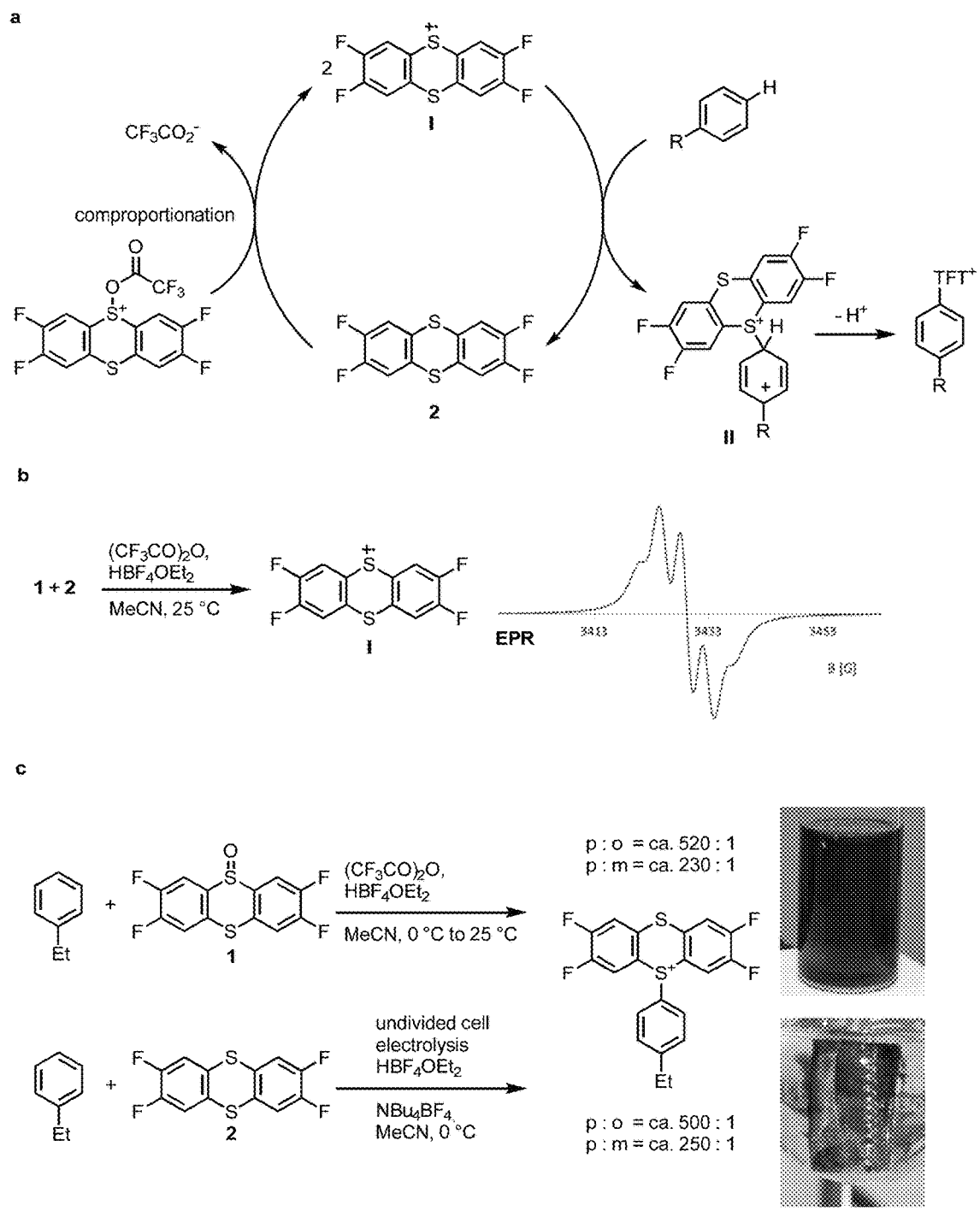

FIG. 4: Reaction mechanism and mechanistic experiments:
a) Proposed mechanism;
b) Comproportionation of TFT-S-oxide and TFT under reaction conditions, EPR spectrum;
c) Comparison of chemical and electrochemical thianthrenation.
Pictures:
Top: typical color of the reaction mixture of TFT-S-oxide with arenes (reaction almost complete);
Bottom: Purple color of TFT radical cations formed at the surface of the Pt-anode during electrolysis of TFT in presence of HBF$_4$OEt$_2$, NBu$_4$BF$_4$, and ethylbenzene in MeCN at 25° C., the picture was taken ca. 10 s after turning the current on.

As shown in FIG. 1 for Bromo and boryl substituents being among the most useful linchpins in organic chemistry, two of the most selective transformations for bromination (*Angew. Chem. Int. Ed.*, 49, 2028-2032 (2010)) and borylation (*J. Am. Chem. Soc.*, 137, 5193-5198 (2015)) have been chosen and been evaluated for their selectivity for functionalization of ethylbenzene. Transition-metal-mediated electrophilic bromination is mostly controlled electronically and thus functionalizes positions ortho and para to electron donating groups and meta to electron withdrawing groups, whereas iridium catalyzed borylation reactions are mostly sterically controlled and can afford high selectivity for certain substitution patterns, such as for 1,3-disubstituted arenes (*Chem. Rev.*, 110, 890-931 (2010)). The inventors present here a C—H functionalization reaction that can proceed in >99% selectivity, even for monosubstituted arenes, to afford novel aryltetrafluorothianthrenium salts (Ar-TFT$^+$).

Figure 2:
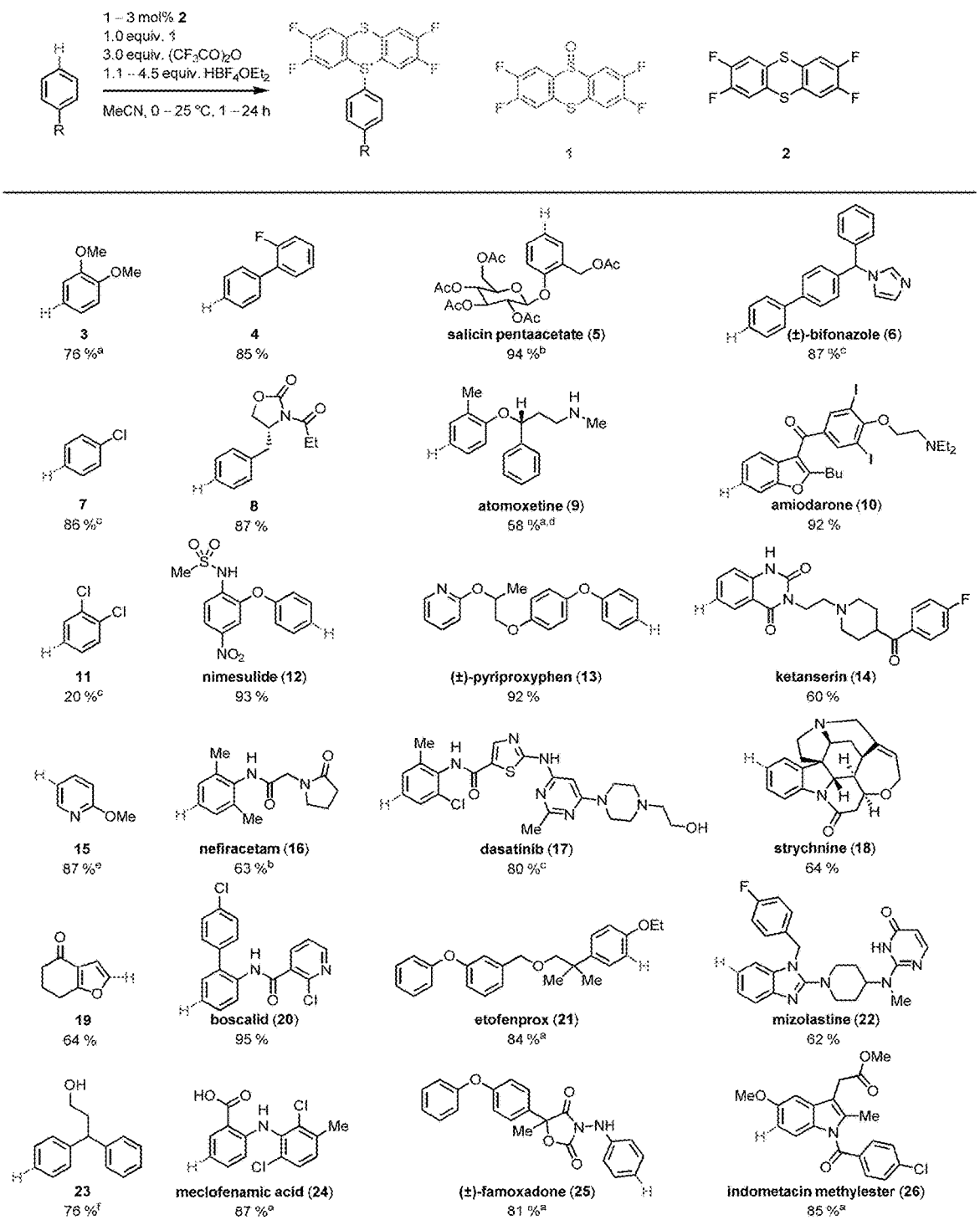
FIG. 2: Substrate-scope of the inventive thianthrenation process.
Figure 3:
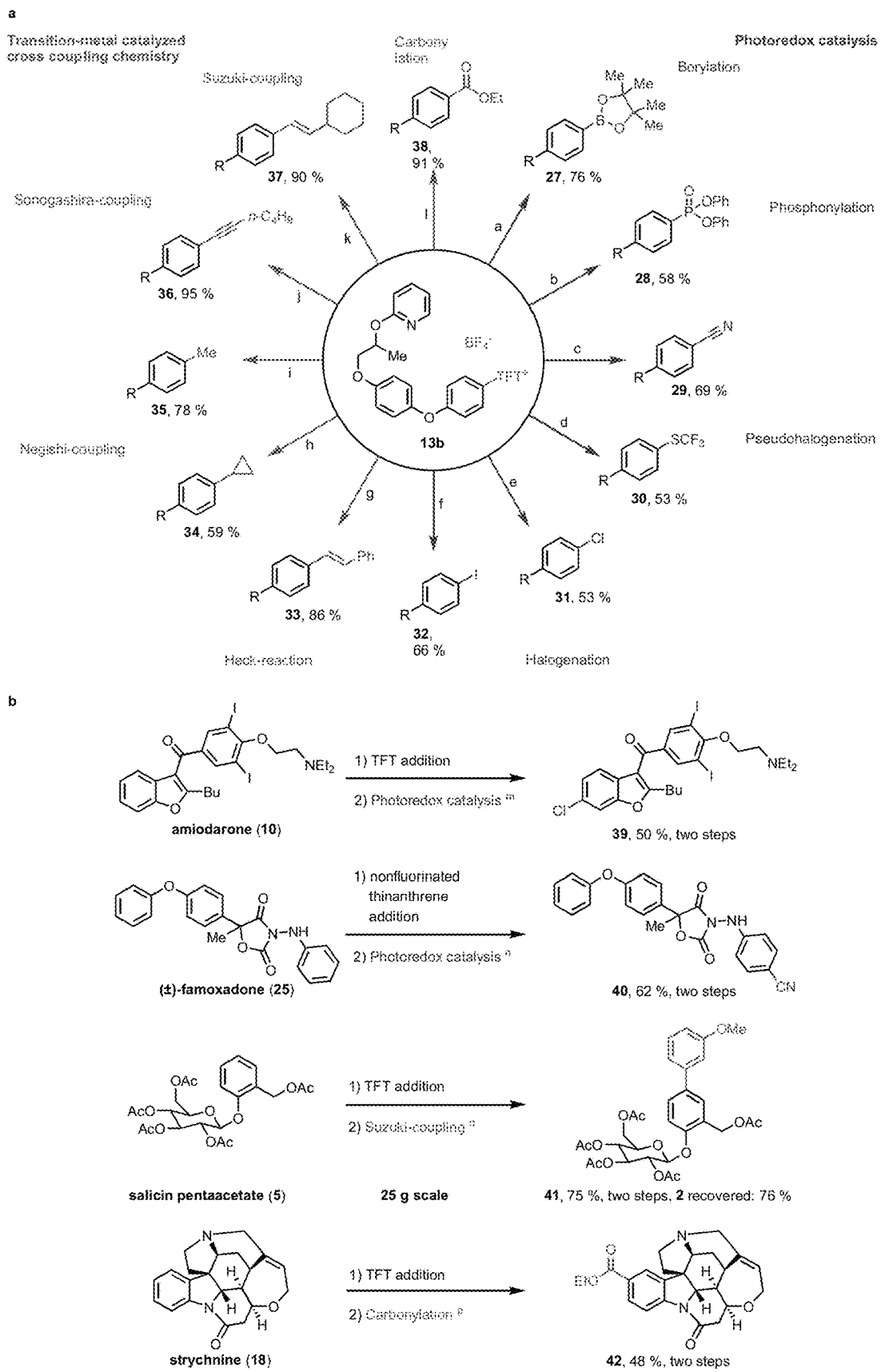
FIG. 3: Application of thianthrenation to functionalize complex arenes.

As shown in FIG. 2, a sulfoxide-based approach is disclosed to access thianthrene radical cations from the new thianthrene derivative 1 that can be prepared on scale in two steps from 1,2-difluorobenzene and disulfur dichloride via tetrafluorothianthrene 2. The tetrafluorothiantrene radical cation generated in situ reacts chemoselectively to functionalize arenes in preference to undergoing deleterious side reactions. The high degree of chemoselectivity enables a substrate scope that, with respect to structural complexity, rivals the state-of-the-art of contemporary aromatic C—H functionalization chemistry.

As illustrated in FIG. 4, the inventors propose that thianthrenation proceeds in three steps: generation of radical cations (I), formation of a dicationic adduct (II), and finally irreversible deprotonation to form product (FIG. 4*a*). Inverse first order in thianthrene in the rate law of the reaction of nonfluorinated thianthrene radicals with anisole rules out radical addition followed by hydrogen atom abstraction. A small primary kinetic hydrogen isotope effect (KIE=1.7 and 1.9 for intra- and intermolecular competition experiments, respectively), together with the inverse first order in thianthrene, rules out radical addition, followed by deprotonation and subsequent oxidation. In support of the proposed mechanism, the inventors observed the generation of radical cations by comproportionation of TFT-S-oxide 1 and TFT 2 under the reaction conditions by EPR spectroscopy (FIG. 4*b*). Moreover, TFT radicals could also be generated and observed by anodic oxidation of TFT 2, and in the presence of arene the formation of TFT-salts was observed in selectivities similar to those observed under standard reaction conditions, which provides evidence that both reactions proceed via the same reactive species (FIG. 4*c*). Radical formation from 1 can also be induced by reductants other than 2, e.g. solvents or trace impurities, because the radicals were also detected in the initial absence of 1. Under typical reaction conditions, radical concentrations of more than 20% of the total TFT concentration were detected about one hour after combining the reagents, also the deep purple color of such mixtures indicative of I did not fade away within one week at 25° C., which indicates that the TFT radical I is persistent. Dication II could be formed from radical addition and subsequent oxidation, or by single electron oxidation of the arene by radical cation I followed by recombination with a second radical I, or by the initial disproportionation of I to a thianthrene dication, followed by arene addition; our mechanism experiments cannot distinguish between these pathways. A Hammett analysis indicated that positive charge is accumulated on the aromatic ring during the reaction, which supports a mechanism proceeding via a cationic intermediate like II. The unusually steep slope of $\rho=-11$, when using $\sigma^+$ values as reported (J. Am. Chem. Soc., 80, 4979-4987 (1958)), means that the rate of reaction varies over more than nine orders of magnitude between anisole and chlorobenzene; the reaction time for electron-poor arenes such as chlorobenzene is 3 h. Conventional radicals, such as for example the phenyl radical are more promiscuous with respect to reactivity other than arene addition, such as hydrogen abstraction, which is why many side reactions are observed with conventional radicals. A reaction via radicals can therefore only span more than nine orders of magnitude in rate if the radical is sufficiently stable toward undesired pathways. As such, both the observed characteristics of the thianthrenation reaction, as well as the mechanistic data obtained, are consistent with the inventor's original design to identify a radical that can react in an endergonic step with a late transition state to elicit high positional selectivity, where para versus meta selectivity is mostly governed by an electronic bias, and the size of the reactive species additionally favors para over ortho attack.

The present invention is further illustrated by the following Examples.

Materials and Methods

All air- and moisture-insensitive reactions were carried out under an ambient atmosphere and monitored by thin-layer chromatography (TLC). High-resolution mass spectra were obtained using Q Exactive Plus from Thermo. Concentration under reduced pressure was performed by rotary evaporation at 25-40° C. at an appropriate pressure. Purified compounds were further dried under vacuum ($10^{-6}$-$10^{-3}$ bar). Yields refer to purified and spectroscopically pure compounds, unless otherwise stated.

Solvents

Dichloromethane, and methanol were purchased from Sigma-Aldrich and used as received. Anhydrous solvents were obtained from Phoenix Solvent Drying Systems. All deuterated solvents were purchased from Euhso-Top. Anhydrous acetonitrile-$d_3$ was dried by storage over molecular sieves.

Chromatography

Thin layer chromatography (TLC) was performed using EMD TLC plates pre-coated with 250 □m thickness silica gel 60 $F_{254}$ plates and visualized by irradiation UV light or by dipping the TLC plate into a dilute, alkaline, aqueous $KMnO_4$-solution. Flash chromatography was performed using silica gel (40-63 μm particle size) purchased from Geduran.

Electrochemistry

For analytical experiments, a BASI epsilon E2 device was used in combination with a BASI Cell Stand C3, purchased from Bioanalytic systems Inc. For cyclic voltammetry a MF-2013 electrode (99.95% Pt, 1.6 mm diameter) from Bioanalytic systems Inc. was used as working electrode. Potentials were measured versus a Ag/AgCl/NaCl$_{(aq)}$ (3 M) reference electrode, MF-2052 electrode RE-5B form Bioanalytic systems Inc. For bulk electrolysis a laboratory power supply unit, Peaktech 6070, purchased from Reichelt Elektronik, was used.

Photochemistry

All reactions with blue light were carried out using a photoreactor equipped with a blue LED module (KT-Elektronik, "100 W Power LED blau 450 nm Aquarium", 450 nm, 100 W), consisting out of 100 LED-chips. The power of the LED was adjusted using a linear regulator. To avoid overheating of the reaction mixture, vials were cooled with two Peltier-elements (TEC1-12706) while being irradiated with blue light. The radiant flux was quantified by calorimetry. The exposure of the reaction mixtures to blue light is given in Einsteins per millimole (E/mmol).

EPR Spectroscopy

EPR experiments have been performed at T=296 K on a Bruker Elexsys E500 spectrometer and a ST9402 resonator. The microwave frequency amounted to 9.66 GHz, a microwave power of 2 mW, and a modulation amplitude of 0.1 mT was used. Lower modulation amplitudes have been used as well, but did not lead to the observation of additional hyperfine structure.

NMR Spectroscopy

NMR spectra were recorded on a Bruker Ascend™ 500 spectrometer operating at 500 MHz, 471 MHz, 203 MHz, and 126 MHz, for $^1H$, $^{19}F$, $^{31}P$, and $^{13}C$ acquisitions, respectively. Chemical shifts are reported in ppm with the solvent residual peak as the internal standard. For $^1H$ NMR: $CDCl_3$, □□7.260; $CD_3CN$, □□1.940; $CD_2Cl_2$, □□5.320; For $^{13}C$ NMR: $CDCl_3$, □□77.16; $CD_3CN$, □ 1.32; $CD_2Cl_2$, □□53.84. $^{19}F$ NMR spectra were referenced using a unified chemical shift scale based on the $^1H$ resonance of tetramethylsilane (1% v/v solution in the respective solvent). Data is reported as follows: s=singlet, d=doublet, t=triplet, q=quartet, quin=quintet, sext=sextet, sept=septet, m=multiplet, bs=broad singlet; coupling constants in Hz; integration. Multiplets resulting from coupling to several magnetically non identical atoms with a coincidentally equal (within the limits of detection) coupling constant are indicated with ψ as well as splittings not resulting from a coupling to another spin. All $^{19}F$ spectra used for quantification were acquired with a reacquisition delay of 20 s.

Starting Materials

All substrates were used as received from commercial suppliers, unless otherwise stated. Chemicals were purchased from Sigma-Aldrich, Chempur, TCI or Alfa Aesar.

Experimental Procedures and Compound Characterization 2,3,7,8-Tetrafluorothianthrene (2)

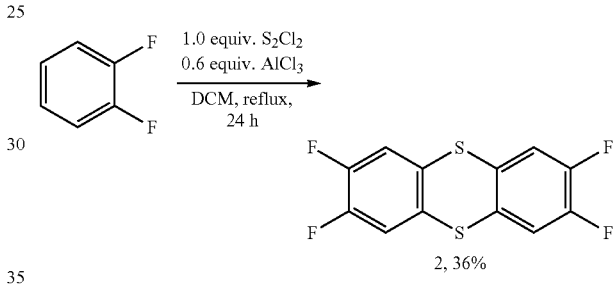

Under argon atmosphere, a 1 L round-bottom flask equipped with a teflon coated magnetic stirbar was charged with dry DCM (0.60 L, c=2.0 M), 1,1-difluorobenzene (118 ml, 0.14 kg, 1.2 mol, 1.0 equiv.), and disulfurdichloride (96 ml, 0.16 kg, 1.2 mol, 1.0 equiv.). The flask was attached to a Soxhlet-extractor (total height: 36 cm, diameter: 5 cm, maximum volume of solid to be extracted: ca. 80 ml) and a reflux condenser. The Soxhlet-extractor was charged with aluminium chloride (0.100 kg, 0.75 mol, 0.63 equiv.). The solution was heated at reflux (oil-bath temperature 75° C.) for 24 h and subsequently kept at 25° C. for another 24 h. The resulting dark blue mixture was carefully poured onto ice (ca. 0.5 kg). After all ice had molten, the mixture was filtered through a glass-frit. The obtained solid was washed with $Et_2O$ (ca. 50 ml). The layers of the filtrate were separated using a separatory funnel and the organic phase was concentrated (final volume ca. 100 ml) under reduced pressure, resulting in the formation of a colorless crystalline precipitate. The solid was collected by filtration through a glass-frit, and was subsequently washed with $Et_2O$ (ca. 40 ml), followed by sucking to dryness. The combined solids were dissolved in the lowest possible volume of EtOAc (ca. 1 L) at reflux at atmospheric pressure. The hot solution was decanted to separate the liquid from yellow precipitate (sulfur). Subsequently the solution was cooled to room temperature. Subsequently, the flask was kept at 0° C. for ca. 1 h. The obtained crystals were collected by filtration, and dried in vacuo. The remaining EtOAc solution was concentrated to a final volume of ca. 200 ml and was cooled to 0° C. The obtained crystals were collected by filtration, and dried in vacuo to afford a total of 62 g (36%) of tetrafluorothianthrene 2 (product still contains sulfur that is separated in the following step) as colorless needle-shaped crystals.

$R_f$=0.75 (silica gel, i-hexane/EtOAc, 10:1 (v/v)).

Melting Point: 202° C. [DCM/pentane].

NMR Spectroscopy:

$^1$H NMR (500 MHz, CDCl$_3$, 298 K, δ): 7.31 (t, J=8.5 Hz, 4H).

$^{13}$C {$^1$H} NMR (126 MHz, CDCl$_3$, 298 K, δ): 150.2 (dd, J=254.4 Hz, 15.3 Hz), 131.5 (ψt, J=5.0 Hz), 117.8 (dd, J=14.0 Hz, 6.8 Hz).

$^{19}$F NMR (471 MHz, CDCl$_3$, 298 K, δ): −136.9 (t, J=8.5 Hz).

HRMS-EI (m/z) calc'd for $C_{12}H_4F_4S_2^+$ [M]$^+$, 287.969059; found, 287.968875; deviation: 0.6 ppm.

Elemental analysis: calc'd for $C_{12}H_4F_4S_2$: C: 50.00%, H: 1.40%, S: 22.24%, found: C: 49.96%, H: 1.47%, S: 22.47%. [sample was purified by chromatography on silica gel eluting with pentane/DCM].

2,3,7,8-Tetrafluorothianthrene-S-oxide (1)

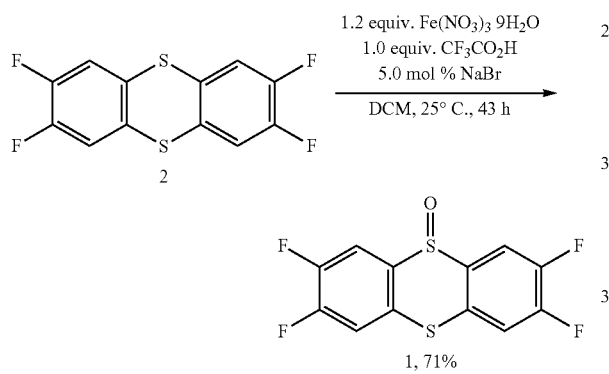

1, 71%

Oxidation of 2 was carried out using a modified procedure for sulfide oxidation (27). Under an ambient atmosphere, a 500 mL round-bottom flask equipped with a teflon coated magnetic stirbar was charged with DCM (0.35 L, c=0.49 M), tetrafluorothianthrene 2 (50.0 g, 0.17 mol, 1.0 equiv.), sodium bromide (0.89 g, 8.7 mmol, 5.1 mol %), and iron(III) nitrate nonahydrate (86 g, 0.21 mol, 1.2 equiv.). To the mixture was added trifluoroacetic acid (13.3 mL, 20 g, 0.17 mol, 1.0 equiv.). The reaction mixture was stirred at 25° C. until reaching completion (progress monitored by TLC; i-hexane/EtOAc, 10:1; KMnO$_4$ stain, 43 h). Upon completion, water (ca. 300 mL) was added. The suspension was filtered, the filtrate was poured into a separatory funnel and the layers were separated. The aqueous layer was extracted with DCM (200 mL). The filter cake was added to the combined organic layers, and the suspension was concentrated under reduced pressure. MeCN (50 ml) was added to the residue, and the resulting suspension was filtered through a glass-frit. The solid was washed with MeCN (ca. 30 ml) and subsequently dried in vacuo. The resulting solid was dissolved in the lowest possible volume of toluene (ca. 0.5 L) at reflux at atmospheric pressure. Subsequently, the flask was wrapped in aluminum foil and allowed to cool to room temperature. The obtained crystals were collected by filtration, washed with Et$_2$O (50 ml), and dried in vacuo to afford a first portion of product. The filtrate was evaporated. To the solid was added acetone (ca. 500 ml) and the mixture was stirred at reflux for 5 min. The mixture was allowed to stand for 5 min, subsequently the mixture was decanted. The solution was evaporated and the resulting colorless solid was recrystallized from toluene, the crystals were washed with Et$_2$O, and dried in vacuo, to afford a second portion of product, accumulating to a total of 37.7 g (71%) of tetrafluorothianthrene-S-oxide 1 as colorless crystals.

$R_f$=0.39 (silica gel, i-hexane/EtOAc, 10:1 (v/v)).

Melting Point: 255° C.

NMR Spectroscopy:

$^1$H NMR (500 MHz, CDCl$_3$, 298 K, δ): 7.74 (dd, J=8.8 Hz, 7.3 Hz, 2H), 7.49 (dd, J=9.0 Hz, 6.5 Hz, 2H).

$^{13}$C {$^1$H} NMR (126 MHz, CDCl$_3$, 298 K, δ): 151.5 (dd, J=256.8 Hz, 13.2 Hz), 151.3 (dd, J=256.4 Hz, 13.6 Hz), 138.5-138.3 (m), 124.3 (dd, J=7.1 Hz, 4.3 Hz), 118.8 (d, J=20.4 Hz), 114.6-114.3 (m).

$^{19}$F NMR (471 MHz, CDCl$_3$, 298 K, δ): −132.8 (dψt, J=20.0 Hz, 8.0 Hz), −133.7 (ddd, J=20.0 Hz, 9.0 Hz, 6.5 Hz).

HRMS-EI (m/z) calc'd for $C_{12}H_4F_4OS_2^+$ [M]$^+$, 303.963974; found, 303.963826; deviation: 0.5 ppm.

Thianthrene-S-oxide (S2)

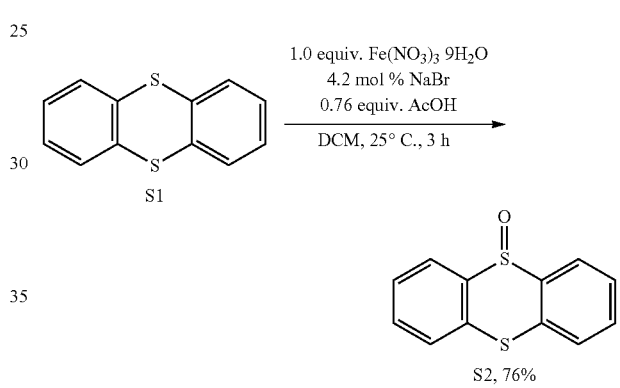

S2, 76%

Oxidation of S1 was carried out using a modified procedure for sulfide oxidation (27). Under an ambient atmosphere, a 100 mL round-bottom flask equipped with a teflon coated magnetic stirbar was charged with DCM (50 mL, c=0.46 M), thianthrene (S1) (5.0 g, 23 mmol, 1.0 equiv.), sodium bromide (0.10 g, 0.97 mmol, 4.2 mol %), iron(III) nitrate nonahydrate (9.3 g, 23 mmol, 1.0 equiv.), and acetic acid (1.0 mL, 1.1 g, 17 mmol, 0.76 equiv.). The reaction mixture was stirred at 25° C. for 3 h. The reaction mixture was diluted with water (50 ml), and was poured into a separatory funnel. The aqueous and the organic layer were separated. The aqueous layer was extracted with DCM (ca. 10 ml). The organic layers were combined, dried over Na$_2$SO$_4$, filtered, and the solvent was removed under reduced pressure. The resulting solid was recrystallized from EtOAc. The obtained crystals were collected by filtration, washed with Et$_2$O (10 ml), and dried in vacuo to afford 4.1 g (76%) of thianthrene-S-oxide (S2) as colorless needle-shaped crystals.

NMR Spectroscopy:

$^1$H NMR (500 MHz, CDCl$_3$, 298 K, δ): 7.89 (dd, J=7.8 Hz, 1.4 Hz, 2H), 7.57 (dd, J=7.8 Hz, 1.2 Hz, 2H), 7.50 (ψtd, J=7.6 Hz, 1.2 Hz, 2H), 7.37 (ψtd, J=7.5 Hz, 1.4 Hz, 2H).

$^{13}$C {$^1$H} NMR (126 MHz, CDCl$_3$, 298 K, δ): 141.4, 129.8, 129.0, 128.4, 124.4.

HRMS-EI (m/z) calc'd for $C_{12}H_8OS_2^+$ [M]$^+$, 232.001660; found, 232.001795, deviation: 0.6 ppm.

Representative Procedure for the Thianthrenation of Arenes with Thianthrene-S-Oxide

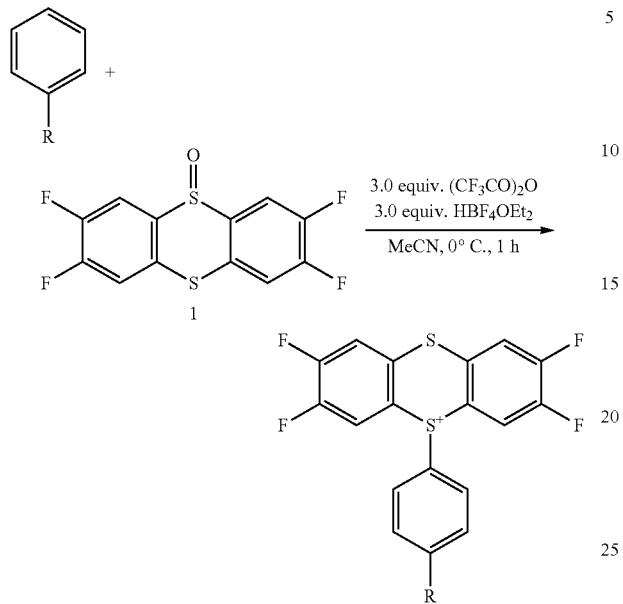

Under an ambient atmosphere, a 20 ml glass-vial was charged with arene (0.50 mmol, 1.0 equiv.) and dry MeCN (2.0-4.0 ml, c=0.13-0.25 M). After cooling to 0° C., HBF$_4$OEt$_2$ (1.2 equiv.+1.0 equiv. per basic functional group) was added to the vial while stirring the reaction mixture. Other acids like triflic acid (TfOH) may be used instead of HBF$_4$.OEt$_2$. For acid sensitive substrates BF$_3$.OEt$_2$ or trimethylsilyltriflate (TMSOTf) may be used. After all solids had dissolved, tetrafluorothianthrene reagent (97% tetrafluorothianthrene-S-oxide 1, 3% tetrafluorothianthrene, 157 mg, 0.50 mmol, 1.0 equiv; pure sulfoxide 1 works similarly well; for electron rich substrates nonfluorinated thianthrene-S-oxide can be used instead of tetrafluorothianthrene reagent) was added in one portion to the solution at 0° C., leading to a suspension. Subsequently, trifluoroacetic anhydride (0.21 ml, 0.32 g, 1.5 mmol, 3.0 equiv.) was added in one portion at 0° C., resulting in a color change to deep purple. The vial was sealed with a screw-cap. The mixture was stirred at 0° C. for 1 h, subsequently, the reaction mixture was warmed to 25° C. and stirred until all solid dissolved and the intensity of the purple color decreased. The solution was diluted with 5 ml DCM and poured onto a mixture of 30 ml DCM, 20 ml saturated aqueous Na$_2$CO$_3$ solution, and 10 ml water. After stirring for 5 min at 25° C., the mixture was poured into a separatory funnel, and the layers were separated. The DCM layer was washed with aqueous NaBF$_4$ solution (2×ca. 20 ml, 5% w/w) and with water (2×ca. 20 ml). Washing with NaBF$_4$ solution is only required if it is of interest, that the product contains only one type of counterion, solutions containing other ions, like triflate or hexafluorophosphate may be used as well. The DCM layer was dried over Na$_2$SO$_4$, filtered, and the solvent was removed under reduced pressure. In order to obtain analytically pure samples of thianthrenium salts, the residue was purified by chromatography on silica gel eluting with DCM/i-PrOH, subsequently, the product was dissolved in 2 ml DCM and precipitated with 20 ml Et$_2$O. In most cases the thianthrenium salts can be used in subsequent transformations without chromatographic purification or precipitation. The solid was dried in vacuo to afford the thianthrenium salt.

Representative Procedure for the Electrochemical Thianthrenation of Arenes

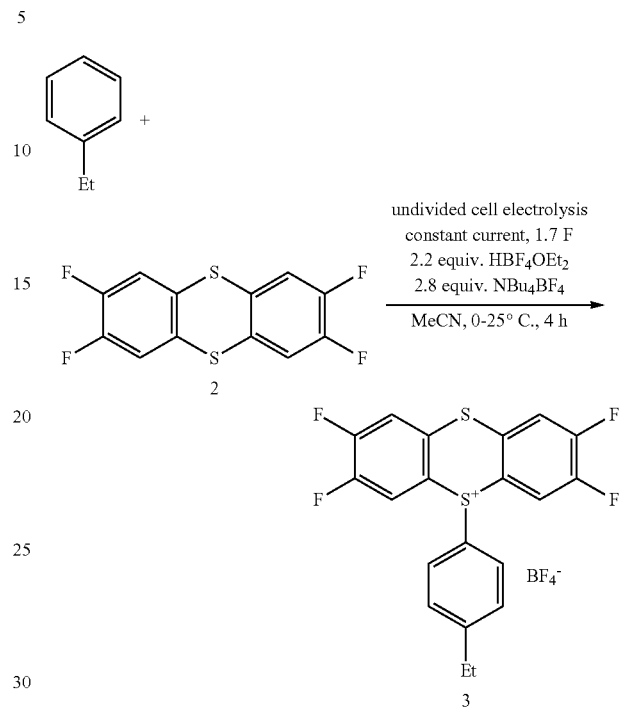

Under an Ar-atmosphere, a flamedried 50 ml Schlenk-flask was charged with tetrafluorothianthrene 2 (144 mg, 0.50 mmol, 1.0 equiv.), and tetrabutylammonium tetrafluoroborate (465 mg, 1.4 mmol, 2.8 equiv.). Under argon-atmosphere, dry MeCN (40 ml, c=0.013 M) was added, followed by the addition of HBF$_4$OEt$_2$ (0.15 ml, 0.18 g, 1.1 mmol, 2.2 equiv.), and ethylbenzene (62 µl, 54 mg, 0.51 mmol, 1.0 equiv.). The mixture was cooled to 0° C., and electrolyzed (anode: Pt-web ca. 20×30 mm, cathode: Pt-wire, length ca. 200 mm, diameter ca. 0.5 mm) at 0° C. at a constant current of 10 mA for 2.3 h (84 C, 1.7 F). The purple solution was allowed to warm to 25° C., and it was allowed to stand at 25° C. for 2 h. The solution was concentrated under reduced pressure, and subsequently diluted with DCM (ca. 10 ml). The organic layer was washed with water (ca. 10 ml). The solvent was removed, and the residue was analyzed by $^1$H and $^{19}$F NMR. The yield was determined by NMR spectroscopy using fluorobenzene as internal standard. Compound 3 was obtained in 21% yield (25% current efficiency).

Representative Procedure for the Thianthrenation Using Dimesylperoxide

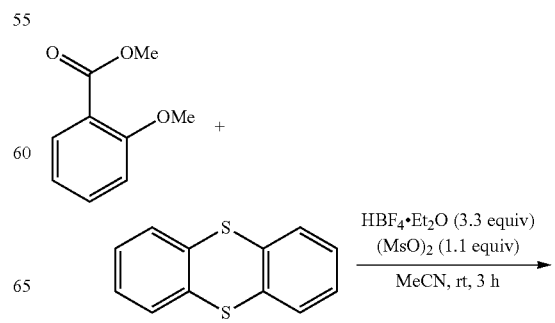

-continued

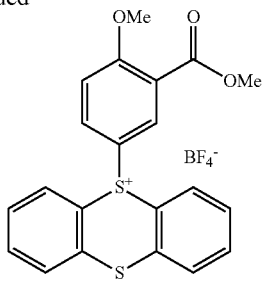

Under an ambient atmosphere, a 50 ml round-bottom flask was charged with a Teflon-coated stir bar, thianthrene (0.865 g, 4.0 mmol, 1.0 equiv), methyl-2-methylbenzoate (0.665 g, 4.0 mmol, 1.0 equiv.), and acetonitrile (10 mL). At room temperature (29° C.), tetrafluoroboric acid diethyl ether complex (1.8 mL, 13.2 mmol, 3.3 equiv) was added, followed by the slow addition of a solution of bis(methanesulfonyl) peroxide (0.837 g, 4.4 mmol, 1.1 equiv) in acetonitrile (10 mL). After the addition of the bis(methanesulfonyl) peroxide, the reaction mixture became homogeneous and a deep blue color. The round-bottom flask was sealed with a septum and stirred at ambient temperature (29° C.) until methyl-2-benzoate was no longer visible by thin-layer chromatography (approx. 3 h). The reaction mixture was concentrated under reduced pressure, and taken up in methylene chloride (25 mL). The organic phase washed three times with water, dried over sodium sulfate, and concentrated via rotary evaporator. The resulting foamy white solid was left overnight under high vacuum affording the title compound as a hygroscopic white solid (1.51 g, 81% yield).

NMR Spectroscopy:
$^1$H NMR (500 MHz, Chloroform-d) δ 8.53-8.46 (m, 2H), 7.80-7.66 (m, 6H), 7.58 (dd, J=9.1, 2.5 Hz, 1H), 7.48 (d, J=2.8 Hz, 1H), 7.05 (d, J=9.2 Hz, 1H), 3.84 (s, 3H), 3.75 (s, 3H).

Representative Procedure for Thianthrenation of Arenes Using Selectfluor

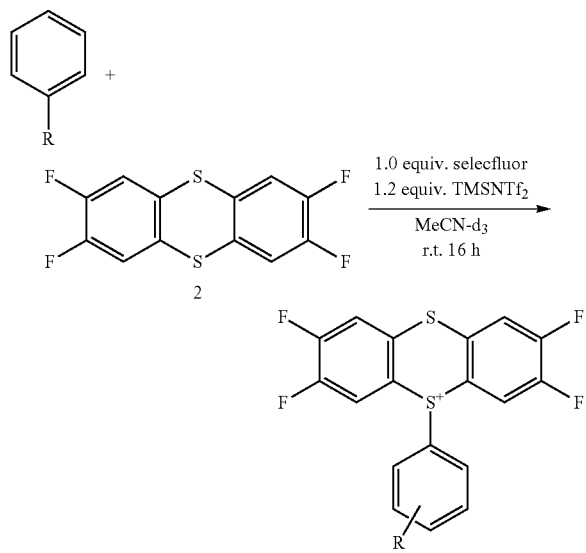

In a glovebox, a 4 ml glass-vial was charged with tetrafluorothianthrene (28.8 mg, 0.10 mmol. 1.0 equiv.), selectfluor (35.4 mg, 0.10 mmol, 1.0 equiv.) and 0.8 ml of MeCN-d$_3$ (c=0.13 M). Subsequently, the arene (0.10 mmol, 1.0 equiv.) was added using an Eppendorf-pipette, followed by addition of a stock solution of TMSNTf$_2$ in MeCN-d$_3$ (c=0.60 M, 0.20 ml, 0.12 mmol, 1.2 equiv.). The vial was sealed with a septum cap and the reaction mixture was left to stir at ambient temperature overnight (16 h). The yield and conversion of the reaction were determined by $^1$H-NMR analysis of the crude reaction mixture. Alternatively to TMSNTf$_2$ one can also use HBF$_4$OEt$_2$, HNTf$_2$, LiNTf$_2$ or TMSOTf 1,2-Dimethoxybenzene derived thianthrenium salt 3a

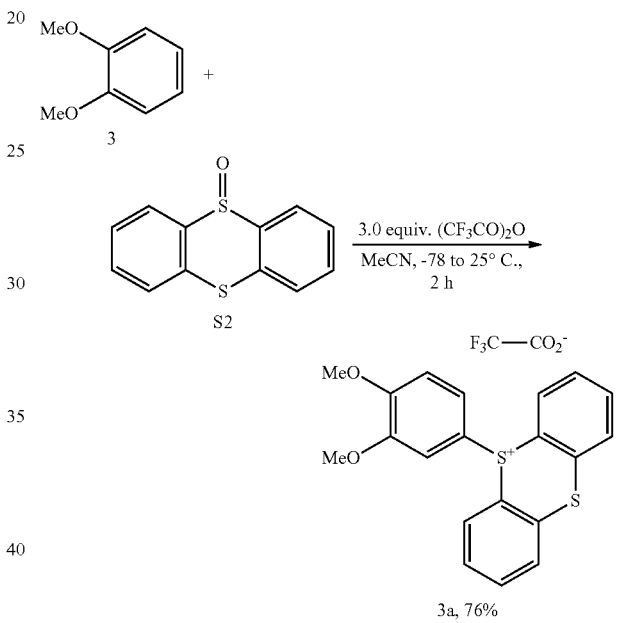

Under an ambient atmosphere, a 20 ml glass-vial was charged sequentially with 1,2-dimethoxybenzene (3) (69 mg, 0.50 mmol, 1.0 equiv.), thianthrene-S-oxide (S2) (116 mg, 0.50 mmol, 1.0 equiv.), and dry MeCN (2.0 ml, c=0.25 M). After all solids had dissolved (ca. 1 min), the solution was cooled to −78° C., and trifluoroacetic anhydride (0.21 ml, 0.32 g, 1.5 mmol, 3.0 equiv.) was added in one portion at −78° C. The mixture was allowed to warm to 0° C. over a period of 2 h. Then, the solution was diluted with 5 ml DCM and poured into a separatory funnel. The organic layer was washed with 50 ml water. The solvent was removed under reduced pressure, and the oily residue was purified by chromatography on silica gel eluting with DCM/i-PrOH (gradient from 10:1 to 1:1 (v/v)). The obtained product was dissolved in 5 ml DCM, and precipitated with 40 ml pentane. The oily precipitate was dried in vacuo to afford 177 mg (76%) of 3a as highly viscous, colorless oil.

NMR Spectroscopy:
$^1$H NMR (500 MHz, CD$_3$CN, 298 K, δ): 8.30 (dd, J=8.0 Hz, 1.4 Hz, 2H), 7.92 (dd, J=8.0 Hz, 1.4 Hz, 2H), 7.83 (ψtd, J=7.7 Hz, 1.4 Hz, 2H), 7.74 (ψtd, J=7.7 Hz, 1.4 Hz, 2H), 6.99 (d, J=8.8 Hz, 1H), 6.88 (dd, J=8.7 Hz, 2.5 Hz, 1H), 6.83 (d, J=2.5 Hz, 1H), 3.80 (s, 3H), 3.64 (s, 3H).

$^{13}$C {$^1$H} NMR (126 MHz, CD$_3$CN, 298 K, δ): 160.9 (q, J=32.2 Hz), 154.6, 151.7, 136.7, 135.7, 135.1, 131.3, 130.9, 124.2, 120.8, 118.5 (q, J=297.0 Hz), 114.3, 113.4, 112.1, 56.94, 56.89.

$^{19}$F {$^1$H} NMR (471 MHz, CD$_3$CN, 298 K, δ): −76.3 (s).

HRMS-ESI (m/z) calc'd for C$_{20}$H$_{17}$O$_2$S$_2^+$ [M-TFA]$^+$, 353.066450; found, 353.066590; deviation: 0.4 ppm.

2-Fluorobiphenyl Derived Thianthrenium Salt 4a

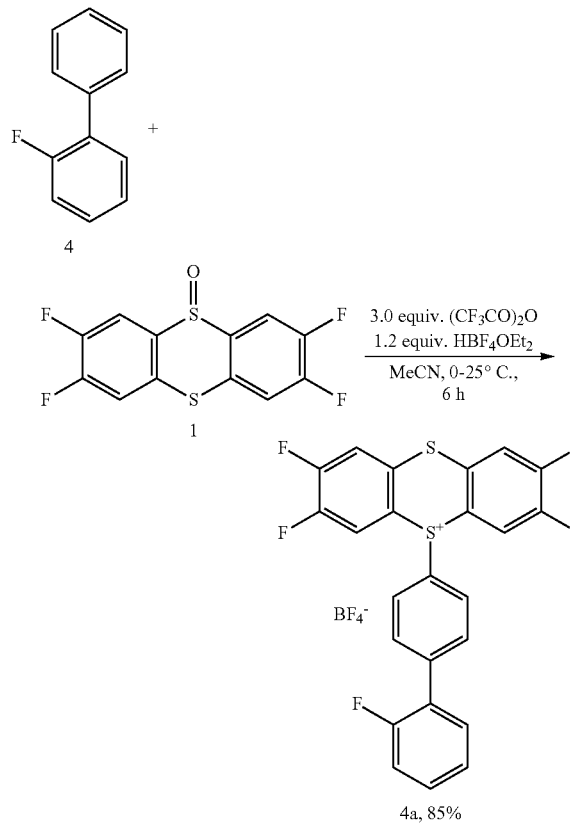

Under an ambient atmosphere, a 20 ml glass-vial was charged with 2-fluorobiphenyl (4) (86 mg, 0.50 mmol, 1.0 equiv.) and dry MeCN (2.0 ml, c=0.25 M). Trifluoroacetic anhydride (0.21 ml, 0.32 g, 1.5 mmol, 3.0 equiv.) was added while stirring the reaction mixture. After cooling to 0° C., tetrafluorothianthrene reagent (97% (w/w) tetrafluorothianthrene-S-oxide 1, 3% (w/w) tetrafluorothianthrene 2, 157 mg, 0.50 mmol, 1.0 equiv.) was added in one portion, followed by the addition of HBF$_4$OEt$_2$ (82 μl, 97 mg, 0.60 mmol, 1.2 equiv.) in one portion at 0° C., leading to a purple suspension. The vial was sealed with a screw-cap, and the mixture was stirred at 0° C. for 1 h, followed by stirring at 25° C. for 5 h, until a slight purple solution was obtained. The reaction mixture was concentrated under reduced pressure, and subsequently, diluted with 5 ml DCM. The DCM phase was poured onto a saturated aqueous NaHCO$_3$ solution (ca. 10 ml). The mixture was poured into a separatory funnel and the layers were separated. The DCM layer was washed with aqueous NaBF$_4$ solution (2×ca. 10 ml, 5% w/w), and with water (2×ca. 10 ml). The DCM layer was dried over Na$_2$SO$_4$, filtered, and the solvent was removed under reduced pressure. The residue was purified by chromatography on silica gel eluting with DCM/i-PrOH, (30:1 (v/v)). The product was dissolved in 5 ml DCM and precipitated with 20 ml Et$_2$O. The suspension was decanted, and the solid was dried in vacuo to afford 232 mg (85%) of 4a as a colorless solid.

NMR Spectroscopy:

$^1$H NMR (500 MHz, CD$_3$CN, 298 K, δ): 8.48 (dd, J=9.1 Hz, 7.2 Hz, 2H), 7.97 (dd, J=9.9 Hz, 7.1 Hz, 2H), 7.69 (dd, J=8.9 Hz, 1.5 Hz, 2H), 7.48-7.41 (m, 2H), 7.33 (d, J=9.0 Hz, 2H), 7.28 (ψtd, J=7.6 Hz, 1.2 Hz, 1H), 7.21 (ddd, J=11.1 Hz, 8.2 Hz, 0.9 Hz, 1H).

$^{13}$C {$^1$H} NMR (128 MHz, CD$_3$CN, 298 K, δ): 160.5 (d, J=247.3 Hz), 154.9 (dd, J=261.8 Hz, 13.1 Hz), 151.6 (dd, J=255.7 Hz, 13.6 Hz), 141.8, 135.4 (dd, J=8.6 Hz, 3.8 Hz), 132.1 (d, J=8.7 Hz), 131.9-131.8 (m), 129.6, 127.0 (d, J=12.6 Hz), 126.1 (d, J=3.6 Hz), 125.8 (dd, J=22.3 Hz, 2.5 Hz), 122.8, 121.3 (d, J=21.8 Hz), 117.2 (d, J=22.6 Hz), 115.3 (dd, J=7.2 Hz, 3.5 Hz).

$^{19}$F {$^1$H} NMR (471 MHz, CD$_3$CN, 298 K, δ): −150.9 (bs), −150.8 (bs), −133.7 (d, J=20.4 Hz), −125.2 (d, J=20.4 Hz), −119.3 (s).

HRMS-ESI (m/z) calc'd for C$_{24}$H$_{12}$F$_5$S$_2^+$ [M-BF$_4$]$^+$, 459.029520; found, 459.029513; deviation: 0.02 ppm.

Salicin Pentaacetate (5)

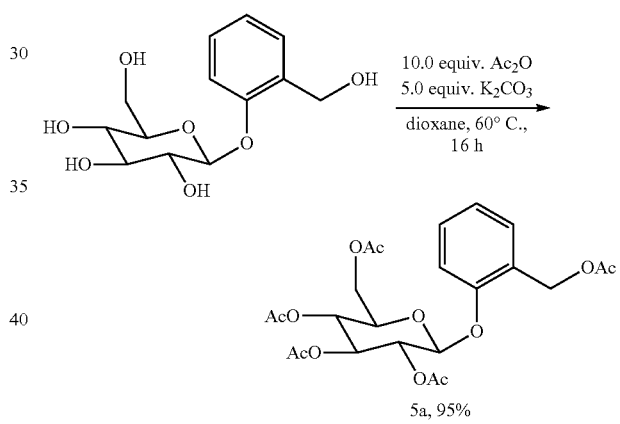

Under an ambient atmosphere, a 250 ml roundbottom flask was charged sequentially with salicine (10.0 g, 35 mmol, 1.0 equiv.), K$_2$CO$_3$ (24.0 g, 0.18 mol, 2.0 equiv.), and dioxane (140 ml, c=0.25 M). Acetic anhydride (33.1 ml, 36 g, 0.35 mol, 10 equiv.) was added in one portion to the reaction mixture. The colorless suspension was stirred at 60° C. for 16 h before the reaction mixture was concentrated under reduced pressure, diluted with EtOAc (150 ml), and washed with water (ca. 250 ml). The mixture was poured into a separatory funnel, and the layers were separated. The ethylacetate layer was dried over Na$_2$SO$_4$, filtered, and the solvent was removed under reduced pressure. The crude product was recrystallized from EtOAc/i-hexane (1:1, ca. 100 ml). The crystals were washed with pentane (ca. 50 ml) and dried in vacuo to afford 16.5 g (95%) of 5a as colorless crystals.

NMR Spectroscopy:

$^1$H NMR (500 MHz, CDCl$_3$, 298 K, δ): 7.32 (dd, J=7.8 Hz, 1.7 Hz, 1H), 7.27-7.23 (m, 1H), 7.08-7.04 (m, 2H), 5.31-5.25 (m, 2H), 5.19-5.12 (m, 1H), 5.09 (d, J=12.9 Hz, 1H), 5.06 (d, J=7.5 Hz, 1H), 5.02 (d, J=12.9 Hz, 1H), 4.26 (dd, J=12.3 Hz, 5.3 Hz, 1H), 4.16 (dd, J=12.3 Hz, 2.5 Hz,

1H), 3.84 (ddd, J=10.0 Hz, 5.3 Hz, 2.5 Hz, 1H), 2.06 (s, 6H), 2.04 (s, 3H), 2.02 (s, 3H), 2.01 (s, 3H).

$^{13}$C {$^1$H} NMR (126 MHz, CDCl$_3$, 298 K, δ): 170.7, 170.5, 170.2, 169.4, 169.3, 154.6, 129.6, 129.5, 126.3, 123.6, 115.9, 99.4, 72.7, 72.0, 71.0, 68.4, 61.9, 61.1, 21.0, 20.7, 20.6 (3 C-atoms).

HRMS-ESI (m/z) calc'd for C$_{23}$H$_{28}$O$_{12}$Na$^+$ [M+Na]$^+$, 519.147580; found 519.147299; deviation: 0.5 ppm.

Salicin Pentaacetate Derived Thianthrenium Salt 5a

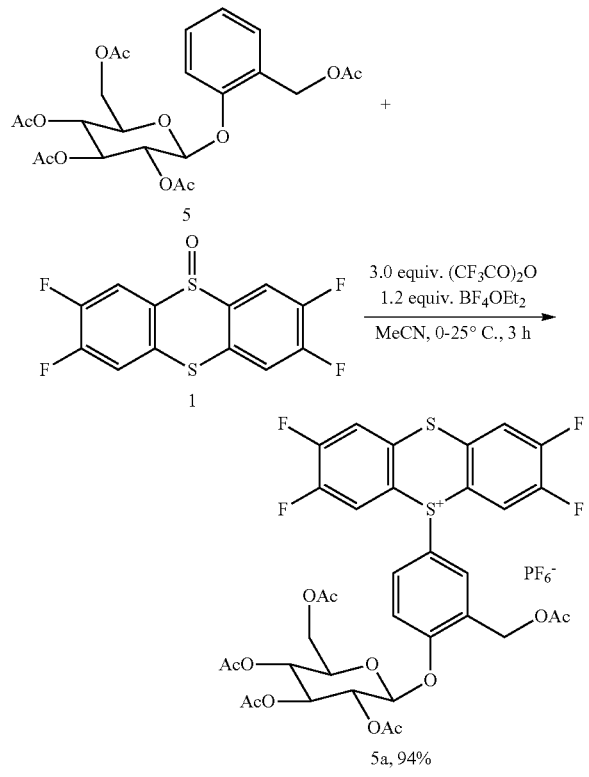

Under an ambient atmosphere, a 20 ml glass-vial was charged with salicin pentaacetate (5) (248 mg, 0.50 mmol, 1.0 equiv.), and dry MeCN (2.0 ml, c=0.25 M). Trifluoroacetic anhydride (0.21 ml, 0.32 g, 1.5 mmol, 3.0 equiv.) was added while stirring the reaction mixture. After cooling to 0° C., tetrafluorothianthrene reagent (97% (w/w) tetrafluorothianthrene-S-oxide 1, 3% (w/w) tetrafluorothianthrene 2, 157 mg, 0.50 mmol, 1.0 equiv.) was added in one portion, followed by the addition of BF$_3$OEt$_2$ (74 μl, 85 mg, 0.60 mmol, 1.2 equiv.) in one portion at 0° C., leading to a purple suspension. The vial was sealed with a screw-cap, and the mixture was stirred at 0° C. for 1 h, followed by stirring at 25° C. for 2 h, until a slight purple solution was obtained. The reaction mixture was poured onto a vigorously stirred biphasic mixture of DCM (ca. 5 ml), and saturated aqueous Na$_2$CO$_3$ solution (ca. 10 ml). The resulting mixture was poured into a separatory funnel, and the layers were separated. The DCM layer was washed with aqueous NaPF$_6$ solution (2×ca. 10 ml, 5% w/w), and with water (2×ca. 10 ml). The DCM layer was dried over Na$_2$SO$_4$, filtered, and the solvent was removed under reduced pressure. The residue was purified by chromatography on silica gel eluting with DCM/i-PrOH, (30:1). The product was dissolved in 5 ml DCM and precipitated with 20 ml Et$_2$O. The suspension was decanted, and the solid was dried in vacuo to afford 434 mg (94%) of 5a as a colorless solid.

NMR Spectroscopy:

$^1$H NMR (500 MHz, CD$_3$CN, 298 K, δ): 8.37 (dd, J=9.1 Hz, 7.1 Hz, 2H), 7.96 (ddψd, J=9.8 Hz, 7.0 Hz, 1.8 Hz, 2H), 7.27-7.19 (m, 3H), 5.40 (d, J=7.8 Hz, 1H), 5.37 (ψt, J=9.7 Hz, 1H), 5.21 (dd, J=9.7 Hz, 7.8 Hz, 1H), 5.11 (ψt, J=9.7 Hz, 1H), 4.89 (s, 2H), 4.24-4.19 (m, 1H), 4.12-4.06 (m, 2H), 2.00 (s, 6H), 1.99 (s, 3H), 1.97 (s, 3H), 1.95 (s, 3H).

$^{13}$C {$^1$H} NMR (126 MHz, CD$_3$CN, 298 K, δ): 171.2 (2 C-atoms), 170.9, 170.6, 170.4, 158.7, 154.8 (ddψd, J=262.3 Hz, 12.9 Hz, 2.6 Hz), 153.0 (dd, J=255.9, 13.5 Hz), 135.0 (dψt, J=8.3 Hz, 4.1 Hz), 131.5, 130.4, 129.8, 125.2 (dψdd, J=22.0 Hz, 7.2 Hz, 1.6 Hz), 121.1 (dψd, J=21.7 Hz, 3.0 Hz), 117.2, 115.8, 115.7 (ψddd, J=14.4 Hz, 7.2 Hz, 3.3 Hz), 98.4, 73.0, 72.7, 71.4, 68.4, 62.5, 60.7, 20.93, 20.91, 20.89, 20.86, 20.85.

$^{19}$F {$^1$H} NMR (471 MHz, CD$_3$CN, 298 K, δ): −73.1 (d, J=708 Hz), −126.2 (dψd, J=20.4 Hz, 9.1 Hz), −134.4 (dψd, J=20.2 Hz, 12.2 Hz).

$^{31}$P {$^1$H} NMR (203 MHz, CD$_3$CN, 298 K, δ): −145.4 (sept, J=708 Hz).

HRMS-ESI (m/z) calc'd for C$_{35}$H$_{31}$F$_4$O$_{12}$S$_2^+$ [M-PF$_6$]$^+$, 783.119540; found, 783.118764; deviation: 1.0 ppm.

Bifonazole Derived Thianthrenium Salt 6a

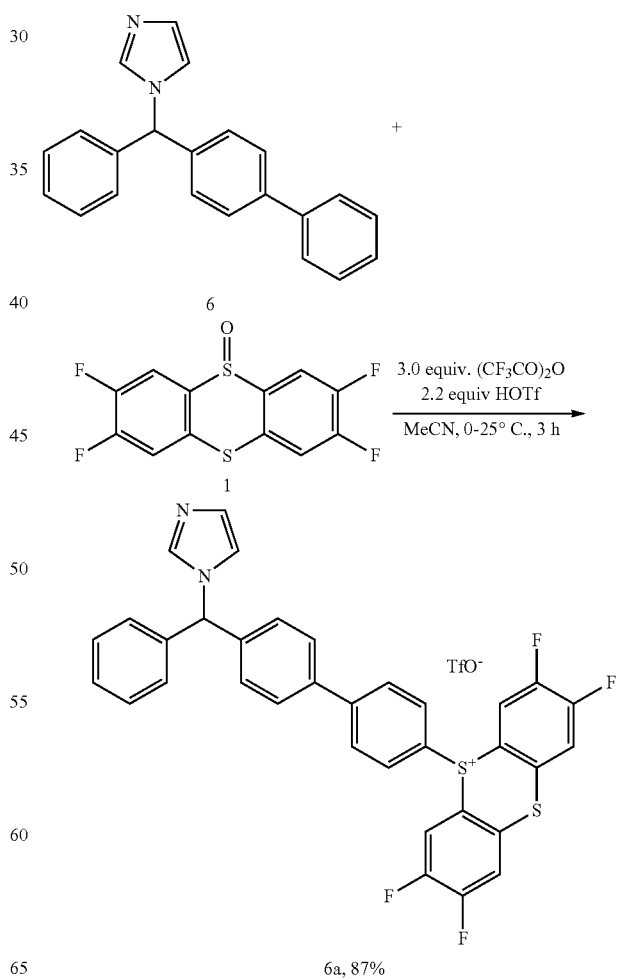

Under an ambient atmosphere, a 20 ml glass-vial was charged sequentially with bifonazole (6) (155 mg, 0.50 mmol, 1.0 equiv.), dry MeCN (2.0 ml, c=0.25 M), and trifluoroacetic anhydride (0.21 ml, 0.32 g, 1.5 mmol, 3.0 equiv.). The mixture was cooled to 0° C., followed by addition of tetrafluorothianthrene reagent (97% (w/w) tetrafluorothianthrene-S-oxide 1, 3% (w/w) tetrafluorothianthrene 2, 157 mg, 0.50 mmol, 1.0 equiv.), and HOTf (97 μl, 0.17 g, 1.1 mmol, 2.2 equiv.). The vial was sealed, and the mixture was stirred at 0° C. for 1 h, then it was stirred at 25° C. for 2 h. The reaction mixture was concentrated under reduced pressure to a final volume of ca. 0.5 ml and then diluted with 5 ml DCM. The DCM phase was washed with saturated NaHCO$_3$-solution (ca. 10 ml) leading to the formation of a colorless precipitate. The DCM phase was evaporated and the obtained solid residue was dissolved in 5 ml EtOH and NaOTf (0.5 g) was added. DCM (ca. 10 ml) was added to the solution. Subsequently, the solution was washed with water (ca. 10 ml), NaOTf-solution (2% w/w, ca. 10 ml), and water (ca. 10 ml). During the washing a precipitate formed, which was collected by filtration. The solid was washed with DCM (5 ml) and water (5 ml). The solid was dried in vacuo to afford 323 mg (87%) of 6a as a colorless solid.

NMR Spectroscopy:

$^1$H NMR (500 MHz, CD$_3$CN, 298 K, δ): 8.47 (dd, J=9.1 Hz, 7.1 Hz, 2H), 8.43 (t, J=1.5 Hz, 1H), 7.98 (dd, J=9.9 Hz, 7.0 Hz, 2H), 7.78 (d, J=8.8 Hz, 2H), 7.71 (d, J=8.4 Hz, 2H), 7.50 (dd, J=2.1 Hz, 1.5 Hz, 1H), 7.48-7.45 (m, 3H), 7.35-7.30 (m, 5H), 7.28-7.26 (m, 2H), 6.99 (s, 1H).

$^{13}$C {$^1$H} NMR (126 MHz, CD$_3$CN, 298 K, δ): 154.9 (dd, J=262.1 Hz, 13.2 Hz), 151.6 (dd, J=255.7, 13.5 Hz), 145.7, 139.7, 138.5, 137.3, 136.3, 135.3 (dd, J=8.7 Hz, 3.8 Hz), 130.5, 130.4, 130.0, 129.97, 129.8, 129.3, 129.1, 125.7 (dd, J=22.1, 2.3 Hz), 123.0, 122.6, 122.0 (q, J=320.5 Hz), 121.6, 121.2 (d, J=21.7 Hz), 115.4 (dd, J=7.2, 3.5 Hz), 67.4.

$^{19}$F {$^1$H} NMR (471 MHz, CD$_3$CN, 298 K, δ): −80.2 (s), −126.2 (d, J=20.5 Hz), −134.6 (d, J=20.3 Hz).

HRMS-ESI (m/z) calc'd for C$_{34}$H$_{21}$N$_2$F$_4$S$_2$$^+$ [M-OTf]$^+$, 597.107691; found, 597.108080; deviation: 0.7 ppm.

Chlorobenzene Derived Thianthrenium Salt 7a

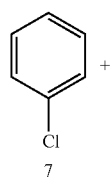

7

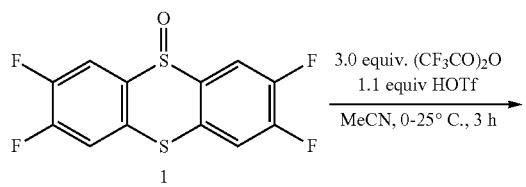

1

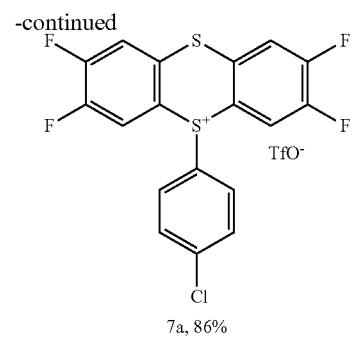

7a, 86%

Under an ambient atmosphere, a 20 ml glass-vial was charged sequentially with chlorobenzene (7) (56 mg, 0.50 mmol, 1.0 equiv.), dry MeCN (2.0 ml, c=0.25 M), and trifluoroacetic anhydride (0.21 ml, 0.32 g, 1.5 mmol, 3.0 equiv.). The solution was cooled to 0° C., followed by addition of tetrafluorothianthrene reagent (97% (w/w) tetrafluorothianthrene-S-oxide 1, 3% (w/w) tetrafluorothianthrene 2, 157 mg, 0.50 mmol, 1.0 equiv.), and HOTf (49 μl, 83 mg, 0.55 mmol, 1.1 equiv.). The mixture was stirred at 0° C. for 1 h, subsequently it was stirred at 25° C. for 2 h. The reaction mixture was concentrated under reduced pressure to a final volume of ca. 0.5 ml, and diluted with 5 ml DCM. The DCM phase was washed with saturated NaHCO$_3$-solution (ca. 10 ml), aqueous NaOTf-solution (3%, w/w, ca. 10 ml), and water (ca. 10 ml). The DCM phase was dried over Na$_2$SO$_4$, and the solvent was removed under reduced pressure. The residue was purified by chromatography on silica gel eluting with DCM/MeOH (10:1 (v/v)) to afford 237 mg (86%) of 7a as colorless oil, which crystallized after several hours.

NMR Spectroscopy:

$^1$H NMR (500 MHz, CD$_3$CN, 298 K, δ): 8.46 (dd, J=9.1 Hz, 7.2 Hz, 2H), 7.96 (dd, J=9.9 Hz, 7.0 Hz, 2H), 7.52 (d, J=9.1 Hz, 2H), 7.20 (d, J=9.1 Hz, 2H).

$^{13}$C {$^1$H} NMR (126 MHz, CD$_3$CN, 298 K, δ): 154.8 (dd, J=262.1 Hz, 13.2 Hz), 151.5 (dd, J=255.6 Hz, 13.6 Hz), 140.5, 135.4 (dd, J=8.6 Hz, 3.9 Hz), 131.5, 131.1, 125.9 (dd, J=22.3 Hz, 2.6 Hz), 122.5, 122.1 (q, J=320.08 Hz), 121.2 (d, J=22.0 Hz), 115.4 (dd, J=7.4 Hz, 3.4 Hz).

$^{19}$F {$^1$H} NMR (471 MHz, CD$_3$CN, 298 K, δ): −80.1 (s), −126.0 (d, J=20.3 Hz), −134.6 (d, J=20.3 Hz).

HRMS-ESI (m/z) calc'd for C$_{18}$H$_8$ClF$_4$S$_2$$^+$ [M-TfO]$^+$, 398.968662; found, 398.968930; deviation: 0.7 ppm.

Benzyloxazolidinone Derived Thianthrenium Salt 8a

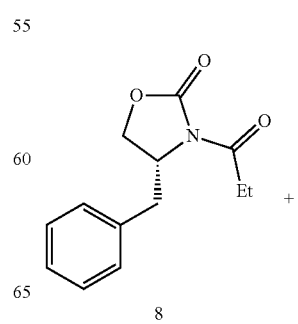

8

-continued

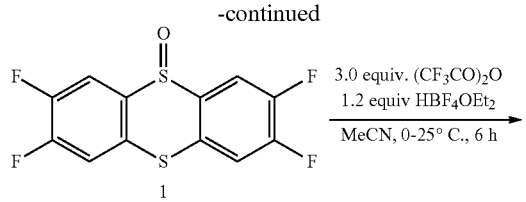

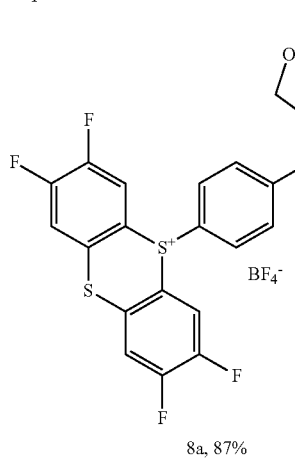

8a, 87%

Under an ambient atmosphere, a 20 ml glass-vial was charged with benzyloxazolidinone 8 (117 mg, 0.50 mmol, 1.0 equiv.) and dry MeCN (2.0 ml, c=0.25 M). Trifluoroacetic anhydride (0.21 ml, 0.32 g, 1.5 mmol, 3.0 equiv.) was added while stirring the reaction mixture. After cooling to 0° C., tetrafluorothianthrene reagent (97% (w/w) tetrafluorothianthrene-S-oxide 1, 3% (w/w) tetrafluorothianthrene 2, 157 mg, 0.50 mmol, 1.0 equiv.) was added in one portion, followed by the addition of $HBF_4OEt_2$ (82 µl, 97 mg, 0.6 mmol, 1.2 equiv.) in one portion at 0° C., leading to a purple suspension. The vial was sealed with a screw-cap, and the mixture was stirred at 0° C. for 1 h, followed by stirring at 25° C. for 5 h, until a slight purple solution was obtained. The reaction mixture was concentrated under reduced pressure, and was diluted with 5 ml DCM. The DCM phase was poured onto a saturated aqueous $NaHCO_3$ solution (ca. 10 ml). Subsequently, the mixture was poured into a separatory funnel, and the layers were separated. The DCM layer was washed with aqueous $NaBF_4$ solution (2×ca. 10 ml, 5% w/w), and with water (2×ca. 10 ml). The DCM layer was dried over $Na_2SO_4$, filtered, and the solvent was removed under reduced pressure. The residue was purified by chromatography on silica gel eluting with DCM/i-PrOH (30:1 (v/v)). The product was dissolved in 5 ml DCM, and precipitated with 20 ml $Et_2O$. The suspension was decanted, and the solid was dried in vacuo to afford 263 mg (87%) of 8a as a colorless solid.

NMR Spectroscopy:

$^1$H NMR (500 MHz, $CD_3CN$, 298 K, δ): 8.40 (ddψd, J=9.1 Hz, 7.2 Hz, 0.8 Hz, 2H), 7.95 (ddψd, J=9.9 Hz, 7.1 Hz, 2.5 Hz, 2H), 7.34 (d, J=8.7 Hz, 2H), 7.14 (d, J=8.7 Hz, 2H), 3.06 (d, J=5.5 Hz, 2H), 4.66 (dtd, J=8.2 Hz, 5.5 Hz, 2.6 Hz, 1H), 4.27 (dd, J=9.2 Hz, 8.1 Hz, 1H), 4.07 (dd, J=9.2 Hz, 2.6 Hz, 1H), 2.84-2.71 (m), 1.05 (t, J=7.3 Hz, 3H).

$^{13}$C {$^1$H} NMR (126 MHz, $CD_3CN$, 298 K, δ): 174.7, 154.8 (dd, J=261.3 Hz, 13.3 Hz), 154.5, 151.6 (dd, J=255.6 Hz, 13.9 Hz), 143.7, 135.4-135.3 (m), 132.7, 129.5, 125.6 (dd, J=22.2 Hz, 2.4 Hz), 121.9, 121.2 (d, J=21.9 Hz), 115.6-115.4 (m), 67.5, 55.1, 37.9, 29.7, 8.7.

$^{19}$F {$^1$H} NMR (471 MHz, $CD_3CN$, 298 K, δ): −126.2 (dψd, J=20.5 Hz, 6.7 Hz), −134.7 (dψd, J=20.3 Hz, 2.5 Hz), −151.4 (bs), −151.5 (bs).

HRMS-ESI (m/z) calc'd for $C_{25}H_{18}F_4NO_3S_2^+$ [M-$BF_4$]$^+$, 520.066030; found, 520.065878; deviation: 0.3 ppm.

Atomoxetine Derived Thianthrenium Salt 9a

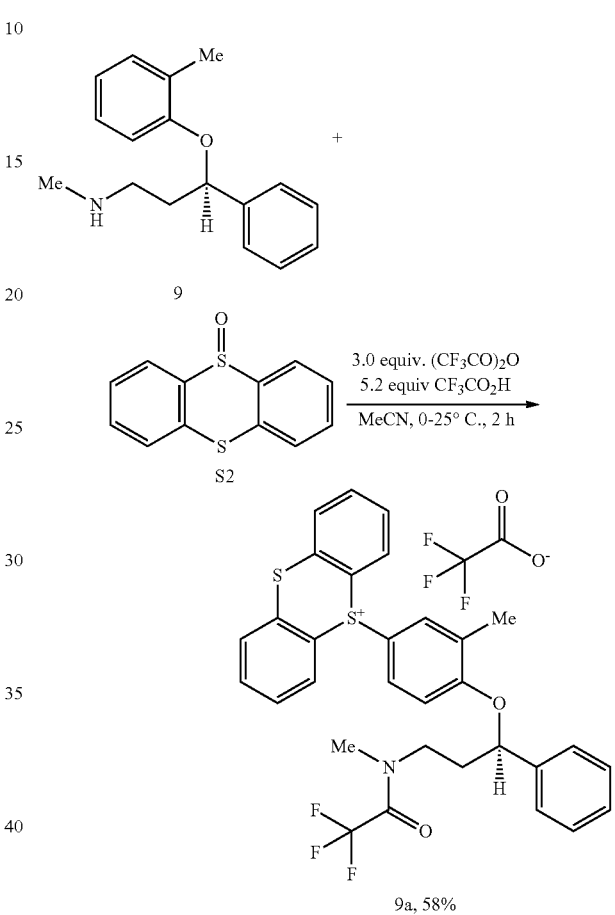

9a, 58%

Atomoxetine hydrochloride 9.HCl (146 mg, 0.50 mmol, 1.0 equiv.) was dissolved in a mixture of saturated $Na_2CO_3$ solution (2 ml) and EtOAc (2 ml). The layers were separated by decantation. The aqueous phase was extracted with EtOAc (3 ml). The combined organic layers were dried over $K_2CO_3$, filtered, and the solvent was removed. The oily residue was dissolved in MeCN (2.0 ml, c=0.25 M), and was transferred under an ambient atmosphere into a 20 ml glass-vial. Subsequently, trifluoroacetic acid (0.20 ml, 0.30 g, 2.6 mmol, 5.2 equiv.) was added. The mixture was cooled to 0° C. Subsequently, thianthrene-S-oxide (S2) (116 mg, 0.50 mmol, 1.0 equiv.), and trifluoroacetic anhydride (0.21 ml, 0.31 g, 1.5 mmol, 3.0 equiv.) were added at 0° C. The purple reaction mixture was stirred at 0° C. for 1 h, subsequently, at 25° C. for 1 h. The reaction mixture was diluted with DCM (5 ml), and was quenched by addition of water (3 ml), and saturated $Na_2CO_3$ solution (5 ml). The mixture was stirred at 25° C. for 20 min, before the layers were separated. The aqueous layer was extracted with DCM (5 ml). The combined DCM layers were dried over $Na_2SO_4$, filtered, and the solvent was removed under reduced pressure. The residue was purified by chromatography on silica gel eluting with DCM/i-PrOH (3:1, (v/v)), to afford 198 mg (58%) of compound 9a as colorless foam.

NMR Spectroscopy: (mixture of 2 rotamers)

$^1$H NMR (500 MHz, CD$_3$CN, 298 K, δ): 8.33-8.27 (m, 2H), 7.83-7.74 (m, 4H), 7.72-7.68 (m, 2H), 7.36-7.31 (m, 2H), 7.30-7.24 (m, 2H), 7.22-7.18 (m, 1H), 7.14-7.11 (m, 1H), 6.90-6.86 (m, 1H), 6.80, 6.78 (s, s, 1H), 5.43, 5.36 (dd, J=8.9 Hz, 3.7 Hz, dd, J=8.8 Hz, 4.0 Hz, 1H), 3.74-3.49 (m, 2H), 3.06, 2.95 (q, J=1.7 Hz, s, 3H), 2.31-2.05 (m, 5H), $^{13}$C {$^1$H} NMR (128 MHz, CD$_3$CN, 298 K, δ): 160.6, 160.4, 160.3 (q, J=31.3 Hz), 157.3 (q, J=35.0 Hz), 157.1 (q, J=34.9 Hz), 141.1, 140.9, 136.8, 135.7, 135.5, 135.4, 131.9, 131.7, 131.3, 131.08, 131.06, 130.8, 129.81, 129.76, 129.20, 129.15, 128.9, 126.9, 126.8, 120.14, 120.12, 120.08, 120.04, 118.8 (q, J=299 Hz), 117.7 (q, J=287 Hz), 117.6 (q, J=288 Hz), 115.22, 115.21, 114.3, 114.2, 78.7, 78.4, 47.1 (q, J=3.5 Hz), 47.0, 37.5, 35.8, 35.5 (q, J=4.0 Hz), 34.9, 16.7, 16.6.

$^{19}$F {$^1$H} NMR (471 MHz, CD$_3$CN, 298 K, δ): −70.3, −70.2, −75.9.

HRMS-ESI (m/z) calc'd for C$_{31}$H$_{27}$F$_3$NO$_2$S$_2^+$ [M-TFA]$^+$, 566.142984; found, 566.143320, deviation: 0.6 ppm.

Amiodarone Derived Thianthrenium Salt 10a

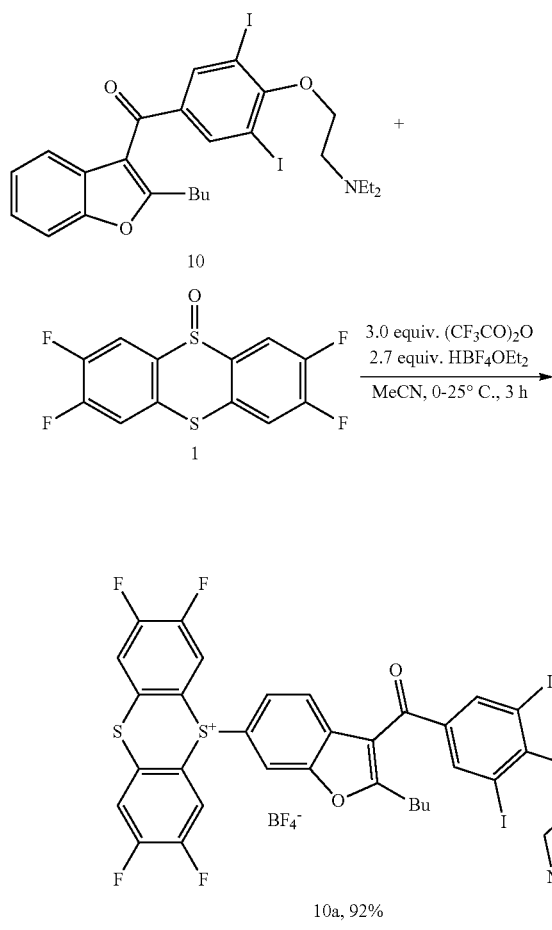

Under an ambient atmosphere, a 20 ml glass-vial was charged with amiodarone hydrochloride 10.HCl (500 mg, 0.73 mmol, 1.47 equiv.), DCM (5.0 ml, c=0.15 M), and aqueous K$_2$CO$_3$ solution (ca. 10 ml, 10% w/w). After stirring for 5 h, the layers were separated. The organic layer was evaporated to dryness, and the residue was dried in vacuo to afford amiodarone 10 as a free base. Under an ambient atmosphere, a 20 ml glass-vial was charged with amiodarone 10 (340 mg, 0.500 mmol, 1.00 equiv.), and dry MeCN (2.0 ml, c=0.25 M). HBF$_4$OEt$_2$ (102 µl, 0.12 g, 0.75 mmol, 1.5 equiv.), and trifluoroacetic anhydride (0.21 ml, 0.32 g, 1.5 mmol, 3.0 equiv.) were added sequentially while stirring the reaction mixture. After cooling to 0° C., tetrafluorothianthrene reagent (97% (w/w) tetrafluorothianthrene-S-oxide 1, 3% (w/w) tetrafluorothianthrene 2, 157 mg, 0.50 mmol, 1.0 equiv.) was added in one portion, followed by the addition of HBF$_4$OEt$_2$ (82 µl, 97 mg, 0.60 mmol, 1.2 equiv.) in one portion at 0° C., leading to a purple suspension. The vial was sealed with a screw-cap, and the mixture was stirred at 0° C. for 1 h, followed by stirring at 25° C. for 2 h, until a slight purple solution was obtained. The reaction mixture was concentrated under reduced pressure, and diluted with 5 ml DCM. The DCM phase was poured onto an aqueous K$_2$CO$_3$ solution (ca. 10 ml, 10% w/w). The mixture was poured into a separatory funnel, and the layers were separated. The DCM layer was washed with aqueous NaBF$_4$ solution (2×ca. 10 ml, 5% w/w), and with water (2×ca. 10 ml). The DCM layer was dried over Na$_2$SO$_4$, filtered, and the solvent was removed under reduced pressure. The residue was purified by chromatography on silica gel eluting with DCM/i-PrOH (30:1 (v/v)). The product was dissolved in 5 ml DCM, and precipitated with 20 ml Et$_2$O. The suspension was decanted, and the solid was dried in vacuo to afford 469 mg (92%) of 10a as colorless foam.

NMR Spectroscopy:

$^1$H NMR (500 MHz, CD$_3$CN, 298 K, δ): 8.48 (dd, J=9.1 Hz, 7.1 Hz, 2H), 8.15 (s, 2H), 7.97 (dd, J=9.8 Hz, 7.0 Hz, 2H), 7.63 (d, J=8.7 Hz, 1H), 7.48 (d, J=2.0 Hz, 1H), 7.15 (dd, J=8.6 Hz, 2.0 Hz, 1H), 4.35 (t, J=5.0 Hz, 2H), 3.70 (t, J=5.1 Hz, 2H), 3.44 (q, J=7.3 Hz, 4H), 2.72 (t, J=7.8 Hz, 2H), 1.69-1.62 (m, 2H), 1.37 (t, J=7.3 Hz, 6H), 1.26 (ψsext, J=7.4 Hz, 2H), 0.83 (t, J=7.4 Hz, 3H).

$^{13}$C {$^1$H} NMR (126 MHz, CD$_3$CN, 298 K, δ): 187.8, 170.7, 161.3, 154.8 (dd, J=262.1, 13.1 Hz), 154.0, 151.6 (dd, 255.7 Hz, 13.6 Hz), 141.4, 135.2 (dd, J=8.6 Hz, 3.8 Hz), 132.7, 125.7 (dd, J=22.3 Hz, 1.5 Hz), 124.7, 124.0, 121.2 (dd, J=21.8 Hz), 119.0, 116.9, 115.7 (dd, J=7.2 Hz, 3.3 Hz), 113.1, 91.5, 67.8, 52.6, 49.6, 30.3, 29.0, 23.1, 13.9, 9.5.

$^{19}$F {$^1$H} NMR (471 MHz, CD$_3$CN, 298 K, δ): −126.1 (d, J=20.6 Hz), −134.4 (d, J=20.2 Hz), −151.6 (bs), −151.7 (bs).

HRMS-ESI (m/z) calc'd for C$_{37}$H$_{32}$F$_4$I$_2$NO$_3$S$_2^+$ [M-BF$_4$]$^+$, 931.985300; found, 931.984373; deviation: 1.0 ppm.

Dichlorobenzene Derived Thianthrenium Salt 11a

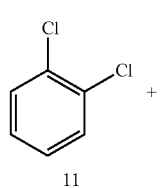

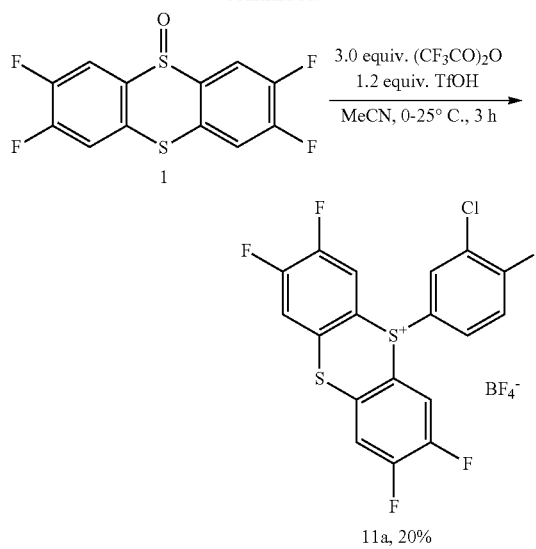

11a, 20%

Under an ambient atmosphere, a 20 ml glass-vial was charged with dichlorbenzene (11) (56 µl, 74 mg, 0.50 mmol, 1.0 equiv.), and dry MeCN (2.0 ml, c=0.25 M). Trifluoroacetic anhydride (0.21 ml, 0.32 g, 1.5 mmol, 3.0 equiv.) was added while stirring the reaction mixture. After cooling to 0° C., tetrafluorothianthrene reagent (97% (w/w) tetrafluorothianthrene-S-oxide 1, 3% (w/w) tetrafluorothianthrene 2, 157 mg, 0.50 mmol, 1.0 equiv.) was added in one portion, followed by the addition of triflic acid (53 µl, 90 mg, 0.6 mmol, 1.2 equiv.) in one portion at 0° C., leading to a purple suspension. The vial was sealed with a screw-cap, and the mixture was stirred at 0° C. for 1 h, followed by stirring at 25° C. for 2 h until a slight purple solution was obtained. The reaction mixture was concentrated under reduced pressure, and diluted with 5 ml DCM. The DCM phase was poured onto a saturated aqueous NaHCO₃ solution (ca. 10 ml). The mixture was poured into a separatory funnel, and the layers were separated. The DCM layer was washed with aqueous NaBF₄ solution (2×ca. 10 ml, 5% w/w), and with water (2×ca. 10 ml). The DCM layer was dried over Na₂SO₄, filtered, and the solvent was removed under reduced pressure. The residue was purified by chromatography on silica gel eluting with DCM/i-PrOH (30:1 (v/v)). The product was dissolved in 5 ml DCM, and precipitated with 20 ml Et₂O. The solid was dried in vacuo to afford 53 mg (20%) of 11a as a colorless solid.

NMR Spectroscopy:

$^1$H NMR (500 MHz, CD$_3$CN, 298 K, δ): 8.42 (dd, J=9.1 Hz, 7.2 Hz, 2H), 7.97 (dd, J=9.9 Hz, 7.1 Hz, 2H), 7.64 (d, J=8.8 Hz, 1H), 7.38 (d, J=2.5 Hz, 1H), 7.09 (dd, J=8.8 Hz, 2.6 Hz, 1H).

$^{13}$C {$^1$H} NMR (126 MHz, CD$_3$CN, 298 K, δ): 155.0 (dd, J=262.3 Hz, 13.2 Hz), 151.7 (dd, J=255.9 Hz, 13.6 Hz), 139.0, 135.7 (dd, J=8.7 Hz, 3.9 Hz), 135.6, 133.0, 130.7, 129.0, 126.0 (dd, J=22.3 Hz, 2.5 Hz), 123.6, 121.5 (d, J=21.9 Hz), 114.8 (dd, J=7.3 Hz, 3.4 Hz).

$^{19}$F {$^1$H} NMR (471 MHz, CD$_3$CN, 298 K, δ): −124.7 (d, J=20.3 Hz), −133.4 (d, J=20.3 Hz), −151.5 (bs), −151.6 (bs).

HRMS-ESI (m/z) calc'd for C$_{18}$H$_7$Cl$_2$F$_4$S$_2^+$ [M-BF$_4$]$^+$, 432.930270; found, 432.929690; deviation: 1.3 ppm.

Nimesulide Derived Thianthrenium Salt 12a

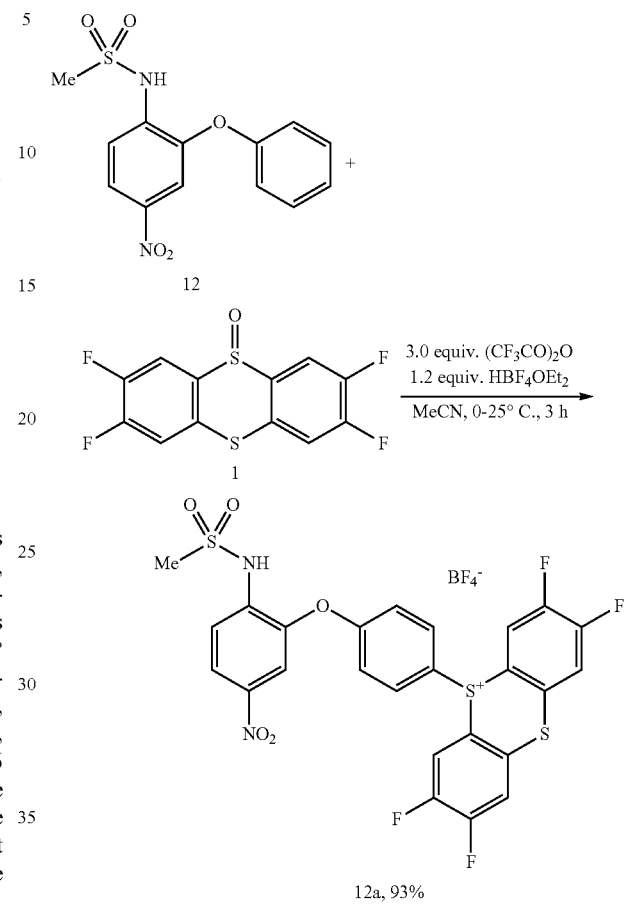

12a, 93%

Under an ambient atmosphere, a 20 ml glass-vial was charged with nimesulide (12) (154 mg, 0.50 mmol, 1.0 equiv.), and dry MeCN (2.0 ml, c=0.25 M). Trifluoroacetic anhydride (0.21 ml, 0.32 g, 1.5 mmol, 3.0 equiv.) was added while stirring the reaction mixture. After cooling to 0° C., tetrafluorothianthrene reagent (97% (w/w) tetrafluorothianthrene-S-oxide 1, 3% (w/w) tetrafluorothianthrene 2, 157 mg, 0.50 mmol, 1.0 equiv.) was added in one portion, followed by the addition of HBF$_4$.OEt$_2$ (82 µl, 97 mg, 0.60 mmol, 1.2 equiv.) in one portion at 0° C., leading to a purple suspension. The vial was sealed with a screw-cap, and the mixture was stirred at 0° C. for 1 h, followed by stirring at 25° C. for 2 h until a slight purple solution was obtained. The reaction mixture was concentrated under reduced pressure, and diluted with 5 ml DCM. The DCM phase was poured onto a saturated aqueous NaHCO₃ solution (ca. 10 ml). The mixture was poured into a separatory funnel, and the layers were separated. The DCM layer was washed with aqueous NaBF₄ solution (2×ca. 10 ml, 5% w/w), and with water (2×ca. 10 ml). The DCM layer was dried over Na₂SO₄, filtered, and the solvent was removed under reduced pressure. The residue was purified by chromatography on silica gel eluting with DCM/i-PrOH (30:1 (v/v)). The product was dissolved in 2 ml DCM and precipitated with 20 ml Et₂O. The solid was dried in vacuo to afford 319 mg (93%) of 12a as yellow foam.

NMR Spectroscopy:

$^1$H NMR (500 MHz, CD$_3$CN, 298 K, δ): 8.38 (dd, J=9.0 Hz, 7.2 Hz, 2H), 7.94 (dd, J=9.9 Hz, 7.0 Hz, 2H), 7.71-7.61 (m, 2H), 7.53 (d, J=9.3 Hz, 1H), 7.36 (d, J=9.3 Hz, 2H), 7.19 (d, J=9.13 Hz, 2H), 3.24 (s, 3H).

$^{13}$C {$^1$H} NMR (126 MHz, CD$_3$CN, 298 K, δ): 156.9, 154.8 (dd, J=262.0 Hz, 13.0 Hz), 151.6 (dd, J=255.7 Hz, 13.4 Hz), 150.1, 146.7, 135.2 (dd, J=8.5 Hz, 3.8 Hz), 134.4, 132.7, 130.6, 125.5 (dd, J=22.1 Hz, 2.5 Hz), 121.2 (d, J=21.9 Hz), 124.6, 115.4, 115.3 (dd, J=7.2 Hz, 3.3 Hz), 113.1, 41.6. One quartary carbon signal not detected, probably overlaps with solvent signal.

$^{19}$F {$^1$H} NMR (471 MHz, CD$_3$CN, 298 K, δ): −126.2 (d, J=20.6 Hz), −134.6 (d, J=20.6 Hz), −152.1 (bs), −152.1 (bs).

HRMS-ESI (m/z) calc'd for C$_{25}$H$_{15}$N$_2$O$_5$F$_4$S$_3^+$ [M-BF$_4$]$^+$, 595.007500; found, 595.007379; deviation: 0.2 ppm.

Pyriproxyfen Derived Thianthrenium Salt 13a

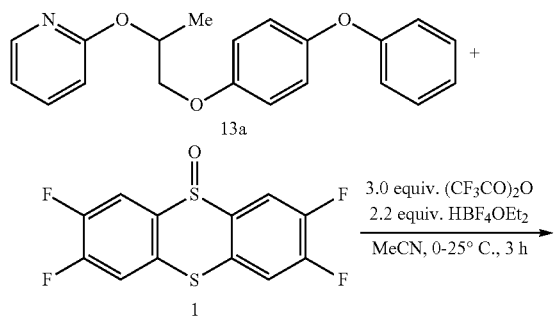

Under an ambient atmosphere, a 20 ml glass-vial was charged with pyriproxyfen (13) (161 mg, 0.50 mmol, 1.0 equiv.), and dry MeCN (2.0 ml, c=0.25 M). HBF$_4$OEt$_2$ (68 μl, 81 mg, 0.50 mmol, 1.0 equiv.), and trifluoroacetic anhydride (0.21 ml, 0.32 g, 1.5 mmol, 3.0 equiv.) were added while stirring the reaction mixture. After cooling to 0° C., tetrafluorothianthrene reagent (97% (w/w) tetrafluorothianthrene-S-oxide 1, 3% (w/w) tetrafluorothianthrene 2, 157 mg, 0.50 mmol, 1.0 equiv.) was added in one portion, followed by the addition of HBF$_4$.OEt$_2$ (82 μl, 97 mg, 0.6 mmol, 1.2 equiv.) in one portion at 0° C., leading to a purple suspension. The vial was sealed with a screw-cap, and the mixture was stirred at 0° C. for 1 h, followed by stirring at 25° C. for 2 h until a slight purple solution was obtained. The reaction mixture was concentrated under reduced pressure, and subsequently, diluted with 5 ml DCM. The DCM phase was poured onto a saturated aqueous NaHCO$_3$ solution (ca. 10 ml). The mixture was poured into a separatory funnel, and the layers were separated. The DCM layer was washed with aqueous NaBF$_4$ solution (2×ca. 10 ml, 5% w/w), and with water (2×ca. 10 ml). The DCM layer was dried over Na$_2$SO$_4$, filtered, and the solvent was removed under reduced pressure. The residue was purified by chromatography on silica gel eluting with DCM/i-PrOH (30:1 (v/v)). The product was dissolved in 2 ml DCM, and precipitated with 20 ml Et$_2$O. The solid was dried in vacuo to afford 320 mg (92%) of 13a as colorless solid.

NMR Spectroscopy:

$^1$H NMR (500 MHz, CD$_3$CN, 298 K, δ): 8.35 (dd, J=9.1 Hz, 7.2 Hz, 2H), 8.11 (ddd, J=5.0 Hz, 2.0 Hz, 0.8 Hz, 1H), 7.94 (dd, J=9.9 Hz, 7.1 Hz, 2H), 7.62 (ddd, J=8.4 Hz, 7.1 Hz, 2.0 Hz, 1H), 7.22 (d, J=9.3 Hz, 2H), 6.98-6.96 (m, 6H), 6.90 (ddd, J=7.1 Hz, 5.0 Hz, 0.9 Hz, 1H), 6.69 (dψt, J=8.4 Hz, 0.9 Hz, 1H), 5.54 (ψquind, J=6.4 Hz, 4.1 Hz), 4.16 (dd, J=10.3 Hz, 6.0 Hz, 1H), 4.11 (dd, J=10.3 Hz, 4.1 Hz, 1H), 1.39 (d, J=6.4 Hz, 3H).

$^{13}$C {$^1$H} NMR (126 MHz, CD$_3$CN, 298 K, δ): 164.3, 164.1, 157.5, 154.7 (dd, J=261.6 Hz, 13.1 Hz), 151.55 (dd, J=255.6 Hz, 13.5 Hz), 148.7, 147.8, 140.1, 134.8 (dd, J=8.5 Hz, 3.8 Hz), 131.9, 125.1 (dd, J=22.1 Hz, 2.0 Hz), 122.8, 121.1 (d, J=21.9 Hz), 119.3, 118.0 117.1, 115.9 (dd, J=7.1 Hz, 3.3 Hz), 114.5, 112.2, 71.9, 70.2, 17.0.

$^{19}$F {$^1$H} NMR (471 MHz, CD$_3$CN, 298 K, δ): −126.5 (d, J=20.5 Hz), −134.6 (d, J=20.3 Hz), −151.9 (bs), −152.0 (bs).

HRMS-ESI (m/z) calc'd for C$_{32}$H$_{22}$F$_4$NO$_3$S$_2^+$ [M-BF$_4$]$^+$, 608.097740; found, 608.097178; deviation: 0.9 ppm.

Ketanserin Derived Thianthrenium Salt 14a

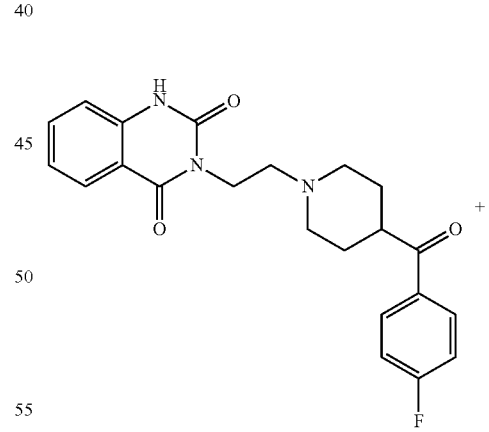

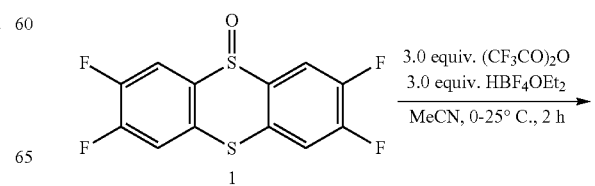

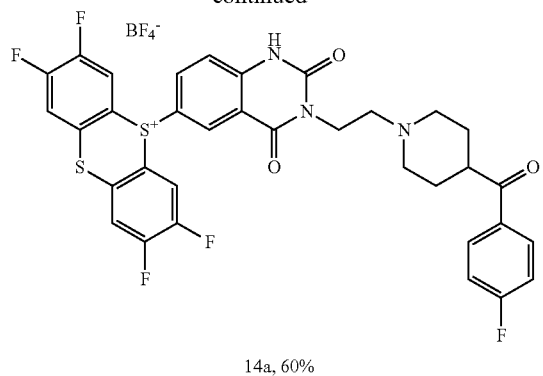

14a, 60%

Under an ambient atmosphere, a 20 ml glass-vial was subsequently charged with ketanserin (14) (99 mg, 0.25 mmol, 1.0 equiv.), and dry MeCN (2.0 ml, c=0.13 M). After all starting material had dissolved (ca. 1 min), the solution was cooled to 0° C., and HBF$_4$.OEt$_2$ (0.10 ml, 0.12 g, 0.75 mmol, 3.0 equiv.), trifluoroacetic anhydride (0.10 ml, 0.16 g, 0.75 mmol, 3.0 equiv.), and tetrafluorothianthrene reagent (97% (w/w) tetrafluorothianthrene-S-oxide 1, 3% (w/w) tetrafluorothianthrene 2, 78 mg, 0.25 mmol, 1.0 equiv.) were added sequentially, leading to a deep purple suspension. The mixture was stirred at 0° C. for 1 h, then, it was stirred at 25° C., until an almost colorless, clear solution was obtained (1 h). DCM (5 ml), and saturated Na$_2$CO$_3$ solution (5 ml) were added to the reaction mixture. The layers were separated, and the DCM-layer was washed with NaBF$_4$ solution (5% w/w, 2×15 ml), and with water (2×15 ml). The DCM layer was dried over Na$_2$SO$_4$, and the solvent was removed under reduced pressure. The residue was purified by chromatography on silica gel eluting with DCM/i-PrOH (gradient from 10:1 to 3:1 (v/v)). The product was dissolved in 5 ml DCM, and precipitated with 30 ml Et$_2$O. The solution was decanted, and the precipitate was dried in vacuo to afford 116 mg (60%) of 14a as a colorless solid.

NMR Spectroscopy:

$^1$H NMR (500 MHz, CD$_3$CN, 298 K, δ): 8.43 (dd, J=9.1 Hz, 7.1 Hz, 2H), 8.00-7.96 (m, 4H), 7.86 (d, J=2.5 Hz, 1H), 7.40 (dd, J=9.0 Hz, 2.6 Hz, 1H), 7.27 (d, J=9.0 Hz, 1H), 7.19 (ψt, J=8.8 Hz, 2H), 4.00 (t, J=6.8 Hz, 2H), 3.26 (tt, J=11.6 Hz, 3.7 Hz, 1H), 2.99 (dψt, J=11.7 Hz, 3.4 Hz, 2H), 2.55 (t, J=6.8 Hz, 2H), 2.16 (ψtd, J=11.7 Hz, 2.4 Hz, 2H), 1.77-1.71 (m, 2H), 1.58-1.46 (m, 2H).

$^{13}$C {$^1$H} NMR (126 MHz, CD$_3$CN, 298 K, δ): 202.3, 167.5 (d, 251.9 Hz), 161.5, 154.8 (dd, J=262.2 Hz, 13.1 Hz), 151.6 (dd, J=256.0 Hz, 13.0 Hz), 150.8, 144.1, 135.1 (dd, J=8.6 Hz, 3.9 Hz), 134.8, 133.6 (d, J=2.9 Hz), 132.0 (d, J=9.4 Hz), 130.2, 125.4 (dd, J=22.1 Hz, 2.3 Hz), 121.3 (d, J=21.8 Hz), 118.7, 116.9, 116.6 (d, J=22.0 Hz), 116.1, 115.6 (dd, J=7.2 Hz, 3.3 Hz), 56.0, 53.9, 44.0, 39.3, 29.5.

$^{19}$F {$^1$H} NMR (471 MHz, CD$_3$CN, 298 K, δ): −108.6 (s), −125.9 (d, J=20.2 Hz), −134.1 (d, J=20.6 Hz), −152.8 (bs, 2 signals).

HRMS-ESI (m/z) calc'd for C$_{34}$H$_{25}$N$_3$O$_3$F$_5$S$_2^+$ [M−BF$_4$]$^+$, 682.125204; found, 682.125270; deviation: 0.1 ppm.

Methoxypyridine Derived Thianthrenium Salt 15a

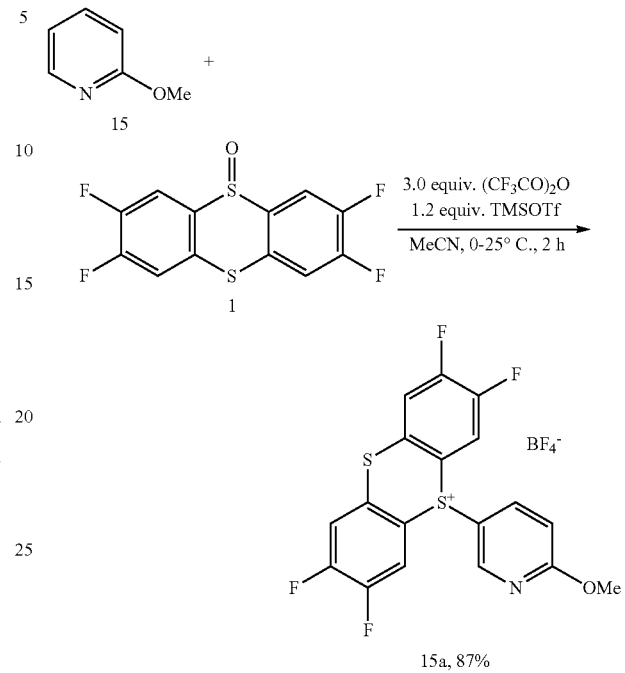

15a, 87%

Aflame-dried, 20 ml argon-filled Schlenk-tube was charged with 2-methoxypyridine (15) (55 mg, 0.50 mmol, 1.0 equiv.), and dry MeCN (2.0 ml, c=0.25 M). Trifluoroacetic anhydride (0.21 ml, 0.32 g, 1.5 mmol, 3.0 equiv.) was added while stirring the reaction mixture. After cooling to 0° C., tetrafluorothianthrene reagent (97% (w/w) tetrafluorothianthrene-S-oxide 1, 3% (w/w) tetrafluorothianthrene 2, 157 mg, 0.50 mmol, 1.0 equiv.) was added in one portion, followed by the addition of trimethylsilyl-trifluormethanesulfonate (181 μl, 0.22 g, 1.0 mmol, 2.0 equiv.) in one portion at 0° C., leading to a dark suspension. The vial was sealed and the mixture was stirred at 0° C. for 1 h, followed by stirring at 25° C. for 1 h. The reaction mixture was concentrated under reduced pressure, and diluted with 5 ml DCM. The DCM phase was poured onto a saturated aqueous NaHCO$_3$ solution (ca. 10 ml). The mixture was poured into a separatory funnel, and the layers were separated. The DCM layer was washed with aqueous NaBF$_4$ solution (2×ca. 10 ml, 5% w/w), and with water (2×ca. 10 ml). The DCM layer was dried over Na$_2$SO$_4$, filtered, and the solvent was removed under reduced pressure. The residue was purified by chromatography on silica gel eluting with DCM/i-PrOH, (30:1 (v/v)). The product was dissolved in 5 ml DCM, and precipitated with 20 ml Et$_2$O. The precipitate was dried in vacuo to afford 211 mg (87%) of 15a as colorless solid.

NMR Spectroscopy:

$^1$H NMR (500 MHz, CD$_3$CN, 298 K, δ): 8.35 (dd, J=9.1 Hz, 7.2 Hz, 2H), 8.06 (dd, J=2.9 Hz, 0.5 Hz, 1H), 7.97 (dd, J=9.9 Hz, 7.1 Hz, 2H), 7.54 (dd, J=9.2 Hz, 2.9 Hz, 1H), 6.91 (dd, J=9.2, 0.6 Hz, 1H), 3.93 (s, 3H).

$^{13}$C {$^1$H} NMR (128 MHz, CD$_3$CN, 298 K, δ): 168.1, 154.8 (dd, J=261.6 Hz, 13.1 Hz), 151.7 (dd, J=155.6 Hz, 13.7 Hz), 149.5, 139.6, 134.9 (dd, J=8.8 Hz, 4.0 Hz), 125.0 (dd, J=22.3 Hz, 2.4 Hz), 121.3 (d, J=21.9 Hz), 115.5 (dd, J=7.2 Hz, 3.6 Hz), 114.2, 112.1, 55.5.

$^{19}$F {$^1$H} NMR (471 MHz, CD$_3$CN, 298 K, δ): −125.6 (d, J=20.4 Hz), −133.6 (d, J=20.4 Hz), −151.1 (bs), −151.1 (bs).

HRMS-ESI (m/z) calc'd for C$_{18}$H$_{10}$F$_4$NOS$_2{}^+$ [M-BF$_4$]$^+$, 396.013700; found, 396.013448; deviation: 0.6 ppm.

Nefiracetam Derived Thianthrenium Salt 16a

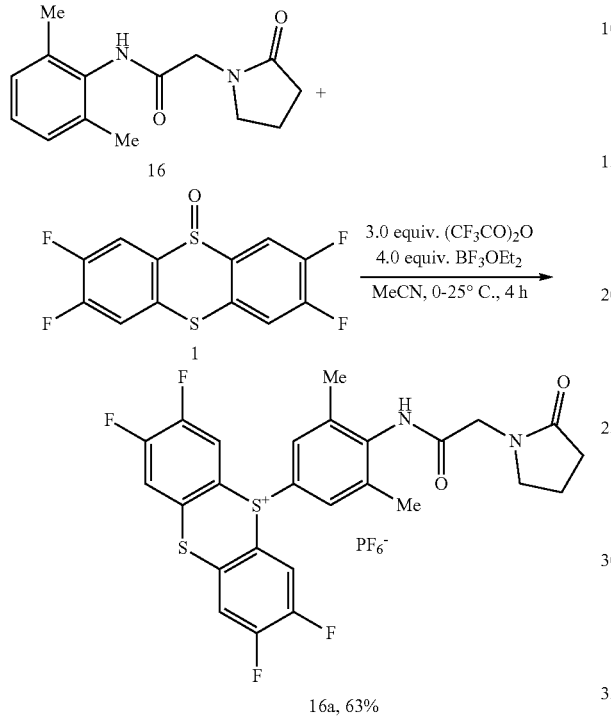

Under an ambient atmosphere, a 20 ml glass-vial was charged with nefiracetam (16) (123 mg, 0.50 mmol, 1.0 equiv.), and dry MeCN (2.0 ml, c=0.25 M). At 0° C., BF$_3$·OEt$_2$ (0.25 ml, 0.28 g, 2.0 mmol, 4.0 equiv.) was added over a period of ca. 30 s. After a clear solution had formed (ca. 2 min), tetrafluorothianthrene reagent (97% (w/w) tetrafluorothianthrene-S-oxide 1, 3% (w/w) tetrafluorothianthrene 2, 157 mg, 0.50 mmol, 1.0 equiv.), and trifluoroacetic anhydride (0.21 ml, 0.32 g, 1.5 mmol, 3.0 equiv.) were added sequentially, leading to a deep purple suspension. The vial was sealed with a screw-cap, and the mixture was stirred at 0° C. for 1 h, followed by stirring at 25° C. for 3 h, before a clear, and almost colorless solution was obtained. The solution was diluted with DCM (5 ml), saturated Na$_2$CO$_3$ solution (10 ml), and water (5 ml). After stirring for 1 h at 25° C., the layers were separated, and the DCM-phase was sequentially washed with NH$_4$PF$_6$ solution (10% (w/w), 2×ca. 5 ml) and water (2×15 ml). The organic layer was dried over Na$_2$SO$_4$ and the solvent was removed. The residue was purified by chromatography on silica gel eluting with DCM/i-PrOH (gradient form 10:1 to 5:1 (v/v)). The product was dissolved in 2 ml DCM, and precipitated with 30 ml Et$_2$O. The suspension was decanted, and the precipitate was dried in vacuo to afford 215 mg (63%) of 16a as colorless, highly viscous oil.

NMR Spectroscopy:

$^1$H NMR (500 MHz, CD$_3$CN, 298 K, δ): 8.42 (dd, J=9.0 Hz, 7.1 Hz, 2H), 8.22 (s, 1H), 7.96 (dd, J=9.9 Hz, 7.0 Hz, 2H), 6.93 (s, 2H), 3.98 (s, 2H), 3.45 (t, J=7.0 Hz, 2H), 2.25 (t, J=8.1 Hz, 2H), 2.12 (s, 6H), 2.00 (ψquin, J=7.5 Hz, 2H).

$^{13}$C {$^1$H} NMR (126 MHz, CD$_3$CN, 298 K, δ): 176.9, 168.1, 154.9 (dd, J=261.9, 13.1 Hz), 151.7 (dd, 255.5 Hz, 13.4 Hz), 140.6, 140.4, 135.3 (dd, J=8.5 Hz, 3.7 Hz), 128.1, 125.7 (dd, J=22.0 Hz, 2.3 Hz), 121.3 (dd, J=22.0 Hz), 121.0, 115.2 (dd, J=7.2 Hz, 3.2 Hz), 48.9, 47.0, 30.9, 18.7, 18.6.

$^{19}$F {$^1$H} NMR (471 MHz, CD$_3$CN, 298 K, δ): −73.1 (d, J=708 Hz), −126.1 (d, J=20.6 Hz), −134.5 (d, J=20.2 Hz).

$^{31}$P {$^1$H} NMR (203 MHz, CD$_3$CN, 298 K, δ): −145.4 (sept, J=708 Hz).

HRMS-ESI (m/z) calc'd for C$_{26}$H$_{21}$N$_2$O$_2$F$_4$S$_2{}^+$ [M-PF$_6$]$^+$, 533.097511; found, 533.097850; deviation: 0.6 ppm.

Dasatinib Derived Thianthrenium Salt 17a

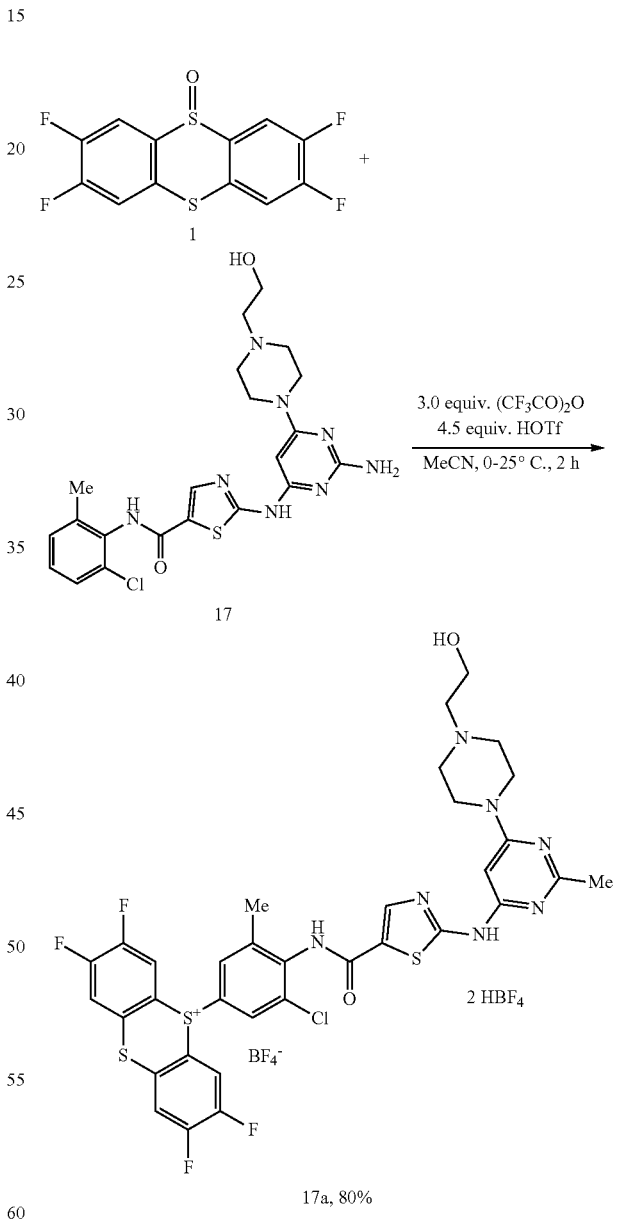

Under an ambient atmosphere, a 20 ml glass-vial was charged with dasatinib (17) (244 mg, 0.50 mmol, 1.0 equiv.), and dry MeCN (2.0 ml, c=0.25 M). At 0° C., trifluoromethanesulfonic acid (0.20 ml, 0.34 g, 2.3 mmol, 4.5 equiv.) was added over a period of ca. 30 s. After a clear solution had formed (ca. 5 min), trifluoroacitic acid anhydride (0.21 ml, 0.32 g, 1.5 mmol, 3.0 equiv.) was added, and the solution was stirred for 15 min at 0° C. Subsequently tetrafluorothianthrene reagent (99% (w/w) tetrafluorothianthrene-S-oxide 1, 1% (w/w) tetrafluorothianthrene 2, 154 mg, 0.50 mmol, 1.0 equiv.) was added, leading to a deep purple suspension. The mixture was stirred at 0° C. for 1 h, followed by stirring at 25° C. for 30 min. The reaction mixture was diluted with DCM (5 ml), and it was quenched by addition of $Na_2CO_3$ solution (sat., ca. 10 ml), and aqueous $NaBF_4$ solution (20% (w/w), 2 ml). The mixture, consisting of a highly viscous sticky oil, an organic phase, and an aqueous phase, was stirred at 25° C. for 10 min. The aqueous layer was removed by decantation. Subsequently, aqueous $Na_2CO_3$ solution (sat., 5 ml), and aqueous $NaBF_4$ solution (20% (w/w), 5 ml) were added. After stirring for 5 min, the aqueous layer was removed by decantation. The solvent was removed. The residue was suspended in 2 ml MeCN, and $HBF_4OEt_2$ was added dropwise until a clear solution was obtained (ca. 0.2 ml). The solution was added dropwise to $Et_2O$ (30 ml). The precipitate was collected by filtration through a glass frit. The solid was dissolved in MeCN (3 ml), and aqueous $NaBF_4$ solution (20% (w/w), 20 ml), and aqueous $Na_2CO_3$ solution (sat., 5 ml) were added. Subsequently, DCM (10 ml) was added. The aqueous layer was removed by decantation. The organic layer was washed with water (ca. 20 ml). The solvent was removed. The residue was suspended in MeCN (2 ml), and $HBF_4OEt_2$ was added dropwise until a clear solution was obtained (ca. 0.2 ml). The solution was added dropwise to $Et_2O$ (30 ml). The precipitate was collected by filtration through a glass frit. The precipitate was dried in vacuo to afford 417 mg (80%) of 17a as colorless solid.

NMR Spectroscopy:

$^1$H NMR (500 MHz, $CD_3CN$, 298 K, δ): 8.73 (s, 1H), 8.44 (dd, J=9.0 Hz, 7.0 Hz, 2H), 8.12 (s, 1H), 7.99 (dd, J=9.7 Hz, 6.9 Hz, 2H), 7.43 (bs, 1H), 7.21 (d, J=2.6 Hz, 1H), 7.09 (d, J=2.6 Hz, 1H), 6.30 (s, 1H), 3.90-3.86 (m, 2H), 3.79-3.42 (m, 6H), 3.35-3.30 (m, 6H), 3.28-3.18 (m, 2H), 2.60 (s, 3H), 2.25 (s, 3H).

$^{13}$C {$^1$H} NMR (126 MHz, $CD_3CN$, 298 K, δ): 165.0, 159.7, 155.0 (dd, J=262.2 Hz, 13.1 Hz), 151.7 (dd, J=255.8 Hz, 13.5 Hz), 142.9, 138.8, 135.6 (dd, J=8.6 Hz, 3.5 Hz), 129.5, 127.4, 126.0 (d, J=22.5 Hz), 123.1, 121.5 (d, J=21.8 Hz), 114.7 (dd, J=7.8 Hz, 3.0 Hz), 84.7, 59.5, 56.0, 52.3, 42.5, 23.2, 19.0. Not all carbon signals detected.

$^{19}$F {$^1$H} NMR (471 MHz, $CD_3CN$, 298 K, δ): −125.7 (d, J=20.5 Hz), −134.3 (d, J=20.2 Hz), −151.3 (s), −151.4 (s).

$^1$H NMR (500 MHz, DMSO-$d_6$, 298 K, δ): 10.14 (s, 1H), 9.71 (bs, 1H), 8.81 (dd, J=9.6 Hz, 7.3 Hz, 2H), 8.38 (dd, J=10.2 Hz, 7.1 Hz, 2H), 8.24 (s, 1H), 7.51 (d, J=2.5 Hz, 1H), 7.26 (d, J=2.5 Hz, 1H), 6.21 (s, 1H), 4.34 (bs, 2H), 3.79-3.75 (m, 2H), 3.61 (bd, J=11.9 Hz, 2H), 3.35 (bt, J=13.0 Hz, 2H), 3.27-3.21 (m, 2H), 3.17-3.07 (m, 2H), 2.46 (s, 3H), 2.23 (s, 3H).

$^{13}$C {$^1$H} NMR (126 MHz, DMSO-$d_6$, 298 K, δ): 164.8, 162.9, 161.3, 159.6, 157.1, 152.9 (dd, J=260.2 Hz, 13.1 Hz), 149.6 (dd, J=253.3 Hz, 13.4 Hz), 141.0, 138.2, 134.2 (probably 2 carbon atoms), 133.5 (dd, J=8.6 Hz, 3.2 Hz), 128.5, 126.7, 125.6 (d, J=22.1 Hz, probably 2 carbon atoms), 123.1, 120.1, 119.3 (d, J=21.8 Hz), 115.1 (dd, J=7.6 Hz, 3.1 Hz), 83.9, 57.6, 54.7, 50.6, 40.9, 25.0, 18.5.

HRMS-ESI (m/z) calc'd for $C_{34}H_{31}ClN_7O_2F_4S_3^{3+}$ [M-3$BF_4$]$^+$, 258.710318; found, 258.710430; deviation: 0.4 ppm.

Strychnine Derived Thianthrenium Salt 18a

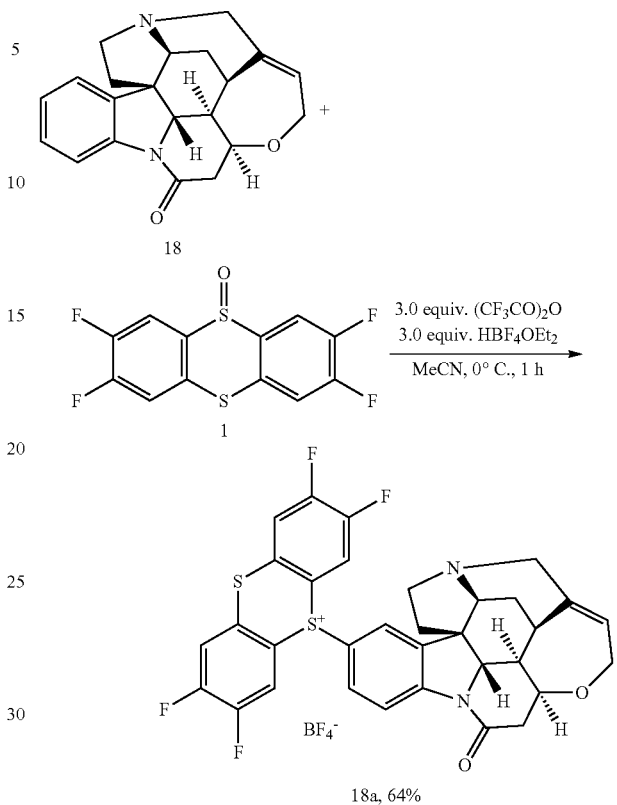

Under an ambient atmosphere, a 20 ml glass-vial was charged with strychnine (18) (167 mg, 0.50 mmol, 1.0 equiv.), and dry MeCN (4.0 ml, c=0.13 M). After cooling to 0° C., $HBF_4OEt_2$ (0.20 ml, 0.24 g, 1.5 mmol, 3.0 equiv.) was added while stirring the reaction mixture. After all solid had dissolved (ca. 1 min), tetrafluorothianthrene reagent (97% (w/w) tetrafluorothianthrene-S-oxide 1, 3% (w/w) tetrafluorothianthrene 2, 157 mg, 0.50 mmol, 1.0 equiv.) was added in one portion at 0° C., followed by the addition of trifluoroacetic anhydride (0.21 ml, 0.32 g, 1.5 mmol, 3.0 equiv.) in one portion at 0° C., leading to a purple suspension. The vial was sealed with a screw-cap, and the mixture was stirred at 0° C. until a clear, and colorless solution was obtained (1 h). The solution was diluted with 5 ml DCM, and poured onto a mixture of DCM (30 ml), saturated aqueous $Na_2CO_3$ solution (20 ml), and water (10 ml). After stirring for 5 min at 25° C., the mixture was poured into a separatory funnel, and the layers were separated. The DCM layer was washed with aqueous $NaBF_4$ solution (2×ca. 20 ml, 5% w/w), and with water (2×ca. 20 ml). The DCM layer was dried over $Na_2SO_4$, filtered, and the solvent was removed under reduced pressure. The residue was purified by chromatography on silica gel eluting with DCM/i-PrOH/$NEt_3$ (160:40:15 (v/v/v)). The product was dissolved in 2 ml DCM, and precipitated with 20 ml $Et_2O$. The suspension was decanted, and the solid was dried in vacuo to afford 228 mg (64%) of 18a as colorless solid.

NMR Spectroscopy:

$^1$H NMR (500 MHz, $CD_3CN$, 298 K, δ): 8.30 (ddψd, J=8.8 Hz, 7.2 Hz, 1.3 Hz, 2H), 8.05 (d, J=8.8 Hz, 1H), 7.95 (dψt, J=9.9 Hz, 6.8 Hz, 2H), 7.19 (dd, J=8.8 Hz, 2.3 Hz, 1H), 7.14 (d, J=2.3 Hz, 1H), 6.06 (ψt, J=7.2 Hz, 1H), 4.30 (ψtd, J=8.3 Hz, 3.2 Hz, 1H), 4.12 (dd, J=14.0 Hz, 6.9 Hz, 1H), 4.06 (dd, J=14.1 Hz, 6.3 Hz, 1H), 4.02 (d, J=10.8 Hz, 1H), 3.98 (bs, 1H), 3.77 (dψq, J=14.4 Hz, 1.7 Hz, 1H), 3.37 (dd, J=11.0 Hz, 7.7 Hz, 1H), 3.27 (bs, 1H), 3.02 (dd, J=17.6 Hz, 8.4 Hz, 1H), 2.99-2.92 (m, 2H), 2.60 (dd, J=17.6 Hz, 3.2 Hz, 1H), 2.35 (dψt, J=15.0 Hz, 4.3 Hz, 1H), 1.99-1.95 (m, 1H), 1.82 (ψtd, J=12.9 Hz, 7.7 Hz, 1H), 1.39 (dm, J=15.5 Hz, 1H), 1.35 (dψt, J=10.8 Hz, 3.3 Hz, 1H).

$^{13}C\{^1H\}$ NMR (126 MHz, CD$_3$CN, 298 K, δ): 170.9, 154.7 (dd, J=261.3 Hz, 13.2 Hz), 151.7 (dd, J=255.4 Hz, 13.5 Hz), 147.9, 138.0, 136.4, 134.9-134.7 (m), 131.8, 131.6, 125.0 (dd, J=22.2 Hz, 4.5 Hz), 124.9, 121.2 (dd, J=21.8 Hz, 1.9 Hz), 117.6, 116.4-116.2 (m), 115.8, 77.5, 65.0, 62.2, 61.4, 53.3, 52.7, 51.6, 47.8, 42.8, 42.5, 31.5, 26.7.

$^{19}F\{^1H\}$ NMR (471 MHz, CD$_3$CN, 298 K, δ): −126.7 (dψd, J=20.3 Hz, 6.6 Hz), −134.6 (dψd, J=20.1 Hz, 4.5 Hz), −152.2 (bs, two signals).

HRMS-ESI (m/z) calc'd for $C_{33}H_{25}F_4N_2O_2S_2^+$ [M-BF$_4$]$^+$, 621.128812; found, 621.12900; deviation: 0.3 ppm.

Tetrahydrobenzofuranone Derived Thianthrenium Salt 19a

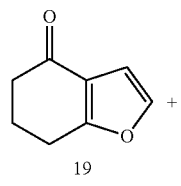

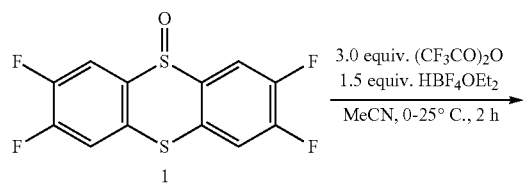

19a, 64%

Under an ambient atmosphere, a 20 ml glass-vial was charged with tetrahydrobenzofuranone 19 (66 μl, 68 mg, 0.50 mmol, 1.0 equiv.), and dry MeCN (2.0 ml, c=0.25 M). Trifluoroacetic anhydride (0.21 ml, 0.32 g, 1.5 mmol, 3.0 equiv.) was added while stirring the reaction mixture. After cooling to 0° C., tetrafluorothianthrene reagent (97% (w/w) tetrafluorothianthrene-S-oxide 1, 3% (w/w) tetrafluorothianthrene 2, 157 mg, 0.50 mmol, 1.0 equiv.) was added in one portion, followed by the addition of HBF$_4$OEt$_2$ (102 μl, 0.12 g, 0.75 mmol, 1.5 equiv.) in one portion at 0° C., leading to a purple suspension. The vial was sealed with a screw-cap, and the mixture was stirred at 0° C. for 1 h, followed by stirring at 25° C. for 1 h, until a slight purple solution was obtained. The reaction mixture was concentrated under reduced pressure, and diluted with 5 ml DCM. The DCM phase was poured onto a saturated aqueous NaHCO$_3$ solution (ca. 10 ml). The mixture was poured into a separatory funnel, and the layers were separated. The DCM layer was washed with aqueous NaBF$_4$ solution (2×ca. 10 ml, 5% w/w), and with water (2×ca. 10 ml). The DCM layer was dried over Na$_2$SO$_4$, filtered, and the solvent was removed under reduced pressure. The residue was purified by chromatography on silica gel eluting with DCM/i-PrOH, (30:1). The product was dissolved in 5 ml DCM, and precipitated with 20 ml Et$_2$O. The suspension was decanted, and the solid was dried in vacuo to afford 164 mg (64%) of 19a as colorless solid.

NMR Spectroscopy:

$^1H$ NMR (500 MHz, CD$_3$CN, 298 K, δ): 8.28 (dd, J=9.1 Hz, 7.2 Hz, 2H), 7.97 (dd, J=10.0 Hz, 7.0 Hz, 2H), 7.40 (s, 1H), 2.84 (t, J=6.3 Hz, 2H), 2.46-2.43 (m, 2H), 2.12 (ψquin, J=6.4 Hz, 2H).

$^{13}C\{^1H\}$ NMR (128 MHz, CD$_3$CN, 298 K, δ): 193.2, 176.1, 154.9 (dd, J=262.2 Hz, 13.1 Hz), 151.5 (dd, J=255.5 Hz, 13.7 Hz), 135.1 (dd, J=8.6 Hz, 3.9 Hz), 130.7, 124.3 (dd, J=22.4 Hz, 2.5 Hz), 123.7, 121.7, 120.7 (d, J=21.9 Hz), 113.5 (dd, J=7.1 Hz, 3.5 Hz), 38.0, 24.3, 22.5.

$^{19}F\{^1H\}$ NMR (471 MHz, CD$_3$CN, 298 K, δ): −125.1 (d, J=20.5 Hz), −133.7 (d, J=20.3 Hz), −151.1 (bs), −151.2 (bs).

HRMS-ESI (m/z) calc'd for $C_{20}H_{11}F_4O_2S_2^+$ [M-BF$_4$]$^+$, 423.013440; found, 423.013114; deviation: 0.8 ppm.

Boscalid Derived Thianthrenium Salt 20a

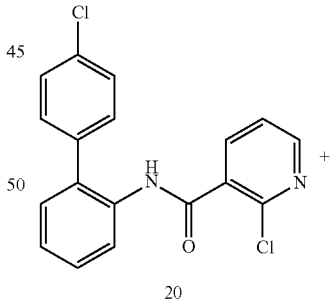

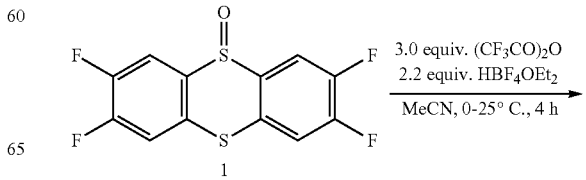

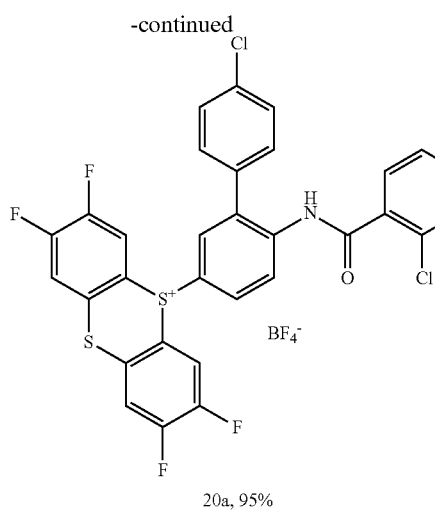

20a, 95%

Under an ambient atmosphere, a 20 ml glass-vial was charged with boscalid (20) (172 mg, 0.50 mmol, 1.0 equiv.), and dry MeCN (2.0 ml, c=0.25 M). HBF$_4$.OEt$_2$ (68 μl, 81 mg, 0.60 mmol, 1.0 equiv.), and trifluoroacetic anhydride (0.21 ml, 0.32 g, 1.5 mmol, 3.0 equiv.) were added while stirring the reaction mixture. After cooling to 0° C., tetrafluorothianthrene reagent (97% (w/w) tetrafluorothianthrene-S-oxide 1, 3% (w/w) tetrafluorothianthrene 2, 157 mg, 0.50 mmol, 1.0 equiv.) was added in one portion, followed by the addition of HBF$_4$.OEt$_2$ (82 μl, 97 mg, 0.60 mmol, 1.2 equiv.) in one portion at 0° C., leading to a purple suspension. The vial was sealed, and the mixture was stirred at 0° C. for 1 h, followed by stirring at 25° C. for 3 h until a slight purple solution was obtained. The reaction mixture was concentrated under reduced pressure, and subsequently, diluted with 5 ml DCM. The DCM phase was poured onto a saturated aqueous NaHCO$_3$ solution (ca. 10 ml). The mixture was poured into a separatory funnel, and the layers were separated. The DCM layer was washed with aqueous NaBF$_4$ solution (2×ca. 10 ml, 5% w/w), and with water (2×ca. 10 ml). The DCM layer was dried over Na$_2$SO$_4$, filtered, and the solvent was removed under reduced pressure. The residue was purified by chromatography on silica gel eluting with DCM/i-PrOH, (30:1). The product was dissolved in 5 ml DCM, and precipitated with 20 ml Et$_2$O. The suspension was decanted, and the solid was dried in vacuo to afford 342 mg (95%) of 20a as colorless solid.

NMR Spectroscopy:

$^1$H NMR (500 MHz, CD$_3$CN, 298 K, δ): 8.50 (bs, 1H), 8.42 (dd, J=9.0 Hz, 7.2 Hz, 2H), 8.38 (dd, J=4.8 Hz, 1.9 Hz, 1H), 8.27 (d, J=9.0 Hz, 1H), 7.97 (dd, J=9.9 Hz, 7.0 Hz, 2H), 7.82 (dd, J=7.6 Hz, 1.9 Hz, 1H), 7.44 (d, J=8.6 Hz, 2H), 7.37 (dd, J=7.6 Hz, 4.8 Hz, 1H), 7.31 (d, J=8.6 Hz, 2H), 7.27 (dd, J=9.0 Hz, 2.7 Hz, 1H), 7.19 (d, J=2.6 Hz, 1H).

$^{13}$C {$^1$H} NMR (126 MHz, CD$_3$CN, 298 K, δ): 165.2, 154.8 (dd, J=261.8 Hz, 13.1 Hz), 152.0, 151.6 (dd, J=255.6 Hz, 13.5 Hz), 147.6, 140.3, 139.1, 136.5, 135.5, 133.3-133.2 (m, 2 chemically different C-atoms), 132.7, 132.2, 131.2, 130.1, 129.6, 125.7-125.5 (m, 2 chemically different C-atoms), 123.9, 121.3 (d, J=21.8 Hz), 118.8, 115.4 (dd, J=7.1 Hz, 3.3 Hz).

$^{19}$F {$^1$H} NMR (471 MHz, CD$_3$CN, 298 K, δ): −126.1 (d, J=20.5 Hz), −134.4 (d, J=20.3 Hz), −151.6 (bs), −151.7 (bs).

HRMS-ESI (m/z) calc'd for C$_{30}$H$_{15}$Cl$_2$F$_4$N$_2$OS$_2^+$ [M-BF$_4$]$^+$, 628.993940; found, 628.993353; deviation: 0.9 ppm.

Etofenprox Derived Thianthrenium Salt 21a

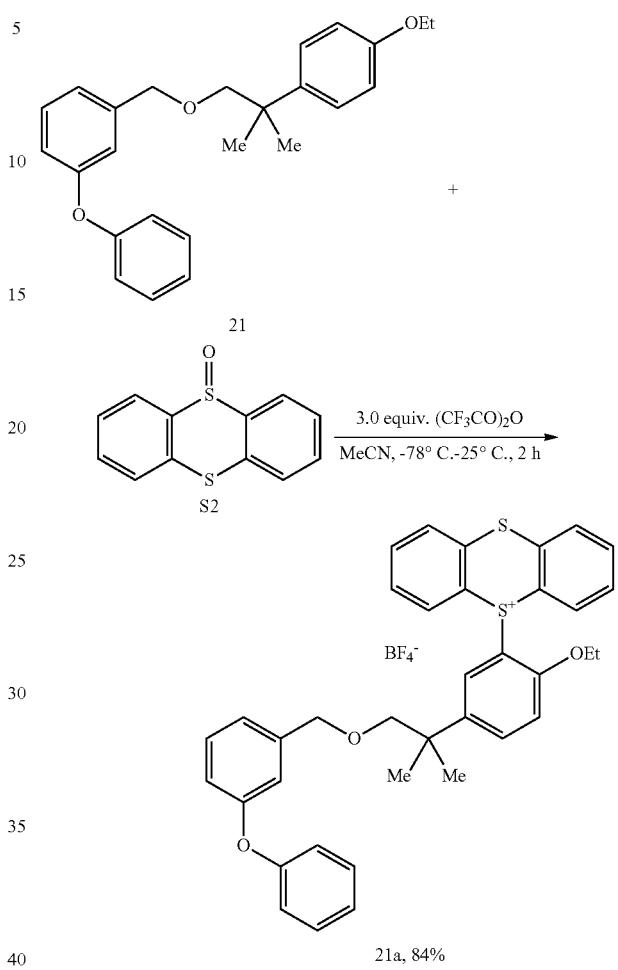

21a, 84%

Under an ambient atmosphere, a 20 ml glass-vial was charged with etofenprox (21) (188 mg, 0.50 mmol, 1.0 equiv.), and dry MeCN (2.0 ml, c=0.25 M). After cooling to −78° C., trifluoroacetic anhydride (0.21 ml, 0.32 g, 1.5 mmol, 3.0 equiv.) was added to the frozen the reaction mixture. Thianthrene reagent (97% (w/w) thianthrene-S-oxide (S2), 3% (w/w) thianthrene (S1), 116 mg, 0.50 mmol, 1.0 equiv.) was added in one portion at −78° C. The vial was sealed with a screw-cap, and the mixture was allowed to stand at −78° C. for 1 h, followed by warming the reaction mixture to 25° C. over a period of 1 h. After stirring the deep purple reaction mixture at 25° C. for 1 h, the reaction mixture was concentrated under reduced pressure, and diluted with 5 ml DCM. The DCM phase was poured onto a saturated aqueous NaHCO$_3$ solution (ca. 10 ml). The mixture was poured into a separatory funnel, and the layers were separated. The DCM layer was washed with aqueous NaBF$_4$ solution (2×ca. 10 ml, 5% w/w), and with water (2×ca. 10 ml). The DCM layer was dried over Na$_2$SO$_4$, filtered, and the solvent was removed under reduced pressure. The residue was purified by chromatography on silica gel eluting with DCM/i-PrOH, (30:1). The product was dissolved in 5 ml DCM, and precipitated with 20 ml Et$_2$O. The suspension was decanted, and the solid was dried in vacuo to afford 279 mg (84%) of 21a as colorless solid.

NMR Spectroscopy:

$^1$H NMR (500 MHz, CD$_3$CN, 298 K, δ): 8.21 (dd, J=7.9 Hz, 1.4 Hz, 2H), 7.85 (dd, J=7.9 Hz, 1.4 Hz, 2H), 7.80 (ψtd, J=7.7 Hz, 1.4 Hz, 2H), 7.72 (ddd, J=7.9 Hz, 7.5 Hz, 1.4 Hz, 2H), 7.58 (dd, J=8.7 Hz, 2.3 Hz, 1H), 7.38-7.34 (m, 2H), 7.30 (ψt, J=7.9 Hz, 1H), 7.14 (tt, J=7.7 Hz, 1.1 Hz, 1H), 7.07 (d, J=8.8 Hz, 1H), 6.99-6.97 (m, 2H), 6.92-6.98 (m, 2H), 6.71 (ψt, J=1.8 Hz, 1H), 6.58 (d, J=2.3 Hz, 1H), 4.26 (s, 2H), 4.17 (q, J=7.0 Hz, 2H), 3.24 (s, 2H), 1.41 (t, J=7.0 Hz, 3H), 1.06 (s, 6H).

$^{13}$C {$^1$H} NMR (126 MHz, CD$_3$CN, 298 K, δ): 158.2, 158.1, 156.3, 142.1, 141.9, 138.1, 136.1, 135.7, 134.8, 131.2, 131.0, 130.8, 130.7, 128.0, 124.5, 123.1, 119.8, 118.6, 118.19, 118.17, 115.0, 108.4, 79.9, 73.0, 67.1, 39.4, 26.2, 14.8.

$^{19}$F {$^1$H} NMR (471 MHz, CD$_3$CN, 298 K, δ): −151.5 (bs), −151.6 (bs).

HRMS-ESI (m/z) calc'd for C$_{37}$H$_{35}$F$_4$O$_3$S$_2^+$ [M-BF$_4$]$^+$, 591.202600; found, 591.202215; deviation: 0.7 ppm.

Mizolastine Derived Thianthrenium Salt 22a

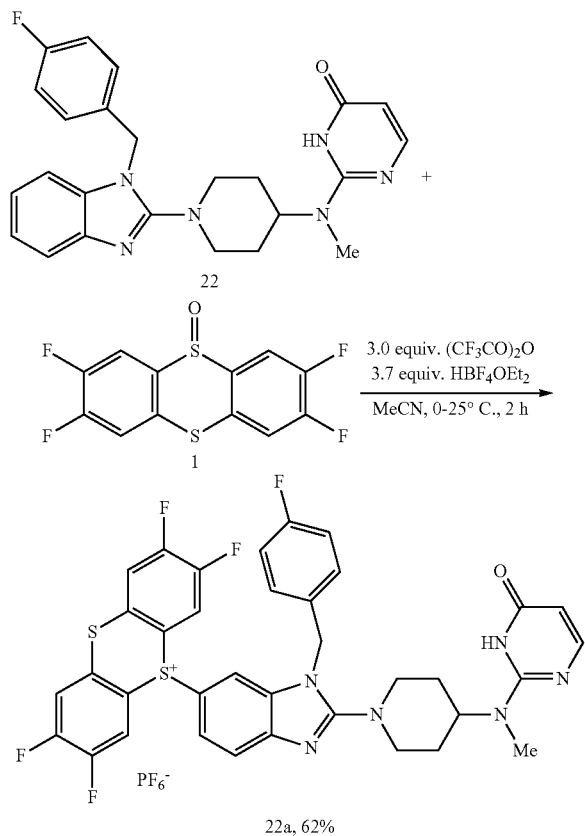

Under an ambient atmosphere, a 20 ml glass-vial was charged with mizolastine (22) (108 mg, 0.25 mmol, 1.0 equiv.), and dry MeCN (1.0 ml, c=0.25 M). HBF$_4$OEt$_2$ (85 μl, 0.10 g, 0.63 mmol, 2.5 equiv.), and trifluoroacetic anhydride (104 μl, 0.16 g, 0.75 mmol, 3.0 equiv.) were added while stirring the reaction mixture. After cooling to 0° C., tetrafluorothianthrene reagent (97% (w/w) tetrafluorothianthrene-S-oxide 1, 3% (w/w) tetrafluorothianthrene 2, 78 mg, 0.25 mmol, 1.0 equiv.) was added in one portion, followed by the addition of HBF$_4$.OEt$_2$ (41 μl, 49 mg, 0.30 mmol, 1.2 equiv.) in one portion at 0° C., leading to a purple suspension. The vial was sealed with a screw-cap, and the mixture was stirred at 0° C. for 1 h, followed by stirring at 25° C. for 1 h, until a slight purple solution was obtained. The reaction mixture was concentrated under reduced pressure, and diluted with 5 ml DCM. The DCM phase was poured onto a saturated aqueous NaHCO$_3$ solution (ca. 10 ml). The mixture was poured into a separatory funnel, and the layers were separated. The DCM layer was washed with aqueous NaBF$_4$ solution (2×ca. 10 ml, 5% w/w), and with water (2×ca. 10 ml). The DCM layer was dried over Na$_2$SO$_4$, filtered, and the solvent was removed under reduced pressure. The residue was purified by chromatography on silica gel eluting with DCM/MeOH/HBF$_4$.OEt$_2$, (300:10:1 (v/v/v)). The product was dissolved in 5 ml DCM, and precipitated with 20 ml Et$_2$O. The precipitate was analyzed by $^1$H and $^{19}$F NMR spectroscopy and showed an impurity that is assumed to be a constitutional isomer, ratio: 16:1 based on integration of the $^1$H signals of the thianthrenyl group; major product: 8.36 (ψt, J=8.0 Hz) and 7.89 (dd, J=9.7, 6.8 Hz); minor product: 8.45 (ψt, J=8.1 Hz) and 7.98 (ψt, J=8.3 Hz). The precipitate was purified via HPLC (50 mm Eclipse Plus C18, 1.8 μm, 4.6 mm inner diameter), eluting with MeCN/NH$_4$HCO$_3$ (aqueous, 20 mM, pH=9.0, 7:13 (v/v)) at a rate of 1 ml/min at 308 K. The product containing solutions were concentrated under reduced pressure to remove MeCN. To the resulting, product containing solutions was added NaPF$_6$ (ca. 2 g/L), and the solutions were extracted with DCM. The extract was dried over Na$_2$SO$_4$, and solvent was removed under reduced pressure. The solid was dried in vacuo to afford 135 mg (62%) of 22a as colorless solid. The minor product could not be obtained in pure form.

NMR Spectroscopy:

$^1$H NMR (500 MHz, CD$_3$CN, 298 K, δ): 8.16 (dd, J=9.0 Hz, 7.0 Hz, 2H), 7.86 (dd, J=9.8 Hz, 6.9 Hz, 2H), 7.66 (bs, 1H), 7.55 (d, J=8.6 Hz, 1H), 7.09 (dd, J=8.6 Hz, 2.2 Hz, 1H), 7.07-7.01 (m, 4H), 6.69 (s, 1H), 5.65 (d, J=6.5 Hz, 1H), 5.17 (s, 2H), 4.60 (bs, 1H), 3.73 (d, J=12.7 Hz, 2H), 3.62-3.55 (m, 2H), 3.20-3.11 (m, 2H), 2.90 (s, 3H), 1.72 (d, J=12.5 Hz, 2H).

$^{13}$C {$^1$H} NMR (128 MHz, CD$_3$CN, 298 K, δ): 163.2 (d, J=244.5 Hz), 162.3, 154.5 (dd, J=261.4 Hz, 13.3 Hz), 151.1 (dd, J=255.8 Hz, 13.5 Hz), 147.6, 137.4, 134.3 (dd, J=8.2 Hz, 3.8 Hz), 132.6 (d, J=3.1 Hz), 129.7 (d, J=8.3 Hz), 124.5 (d, J=21.9 Hz), 123.7, 120.9 (d, J=21.7 Hz), 119.8, 117.0 (dd, J=6.9 Hz, 3.5 Hz), 116.5 (d, J=21.9 Hz), 111.9, 103.0 (b), 53.8, 50.8, 48.6, 29.9, 29.0.

$^{19}$F {$^1$H} NMR (471 MHz, CD$_3$CN, 298 K, δ): −116.6 (s), −127.0 (d, J=20.6 Hz), −134.6 (d, J=20.6 Hz).

$^{31}$P {$^1$H} NMR (203 MHz, CD$_3$CN, 298 K, δ): −145.5 (sept, J=707 Hz).

HRMS-ESI (m/z) calc'd for C$_{38}$H$_{28}$F$_5$N$_6$OS$_2^+$ [M-PF$_6$]$^+$, 719.168390; found, 719.168070; deviation: 0.4 ppm.

3,3-Diphenyl-1-propanol Derived Thianthrenium Salt 23a

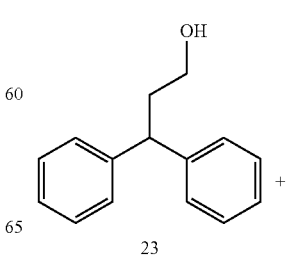

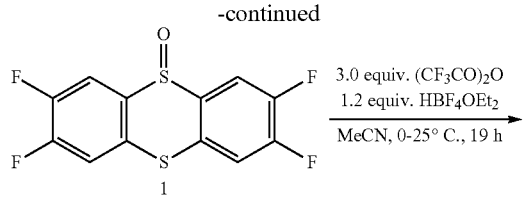

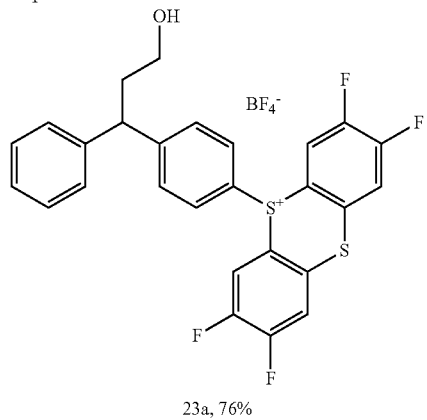

23a, 76%

Under an ambient atmosphere, a 20 ml glass-vial was charged with 3,3-diphenyl-1-propanol (23) (106 mg, 0.50 mmol, 1.0 equiv.), and dry MeCN (2.0 ml, c=0.25 M). Trifluoroacetic anhydride (0.21 ml, 0.32 g, 1.5 mmol, 3.0 equiv.) was added, and the reaction mixture was stirred for 30 min. After cooling to 0° C., tetrafluorothianthrene reagent (97% (w/w) tetrafluorothianthrene-S-oxide 1, 3% (w/w) tetrafluorothianthrene 2, 141 mg, 0.45 mmol, 0.90 equiv.) was added in one portion, followed by the addition of HBF$_4$OEt$_2$ (82 μl, 97 mg, 0.60 mmol, 1.2 equiv.) in one portion at 0° C., leading to a purple suspension. The vial was sealed with a screw-cap, and the mixture was stirred at 0° C. for 1 h, followed by stirring at 25° C. for 18 h, until a slight purple solution was obtained. The reaction mixture was concentrated under reduced pressure, and diluted with 15 ml DCM. The DCM phase was poured onto a saturated aqueous NaHCO$_3$ solution (ca. 10 ml). The mixture was poured into a separatory funnel, and the layers were separated. The DCM layer was washed with aqueous NaBF$_4$ solution (2×ca. 10 ml, 5% w/w), and with water (2×ca. 10 ml). The DCM layer was dried over Na$_2$SO$_4$, filtered, and the solvent was removed under reduced pressure. The residue was purified by chromatography on silica gel eluting with DCM/i-PrOH, (30:1 (v/v)). The product was dissolved in 5 ml DCM, and precipitated with 20 ml Et$_2$O. The suspension was decanted, and the solid was dried in vacuo to afford 222 mg (76%) of 23a as colorless solid.

NMR Spectroscopy:

$^1$H NMR (500 MHz, CD$_3$CN, 298 K, δ): 8.39 (dd, J=9.1 Hz, 7.2 Hz, 2H), 7.93 (ddψd, J=9.9 Hz, 7.0 Hz, 2.2 Hz, 2H), 7.45 (d, J=8.7 Hz, 2H), 7.29-7.23 (m, 4H), 7.20-7.14 (m, 3H), 4.22 (t, 7.8 Hz, 1H), 3.36-3.32 (m, 2H), 2.65 (bs, 1H), 2.25-2.13 (m, 2H).

$^{13}$C {$^1$H} NMR (126 MHz, CD$_3$CN, 298 K, δ): 154.8 (dd, J=261.8 Hz, 13.1 Hz), 152.7, 151.6 (dd, J=255.5 Hz, 13.5 Hz), 144.3, 135.2-135.1 (m), 131.0, 129.8, 129.5, 128.8, 127.8, 125.5 (d, J=22.1 Hz), 121.2 (d, J=21.9 Hz), 120.8, 115.3-115.2 (m), 60.1, 47.6, 38.4.

$^{19}$F {$^1$H} NMR (471 MHz, CD$_3$CN, 298 K, δ): −126.3 (dd, J=20.4 Hz, 5.5 Hz), −134.6 (dd, J=20.5 Hz, 3.8 Hz), −152.0 (bs), −152.1 (bs).

HRMS-ESI (m/z) calc'd for C$_{27}$H$_{19}$F$_4$OS$_2^+$ [M-BF$_4$]$^+$, 499.081040; found, 499.080799; deviation: 0.5 ppm.

Meclofenamic Acid Derived Thianthrenium Salt 24a

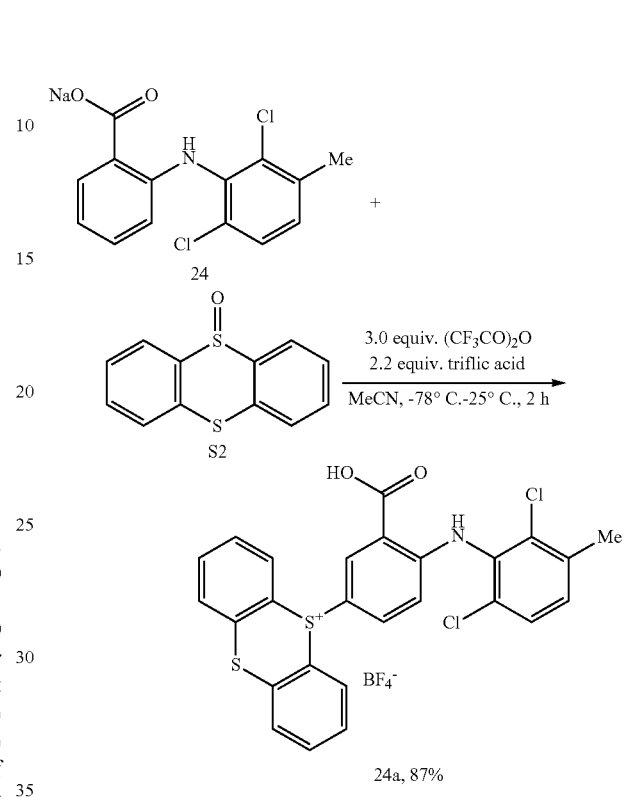

24a, 87%

Under an ambient atmosphere, a 20 ml glass-vial was charged with meclofenamic acid sodium salt (24) (159 mg, 0.50 mmol, 1.0 equiv.), and dry MeCN (2.0 ml, c=0.25 M). After cooling to −78° C., trifluoroacetic anhydride (0.21 ml, 0.32 g, 1.5 mmol, 3.0 equiv.) was added to the frozen the reaction mixture. Thianthrene reagent (97% (w/w) thianthrene-S-oxide (S2), 3% (w/w) thianthrene (S1), 116 mg, 0.50 mmol, 1.0 equiv.) was added in one portion, followed by the addition of triflic acid (84 μl, 0.13 g, 1.1 mmol, 2.2 equiv.) in one portion at −78° C. The vial was sealed with a screw-cap, and the mixture was allowed to stand at −78° C. for 1 h, followed by warming the reaction mixture to 25° C. over a period of 1 h. Subsequently, the mixture was stirred for 1 h at 25° C. The reaction mixture was concentrated under reduced pressure, and diluted with 5 ml DCM. The DCM phase was poured onto a saturated aqueous NaHCO$_3$ solution (ca. 10 ml). The mixture was poured into a separatory funnel and the layers were separated. The DCM layer was washed with aqueous NaBF$_4$ solution (2×ca. 10 ml, 5% w/w), and with water (2×ca. 10 ml). The DCM layer was dried over Na$_2$SO$_4$, filtered, and the solvent was removed under reduced pressure. The residue was purified by chromatography on silica gel eluting with DCM/i-PrOH/ HBF$_4$OEt$_2$ (500:15:2 (v/v/v)). The product was dissolved in 5 ml DCM, and precipitated with 20 ml Et$_2$O. The solid was dried in vacuo to afford 270 mg (87%) of 24a as colorless solid.

NMR Spectroscopy:

$^1$H NMR (500 MHz, CD$_3$CN, 298 K, δ): 9.96 (bs, 1H), 9.79 (bs, 1H), 8.21 (d, J=8.0 Hz, 2H), 7.95-7.88 (m, 3H), 7.84 (ψt, J=7.7 Hz, 2H), 7.76 (ψt, J=7.7 Hz, 2H), 7.39 (d,

J=8.3 Hz, 1H), 7.30 (d, J=8.3 Hz, 1H), 7.14 (dd, J=9.3 Hz, 2.8 Hz, 1H), 6.34 (d, J=9.4 Hz, 1H), 2.36 (s, 3H).

$^{13}C$ {$^{1}H$} NMR (128 MHz, CD$_3$CN, 298 K, δ): 168.4, 152.7, 138.2, 136.7, 135.8, 135.3, 134.9, 134.0, 132.2, 131.6, 131.5, 131.0, 129.1, 120.7, 116.8, 112.8, 109.4, 20.5.

$^{19}F$ {$^{1}H$} NMR (471 MHz, CD$_3$CN, 298 K, δ): −151.6 (bs), −151.6 (bs).

HRMS-ESI (m/z) calc'd for $C_{26}H_{18}Cl_2F_4NO_2S_2^+$ [M-BF$_4$]$^+$, 510.015680; found, 510.015055; deviation: 1.2 ppm.

Famoxadone Derived Thianthrenium Salt 25a

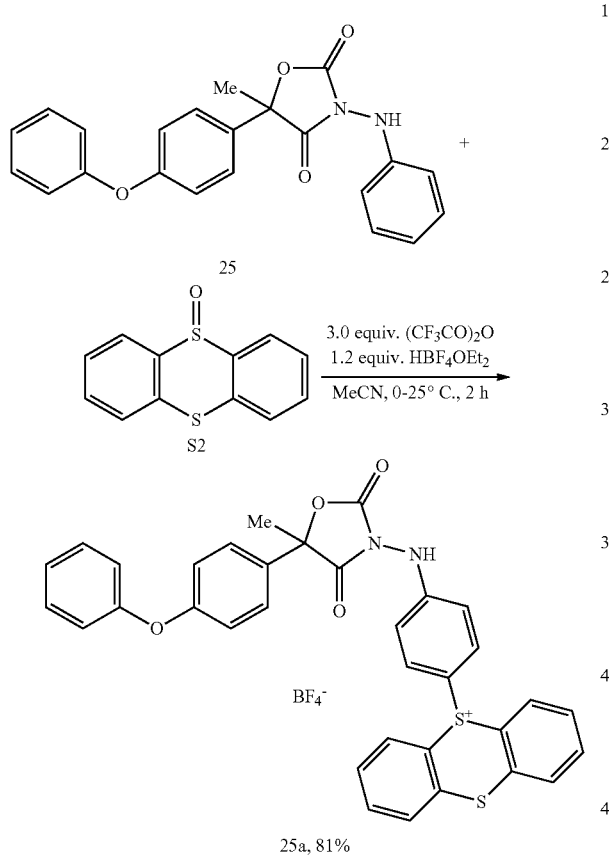

Under an ambient atmosphere, a 20 ml glass-vial was charged with famoxadone (25) (187 mg, 0.50 mmol, 1.0 equiv.), and dry MeCN (2.0 ml, c=0.25 M). Trifluoroacetic anhydride (0.21 ml, 0.32 g, 1.5 mmol, 3.0 equiv.) was added while stirring the reaction mixture. After cooling to 0° C., thianthrene reagent (97% (w/w) thianthrene-S-oxide S2, 3% (w/w) thianthrene S1, 116 mg, 0.50 mmol, 1.0 equiv.) was added in one portion, followed by the addition of HBF$_4$OEt$_2$ (82 μl, 97 mg, 0.60 mmol, 1.2 equiv.) in one portion at 0° C., leading to a purple suspension. The vial was sealed with a screw-cap, and the mixture was stirred at 0° C. for 1 h, followed by stirring at 25° C. for 1 h, until a slight purple solution was obtained. The reaction mixture was concentrated under reduced pressure, and diluted with 5 ml DCM. The DCM phase was poured onto a saturated aqueous NaHCO$_3$ solution (ca. 10 ml). The mixture was poured into a separatory funnel, and the layers were separated. The DCM layer was washed with aqueous NaBF$_4$ solution (2×ca. 10 ml, 5% w/w), and with water (2×ca. 10 ml). The DCM layer was dried over Na$_2$SO$_4$, filtered, and the solvent was removed under reduced pressure. The residue was purified by chromatography on silica gel eluting with DCM/i-PrOH, (30:1 (v/v)). The product was dissolved in 5 ml DCM, and precipitated with 20 ml Et$_2$O. The suspension was decanted, and the solid was dried in vacuo to afford 275 mg (81%) of 25a as colorless solid.

NMR Spectroscopy:

$^{1}H$ NMR (600 MHz, CD$_3$CN, 298 K, δ): 8.23 (dddψd, J=8.0 Hz, 1.3 Hz, 0.8 Hz, 0.4 Hz, 2H), 7.92 (dddψd, J=8.0 Hz, 2.1 Hz, 1.3 Hz, 0.4 Hz, 2H), 7.84 (ddψt, J=8.0 Hz, 7.5 Hz, 1.4 Hz, 2H), 7.76 (dddψd, J=7.9 Hz, 7.5 Hz, 1.3 Hz, 0.4 Hz, 2H), 7.51-7.49 (m, 2H), 7.48 (bs), 7.41-7.38 (m, 2H), 7.21-7.18 (m, 1H), 7.06 (d, J=9.1 Hz, 2H), 7.03-7.01 (m, 4H), 6.79 (d, J=9.1 Hz, 2H), 1.96 (s, 3H).

$^{13}C$ {$^{1}H$} NMR (151 MHz, CD$_3$CN, 298 K, δ): 172.7, 159.5, 157.2, 153.1, 150.3, 137.0, 135.8, 153.3, 131.6, 131.4, 131.4, 131.1, 130.9, 127.6, 125.2, 120.5, 120.2, 119.4, 114.9, 114.3, 86.2, 24.7.

$^{19}F$ {$^{1}H$} NMR (565 MHz, CD$_3$CN, 298 K, δ): −151.4 (bs), −151.5 (bs).

$^{15}N$ NMR (61 MHz, CD$_3$CN, 298 K, δ): −222.7, −293.0. (shifts taken from 2D spectrum).

HRMS-ESI (m/z) calc'd for $C_{34}H_{25}F_4N_2O_4S_2^+$ [M-BF$_4$]$^+$, 589.125410; found, 589.125028; deviation: 0.6 ppm.

Indomethacin Methylester (26)

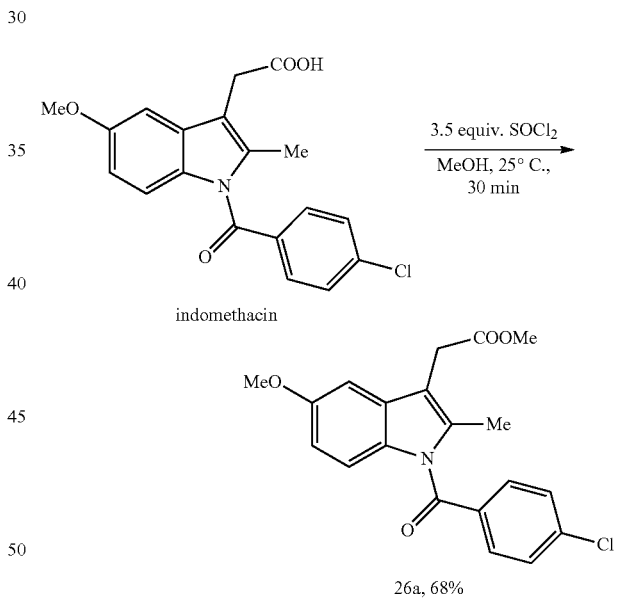

A 100 ml roundbottom flask was charged with MeOH (20 ml, c=0.14 M), and indomethacin (1.00 g, 2.7 mmol, 1.0 equiv.). Thionylchloride (0.70 ml, 1.1 g, 9.7 mmol, 3.5 equiv.) was added dropwise to the suspension over a period of 1 min, leading to a clear solution. After 5 min, a colorless precipitate started to form, and the stirrer was turned off. The mixture was allowed to stand at 25° C. for 30 min, before the colorless crystals were collected by filtration through a glass-frit. The solid was washed with MeOH (20 ml), and dried in vacuo to afford 0.71 g (1.9 mmol, 68%) of 26 as colorless crystals.

NMR Spectroscopy:

$^{1}H$ NMR (500 MHz, CDCl$_3$, 298 K, δ): 7.66 (d, J=8.5 Hz, 2H), 7.47 (d, J=8.5 Hz, 2H), 6.96 (d, J=2.5 Hz, 1H), 6.86 (d,

J=9.0 Hz, 1H), 6.67 (dd, J=9.0 Hz, 2.6 Hz, 1H), 3.84 (s, 3H), 3.70 (s, 3H), 3.67 (s, 2H), 2.39 (s, 3H).

$^{13}$C {$^1$H} NMR (126 MHz, CDCl$_3$, 298 K, δ): 171.4, 168.4, 156.2, 139.4, 136.1, 134.0, 131.3, 130.9, 130.8, 129.2, 115.1, 112.6, 111.7, 101.4, 55.8, 52.3, 30.2, 13.4.

Indomethacin Methylester Derived Thianthrenium Salt 26a

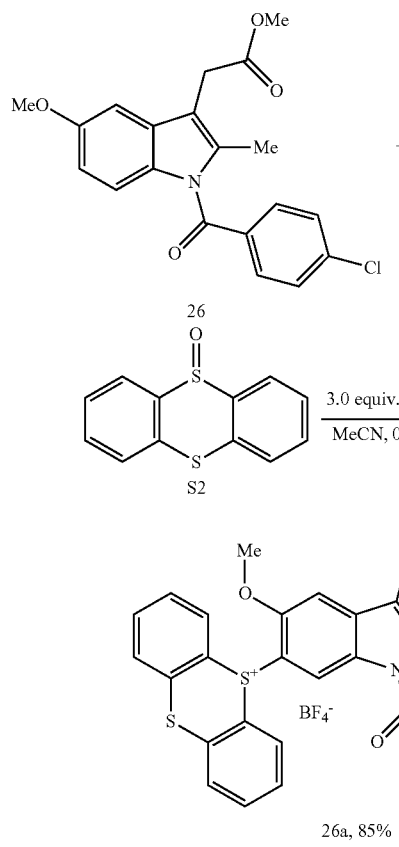

Under an ambient atmosphere, a 20 ml glass-vial was charged with indomethacin methylester (26) (186 mg, 0.50 mmol, 1.0 equiv.), and dry MeCN (2.0 ml, c=0.25 M). After cooling to −78° C., trifluoroacetic anhydride (0.21 ml, 0.32 g, 1.5 mmol, 3.0 equiv.) was added to the frozen the reaction mixture. Thianthrene reagent (97% (w/w) thianthrene-S-oxide (S2), 3% (w/w) thianthrene (S1), 116 mg, 0.50 mmol, 1.0 equiv.) was added in one portion at −78° C. The vial was sealed with a screw-cap, and the mixture was allowed to stand at −78° C. for 1 h, followed by warming the reaction mixture to 25° C. Subsequently, the mixture was stirred for 1 h at 25° C. The reaction mixture was concentrated under reduced pressure, and diluted with 5 ml DCM. The DCM phase was poured onto a saturated aqueous NaHCO$_3$ solution (ca. 10 ml). The mixture was poured into a separatory funnel, and the layers were separated. The DCM layer was washed with aqueous NaBF$_4$ solution (2×ca. 10 ml, 5% w/w), and with water (2×ca. 10 ml). The DCM layer was dried over Na$_2$SO$_4$, filtered, and the solvent was removed under reduced pressure. The residue was purified by chromatography on silica gel eluting with DCM/i-PrOH, (30:1 (v/v)). The product was dissolved in 5 ml DCM, and precipitated with 20 ml Et$_2$O. The suspension was decanted, and the solid was dried in vacuo to afford 286 mg (85%) of 26a as a colorless solid.

NMR Spectroscopy:

$^1$H NMR (500 MHz, CD$_3$CN, 298 K, δ): 8.16 (dψt, J=7.9 Hz, 0.9 Hz, 2H), 7.79-7.77 (m, 4H), 7.73-7.68 (m, 2H), 7.47 (s), 7.27 (s, 1H), 6.16 (s, 1H), 3.97 (s, 3H), 3.73 (s, 2H), 3.64 (s, 3H), 2.36 (s, 3H).

$^{13}$C {$^1$H} NMR (128 MHz, CD$_3$CN, 298 K, δ): 171.8, 168.3, 154.4, 142.7, 140.5, 138.0, 136.5, 135.9, 135.6, 133.6, 132.5, 131.3, 130.7, 130.5, 130.5, 118.2, 115.6, 113.8, 104.4, 103.5, 58.0, 52.7, 29.9, 13.3.

$^{19}$F {$^1$H} NMR (471 MHz, CD$_3$CN, 298 K, δ): −152.6 (bs), −152.7 (bs).

HRMS-ESI (m/z) calc'd for $C_{32}H_{25}ClF_4NO_4S_2^+$ [M-BF$_4$]$^+$, 586.091180; found, 586.090807; deviation: 0.6 ppm.

Borylpyriproxyfen 27

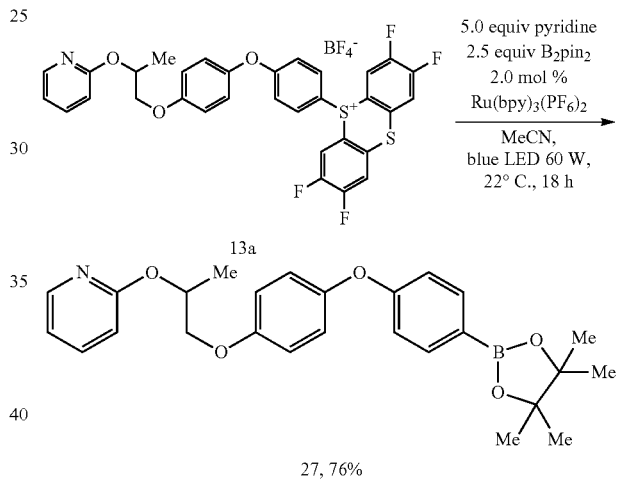

Under an ambient atmosphere, two 4 ml glass-vials equipped with teflon coated magnetic stirbars were in total charged with thianthrenium salt 13a (348 mg, 0.50 mmol, 1.0 equiv.), Ru(bpy)$_3$(PF$_6$)$_2$ (8.6 mg, 0.010 mmol, 2.0 mol %), B$_2$Pin$_2$ (317 mg, 1.3 mmol, 2.5 equiv.), and pyridine (202 µl, 0.20 g, 2.5 mmol, 5.0 equiv.). After adding MeCN (2.0 ml, c=0.13 M) to each vial, the mixtures were degassed by purging with argon for 5 minutes. The vials were irradiated with LEDs (450 nm, 60 W) at 22° C. for 18 h (3 E/mmol). The combined reaction mixtures were concentrated under reduced pressure, and the residue was purified by chromatography on silica gel eluting with i-hexane/EtOAc, (20:1 (v/v)). The product was dried in vacuo to afford 255 mg (76%) of 27 as a colorless solid, still containing B$_2$Pin$_2$. A sample of 27 free of B$_2$Pin$_2$ was prepared by dissolving the product in DCM, followed by addition of trifluoroacetic acid. The mixture was immediately loaded on a short silica column. The column was then eluted with DCM (200 ml). Subsequently elution was continued with DCM/NEt$_3$ (20:1 (v/v)). The eluate was concentrated, and the residue was dried in vacuo. The product was filtered through silica gel eluting with pentane/EtOAc (10:1 (v/v)) to afford B$_2$Pin$_2$ free 27.

NMR Spectroscopy:

$^1$H NMR (500 MHz, CDCl$_3$, 298 K, δ): 8.16 (ddd, J=5.0 Hz, 2.1 Hz, 0.8 Hz, 1H), 7.76 (d, J=8.6 Hz, 2H), 7.56 (ddd, J=8.4 Hz, 7.1 Hz, 2.0 Hz, 1H), 7.00-7.91 (m, 6H), 6.86 (ddd, J=7.1 Hz, 5.1 Hz, 1.0 Hz, 1H), 6.75 (d, J=8.3 Hz, 1H), 5.63-5.58 (m, 1H), 4.20 (dd, J=9.9 Hz, 5.3 Hz, 1H), 4.09 (dd, J=9.9 Hz, 4.9 Hz, 1H), 1.50 (d, J=6.4 Hz, 3H), 1.34 (s, 12H).

$^{13}$C {$^1$H} NMR (128 MHz, CDCl$_3$, 298 K, δ): 163.2, 161.4, 155.6, 149.7, 146.9, 138.8, 136.7, 121.3, 116.9, 116.6, 115.9, 111.8, 83.8, 71.1, 69.3, 25.0, 17.1.

HRMS-ESI (m/z) calc'd for $C_{26}H_{31}BNO_5^+$ [M+H]$^+$, 448.229110; found, 448.228979; deviation: 0.3 ppm.

Phosphonylpyriproxyfen 28

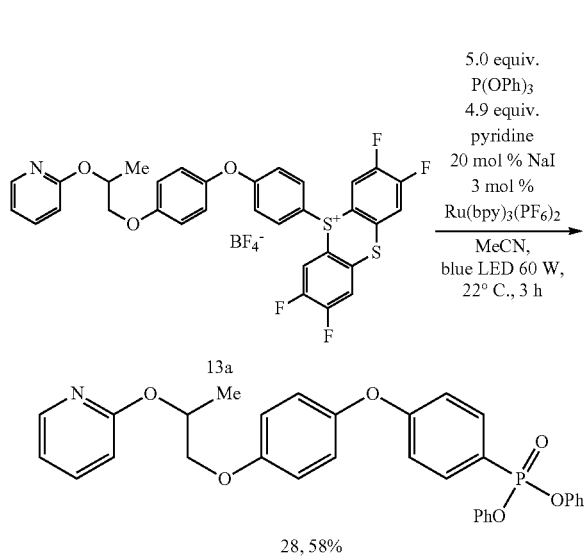

28, 58%

Under an ambient atmosphere, a 4 ml glass vial was charged with thianthrenium salt 13a (174 mg, 0.25 mmol, 1.0 equiv.), sodium iodide (7 mg, 0.05 mmol, 0.2 equiv.), and tris-(2,2-bipyridin)-ruthenium(II)-hexafluorophosphate (6 mg, 0.007 mmol, 3 mol %). The solids were dissolved in MeCN (2.0 ml, c=0.13 M), and triphenylphosphite (0.33 ml, 0.39 g, 1.3 mmol, 5.0 equiv.), and pyridine (0.10 ml, 98 mg, 1.2 mmol, 4.9 equiv.) was added. The vial was sealed with a septum-cap, and the reaction mixture was degassed by bubbling argon through the solution with a needle. The reaction mixture was irradiated with LEDs (450 nm, 60 W) for 3 h (0.5 E/mmol) at 22° C. The reaction mixture was poured onto a mixture of water (15 ml), and EtOAc (15 ml). The layers were separated, and the aqueous layer was extracted with 10 ml EtOAc. The combined organic layers were dried over Na$_2$SO$_4$, and the solvent was removed under reduced pressure. The crude product was purified by chromatography on silica gel eluting with pentane/EtOAc (3:1 (v/v)) to afford 80 mg (58%) of 28 as colorless viscous oil.

NMR Spectroscopy:

$^1$H NMR (500 MHz, CDCl$_3$, 298 K, δ): 8.16 (ddd, J=5.0 Hz, 1.9 Hz, 0.6 Hz, 1H), 7.88 (dd, J=13.4 Hz, 8.8 Hz, 2H), 7.56 (ddd, J=8.7 Hz, 7.1 Hz, 2.0 Hz, 1H), 7.32-7.27 (m, 4H), 7.22-7.18 (m, 4H), 7.16-7.12 (m, 2H), 7.02-6.95 (m, 6H), 6.86 (ddd, J=7.1 Hz, 5.0 Hz, 1.0 Hz, 1H), 6.74 (d, J=8.4 Hz, 1H), 5.64-5.55 (m, 1H), 4.21 (dd, J=9.9 Hz, 5.3 Hz, 1H), 4.10 (dd, J=9.9 Hz, 4.9 Hz, 1H), 1.50 (d, J=6.4 Hz, 3H).

$^{13}$C {$^1$H} NMR (128 MHz, CDCl$_3$, 298 K, δ): 163.1, 163.0 (d, J=3.7 Hz), 156.2, 150.5 (d, J=7.7 Hz), 148.3, 146.8, 138.8, 134.4 (d, J=11.9 Hz), 129.7, 125.1, 121.8, 120.6 (d, J=4.6 Hz), 119.5 (d, J=199 Hz), 116.8, 116.7, 116.6, 116.0, 111.7, 71.0, 69.2, 17.0.

$^{31}$P {$^1$H} NMR (203 MHz, CDCl$_3$, 298 K, δ): 12.1 (s).

HRMS-ESI (m/z) calc'd for $C_{32}H_{29}NO_6P$ [M+H]$^+$, 554.172703; found, 554.172780, deviation: 0.1 ppm.

Cyanopyriproxyfen 29

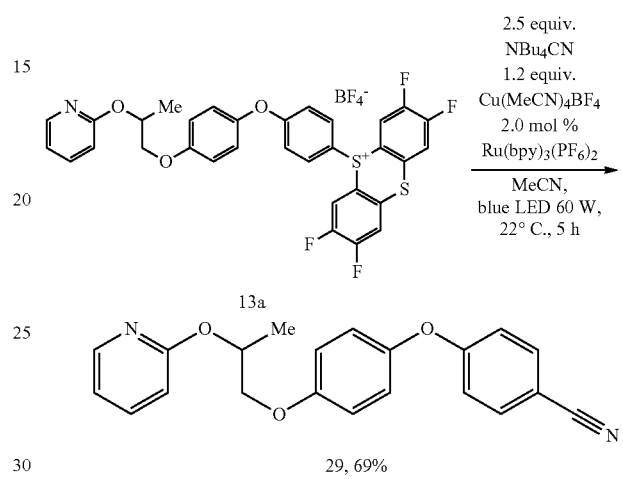

29, 69%

Under an ambient atmosphere, two 4 ml glass-vials equipped with teflon coated magnetic stirbars were in total charged with thianthrenium salt 13a (348 mg, 0.50 mmol, 1.0 equiv.), Ru(bpy)$_3$(PF$_6$)$_2$ (8.6 mg, 0.010 mmol, 2.0 mol %), NBu$_4$CN (336 mg, 1.3 mmol, 2.5 equiv.), and Cu(MeCN)$_4$BF$_4$ (189 mg, 0.60 mmol, 1.2 equiv.). After adding MeCN (2.0 ml, c=0.125 M) to each vial, the mixtures were degassed by purging with argon for 5 minutes. The vials were irradiated with LEDs (450 nm, 60 W) at 22° C. for 5 h (0.8 E/mmol). The combined reaction mixtures were diluted with EtOAc (total ca. 10 ml), and poured onto a saturated aqueous FeSO$_4$.7H$_2$O solution (ca. 10 ml). The mixture was poured into a separatory funnel, and the layers were separated. The organic layer was washed with saturated aqueous NaHCO$_3$ solution (ca. 10 ml), and with water (ca. 10 ml). The organic layer was dried over Na$_2$SO$_4$, filtered, and the solvent was removed under reduced pressure. The residue was purified by chromatography on silica gel eluting with i-hexane/EtOAc, (20:1 (v/v)). The product was dried in vacuo to afford 120 mg (69%) of 29 as a colorless solid.

NMR Spectroscopy:

$^1$H NMR (500 MHz, CDCl$_3$, 298 K, δ): 8.15 (ddd, J=5.0 Hz, 2.1 Hz, 0.8 Hz, 1H), 7.59-7.55 (m, 3H), 6.98 (s, 4H), 6.94 (d, J=8.9 Hz, 2H), 6.87 (ddd, J=7.1 Hz, 5.0 Hz, 1.0 Hz, 1H), 6.74 (dψt, J=8.2 Hz, 0.9 Hz, 1H), 5.63-5.57 (m, 1H), 4.21 (dd, J=9.9 Hz, 5.3 Hz, 1H), 4.09 (dd, J=9.9 Hz, 4.9 Hz, 1H), 1.49 (d, J=6.4 Hz, 3H).

$^{13}$C {$^1$H} NMR (128 MHz, CDCl$_3$, 298 K, δ): 163.2, 162.3, 156.5, 148.1, 146.9, 138.9, 134.2, 121.9, 119.1, 117.3, 117.0, 116.3, 111.8, 105.4, 71.2, 69.3, 17.2.

HRMS-ESI (m/z) calc'd for $C_{21}H_{19}N_2O_3^+$ [M+H]$^+$, 347.139200; found, 347.139017; deviation: 0.5 ppm.

Trifluoromethylthiopyriproxyfen 30

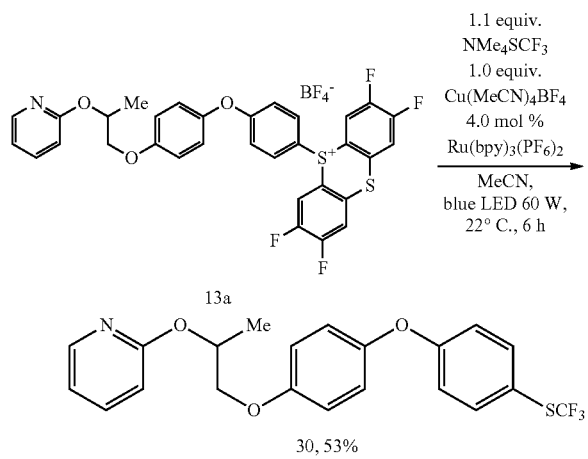

In a nitrogen-filled glovebox, a 4 ml glass-vial, equipped with a teflon coated magnetic stirbar, was charged with thianthrenium salt 13a (174 mg, 0.25 mmol, 1.0 equiv.), Ru(bpy)$_3$(PF$_6$)$_2$ (8.6 mg, 0.010 mmol, 4.0 mol %), NMe$_4$SCF$_3$ (48 mg, 0.28 mmol, 1.1 equiv.), and Cu(MeCN)$_4$BF$_4$ (79 mg, 0.25 mmol, 1.0 equiv.). After adding dry MeCN (2.0 ml, c=0.13 M), the vial was irradiated with LEDs (450 nm, 60 W) at 22° C. for 6 h (1 E/mmol). The reaction mixture was concentrated under reduced pressure, and the residue was purified by chromatography on silica gel eluting with i-hexane/EtOAc, (20:1 (v/v)). The product was dried in vacuo to afford 56 mg (53%) of 30 as colorless viscous oil.

NMR Spectroscopy:

$^1$H NMR (500 MHz, CDCl$_3$, 298 K, δ): 8.15 (ddd, J=5.1 Hz, 2.1 Hz, 0.9 Hz, 1H), 7.60-7.53 (m, 3H), 7.01-6.95 (m, 4H), 6.92 (d, J=8.8 Hz, 2H), 6.87 (ddd, J=7.1 Hz, 5.0 Hz, 1.0 Hz, 1H), 6.75 (d, J=8.3 Hz, 1H), 5.63-5.56 (m, 1H), 4.21 (dd, J=9.8 Hz, 5.3 Hz, 1H), 4.09 (dd, J=9.8 Hz, 4.8 Hz, 1H), 1.49 (d, J=6.4 Hz, 3H).

$^{13}$C {$^1$H} NMR (128 MHz, CDCl$_3$, 298 K, δ): 163.3, 161.5, 156.2, 148.8, 146.9, 138.9, 138.4, 129.7 (q, J=308 Hz), 121.7, 117.8, 117.0, 116.6, 116.1, 111.8, 71.2, 69.3, 17.2. $^{19}$F NMR (471 MHz, CDCl$_3$, 298 K, δ): −43.7.

HRMS-ESI (m/z) calc'd for C$_{21}$H$_{19}$F$_3$NO$_3$S$^+$ [M+H]$^+$, 422.103200; found, 422.103227; deviation: 0.1 ppm.

Chloropyriproxyfen 31

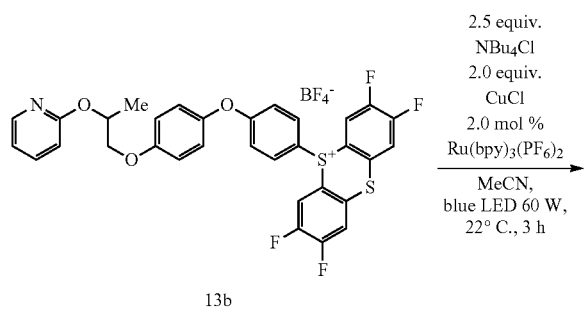

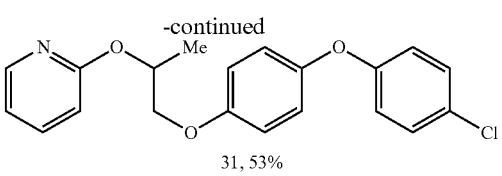

Under an ambient atmosphere, two 4 ml glass-vials, equipped with teflon coated magnetic stirbars, were in total charged with pyriproxyfen tetrafluorothianthrenium tetrafluoroborate 13b (348 mg, 0.50 mmol, 1.0 equiv.), Ru(bpy)$_3$(PF$_6$)$_2$ (8.6 mg, 0.010 mmol, 2.0 mol %), NBu$_4$Cl (347 mg, 1.3 mmol, 2.5 equiv.), and CuCl (99 mg, 1.0 mmol, 2.0 equiv.). After adding MeCN (2.0 ml, c=0.13 M) to each vial, the mixtures were degassed by purging with argon for 5 minutes. The vials were irradiated with LEDs (450 nm, 60 W) at 22° C. for 3 h (0.5 E/mmol). The combined reaction mixtures were concentrated under reduced pressure, and the residue was purified by chromatography on silica gel eluting with i-hexane/EtOAc, (20:1 (v/v)). The product was dried in vacuo to afford 96 mg (53%) of 31 as a colorless solid.

NMR Spectroscopy:

$^1$H NMR (500 MHz, CDCl$_3$, 298 K, δ): 8.15 (ddd, J=5.1 Hz, 2.1 Hz, 0.9 Hz, 1H), 7.57 (ddd, J=8.4 Hz, 7.1 Hz, 2.0 Hz, 1H), 7.24 (d, J=9.0 Hz, 2H), 6.96-6.91 (m, 4H), 6.88-6.84 (m, 3H), 6.74 (d, J=8.4 Hz, 1H), 5.61-5.55 (m, 1H), 4.19 (dd, J=9.9 Hz, 5.3 Hz, 1H), 4.07 (dd, J=9.9 Hz, 4.9 Hz, 1H), 1.48 (d, J=6.4 Hz, 3H).

$^{13}$C {$^1$H} NMR (128 MHz, CDCl$_3$, 298 K, δ): 163.3, 157.3, 155.6, 150.1, 146.9, 138.9, 129.7, 127.5, 120.9, 118.9, 116.9, 116.0, 111.8, 71.1, 69.2, 17.0.

HRMS-ESI (m/z) calc'd for C$_{20}$H$_{19}$ClNO$_3$$^+$ [M+H]$^+$, 356.105010; found, 356.104797; deviation: 0.6 ppm.

Iodopyriproxyten 32

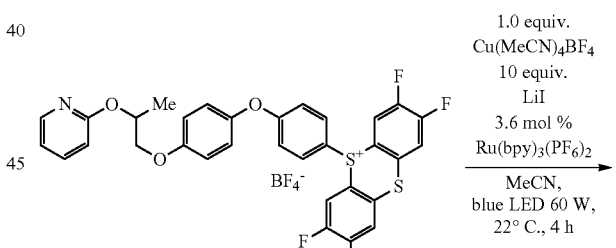

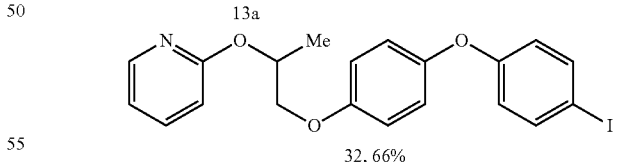

Under an ambient atmosphere, a 4 ml glass vial was charged with pyriproxyfen tetrafluorothianthrenium tetrafluoroborate 13b (174 mg, 0.25 mmol, 1.0 equiv.), LiI (402 mg, 2.5 mmol, 10 equiv.), Cu(MeCN)$_4$BF$_4$ (79 mg, 0.25 mmol, 1.0 equiv.), and tris-(2,2-bipyridin)-ruthenium(II)-hexafluorophosphate (7.8 mg, 0.0091 mmol, 3.6 mol %). The solids were dissolved in a mixture of MeCN (1.5 ml) and DMSO (1.0 ml, c=0.10 M). The vial was sealed with a septum-cap, and the reaction mixture was degassed by bubbling argon through the solution with a needle. The reaction mixture was irradiated with LEDs (450 nm, 60 W) for 4 h (0.7 E/mmol) at 22° C. The reaction mixture was poured onto a mixture of water (25 ml), and EtOAc (25 ml). The layers were separated and the aqueous layer was extracted with 25 ml EtOAc. The combined organic layers were dried over $Na_2SO_4$, and the solvent was removed under reduced pressure. The residue was purified by chromatography on silica gel eluting with pentane/EtOAc (gradient from 200/1 to 50/1 (v/v)) to afford 89 mg (66%) of 32 as colorless solid.

NMR Spectroscopy:

$^1$H NMR (500 MHz, $CDCl_3$, 298 K, δ): 8.15 (ddd, J=5.0 Hz, 2.1 Hz, 0.8 Hz, 1H), 7.59-7.54 (m, 3H), 6.98-6.92 (m, 4H), 6.86 (ddd, J=7.1 Hz, 5.1 Hz, 1.0 Hz, 1H), 6.74 (dψt, J=8.3 Hz, 0.9 Hz, 1H), 6.70 (d, J=8.9 Hz, 2H), 5.63-5.55 (m, 1H), 4.19 (dd, J=9.8 Hz, 5.3 Hz, 1H), 4.08 (dd, J=9.9 Hz, 4.8 Hz, 1H), 1.49 (d, J=6.4 Hz, 3H).

$^{13}$C {$^1$H} NMR (128 MHz, $CDCl_3$, 298 K, δ): 163.3, 158.8, 155.7, 149.7, 146.9, 138.8, 138.6, 121.1, 119.8, 116.9, 116.0, 111.8, 85.0, 71.2, 69.3, 17.1.

HRMS-ESI (m/z) calc'd for $C_{20}H_{19}INO_3^+$ [M+H]$^+$, 448.040416; found, 448.040230, deviation: 0.4 ppm.

Styrenylpyriproxyfen 33 mixture was stirred at 100° C. for 24 h. The reaction mixture was concentrated under reduced pressure and the residue was purified by chromatography on silica gel eluting with i-hexane/EtOAc, (20:1 (v/v)). The product was dried in vacuo to afford 183 mg (86%) of 33 as a colorless solid.

NMR Spectroscopy:

$^1$H NMR (500 MHz, $CDCl_3$, 298 K, δ): 8.18 (ddd, J=5.1 Hz, 2.1 Hz, 0.8 Hz, 1H), 7.58 (ddd, J=8.4 Hz, 7.1 Hz, 2.1 Hz, 1H), 7.51 (d, J=6.9 Hz, 2H), 7.46 (d, J=8.7 Hz, 2H), 7.36 (ψt, J=7.7 Hz, 2H), 7.29-7.24 (m, 1H), 7.11-6.93 (m, 8H), 6.87 (ddd, J=7.1 Hz, 5.0 Hz, 1.0 Hz, 1H), 6.77 (d, J=8.4 Hz, 1H), 5.66-5.60 (m, 1H), 4.22 (dd, J=9.9 Hz, 5.3 Hz, 1H), 4.10 (dd, J=9.9 Hz, 4.9 Hz, 1H), 1.51 (d, J=6.4 Hz, 3H).

$^{13}$C {$^1$H} NMR (128 MHz, $CDCl_3$, 298 K, δ): 163.3, 158.3, 155.5, 150.2, 146.9, 138.8, 137.6, 131.9, 128.8, 128.1, 127.9, 127.6, 127.5, 126.5, 120.9, 117.9, 116.9, 115.9, 111.8, 71.2, 69.4, 17.1.

HRMS-EI (m/z) calc'd for $C_{28}H_{26}NO_3^+$ [M]$^+$, 424.190320; found, 424.190719; deviation: 0.9 ppm.

Cyclopropylpyriproxyfen 34

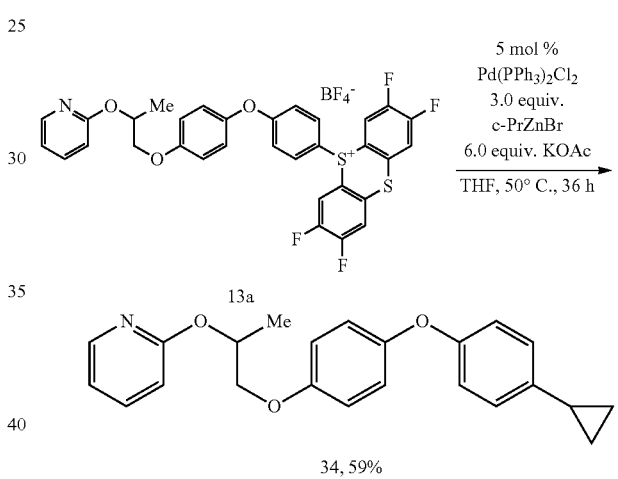

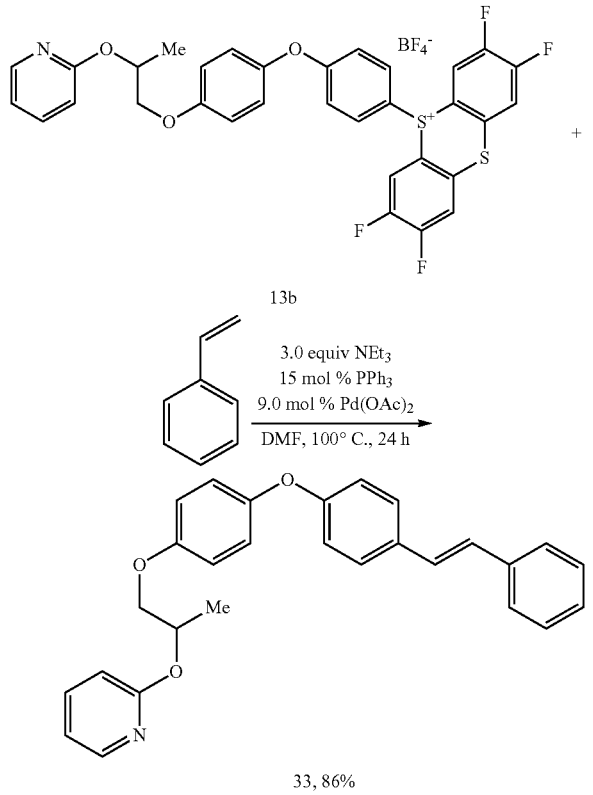

A 10 ml roundbottom flask, equipped with a teflon coated magnetic stirbar, was charged with thianthrenium salt 13a (348 mg, 0.50 mmol, 1.0 equiv.), $Pd(OAc)_2$ (10 mg, 0.045 mmol, 9.0 mol %), and $PPh_3$ (20 mg, 0.075 mmol, 15 mol %). After adding DMF (2.0 ml, c=0.25 M), the mixture was degassed by purging with argon for 5 minutes, followed by the addition of $NEt_3$ (209 µl, 0.15 g, 1.5 mmol, 3.0 equiv.), and styrene (115 µl, 0.10 g, 1.0 mmol, 2.0 equiv.). The A 10 ml Schlenk-tube, equipped with a magnetic stir bar, and fitted with a septum, was charged with $Pd(PPh_3)_2Cl_2$ (17.5 mg, 25 µmol, 5.0 mol %), thianthrenium salt 13a (348 mg, 0.50 mmol, 1.0 equiv.), and KOAc (294 mg, 3.0 mmol, 6.0 equiv.). The flask was evacuated for 4 hours, then, it was filled with argon. After completing three evacuation/backfilling cycles, a THF solution of cyclopropylzinc bromide (0.5 M, 3.0 ml, 1.5 mmol, 3.0 equiv.) was slowly added to the mixture while stirring at 25° C. Subsequently, the mixture was heated to 50° C., and stirred for 36 h at 50° C. The reaction mixture was quenched by the slow addition of ice-cold HCl (1 M, 20 ml), and was extracted with ethyl acetate (3×10 ml). The combined organic layers were dried over anhydrous $Na_2SO_4$, filtered, and the solvent was removed under reduced pressure. The residue was purified by chromatography on silica gel eluting with ethyl acetate/i-hexane (gradient from 1:100 to 1:70 (v/v)) to afford 108 mg (59%) of 34 as colorless oil.

NMR Spectroscopy:

$^1$H NMR (500 MHz, $CDCl_3$, 298 K, δ): 8.15 (ddd, J=5.0 Hz, 2.1 Hz, 0.8 Hz, 1H), 7.56 (ddd, J=8.4 Hz, 7.1 Hz, 2.0 Hz, 1H), 7.01 (d, J=8.6 Hz, 2H), 6.95-6.88 (m, 4H), 6.87-6.82 (m, 3H), 6.74 (d, J=8.3 Hz, 1H), 5.62-5.54 (m, 1H), 4.18 (dd, J=9.9 Hz, 5.3 Hz, 1H), 4.06 (dd, J=9.9 Hz, 4.9 Hz, 1H), 1.87 (tt, J=8.4 Hz, 5.1 Hz, 1H), 1.48 (d, J=6.4 Hz, 3H), 0.95-0.90 (m, 2H), 0.66-0.62 (m, 2H).

$^{13}$C {$^1$H} NMR (128 MHz, CDCl$_3$, 298 K, δ): 163.2, 156.1, 155.0, 150.9, 146.8, 138.7, 138.1, 126.9, 120.3, 117.9, 116.8, 115.7, 111.7, 71.2, 69.3, 17.2, 14.8, 8.8.

HRMS-ESI (m/z) calc'd for $C_{23}H_{24}NO_3^+$ [M+H]$^+$, 362.175150; found, 362.175069; deviation: 0.2 ppm.

Methylpyriproxyfen 35

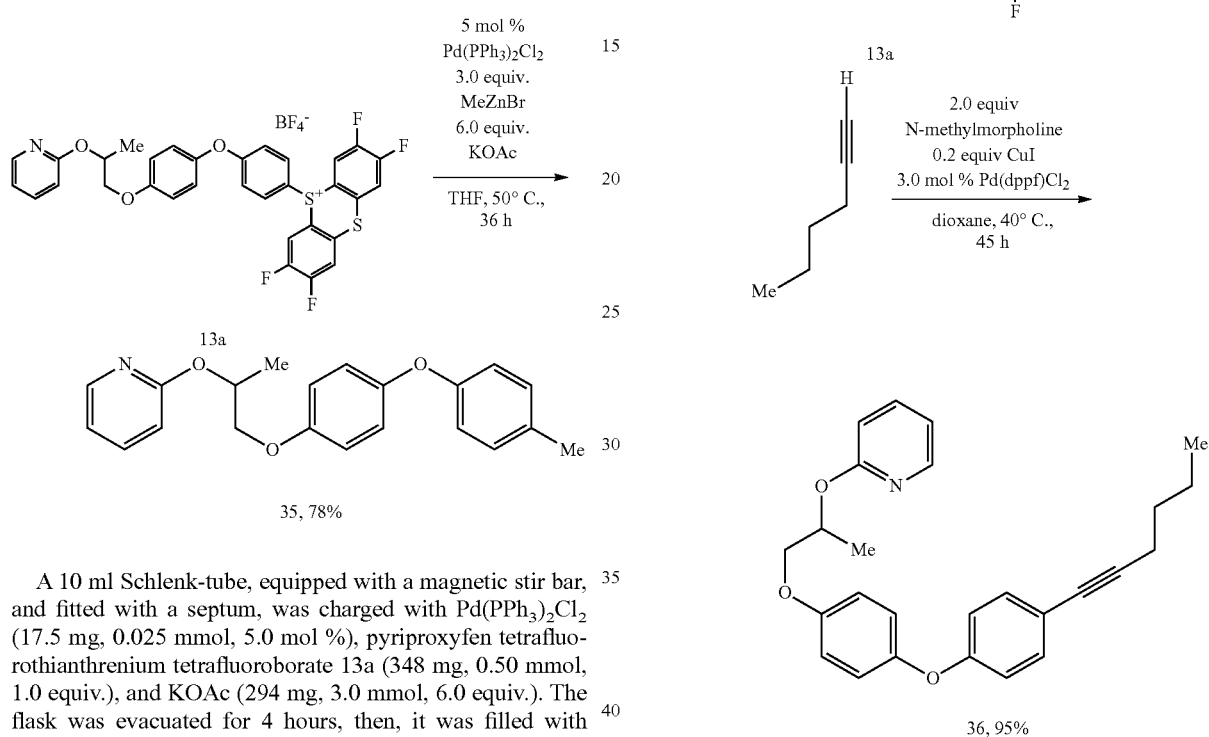

35, 78%

A 10 ml Schlenk-tube, equipped with a magnetic stir bar, and fitted with a septum, was charged with Pd(PPh$_3$)$_2$Cl$_2$ (17.5 mg, 0.025 mmol, 5.0 mol %), pyriproxyfen tetrafluorothianthrenium tetrafluoroborate 13a (348 mg, 0.50 mmol, 1.0 equiv.), and KOAc (294 mg, 3.0 mmol, 6.0 equiv.). The flask was evacuated for 4 hours, then, it was filled with argon. After completing three evacuation/backfilling cycles, anhydrous, and degassed THF (2.25 mL) was added via a syringe. While stirring at 25° C., a THF solution of methylzinc chloride (2.0 M, 0.75 ml, 1.5 mmol, 3.0 equiv.) was added slowly to the reaction mixture. The mixture was heated to 50° C., and stirred for 36 h at 50° C. The reaction mixture was quenched by the slow addition of ice-cold HCl (1 M, 20 ml), and was extracted with ethyl acetate (3×10 ml). The combined organic layers were dried over anhydrous Na$_2$SO$_4$, filtered, and the solvent was removed under reduced pressure. The residue was purified by chromatography on silica gel eluting with ethyl acetate/i-hexane (gradient from 1:100 to 1:80 (v/v)) to afford 131 mg (78%) of 35 as a pale yellow oil.

NMR Spectroscopy:

$^1$H NMR (500 MHz, CDCl$_3$, 298 K, δ): 8.15 (ddd, J=5.0 Hz, 2.0 Hz, 0.8 Hz, 1H), 7.57 (ddd, J=8.4 Hz, 7.1 Hz, 2.0 Hz, 1H), 7.10 (d, J=8.3 Hz, 2H), 6.98-6.88 (m, 4H), 6.88-6.82 (m, 3H), 6.74 (dψt, J=8.3 Hz, 0.9 Hz, 1H), 5.62-5.55 (m, 1H), 4.18 (dd, J=9.9 Hz, 5.4 Hz, 1H), 4.07 (dd, J=9.9 Hz, 4.9 Hz, 1H), 2.31 (s, 3H), 1.48 (d, J=6.4 Hz, 3H).

$^{13}$C {$^1$H} NMR (128 MHz, CDCl$_3$, 298 K, δ): 163.3, 156.2, 155.1, 151.0, 146.9, 138.9, 132.2, 130.2, 120.4, 118.0, 116.9, 115.9, 111.8, 71.2, 69.5, 20.8, 17.2.

HRMS-ESI (m/z) calc'd for $C_{21}H_{22}NO_3^+$ [M+H]$^+$, 336.159490; found, 336.159418; deviation: 0.2 ppm.

Hexynylpyriproxyfen 36

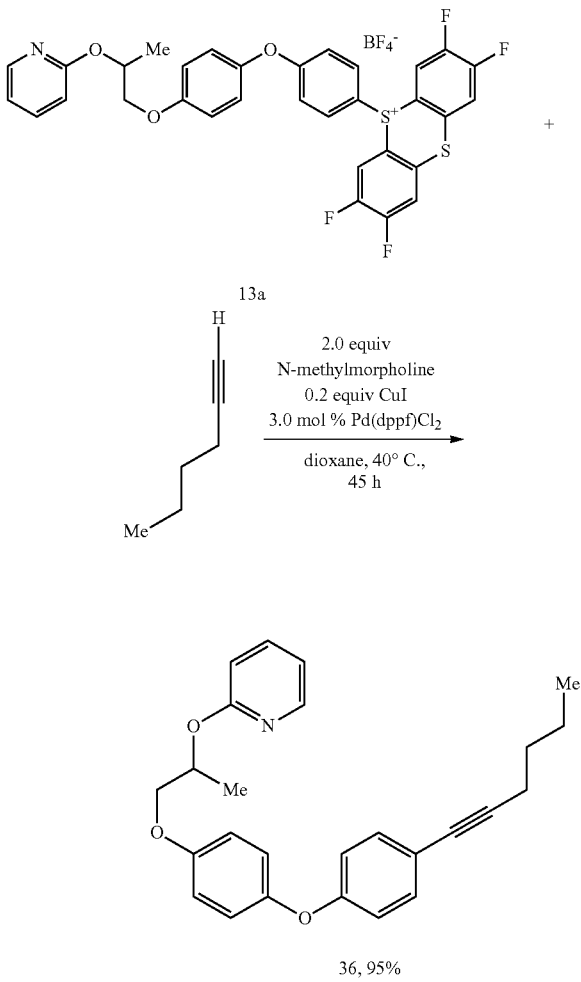

36, 95%

Under an ambient atmosphere, a 10 ml roundbottom flask, equipped with a teflon coated magnetic stirbar, and fitted with a septum, was charged with thianthrenium salt 13a (348 mg, 0.50 mmol, 1.0 equiv.), Pd(dppf)Cl$_2$ (11 mg, 0.015 mmol, 3.0 mol %), and CuI (19 mg, 0.10 mmol, 20 mol %). After adding dioxane (2.0 ml, c=0.25 M), the mixture was degassed by purging with argon for 5 minutes, followed by the addition of N-methylmorpholine (110 μl, 0.10 g, 1.0 mmol, 2.0 equiv.), and 1-hexyne (115 μl, 82 mg, 1.0 mmol, 2.0 equiv.). The mixture was stirred at 40° C. for 45 h. The reaction mixture was concentrated under reduced pressure, and the residue was purified by chromatography on silica gel eluting with i-hexane/EtOAc (20:1 (v/v)). The product was dried in vacuo to afford 191 mg (95%) of 36 as a colorless solid.

NMR Spectroscopy:

$^1$H NMR (500 MHz, CDCl$_3$, 298 K, δ): 8.15 (ddd, J=5.0 Hz, 2.1 Hz, 0.9 Hz, 1H), 7.56 (ddd, J=8.4 Hz, 7.1 Hz, 2.0 Hz, 1H), 7.32 (d, J=8.8 Hz, 2H), 6.97-6.91 (m, 4H), 6.87-6.82 (m, 3H), 6.75 (dψt, J=8.3 Hz, 0.9 Hz, 1H), 5.63-5.56 (m, 1H), 4.19 (dd, J=9.9 Hz, 5.3 Hz, 1H), 4.08 (dd, J=9.9 Hz, 4.9 Hz, 1H), 2.39 (t, J=7.1 Hz, 2H), 1.61-1.54 (m, 2H), 1.51-1.44 (m, 5H), 0.95 (t, J=7.3 Hz, 3H).

$^{13}$C {$^1$H} NMR (128 MHz, CDCl$_3$, 298 K, δ): 163.3, 158.1, 155.6, 149.9, 146.9, 138.8, 133.1, 121.1, 118.2, 117.4, 116.9, 116.0, 111.8, 89.5, 80.2, 71.2, 69.4, 31.0, 22.2, 19.2, 17.1, 13.8.

HRMS-ESI (m/z) calc'd for C$_{26}$H$_{28}$NO$_3^+$ [M+H]$^+$, 402.206450; found, 402.206369; deviation: 0.2 ppm.

Vinylpyriproxyfen 37

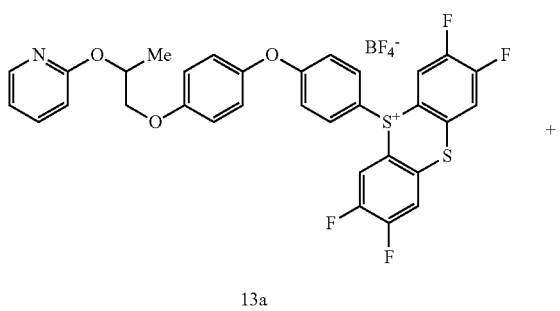

13a

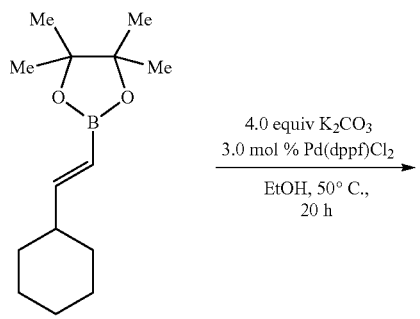

4.0 equiv K$_2$CO$_3$
3.0 mol % Pd(dppf)Cl$_2$

EtOH, 50° C., 20 h

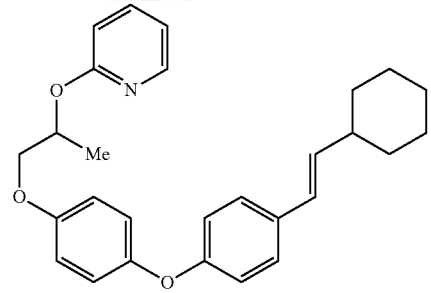

37, 90%

Under an ambient atmosphere, a 10 ml roundbottom flask, equipped with a teflon coated magnetic stirbar, and fitted with a septum, was charged with thianthrenium salt 13a (348 mg, 0.50 mmol, 1.0 equiv.), Pd(dppf)Cl$_2$ (11 mg, 0.015 mmol, 3.0 mol %), K$_2$CO$_3$ (276 mg, 2.0 mmol, 4.0 equiv.), and cyclohexylvinylboronic acid (154 mg, 1.0 mmol, 2.0 equiv.). After adding EtOH (2.0 ml, c=0.25 M) the mixture was degassed by purging with argon for 5 minutes. The mixture was stirred at 50° C. for 20 h. The reaction mixture was concentrated under reduced pressure. The residue was purified by chromatography on silica gel eluting with i-hexane/EtOAc (20:1 (v/v)). The product was dried in vacuo to afford 193 mg (90%) of 37 as a colorless solid.

NMR Spectroscopy:

$^1$H NMR (500 MHz, CDCl$_3$, 298 K, δ): 8.15 (ddd, J=5.0 Hz, 2.1 Hz, 0.8 Hz, 1H), 7.57 (ddd, J=8.4 Hz, 7.1 Hz, 2.1 Hz, 1H), 7.28 (d, J=8.7 Hz, 2H), 6.96-6.90 (m, 4H), 6.89-6.85 (m, 3H), 6.75 (dψt, J=8.3 Hz, 1.0 Hz, 1H), 6.30 (dd, J=15.9 Hz, 1.3 Hz, 1H), 6.07 (dd, J=16.0 Hz, 7.0 Hz, 1H), 5.63-5.56 (m, 1H), 4.19 (dd, J=9.8 Hz, 5.3 Hz, 1H), 4.07 (dd, J=9.9 Hz, 4.9 Hz, 1H), 2.15-2.07 (m, 1H), 1.83-1.72 (m, 4H), 1.71-1.65 (m, 1H), 1.49 (d, J=6.4 Hz, 3H), 1.38-1.26 (m, 2H), 1.24-1.12 (m, 3H).

$^{13}$C {$^1$H} NMR (128 MHz, CDCl$_3$, 298 K, δ): 163.3, 157.4, 155.2, 150.7, 146.9, 138.8, 135.9, 135.9, 132.9, 127.2, 126.5, 120.6, 120.6, 118.0, 116.9, 115.9, 111.8, 71.2, 69.4, 41.3, 33.2, 26.3, 26.2, 17.2.

HRMS-ESI (m/z) calc'd for C$_{28}$H$_{32}$NO$_3^+$ [M+H]$^+$, 430.237710; found, 430.237669; deviation: 0.1 ppm.

Carboxyethylpyriproxyfen 38

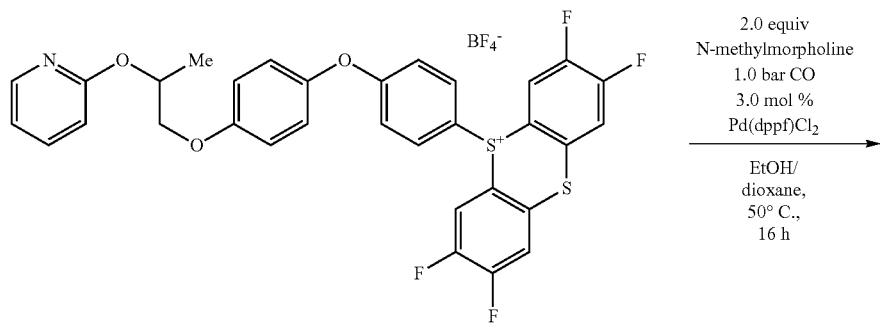

2.0 equiv N-methylmorpholine
1.0 bar CO
3.0 mol % Pd(dppf)Cl$_2$

EtOH/ dioxane, 50° C., 16 h

13a

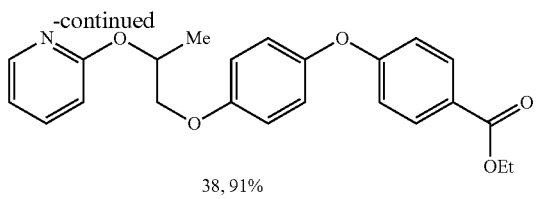

38, 91%

Under an ambient atmosphere, a 20 ml roundbottom flask, equipped with a teflon coated magnetic stirbar, and fitted with a septum, was charged with thianthrenium salt 13a (348 mg, 0.50 mmol, 1.0 equiv.), and Pd(dppf)Cl$_2$ (11 mg, 0.015 mmol, 3.0 mol %). After adding EtOH (2.0 ml), and dioxane (2.0 ml, c=0.13 M) the mixture was degassed by purging with argon for 5 minutes, followed by passing CO (1 bar) through the orange suspension. N-methylmorpholine (101 mg, 1.0 mmol, 2.0 equiv.) was added to the reaction mixture. Subsequently, the mixture was warmed to 50° C. The reaction was stirred at 50° C. for 16 h. The reaction mixture was concentrated under reduced pressure and the residue was purified by chromatography on silica gel eluting with i-hexane/EtOAc (20:1 (v/v)). The product was dried in vacuo to afford 179 mg (91%) of 38 as a colorless solid.

NMR Spectroscopy:

$^1$H NMR (500 MHz, CDCl$_3$, 298 K, δ): 8.15 (ddd, J=5.0 Hz, 2.1 Hz, 0.9 Hz, 1H), 7.92 (dd, J=5.5 Hz, 3.1 Hz, 2H), 7.76 (dd, J=5.5 Hz, 3.0 Hz, 2H), 7.55 (ddd, J=8.4 Hz, 7.1 Hz, 2.0 Hz, 1H), 7.34 (d, J=8.9 Hz, 1H), 7.06-6.99 (m, 4H), 6.97-6.94 (m, 2H), 6.85 (ddd, J=7.1 Hz, 5.0 Hz, 1.0 Hz, 1H), 6.74 (dψt, J=8.4 Hz, 0.8 Hz, 1H), 5.63-5.57 (m, 1H), 4.20 (dd, J=9.9 Hz, 5.3 Hz, 1H), 4.08 (dd, J=9.9 Hz, 4.8 Hz, 1H), 1.49 (d, J=6.4 Hz, 3H).

$^{13}$C {$^1$H} NMR (128 MHz, CDCl$_3$, 298 K, δ): 167.5, 163.2, 158.4, 155.7, 149.6, 146.8, 138.7, 134.4, 131.8, 128.0, 125.7, 123.7, 121.3, 117.7, 116.8, 116.0, 111.7, 71.1, 69.3, 17.1.

HRMS-ESI (m/z) calc'd for C$_{23}$H$_{24}$NO$_5^+$ [M+H]$^+$, 394.164940; found, 394.164899; deviation: 0.1 ppm.

Chloroamiodarone 39

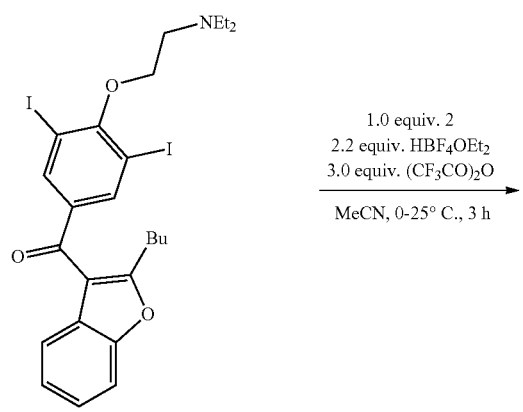

10

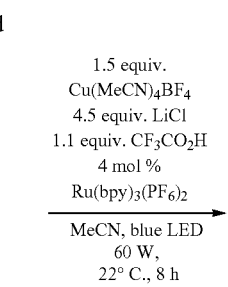

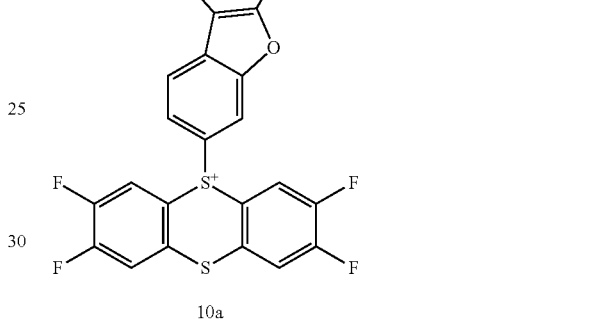

10a

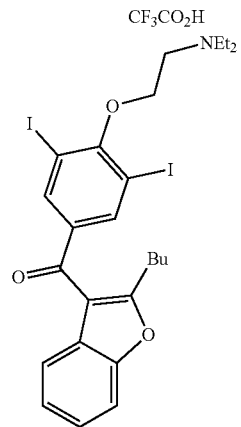

39, 50%

Thianthrenation: Amidarone (10) was prepared from amiodarone hydrochloride by extraction from an aqueous Na$_2$CO$_3$ solution. In a 20 ml glass-vial, equipped with a teflon coated magnetic stirbar, amiodarone (10) (612 mg, 0.95 mmol, 1.0 equiv.) was dissolved in MeCN (3.7 ml, c=0.26 M), subsequently, HBF$_4$OEt$_2$ (0.13 ml, 0.15 g, 0.95 mmol, 1.0 equiv.) was added in one portion. After addition of trifluoroacetic acid anhydride (0.40 ml, 0.60 g, 2.8 mmol, 3.0 equiv.), the reaction mixture was cooled to 0° C., and reagent 2 (289 mg, 0.95 mmol, 1.0 equiv.) was added, followed by addition of HBF$_4$OEt$_2$ (0.15 ml, 0.18 g, 1.1 mmol, 1.2 equiv.). The reaction mixture was stirred for 1 h at 0° C., followed by stirring for 2 h at 25° C. The reaction mixture was concentrated under reduced pressure. The residue was dissolved in 5 ml DCM. The DCM phase was washed with aqueous NaHCO₃ solution (saturated, 10 ml), aqueous NaBF₄ solution (10 ml), and water (10 ml). The organic layer was dried over Na₂SO4 and the solvent was removed under reduced pressure and dried in vauco to afford 914 mg of amiodaronethianthrenium-salt 10a as yellow foam.

Chlorination: A 4 ml glass-vial, equipped with a teflon coated magnetic stirbar, was charged with thianthrenium salt 10a (200 mg, 21.9% of the previously synthesized quantity, <0.21 mmol, 1.0 equiv.), Ru(bpy)₃(PF₆)₂ (6.7 mg, 7.8 μmol, >3.8 mol %), LiCl (40 mg, 0.94 mmol, >4.5 equiv.), Cu(MeCN)₄BF₄ (100 mg, 0.31 mmol, >1.5 equiv.), and MeCN (1.5 ml, c=0.13 M). Subsequently, trifluoroacetic acid (27 mg, 0.23 mmol, >1.1 equiv.) was added. The mixture was degassed by purging with argon for 1 minute. The vial was irradiated with LEDs (450 nm, 60 W) at 22° C. for 8 h (2 E/mmol). To the reaction mixture was added aqueous Na₂CO₃ solution (saturated, 1 ml), water (1 ml), and EtOAc (1 ml). The layers were separated, and the organic layer was extracted with EtOAc (4×1 ml). The combined organic layers were dried over K₂CO₃ and the solvent was removed. The residue was purified by chromatography on silica gel eluting with pentane/EtOAc/CF₃CO₂H, (16:20:1 to 8:28:1). The product 39-TFA was dried in vacuo to afford 83 mg (50% over 2 steps) of 39-TFA as colorless oil.

NMR Spectroscopy:

¹H NMR (500 MHz, CD₃CN, 298 K, δ): 9.79 (bs, 1H), 8.18 (s, 2H), 7.59 (d, J=1.8 Hz, 1H), 7.44 (d, J=8.4 Hz, 1H), 7.25 (dd, J=8.4 Hz, 1.8 Hz, 1H), 4.39 (t, J=4.9 Hz, 2H), 3.71 (bs, 2H), 2.74 (t, J=7.7 Hz, 2H), 1.73-1.65 (m, 2H), 1.37 (t, J=7.1 Hz, 6H), 1.29 (ψsext, J=7.4 Hz, 2H), 0.86 (t, J=7.4 Hz, 3H).

¹³C {¹H} NMR (128 MHz, CD₃CN, 298 K, δ): 188.2, 167.9, 161.2, 154.7, 141.4, 140.0, 131.0, 126.6, 125.3, 123.0, 116.7, 112.5, 91.4, 68.0, 51.9, 49.1, 30.6, 28.9, 23.2, 14.0, 9.3.

¹⁹F NMR (471 MHz, CD₃CN, 298 K, δ): −77.3 (s).

HRMS-ESI (m/z) calc'd for C₂₅H₂₉ClI₂NO₃⁺ [M+H]⁺, 679.991991; found, 679.992330; deviation: 0.5 ppm.

Cyanofamoxadone 40

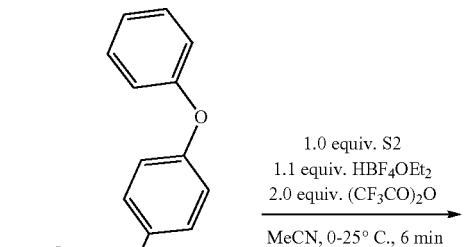

25

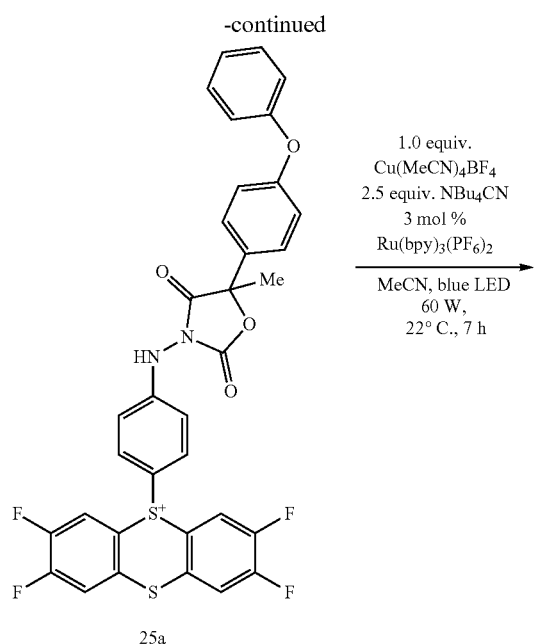

25a

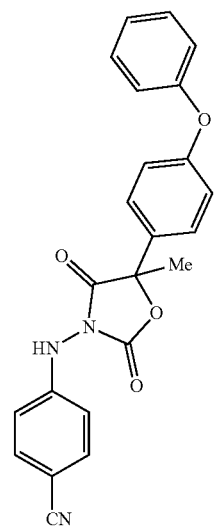

40, 62%

Thianthrenation: A 20 ml glass-vial, equipped with a teflon coated magnetic stirbar, was charged with famoxadone 25 (749 mg, 2.0 mmol, 1.0 equiv.), and (nonfluorinated) thianthrene-S-oxide (S2) (465 mg, 2.0 mmol, 1.0 equiv.) followed by addition of MeCN (2.0 ml, c=1.0 M). The mixture was cooled to 0° C. and HBF₄OEt₂ (0.30 ml, 0.36 g, 2.2 mmol, 1.1 equiv.) was added. After stirring for 30 s, trifluoroacetic acid anhydride (0.56 ml, 0.84 g, 4.0 mmol, 2.0 equiv.) was added at 0° C. in one portion. The mixture was stirred at 0° C. for 1 min, then, it was stirred at 25° C. for another 5 min. The mixture was diluted with 5 ml DCM, and quenched by addition of aqueous Na₂CO₃ solution (saturated, 5 ml). After stirring the biphasic mixture for 5 min at 25° C., the layers were separated by decantation. The aqueous layer was extracted with 5 ml EtOAc. The combined organic layers were dried over Na₂SO₄, and the solvent was removed under reduced pressure, yielding 1.36 g of crude thianthrenium salt 25a as brown foam.

Cyanation: A 4 ml glass-vial, equipped with a teflon coated magnetic stirbar, was charged with crude thianthrenium salt 25a (169 mg, 12.4% of previously synthesized quantity, <0.25 mmol, 1.0 equiv.), Ru(bpy)$_3$(PF$_6$)$_2$ (6.4 mg, 7.5 μmol, <3.0 mol %), NBu$_4$CN (168 mg, 0.63 mmol, <2.5 equiv.), and Cu(MeCN)$_4$BF$_4$ (79 mg, 0.25 mmol, <1.0 equiv.), and MeCN (2.0 ml, c=0.13 M). Subsequently, DMSO (1.0 ml) was added, leading to a clear solution. The mixture was degassed by purging with argon for 2 minutes. The vial was irradiated with LEDs (450 nm, 60 W) at 22° C. for 7 h (1 E/mmol). The reaction mixture was poured onto a mixture of EtOAc (5 ml), and water (5 ml). The layers were separated by decantation. The aqueous layer was extracted with 5 ml EtOAc. The combined organic layers were dried over Na$_2$SO$_4$, filtered through cotton wool, and the solvent was removed under reduced pressure. The residue was purified by chromatography on silica gel eluting with pentane/EtOAc, (3:2 (v/v)). The product was dried in vacuo to afford 62 mg (62% over 2 steps) of 40 as colorless oil.

NMR Spectroscopy:

$^1$H NMR (500 MHz, CDCl$_3$, 298 K, δ): 7.55-7.50 (m, 4H), 7.38 (dd, J=8.6 Hz, 7.4 Hz, 2H), 7.18 (tt, J=7.4 Hz, 1.0 Hz, 1H), 7.08-7.01 (m, 4H), 6.69 (d, J=8.8 Hz, 2H), 6.49 (s, 1H), 2.00 (s, 3H).

$^{13}$C {$^1$H} NMR (128 MHz, CDCl$_3$, 298 K, δ): 171.7, 59.0, 156.1, 152.3, 147.9, 134.0, 130.1, 129.8, 126.1, 124.4, 119.8, 118.9, 118.8, 113.6, 105.8, 85.6, 25.7.

HRMS-ESI (m/z) calc'd for C$_{23}$H$_{16}$N$_3$O$_4^-$ [M−H]$^-$, 398.114631; found, 398.114710; deviation: 0.2 ppm.

Methoxyphenylsalicin Pentaacetate 41

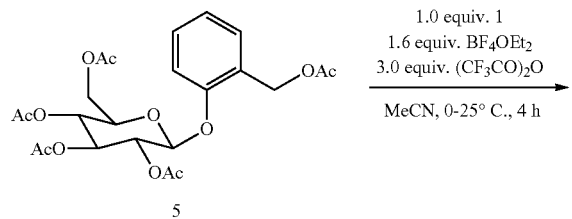

1.0 equiv. 1
1.6 equiv. BF$_4$OEt$_2$
3.0 equiv. (CF$_3$CO)$_2$O

MeCN, 0-25° C., 4 h

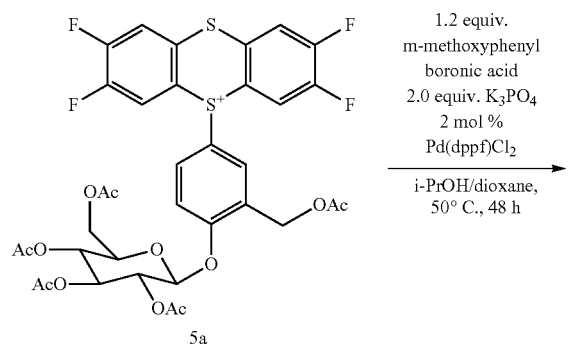

1.2 equiv. m-methoxyphenyl boronic acid
2.0 equiv. K$_3$PO$_4$
2 mol % Pd(dppf)Cl$_2$ i-PrOH/dioxane, 50° C., 48 h

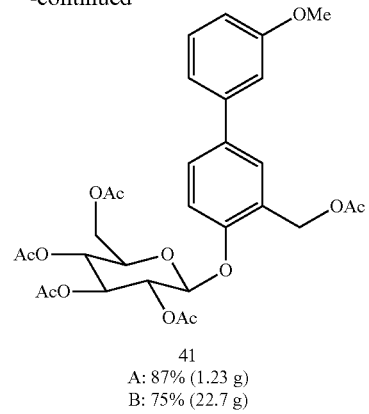

41
A: 87% (1.23 g)
B: 75% (22.7 g)

(A) Thianthrenation: In a 50 ml round bottom flask, equipped with a teflon coated magnetic stirbar, salicin pentaacetate (5) (2.01 g, 4.04 mmol, 1.00 equiv.) was suspended in MeCN (16 ml, c=0.25 M). Subsequently, trifluoroacetic anhydride (1.68 ml, 2.6 g, 12 mmol, 3.0 equiv.) was added. The reaction mixture was cooled to 0° C., followed by addition of tetrafluorothianthrene-S-oxide 1 (1.23 g, 4.0 mmol, 1.0 equiv.). At 0° C., BF$_3$OEt$_2$ (0.80 ml, 0.92 g, 6.5 mmol, 1.6 equiv.) was added in one portion. The mixture was stirred at 0° C. for 1 h, and subsequently 3 h at 25° C. The reaction mixture was added slowly to a vigorously stirred mixture of aqueous NaHCO$_3$ solution (saturated, 80 ml), and DCM (80 ml). The mixture was transferred into a separatory funnel, and layers were separated. The organic layer was subsequently washed with NaHCO$_3$ solution (saturated, 2×100 ml), and water (100 ml). The organic layer was dried over Na$_2$SO$_4$, and the solvent was removed under reduced pressure. The residue was dissolved in DCM, and subsequently precipitated by addition of Et$_2$O. After several minutes, the mixture was decanted, and the residue was dried in vacuo to afford 3.70 g of 5a as colorless foam.

Suzuki-coupling: A 10 ml Schlenk-tube, equipped with a magnetic stir bar, and fitted with a septum, was charged with Pd(dppf)Cl$_2$ (35 mg, 48 μmol, 2.0 mol %), thianthrenium salt 5a (2.15 g, 58.2% of previously synthesized quantity, <2.4 mmol, 1.0 equiv.), 3-methoxyphenyl-boronic acid (438 mg, 2.9 mmol, >1.2 equiv.), and K$_3$PO$_4$ (1.02 g, 4.8 mmol, >2.0 equiv.). The solids were suspended in a mixture of 6.0 ml i-PrOH and 6.0 ml dioxane (c=0.20 M). The reaction mixture was degassed by purging with argon for 45 min, followed by evacuating and backfilling with argon. The mixture was heated to 50° C., and stirred at 50° C. for 48 h. The reaction mixture was allowed to cool to 25° C., and was diluted with aqueous NaHCO$_3$ solution (saturated, 40 ml), and was extracted with ethyl acetate (3×20 ml). The combined organic layers were dried over anhydrous Na$_2$SO$_4$, filtered, and the solvent was removed under reduced pressure. The residue was purified by chromatography on silica gel eluting with EtOAc/i-hexane (gradient from 1:50 to 1:1 (v/v)) to afford 1.23 g (87% over two steps) of 41 as a pale yellow solid, and 0.607 g (89% recovered) of 2 as colorless crystals.

(B) Thianthrenation: In a 500 ml round bottom flask, equipped with a teflon coated magnetic stirbar, salicin pentaacetate (5) (25.0 g, 0.050 mol, 1.0 equiv.) was suspended in 200 ml MeCN (c=0.25 M). Subsequently, trifluoroacetic anhydride (21.0 ml, 32 g, 0.15 mol, 3.0 equiv.) was added. The reaction mixture was cooled to 0° C., followed by addition of tetrafluorothianthrene-S-oxide 1 (15.3 g, 0.50 mol, 1.0 equiv.). At 0° C. BF$_3$OEt$_2$ (9.94 ml, 11 g, 81 mmol, 1.6 equiv.) was added in one portion. The mixture was stirred at 0° C. for 1 h, and subsequently 3 h at 25° C. The reaction mixture was added slowly to a vigorously stirred mixture of aqueous NaHCO$_3$ solution (saturated, 300 ml), and DCM (300 ml). The mixture was transferred into a separatory funnel, and the layers were separated. The organic layer was sequentially washed with NaHCO$_3$ solution (saturated, 2×400 ml), and water (400 ml). The organic layer was dried over Na$_2$SO$_4$, and the solvent was removed under reduced pressure. The residue was dried in vacuo to afford 41.1 g of 5a as colorless foam.

Suzuki-coupling: A 1 L round bottom flask, equipped with a magnetic stir bar, and fitted with a septum, was charged with Pd(dppf)Cl$_2$ (0.669 g, 0.914 mmol, 2.0 mol %), thianthrenium salt 5a (41.1 g, 100% of previously synthesized quantity, <0.050 mol, 1.0 equiv.), 3-methoxyphenyl-boronic acid (8.36 g, 55 mmol, >1.1 equiv.) and K$_3$PO$_4$ (19.5 g, 92 mmol, >1.8 equiv.). The mixture was suspended in a mixture of 114 ml i-PrOH and 114 ml dioxane (c<0.22 M). The reaction mixture was degassed by purging with argon for 45 minutes, followed by evacuating and backfilling with argon. The mixture was heated to 50° C. and was stirred at 50° C. for 48 h. the reaction mixture was allowed to cool to 25° C. overnight. The reaction mixture was filtered through a glass-frit. The solid was sequentially washed with aqueous NaHCO$_3$ solution (saturated, 3×50 ml), water (3×50 ml), and a mixture of EtOH and EtOAc (10:1, 3×50 ml). The organic filtrates were combined. The filter cake was dried in vacuo to afford a first portion of TFT 2 of 5.93 g as colorless crystals. The combined organic filtrates were concentrated and subsequently re-dissolved in EtOAc (400 ml). Subsequently the organic phase was washed with aqueous NaHCO$_3$ solution (saturated, 2×100 ml), water (2×100 ml), dried over anhydrous Na$_2$SO$_4$, filtered, and the solvent was removed under reduced pressure. The residue was dissolved in the lowest possible volume of EtOAc (ca. 100 ml) at 50° C. The solution was cooled to 25° C. before it was kept at −18° C. for 4 h. The resulting precipitate was collected by filtration, and rinsed with EtOH (3×50 ml). The solid was dried in vacuo to afford a second portion of TFT 2 of 4.23 g as colorless crystals. The organic solution was concentrated under reduced. The resulting residue was purified by chromatography on silica gel (dry loading) eluting with EtOAc/i-hexane (gradient from 1:50 to 2:3 (v/v)) to afford 22.7 g (75% over two steps) of 41 as a pale yellow foam, and a third portion of TFT 2 of 0.912 g as colorless crystals, resulting is a total of 11.1 g (76%) of recovered TFT 2.

NMR Spectroscopy:

$^1$H NMR (500 MHz, CDCl$_3$, 298 K, δ): 7.55 (d, J=2.4 Hz, 1H), 7.48 (dd, J=8.4 Hz, 2.4 Hz, 1H), 7.34 (ψt, J=7.9 Hz, 1H), 7.14 (d, J=8.5 Hz, 1H), 7.11 (ddd, J=7.7 Hz, 1.7 Hz, 0.9 Hz, 1H), 7.05 (ψt, J=2.1 Hz, 1H), 6.88 (ddd, J=8.2 Hz, 2.6 Hz, 0.9 Hz, 1H), 5.36-5.29 (m, 2H), 5.22 (m, 4H), 4.29 (dd, J=12.3 Hz, 5.3 Hz, 1H), 4.20 (dd, J=12.3 Hz, 2.6 Hz, 1H), 3.90-3.86 (m, 1H), 3.86 (s, 3H), 2.11 (s, 6H), 2.08 (s, 3H), 2.05 (s, 3H), 2.05 (s, 3H).

$^{13}$C {$^1$H} NMR (128 MHz, CDCl$_3$, 298 K, δ): 170.8, 170.7, 170.3, 169.5, 169.4, 160.1, 154.2, 141.8, 136.7, 130.0, 128.5, 128.2, 126.6, 119.6, 116.3, 113.1, 112.6, 99.5, 72.7, 72.2, 71.1, 68.4, 62.0, 61.2, 55.4, 21.1, 20.8, 20.7, 20.7.

HRMS-ESI (m/z) calc'd for C$_{30}$H$_{34}$O$_{13}$Na$^+$ [M+Na]$^+$, 625.190040; found, 625.189164; deviation: 1.4 ppm.

Carboxyethylstrychnine 42

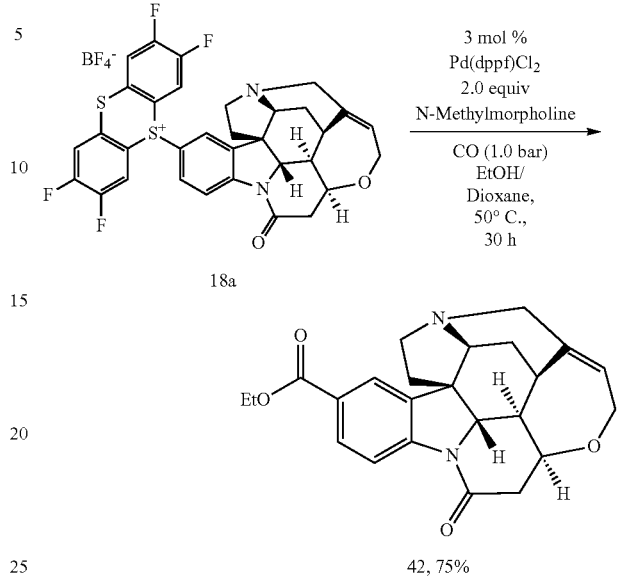

A 10 ml Schlenk-tube, equipped with a magnetic stir bar, and fitted with a septum, was charged with Pd(dppf)Cl$_2$ (3.3 mg, 0.0045 mmol, 3.0 mol %), strychnine tetrafluorothianthrenium tetrafluoroborate 18a (106 mg, 0.15 mmol, 1.0 equiv.). The mixture was dissolved in dry EtOH (0.80 ml), and dry dioxane (0.20 ml) (c=0.15 M), followed by the addition of N-methylmorpholine (33 μl, 0.30 mmol, 3.0 equiv.). The reaction mixture was degassed by freezing in liquid N$_2$, followed by evacuating and backfilling with argon (3 cycles). Subsequently, the vessel was evacuated, and backfilled with CO (1 bar) by the means of a CO balloon. The mixture was heated to 50° C., and stirred for 30 h at 50° C. The reaction was diluted with aqueous NaHCO$_3$ solution (saturated, 20 ml), and was extracted with ethyl acetate (3×10 ml). The combined organic layers were dried over anhydrous Na$_2$SO$_4$, filtered, and the solvent was removed under reduced pressure. The residue was purified by chromatography on silica gel eluting with DCM/EtOH/NEt$_3$ (gradient from 150:1:3 to 90:3:2 (v/v/v)) to afford 46 mg (75%) of 42 as a pale yellow solid.

NMR Spectroscopy:

$^1$H NMR (500 MHz, CDCl$_3$, 298 K, δ): 8.11 (d, J=8.5 Hz, 1H), 7.99 (dd, J=8.5 Hz, 1.8 Hz, 1H), 7.86 (d, J=1.7 Hz, 1H), 5.96 (s, 1H), 4.36 (q, J=7.1 Hz, 2H), 4.30 (dψt, J=8.4 Hz, 3.3 Hz, 1H), 4.17 (dd, J=13.8 Hz, 7.0 Hz, 1H), 4.10-4.03 (m, 2H), 3.94 (d, J=10.5 Hz, 1H), 3.79-3.74 (m, 1H), 3.32-3.29 (m, 1H), 3.20-3.13 (m, 2H), 2.95-2.88 (m, 1H), 2.79 (d, J=14.7 Hz, 1H), 2.69 (dd, J=17.6 Hz, 3.2 Hz, 1H), 2.40 (dψt, J=14.5 Hz, 4.3 Hz, 1H), 1.99-1.92 (m, 1H), 1.48 (d, J=14.6 Hz, 1H), 1.39 (t, J=7.1 Hz, 3H), 1.30 (dψt, J=10.5 Hz, 3.0 Hz, 2H).

$^{13}$C {$^1$H} NMR (128 MHz, CDCl$_3$, 298 K, δ): 169.7, 166.3, 146.1, 140.1, 133.1, 131.2, 127.9, 124.1, 115.7, 77.4, 64.8, 61.1, 60.8, 60.4, 52.8, 51.8, 50.5, 48.3, 42.9, 42.7, 31.7, 27.0, 14.5.

HRMS-ESI (m/z) calc'd for C$_{24}$H$_{27}$N$_2$O$_4$$^+$ [M+H]$^+$, 407.196760; found, 407.196533; deviation: 0.6 ppm.

Suzuki-Coupling of a Triflylated Thianthrenium Salt

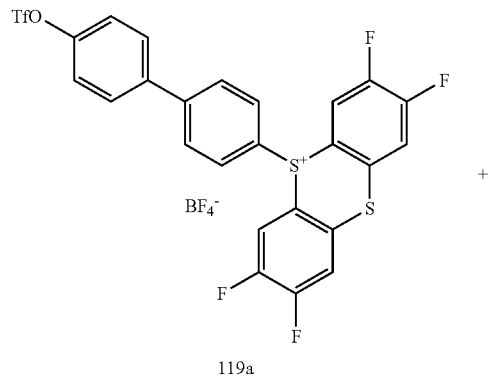

119a

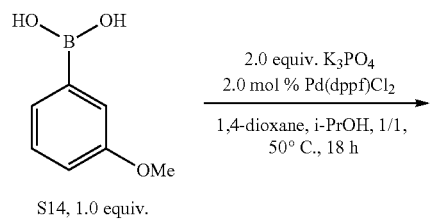

S14, 1.0 equiv.

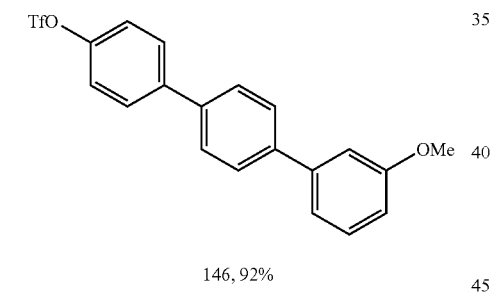

146, 92%

Under an ambient atmosphere, a 4 ml glass-vial equipped with a magnetic stirbar was charged with thianthrenium salt 119a (203 mg, 0.30 mmol, 1.0 equiv.), boronic acid S14 (46 mg, 0.30 mmol, 1.0 equiv.), Pd(dppf)Cl$_2$ (4.4 mg, 6.0 μmol, 2.0 mol %), potassium phosphate (127 mg, 0.60 mmol, 2.0 equiv.), i-PrOH (1.2 ml) and 1,4-dioxane (1.2 ml, c=0.13 M). The mixture was degassed by purging with Ar for 1 min. The vial was sealed, and stirred at 50° C. for 18 h. The mixture was diluted with DCM (10 ml), and washed with water (20 ml). The aqueous layer was extracted with DCM (10 ml). The combined organic layers were dried over MgSO$_4$, filtered, and the solvent was removed under reduced pressure. The residue was dissolved in DCM (5 ml) and purified by column chromatography on silica gel, eluting with i-hexane/EtOAc (9:1 gradient to 7:3, v:v) to afford 113 mg (92%) of 146 as colorless crystals.

NMR Spectroscopy:

$^1$H NMR (500 MHz, CDCl$_3$, 298 K, δ): 7.71-7.68 (m, 4H), 7.64 (d, J=8.4 Hz, 2H), 7.42-7.35 (m, 3H), 7.24 (ddd, J=7.6 Hz, 1.7 Hz, 1.0 Hz, 1H), 7.18 (dd, J=2.5 Hz, 1.6 Hz, 1H), 6.94 (ddd, J=8.2 Hz, 2.6 Hz, 1.0 Hz, 1H), 3.89 (s, 3H).

$^{13}$C {$^1$H} NMR (128 MHz, CDCl$_3$, 298 K, δ): 160.2, 149.1, 142.0, 141.3, 141.0, 138.4, 130.0, 128.0, 127.9, 127.7, 121.8, 119.7, 118.9 (q, J=321 Hz), 113.1, 113.0, 55.5.

$^{19}$F NMR (128 MHz, CDCl$_3$, 298 K, δ): −72.8 (s).

HRMS-EI (m/z) calc'd for C$_{20}$H$_{15}$O$_4$F$_3$S$^+$ [M]$^+$, 408.064318; found, 408.064557; deviation: 0.6 ppm.

Suzuki-Coupling of a Brominated Thianthrenium Salt

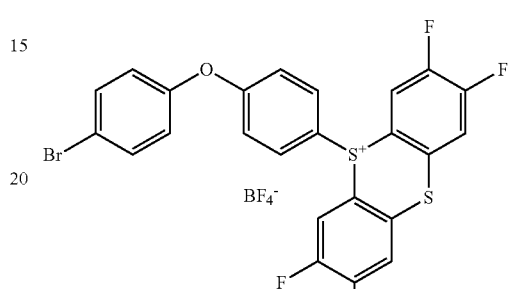

119a

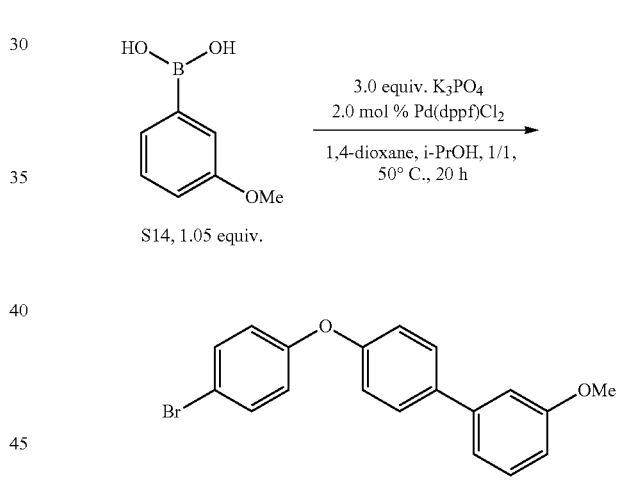

147, 96%

Under an ambient atmosphere, a 20 ml glass-vial, equipped with a teflon-coated magnetic stir bar, was charged with thianthrenium salt 119a (187 mg, 0.30 mmol, 1.0 equiv.), boronic acid S14 (47.9 mg, 0.32 mmol, 1.05 equiv.), K$_3$PO$_4$ (191 mg, 0.90 mmol, 3.0 equiv.), Pd(dppf)Cl$_2$ (4.4 mg, 6.0 μmol, 2.0 mol %), i-PrOH (1.6 ml) and 1,4-dioxane (1.6 ml). The mixture was degassed by purging with Ar for 1 min. The vial was sealed, and the mixture was stirred at 50° C. for 20 h. After the reaction mixture had cooled to 25° C., the mixture was poured into a separatory funnel onto water (15 ml). The aqueous layer was extracted with EtOAc (3×20 ml). The combined organic layers were dried over Na$_2$SO$_4$, filtered, and concentrated under reduced pressure. The residue was purified by chromatography on silica gel eluting with i-hexane/EtOAc (1:0 gradient to 200:1) to afford 103 mg (96%) of 147 as colorless oil, which crystallized after one day.

NMR Spectroscopy:

$^1$H NMR (500 MHz, CDCl$_3$, 298 K, δ): 7.57 (d, J=8.7 Hz, 2H), 7.46 (d, J=8.9 Hz, 2H), 7.37 (ψt, J=7.9 Hz), 7.17 (ddd, J=7.6 Hz, 1.7 Hz, 1.0 Hz, 1H), 7.12 (dd, J=2.6 Hz, 1.7 Hz, 1H), 7.07 (d, J=8.7 Hz, 2H), 6.95 (d, J=8.9 Hz, 2H), 6.91 (ddd, J=8.2 Hz, 2.6 Hz, 0.9 Hz, 1H).

$^{13}$C {$^1$H} NMR (128 MHz, CDCl$_3$, 298 K, δ): 160.0, 156.5, 141.9, 136.7, 132.8, 129.9, 132.8, 128.6, 120.6, 119.5, 119.2, 115.8, 112.8, 112.5, 55.3.

HRMS-EI (m/z) calc'd for C$_{19}$H$_{15}$O$_2$Br$^+$ [M]$^+$, 354.025555; found, 354.025235; deviation: 0.9 ppm.

Minisci-Type Arylation with a Thianthrenium Salt

NMR Spectroscopy:

$^1$H NMR (500 MHz, CDCl$_3$, 298 K, δ): 9.00 (d, J=1.6 Hz, 1H), 8.61 (dd, J=2.5 Hz, 1.6 Hz, 1H), 8.48 (d, J=2.6 Hz, 1H), 8.01 (d, J=8.9 Hz, 2H), 7.47 (d, J=9.0 Hz, 2H), 7.11 (d, J=8.8 Hz, 2H), 6.95 (d, J=9.0 Hz, 2H).

$^{13}$C {$^1$H} NMR (128 MHz, CDCl$_3$, 298 K, δ): 158.9, 155.8, 152.3, 144.3, 142.5, 141.7, 133.0, 131.5, 128.8, 121.2, 119.1, 116.6.

HRMS-ESI (m/z) calc'd for C$_{16}$H$_{12}$BrN$_2$O$^+$ [M+H]$^+$, 327.012762; found, 327.012760; deviation: 0.01 ppm.

Photoredox Mediated Coupling of an Iodinated Thianthrenium Salt

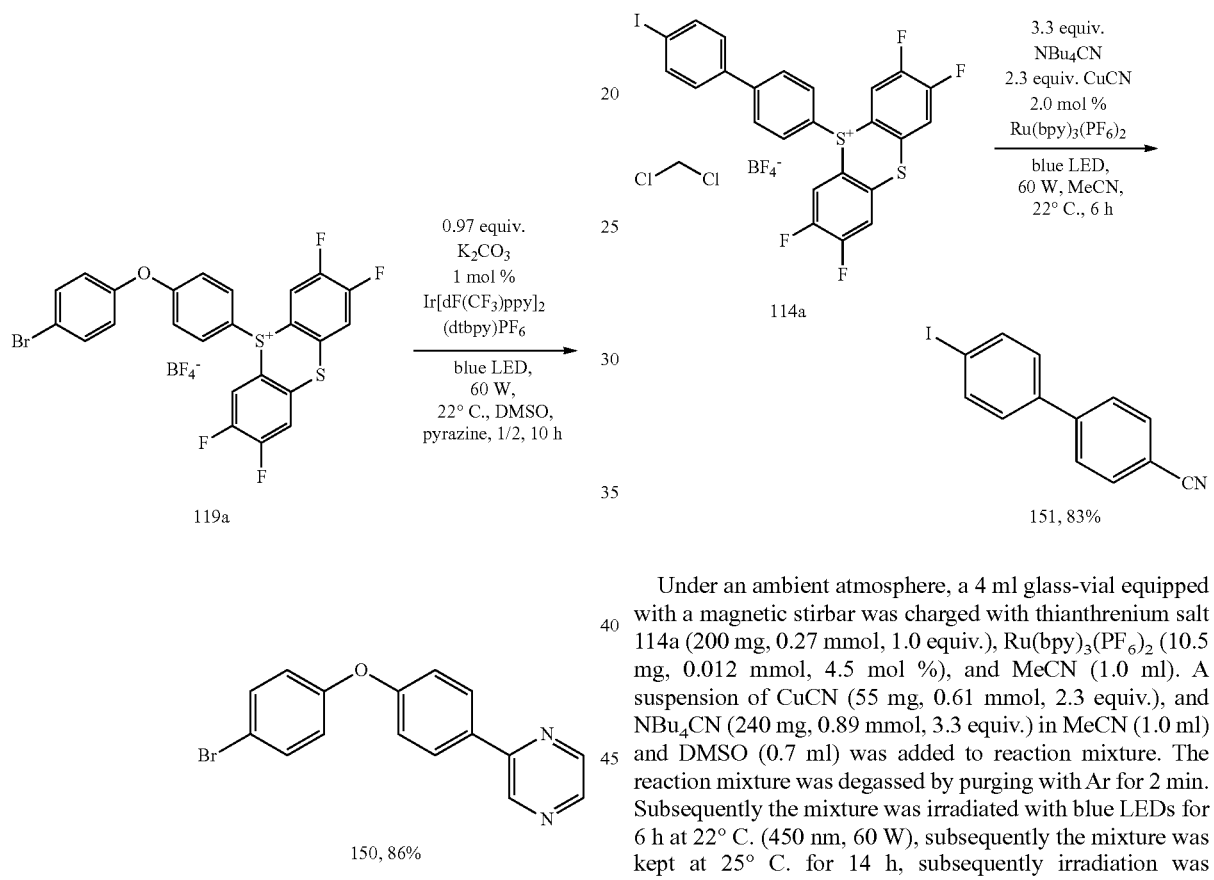

Under an ambient atmosphere, a 4 ml glass-vial equipped with a teflon-coated magnetic stirbar was charged with thianthrenium salt 119a (205 mg, 0.33 mmol, 1.0 equiv.), Ir[dF(CF$_3$)ppy]$_2$(dtbpy)PF$_6$ (5 mg, 0.005 mmol, 1 mol %), K$_2$CO$_3$ (44 mg, 0.32 mmol, 0.97 equiv.), pyrazine (2.3 g), and DMSO (1.3 ml). The reaction mixture was degassed by purging with Ar for 2 min. Subsequently the mixture was irradiated with blue LEDs for 10 h (450 nm, 60 W, 22° C., 1 E/mmol). The reaction mixture was poured into a separatory funnel containing saturated sodium bicarbonate solution (10 ml). The mixture was extracted with EtOAc (5×10 ml). The combined organic layers were dried over Na$_2$SO$_4$, filtered, and the solvent was removed under reduced pressure. The residue was purified by column chromatography on silica gel, eluting with i-hexane/EtOAc (1:0 gradient to 3:1 (v/v)) to afford 93 mg (86%) of 150 as a white solid.

Under an ambient atmosphere, a 4 ml glass-vial equipped with a magnetic stirbar was charged with thianthrenium salt 114a (200 mg, 0.27 mmol, 1.0 equiv.), Ru(bpy)$_3$(PF$_6$)$_2$ (10.5 mg, 0.012 mmol, 4.5 mol %), and MeCN (1.0 ml). A suspension of CuCN (55 mg, 0.61 mmol, 2.3 equiv.), and NBu$_4$CN (240 mg, 0.89 mmol, 3.3 equiv.) in MeCN (1.0 ml) and DMSO (0.7 ml) was added to reaction mixture. The reaction mixture was degassed by purging with Ar for 2 min. Subsequently the mixture was irradiated with blue LEDs for 6 h at 22° C. (450 nm, 60 W), subsequently the mixture was kept at 25° C. for 14 h, subsequently irradiation was continued for 6 h at 22° C. (450 nm, 60 W, total: 2 E/mmol). The reaction mixture was diluted with 100 ml CHCl$_3$ and washed with 50 ml water. The aqueous layer was extracted with CHCl$_3$ (3×20 ml). The combined organic layers were dried over MgSO$_4$, filtered, and the solvent was removed under reduced pressure. The residue was purified by column chromatography on silica gel, eluting with i-hex/EtOAc (1:0 gradient to 3:1). A second column was (silica gel, i-hexane/EtOAc, 1:0 gradient to 23:2, (v:v)) was performed to afford 69 mg (83%) of 151 as colorless crystals.

NMR Spectroscopy:

$^1$H NMR (500 MHz, CDCl$_3$, 298 K, δ): 7.81 (d, J=8.5 Hz, 2H), 7.73 (d, J=8.3 Hz, 2H), 7.64 (d, J=8.4 Hz, 2H), 7.32 (d, J=8.4 Hz, 2H).

$^{13}$C {$^1$H} NMR (128 MHz, CDCl$_3$, 298 K, δ): 144.6, 138.8, 138.4, 132.9, 129.1, 127.6, 118.9, 111.5, 95.0.

HRMS-EI (m/z) calc'd for C$_{13}$H$_8$NI$^+$ [M]$^+$, 304.970146; found, 304.970338; deviation: 0.6 ppm.

Phenylsulfonylpyriproxyfen 139

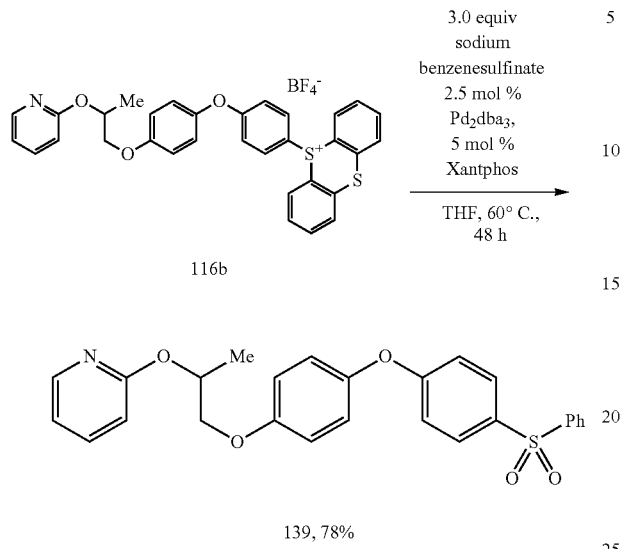

139, 78%

A vial was charged with a teflon-coated stirbar, pyriproxyfen derived thianthrenium salt 116b (160 mg, 0.257 mmol, 1.0 equiv), and benzenesulfinic acid sodium salt (132 mg, 0.804 mmol, 3.1 equiv). The vial was sealed with a septum-cap, evacuated and filled with argon. In a nitrogen filled glove box, a second vial was charged with a teflon-coated stirbar, tris-(dibenzylideneacetone)-dipalladium (6 mg, 0.0067 mmol, 5 mol % palladium), xantphos (8 mg, 0.013 mmol, 5 mol %) and acetonitrile (1 mL), and sealed with a septum-cap. The Pd-containing vial was brought out of the glovebox and heated at 60° C. for 1 h at which point the solution was transferred to the vial containing the pyriproxyfen thianthrenium salt and benzenesulfinic acid sodium salt. The reaction mixture was stirred at 60° C. for 48 h, at which point the solvent was removed under reduced pressure. The gray residue was taken up in ethyl acetate (1 mL) and filtered through a plug of celite. The bed of celite was washed three times with ethyl acetate (3×1 mL) and the combined filtrate was concentrated under reduced pressure. The residue was purified by chromatography on silica gel eluting with a gradient of 0% (v/v) EtOAc in i-hexane to 20% (v/v) EtOAc in i-hexane over 40 column volumes. The solvent was removed from the combined product fractions affording 92 mg (78%) of sulfone 139 as a colorless solid.

NMR Spectroscopy:

$^1$H NMR (500 MHz, CDCl$_3$, 298 K, δ): 8.17-8.12 (m, 1H), 7.96-7.89 (m, 2H), 7.88-7.81 (m, 2H), 7.59-7.52 (m, 2H), 7.49 (m, 2H), 6.99-6.92 (m, 6H), 6.86 (ddd, J=7.1, 5.0, 1.0 Hz, 1H), 6.74 (d, J=8.3 Hz, 1H), 5.59 (m, 1H), 4.20 (dd, J=9.8, 5.3 Hz, 1H), 4.08 (dd, J=9.9, 4.8 Hz, 1H), 1.48 (d, J=6.4 Hz, 3H).

$^{13}$C {$^1$H} NMR (128 MHz, CDCl$_3$, 298 K, δ): 163.2, 163.1, 156.4, 148.2, 146.9, 142.3, 138.9, 134.6, 133.1, 130.0, 129.4, 127.5, 121.9, 117.0, 117.0, 116.2, 111.8, 71.1, 69.3, 17.1.

HRMS-ESI (m/z) calc'd for C$_{26}$H$_{24}$NO$_5$S$^+$ [M+H]$^+$, 462.136971; found, 462.137050; deviation: 0.17 ppm.

Dibromothiophene Derived Thianthrenium Salt 4a

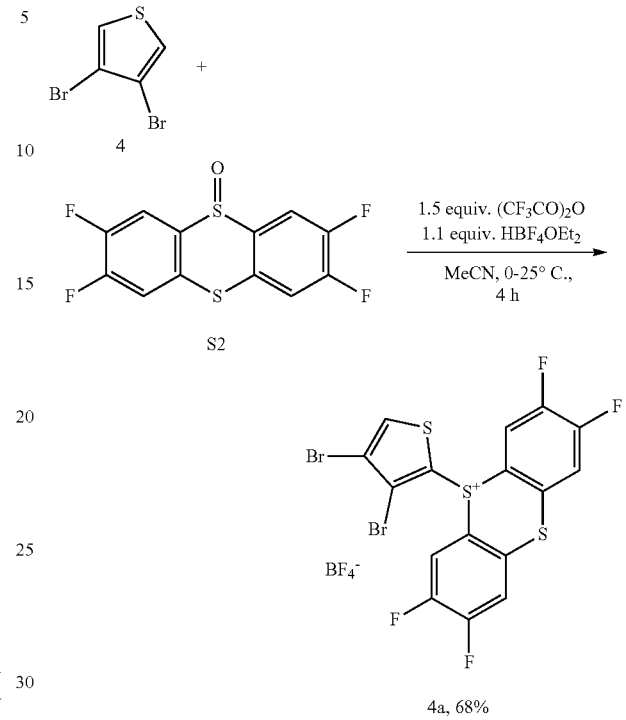

4a, 68%

Under an ambient atmosphere, a 25 ml round bottom flask was subsequently charged with tetrafluorothianthrene reagent (97% (w/w) tetrafluorothianthrene-S-oxide 1, 3% (w/w) tetrafluorothianthrene 2, 152 mg, 0.5 mmol, 1.0 equiv.), MeCN (1.9 ml, 0.26 M), dibromothiophen 4 (121 mg, 0.50 mmol, 1.0 equiv.), and HBF$_4$OEt$_2$ (0.75 ml, 0.55 mmol, 1.1 equiv.). After cooling to 0° C., trifluoroacetic anhydride (0.10 ml, 0.75 mmol, 1.5 equiv.) was added in one portion at 0° C. The reaction mixture stirred at 0° C. for 2 h, subsequently it was allowed to warm to 25° C. and was stirred for another 2 h. The solution was diluted with DCM (5 ml), and was poured into a separatory funnel. The organic layer was washed with water (3×5 ml) and subsequently with NaBF$_4$ solution (10% (w/w), 3×5 ml). The organic layer was dried over Na$_2$SO$_4$, filtered, and the solvent was removed under reduced pressure. The residue was loaded on a silica pad (ca. 15 ml silica gel) and washed with pentane/EtOAc (3:1 (v/v), 150 ml). Subsequently the product was eluted with DCM/MeOH (10:1 (v/v), 100 ml). The solvent was removed under reduced pressure, and the residue was dried in vacuo to afford 209 mg (68%) of 4a as colorless solid.

NMR Spectroscopy:

$^1$H NMR (500 MHz, CDCl$_3$, 298 K, δ): 8.43 (dd, J=9.0 Hz, 7.1 Hz, 2H), 8.05 (s, 1H), 8.01 (dd, J=10.0 Hz, 7.0 Hz, 2H).

$^{13}$C {$^1$H} NMR (128 MHz, CDCl$_3$, 298 K, δ): 155.06 (dd, J=263.0 Hz, 13.1 Hz), 151.4 (dd, J=256.3 Hz, 13.7 Hz), 135.5, 135.4 (dd, J=8.9 Hz, 4.0 Hz), 126.1, 125.1 (dd, J=22.4 Hz, 2.6 Hz), 121.0 (d, J=22.1 Hz), 117.7, 116.8, 113.8 (dd, J=7.2 Hz, 3.5 Hz).

$^{19}$F {$^1$H} NMR (471 MHz, CDCl$_3$, 298 K, δ): −124.7 (d, J=20.7 Hz), −134.0 (d, J=20.2 Hz), −151.5 (bs), −151.6 (bs).

HRMS-ESI (m/z) calc'd for $C_{16}H_5Br_2F_4S_3^+$ [M-BF$_4$]$^+$, 526.785107; found, 526.785500; deviation: 0.8 ppm.

Bromodiphenylether Derived Thianthrenium Salt 9a

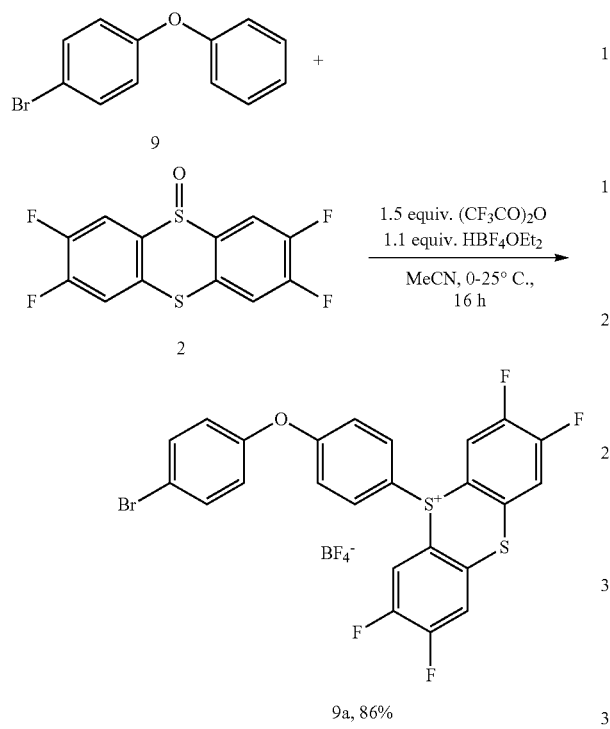

9a, 86%

Under an ambient atmosphere, a 20 ml glass-vial was charged with bromodiphenylether 9 (0.95 ml, 0.82 g, 3.3 mmol, 1.0 equiv.), tetrafluorothianthrene reagent (97% (w/w) tetrafluorothianthrene-S-oxide 1, 3% (w/w) tetrafluorothianthrene 2, 1.0 g, 3.3 mmol, 1.0 equiv.), and MeCN (5.0 ml, c=0.66 M). HBF$_4$·OEt$_2$ (0.49 ml, 0.59 g, 3.6 mmol, 1.1 equiv.) was added in one portion at 25° C. The suspension was cooled to 0° C., and trifluoroacetic anhydride (0.69 ml, 1.0 g, 4.9 mmol, 1.5 equiv.) was added, subsequently the mixture was allowed to warm to 25° C. and the reaction mixture was stirred for 16 h. The mixture was concentrated under reduced pressure, diluted with DCM (15 ml), and washed with water (25 ml) and aqueous NaBF$_4$ solution (2×25 ml, 10% (w/w)). The organic layer was dried over Na$_2$SO$_4$, filtered, and the solvent was removed under reduced pressure. The residue was purified by chromatography on silica gel eluting with DCM/i-PrOH, (1:0 gradient to 9:1 (v/v)) to afford 1.91 g (86%) of 9a as colorless foam.

NMR Spectroscopy:

$^1$H NMR (500 MHz, CD$_3$CN, 298 K, δ): 8.36 (dd, J=9.1 Hz, 7.2 Hz, 2H), 7.96 (dd, J=9.9 Hz, 7.1 Hz, 2H), 7.57 (d, J=8.9 Hz, 2H), 7.24 (d, J=9.2 Hz, 2H), 7.05 (d, J=9.2 Hz, 2H), 6.99 (d, J=8.9 Hz, 2H).

$^{13}$C {$^1$H} NMR (128 MHz, CD$_3$CN, 298 K, δ): 162.9, 155.0, 154.8 (dd, J=161.7 Hz, 13.2 Hz), 151.6 (dd, 255.7 Hz, 13.6 Hz), 135.0 (dd, J=8.5 Hz, 4.0 Hz), 134.4, 132.0, 125.2 (dd, J=22.1 Hz, 2.4 Hz), 123.3, 121.1 (d, J=21.8 Hz), 120.1, 118.7, 115.9-115.8 (m, 2 C-atoms).

$^{19}$F {$^1$H} NMR (471 MHz, CD$_3$CN, 298 K, δ): −126.4 (d, J=20.6 Hz), −134.6 (d, J=20.3 Hz), −152.1 (bs), −152.2 (bs).

HRMS-ESI (m/z) calc'd for $C_{24}H_{12}BrF_4OS_2^+$ [M-BF$_4$]$^+$, 534.944374; found, 534.944710; deviation: 0.6 ppm.

Mesitylene Derived Thianthrenium Salt 13a

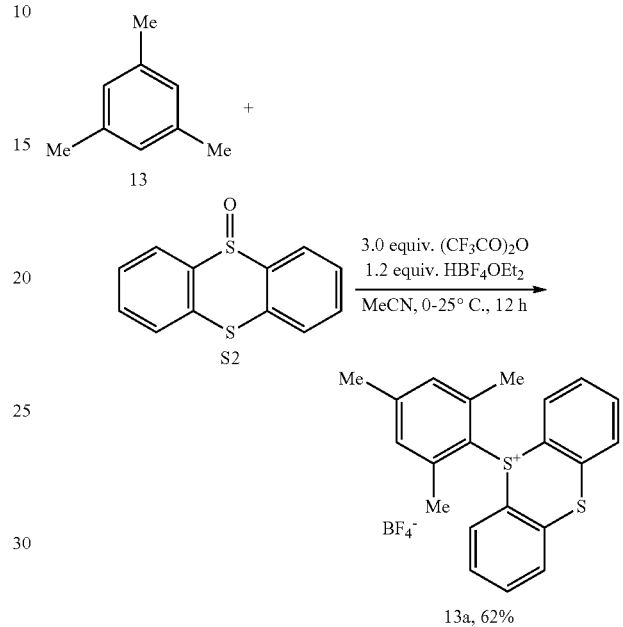

13a, 62%

Under an ambient atmosphere, a 20 ml glass-vial was charged with mesitylene 13 (600 mg, 5.0 mmol, 1.0 equiv.) and MeCN (5.0 ml, 1.0 M). After cooling to 0° C., HBF$_4$·OEt$_2$ (0.82 ml, 6.0 mmol, 1.2 equiv.) was added in one portion to the reaction mixture. After all solids had dissolved, thianthrene-S-oxide S2 (1.16 g, 5.0 mmol, 1.0 equiv.) was added in one portion at 0° C. Subsequently, trifluoroacetic anhydride (2.1 ml, 15 mmol, 3.0 equiv.) was added in one portion at 0° C. The reaction mixture was allowed to warm to 25° C. and was stirred for 12 h. The solution was diluted with DCM (5 ml), and poured onto a mixture of DCM (30 ml) and aqueous NaHCO$_3$ solution (saturated, 20 ml). The mixture was poured into a separatory funnel, and the layers were separated. The organic layer was washed with NaBF$_4$ solution (10% (w/w), 3×20 ml). The organic layer was dried over Na$_2$SO$_4$, filtered, and the solvent was removed under reduced pressure. The residue was purified by chromatography on silica gel eluting with DCM/MeOH (30:1 (v/v)) to afford 1.3 g (62%) of 13a as colorless solid.

NMR Spectroscopy:

$^1$H NMR (500 MHz, CDCl$_3$, 298 K, δ): 7.78 (d, J=7.9 Hz, 2H), 7.67 (ψt, J=7.6 Hz, 2H), 7.54 (ψt, J=7.8 Hz, 2H), 7.33 (s, 2H), 7.11 (d, J=8.2 Hz, 2H), 2.41 (s, 3H), 2.18 (s, 6H).

$^{13}$C {$^1$H} NMR (128 MHz, CDCl$_3$, 298 K, δ): 149.0, 145.1, 133.5, 133.4, 130.3, 130.1, 129.7, 126.3, 123.7, 110.0, 21.5, 21.4.

$^{19}$F {$^1$H} NMR (471 MHz, CDCl$_3$, 298 K, δ): −153.3 (bs), −153.4 (bs).

HRMS-ESI (m/z) calc'd for $C_{21}H_{19}S_2^+$ [M-BF$_4$]$^+$, 335.092270; found, 335.092190; deviation: 0.2 ppm.

85
Iodobiphenyl Derived Thianthrenium Salt 14a

86
Biphenyltriflate Derived Thianthrenium Salt 19a

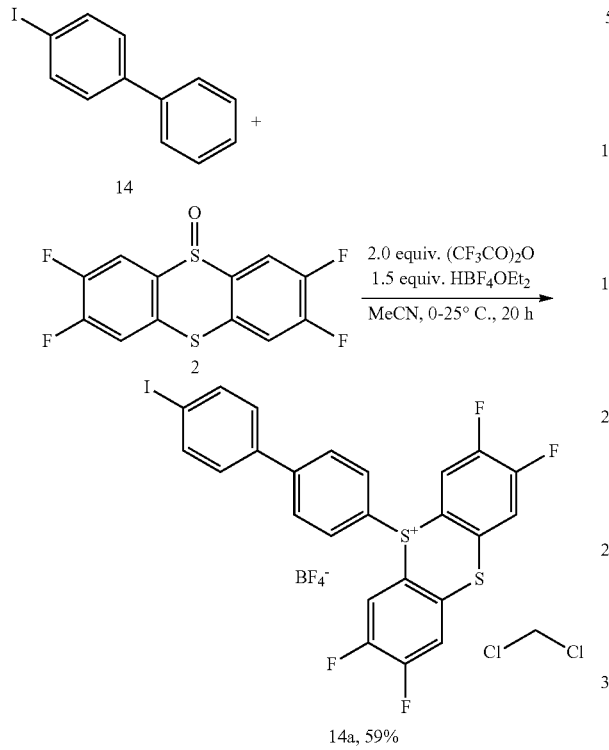

14a, 59%

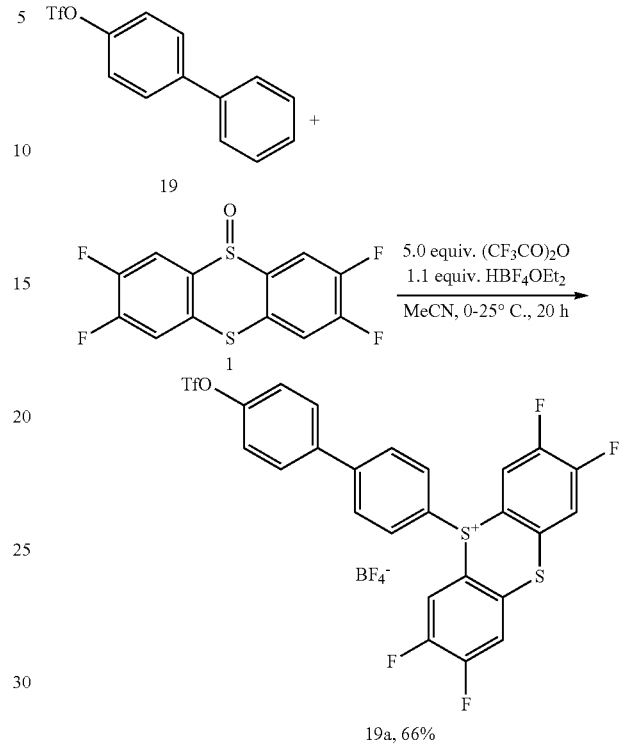

19a, 66%

Under an ambient atmosphere, a 20 ml glass-vial was charged with iodobiphenyl 14 (470 mg, 1.68 mmol, 1.0 equiv.), tetrafluorothianthrene reagent (97% (w/w) tetrafluorothianthrene-S-oxide 1, 3% (w/w) tetrafluorothianthrene 2, 511 mg, 1.68 mmol, 1.0 equiv.), and MeCN (3.5 ml, c=0.48 M). The suspension was cooled to 0° C., and subsequently trifluoroacetic anhydride (0.47 ml, 0.71 g, 3.4 mmol, 2.0 equiv.) and HBF$_4$OEt$_2$ (0.34 ml, 0.41 g, 2.5 mmol, 1.5 equiv.) were added at 0° C. The mixture was stirred at 0° C. for 1 h, and subsequently 19 h at 25° C. The mixture was transferred into a round-bottom flask and was concentrated under reduced pressure, diluted with DCM (10 ml), and washed with aqueous NaHCO$_3$ solution (saturated, 15 ml), and aqueous NaBF$_4$ solution (3×15 ml, 10% (w/w)). The organic layer was diluted with 10 ml EtOAc, leading to the crystallization of the product. The suspension was filtered, and the solid was dried in vacuo to obtain 734 mg (59%) of 14a as colorless solid.

NMR Spectroscopy:

$^1$H NMR (500 MHz, CD$_3$CN, 298 K, δ): 8.45 (dd, J=9.1 Hz, 7.2 Hz, 2H), 7.97 (dd, J=9.9 Hz, 7.0 Hz, 2H), 7.82 (d, J=8.6 Hz, 2H), 7.73 (d, J=8.8 Hz, 2H), 7.39 (d, J=8.5 Hz, 2H), 7.29 (d, J=8.8 Hz, 2H), 5.44 (s, 2H).

$^{13}$C {$^1$H} NMR (128 MHz, CD$_3$CN, 298 K, δ): 155.9 (dd, J=262.2 Hz, 13.0 Hz), 151.6 (dd, J=255.8, 13.5 Hz), 145.7, 139.2, 138.5, 135.3 (dd, J=8.7 Hz, 3.8 Hz), 130.2, 130.0, 129.6, 125.7 (dd, J=22.2 Hz, 2.3 Hz), 122.4, 121.2 (d, J=21.8 Hz), 115.3 (dd, J=7.2 Hz, 3.3 Hz), 95.8, 55.3.

$^{19}$F {$^1$H} NMR (471 MHz, CD$_3$CN, 298 K, δ): −126.1 (d, J=20.1 Hz), −134.5 (d, J=20.6 Hz), −152.1 (bs), −152.1 (bs).

HRMS-ESI (m/z) calc'd for C$_{24}$H$_{12}$F$_4$IS$_2$$^+$ [M-CH$_2$Cl$_2$—BF$_4$]$^+$, 566.935582; found, 566.935280; deviation: 0.5 ppm.

Under an ambient atmosphere, a 20 ml glass-vial was charged with biphenyltrilfate 19 (547 mg, 1.81 mmol, 1.0 equiv.), tetrafluorothianthrene reagent (97% (w/w) tetrafluorothianthrene-S-oxide 1, 3% (w/w) tetrafluorothianthrene 2, 551 mg, 1.81 mmol, 1.0 equiv.), and MeCN (4.0 ml, c=0.45 M). Trifluoroacetic anhydride (1.26 ml, 1.90 g, 9.05 mmol, 5.0 equiv.) was added, subsequently the mixture was cooled to 0° C., and HBF$_4$OEt$_2$ (0.27 ml, 0.32 g, 2.0 mmol, 1.1 equiv.) was added in one portion at 0° C. The mixture was stirred at 0° C. for 1 h, and subsequently at 25° C. for 19 h. The reaction mixture was transferred into a round-bottom flask, and the solvent was removed under reduced pressure. The residue was dissolved in 15 ml DCM. The solution was transferred into a separatory funnel, and was subsequently washed with aqueous NaHCO$_3$ solution (saturated, 20 ml) and aqueous NaBF$_4$ solution (10% (w/w), 3×20 ml). The organic layer was dried over Na$_2$SO$_4$, filtered, and the solvent was removed under reduced pressure. The residue was purified by chromatography on silica gel eluting with DCM/i-PrOH, (1:0 gradient to 9:1 (v/v)) to afford 812 mg (66%) of 19a as colorless solid.

NMR Spectroscopy:

$^1$H NMR (500 MHz, CD$_3$CN, 298 K, δ): 8.46 (dd, J=9.1 Hz, 7.2 Hz, 2H), 7.98 (dd, J=9.9 Hz, 7.0 Hz, 2H), 7.79-7.74 (m, 4H), 7.48 (d, J=8.9 Hz, 2H), 7.32 (d, J=8.9 Hz, 2H).

$^{13}$C {$^1$H} NMR (128 MHz, CD$_3$CN, 298 K, δ): 154.9 (dd, J=261.9 Hz, 13.2 Hz), 151.6 (dd, J=255.6, 13.5 Hz), 151.0, 145.0, 139.6, 135.4 (dd, J=8.6 Hz, 3.8 Hz), 130.6, 130.0 (d, J=11.9 Hz), 125.7 (dd, J=22.1 Hz, 2.4 Hz), 123.2, 121.3, 119.7 (q, J=320 Hz), 115.3 (dd, J=7.2 Hz, 3.4 Hz).

$^{19}$F {$^1$H} NMR (471 MHz, CD$_3$CN, 298 K, δ): −74.7 (s), −126.1 (d, J=20.5 Hz), −134.5 (d, J=20.5 Hz), −152.1 (bs), −152.2 (bs).

HRMS-ESI (m/z) calc'd for $C_{25}H_{12}O_3F_7S_3^+$ [M-BF$_4$]$^+$, 588.983137; found, 588.982620; deviation: 0.9 ppm.

Pyriproxyfen Derived Thianthrenium Salt 16b

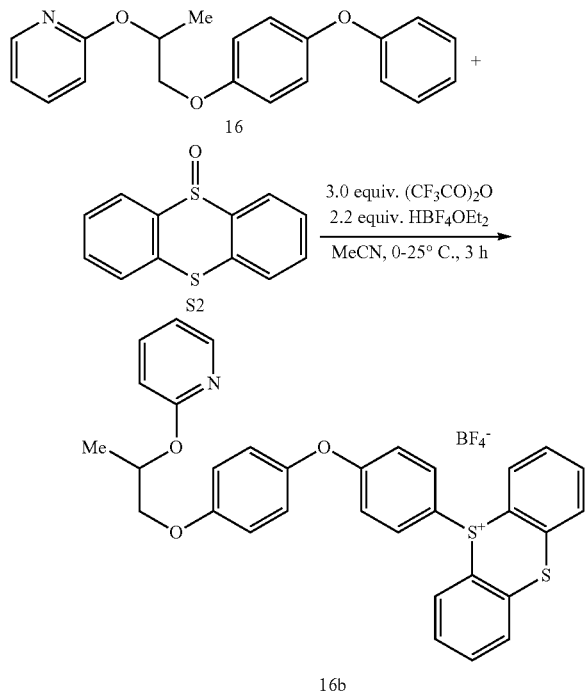

Under an ambient atmosphere, a 20 ml glass-vial was charged with pyriproxyfen (16) (642 mg, 2.00 mmol, 1.0 equiv.), and MeCN (8.0 ml, c=0.25 M). HBF$_4$OEt$_2$ (276 µl, 324 mg, 2 mmol, 1.0 equiv.), and trifluoroacetic anhydride (834 µl, 1.26 g, 6.00 mmol, 3.0 equiv.) were added while stirring the reaction mixture. After cooling to 0° C., thianthrene-S-oxide S2 (464 mg, 1.00 mmol, 1.0 equiv.) was added in one portion, followed by the addition of HBF$_4$OEt$_2$ (327 µl, 389 mg, 2.40 mmol, 1.2 equiv.) in one portion at 0° C., leading to a dark blue suspension. The vial was sealed with a screw-cap, and the mixture was stirred at 0° C. for 1 h, followed by stirring at 25° C. for 2 h until a slight purple solution was obtained. The reaction mixture was concentrated under reduced pressure, and subsequently, diluted with 5 ml DCM. The DCM phase was poured onto a saturated aqueous NaHCO$_3$ solution (ca. 10 ml). The mixture was poured into a separatory funnel, and the layers were separated. The DCM layer was washed with aqueous NaBF$_4$ solution (2×ca. 10 ml, 5% w/w), and with water (2×ca. 10 ml). The DCM layer was dried over Na$_2$SO$_4$, filtered, and the solvent was removed under reduced pressure. The product was dissolved in a minimal amount of DCM, and precipitated with Et$_2$O. The solid was dried in vacuo to afford 1.19 g (95%) of 16b a colorless foam.

NMR Spectroscopy:

$^1$H NMR (500 MHz, CD$_3$CN, 298 K, δ): 8.30 (dd, J=7.9 Hz, 1.2 Hz, 2H), 8.11 (ddd, J=5.0 Hz, 2.0 Hz, 0.7 Hz, 1H), 7.94 (dd, J=7.9 Hz, 1.2 Hz, 2H), 7.86 (td, J=7.7 Hz, 1.4 Hz, 2H), 7.78 (td, J=7.8 Hz, 1.3 Hz, 2H), 7.62 (ddd, J=8.4 Hz, 7.1 Hz, 2.0 Hz, 1H), 7.16-7.10 (m, 2H), 6.98-6.88 (m, 7H), 6.69 (dt, J=8.4 Hz, 0.8 Hz, 1H), 5.54 (m, 1H), 4.15 (dd, J=10.3 Hz, 6.0 Hz, 1H), 4.09 (dd, J=10.3 Hz, 4.1 Hz, 1H), 1.38 (d, J=6.4 Hz, 3H).

$^{13}$C {$^1$H} NMR (128 MHz, CDCl$_3$, 298 K, δ): 164.0, 163.8, 157.3, 148.7, 147.8, 140.1, 137.1, 135.9, 135.4, 131.5, 130.9, 122.7, 120.0, 119.2, 117.9, 117.0, 116.0, 112.1, 71.8, 70.1, 16.9.

HRMS-ESI (m/z) calc'd for $C_{32}H_{26}NO_3S_2^+$ [M-BF$_4$]$^+$, 536.134864; found, 536.13469; deviation: 0.32 ppm.

Thianthrenium Salt TT-1

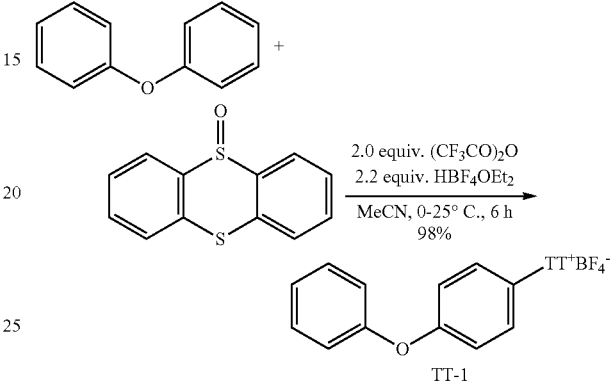

Under ambient atmosphere, a 500 mL round-bottom flask equipped with a magnetic stir bar was charged with diphenyl ether (7.0 mL, 7.5 g, 44 mmol, 1.0 equiv.) and MeCN (0.10 L, c=0.44 M). Trifluoroacetic anhydride (12.2 mL, 18.4 g, 87.8 mmol, 2.0 equiv.) was added at ambient temperature while stirring. After cooling to 0° C., thianthrene S-oxide (10.2 g, 43.9 mmol, 0.99 equiv.) was added in one portion, followed by the addition of HBF$_4$OEt$_2$ (13.2 mL, 15.7 g, 97.0 mmol, 2.2 equiv.) in one portion. The mixture was stirred at 0° C. for 1 h, then at ambient temperature for 5 h. The reaction mixture was concentrated under reduced pressure, and subsequently diluted with DCM (300 mL). The solution was poured onto a saturated aqueous NaHCO$_3$ solution (300 mL), and the layers were separated. The organic phase was washed with aqueous NaBF$_4$ solution (2×300 mL, 10%), and with water (2×300 mL). The organic phase was dried over MgSO$_4$, and the solvent was removed under reduced pressure. The residue was purified by chromatography on silica gel eluting with DCM/MeOH (1:0-10:1 (v/v)) to afford 20 g (98%) of TT-1 as colorless foam.

Rf=0.46 (DCM/MeOH, 94:6 (v/v)).

NMR Spectroscopy:

$^1$H NMR (500 MHz, MeCN-d$_3$, 25° C., δ): 8.32-8.30 (m, 2H), 7.96-7.94 (m, 2H), 7.89-7.85 (m, 2H), 7.81-7.78 (m, 2H), 7.43-7.40 (m, 2H), 7.27-7.23 (m, 2H), 7.04-7.02 (m, 2H), 6.99-6.98 (m, 2H).

$^{13}$C NMR {$^1$H} (126 MHz, MeCN-d$_3$, 25° C., δ): 163.1, 155.6, 137.2, 136.0, 135.6, 131.6, 131.6, 131.4, 130.9, 126.4, 121.3, 120.0, 119.9, 116.7.

$^{19}$F NMR {$^1$H} (471 MHz, MeCN-d$_3$, 25° C., δ): −151.4, −151.5.

HRMS-ESI (m/z) calc'd. for $C_{24}H_{17}OS_2^+$ [M-BF$_4$]$^+$, 385.071530; found, 385.071535; deviation: +0.01 ppm.

Aniline 1a

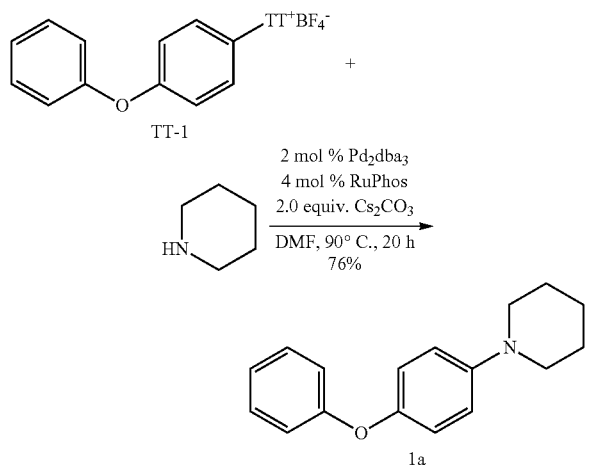

In an argon-filled glovebox, a 4 mL glass-vial equipped with a magnetic stir bar was charged with TT-1 (94 mg, 0.20 mmol, 1.0 equiv.), Pd$_2$dba$_3$ (4 mg, 4 μmol, 2 mol %), RuPhos (4 mg, 9 μmol, 4 mol %), Cs$_2$CO$_3$ (130 mg, 0.40 mmol, 2.0 equiv.), and DMF (1 mL, c=0.2 M). Piperidine (59 μL, 51 mg, 0.60 mmol, 3.0 equiv.) was added, and the sealed vial was taken out from the glovebox. The suspension was stirred at 90° C. for 20 h. The solvent was removed under reduced pressure, and the residue was purified by chromatography on silica gel eluting with hexanes/EtOAc (1:0-30:1 (v/v)) to afford 39 mg (76%) of 1a as yellow oil.

Rf=0.22 (hexanes/EtOAc, 95:5 (v/v)).

NMR Spectroscopy:

$^1$H NMR (500 MHz, CDCl$_3$, 25° C., δ): 7.29 (t, J=8.0 Hz, 2H), 7.03 (t, J=7.0 Hz, 1H), 6.98-6.90 (m, 6H), 3.14-3.07 (m, 4H), 1.78-1.69 (m, 4H), 1.61-1.53 (m, 2H).

$^{13}$C NMR {$^1$H} (126 MHz, CDCl$_3$, 25° C., δ): 158.8, 149.5, 149.1, 129.7, 122.4, 120.6, 118.2, 117.7, 51.6, 26.2, 24.3.

HRMS-ESI (m/z) calc'd. for C$_{17}$H$_{20}$NO$^+$ [M+H]$^+$, 254.153939; found, 254.153990; deviation: −0.20 ppm.

Aminopyridine 1f

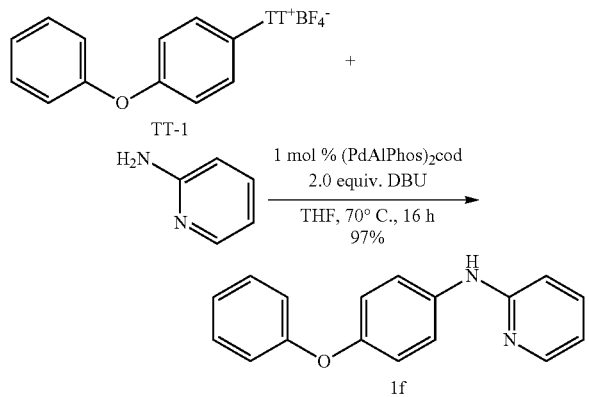

In an argon-filled glovebox, a 4 mL glass-vial equipped with a magnetic stir bar was charged with TT-1 (94 mg, 0.20 mmol, 1.0 equiv.), (PdAlPhos)$_2$cod (4 mg, 2 μmol, 1 mol %), and THF (1 mL, c=0.2 M). 2-Aminopyridine (23 mg, 0.24 mmol, 1.2 equiv.) and DBU (60 μL, 61 mg, 0.40 mmol, 2.0 equiv.) were added, and the sealed vial was taken out from the glovebox. The solution was stirred at 70° C. for 16 h. The solvent was removed under reduced pressure, and the residue was purified by chromatography on silica gel eluting with hexanes/EtOAc (1:0-10:1 (v/v)) to afford 51 mg (97%) of 1f as white solid.

Rf=0.16 (hexanes/EtOAc, 9:1 (v/v)).

NMR Spectroscopy:

$^1$H NMR (500 MHz, CDCl$_3$, 25° C., δ): 8.20-8.19 (m, 1H), 7.49-7.46 (m, 1H), 7.35-7.31 (m, 4H), 7.10-7.07 (m, 1H), 7.03-7.01 (m, 4H), 6.85 (brs, 1H), 6.80-6.78 (m, 1H), 6.73-6.70 (m, 1H).

$^{13}$C NMR {$^1$H} (126 MHz, CDCl$_3$, 25° C., δ): 157.9, 156.7, 152.7, 148.5, 137.8, 136.2, 129.8, 123.0, 122.8, 120.3, 118.4, 114.9, 108.0.

HRMS-ESI (m/z) calc'd. for C$_{17}$H$_{15}$N$_2$O$^+$ [M+H]$^+$, 263.117887; found, 263.118000; deviation: −0.43 ppm.

Oxazolidinone 1i

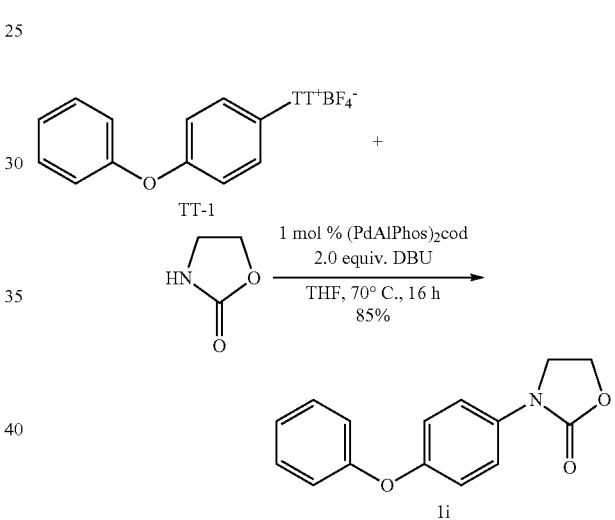

In an argon-filled glovebox, a 4 mL glass-vial equipped with a magnetic stir bar was charged with TT-1 (94 mg, 0.20 mmol, 1.0 equiv.), (PdAlPhos)$_2$cod (4 mg, 2 μmol, 1 mol %), and THF (0.5 mL, c=0.4 M). 2-Oxazolidinone (17 mg, 0.20 mmol, 0.98 equiv.) and DBU (60 μL, 61 mg, 0.40 mmol, 2.0 equiv.) were added, and the sealed vial was taken out from the glovebox. The solution was stirred at 70° C. for 16 h. The solvent was removed under reduced pressure, and the residue was purified by chromatography on silica gel eluting with hexanes/EtOAc (1:0-5:2 (v/v)) to afford 43 mg (85%) of 1i as colorless oil.

Rf=0.23 (hexanes/EtOAc, 7:3 (v/v)).

NMR Spectroscopy:

$^1$H NMR (500 MHz, CDCl$_3$, 25° C., δ): 7.51-7.49 (m, 2H), 7.35-7.31 (m, 2H), 7.11-7.05 (m, 3H), 7.00-6.98 (m, 2H), 4.51-4.47 (m, 2H), 4.08-4.04 (m, 2H).

$^{13}$C NMR {$^1$H} (126 MHz, CDCl$_3$, 25° C., δ): 157.5, 155.6, 153.6, 133.9, 129.9, 123.3, 120.2, 119.8, 118.6, 61.4, 45.7.

HRMS-EI (m/z) calc'd. for C$_{15}$H$_{13}$NO$_3$$^+$ [M]$^+$, 255.088994; found, 255.089320; deviation: −1.28 ppm.

Triazole 1o

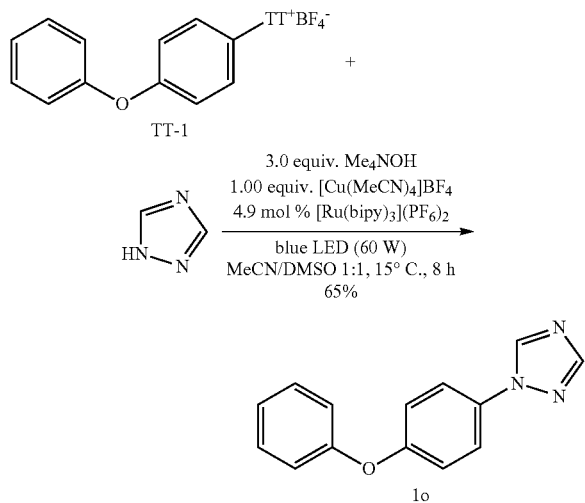

Under ambient atmosphere, a 4 mL glass-vial was charged with 1,2,4-triazole (83 mg, 1.2 mmol, 3.0 equiv.) and tetramethylammonium hydroxide (25% in methanol, 438 mg, 0.51 mL, 1.2 mmol, 3.0 equiv.), and the solvent was removed under reduced pressure. Thianthrenium salt TT-1 (189 mg, 0.400 mmol, 1.00 equiv.), [Cu(MeCN)$_4$]BF$_4$ (126 mg, 0.401 mmol, 1.00 equiv.), [Ru(bipy)$_3$](PF$_6$)$_2$ (17 mg, 20 μmol, 4.9 mol %), acetonitrile (1.0 mL) and dimethylsulfoxide (1.0 mL, $c_{total}$=0.20 M) were added, and the suspension was degassed by bubbling through argon with a cannula for 5 min. While stirring, the suspension was irradiated for 8 h at 15° C. using a blue LED (60 W). The suspension was added to water (30 mL), and the aqueous phase was extracted with DCM (3×20 mL). The organic phase was washed with saturated NaCl solution (30 mL), dried over MgSO$_4$, and the solvent was removed under reduced pressure. The residue was purified by chromatography on silica gel eluting with hexanes/EtOAc (10:0-2:8 (v/v)) to afford 62 mg (65%) of 1o as colorless oil.

Rf=0.15 (hexanes/EtOAc, 7:3 (v/v)).

NMR Spectroscopy:

$^1$H NMR (500 MHz, CDCl$_3$, 25° C., δ): 8.58 (s, 1H), 8.10 (s, 1H), 7.64-7.60 (m, 2H), 7.39-7.35 (m, 2H), 7.18-7.14 (m, 1H), 7.13-7.10 (m, 2H), 7.06-7.04 (m, 2H). $^{13}$C NMR {$^1$H} (126 MHz, CDCl$_3$, 25° C., δ): 157.6, 156.5, 152.3, 140.9, 132.3, 130.1, 124.2, 122.0, 119.6, 119.4.

HRMS-EI (m/z) calc'd. for C$_{14}$H$_{11}$N$_3$O$^+$ [M]$^+$, 237.089661; found, 237.089850; deviation: −0.80 ppm.

Phthalimide 1p

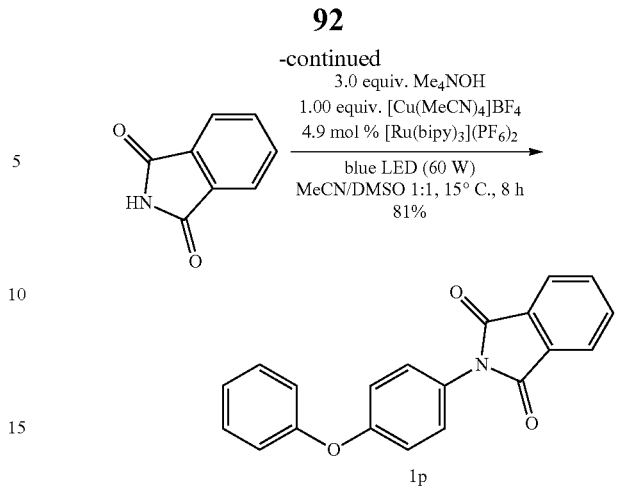

Under ambient atmosphere, a 4 mL glass-vial was charged with phthalimide (177 mg, 1.20 mmol, 3.01 equiv.) and tetramethylammonium hydroxide (25% in methanol, 438 mg, 0.51 mL, 1.2 mmol, 3.0 equiv.), and the solvent was removed under reduced pressure. Thianthrenium salt TT-1 (189 mg, 0.400 mmol, 1.00 equiv.), [Cu(MeCN)$_4$]BF$_4$ (126 mg, 0.401 mmol, 1.00 equiv.), [Ru(bipy)$_3$](PF$_6$)$_2$ (17 mg, 20 μmol, 4.9 mol %), acetonitrile (1.0 mL) and dimethylsulfoxide (1.0 mL, $c_{total}$=0.20 M) were added, and the suspension was degassed by bubbling through argon with a cannula for 5 min. While stirring, the suspension was irradiated for 8 h at 15° C. using a blue LED (60 W). The suspension was added to water (30 mL), and the aqueous phase was extracted with DCM (3×20 mL). The organic phase was washed with saturated NaCl solution (30 mL), dried over MgSO$_4$, and the solvent was removed under reduced pressure. The residue was purified by chromatography on silica gel eluting with hexanes/EtOAc (10:0-2:8 (v/v)) to afford 102 mg (81%) of 1p as colorless oil.

Rf=0.22 (hexanes/EtOAc, 8:2 (v/v)).

NMR Spectroscopy:

$^1$H NMR (500 MHz, CDCl$_3$, 25° C., δ): 7.98-7.94 (m, 2H), 7.81-7.78 (m, 2H), 7.40-7.36 (m, 4H), 7.17-7.08 (m, 5H).

$^{13}$C NMR {$^1$H} (126 MHz, CDCl$_3$, 25° C., δ): 167.5, 157.3, 156.6, 134.5, 131.9, 130.0, 128.2, 126.5, 124.0, 123.9, 119.7, 119.0.

HRMS-ESI (m/z) calc'd. for C$_{20}$H$_{14}$NO$_3^+$ [M+H]$^+$, 316.096819; found, 316.096780; deviation: −0.12 ppm.

Bromopyridone 1r

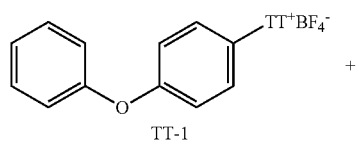

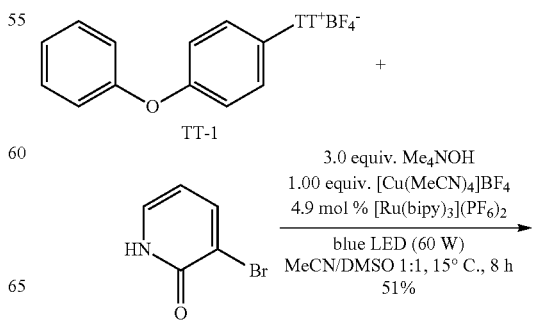

-continued

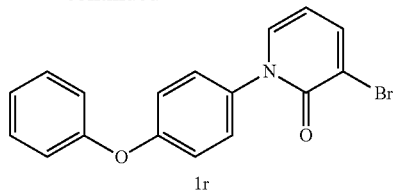

1r

Under ambient atmosphere, a 4 mL glass-vial was charged with 3-bromo-2-hydroxypyridine (209 mg, 1.20 mmol, 3.00 equiv.) and tetramethylammonium hydroxide (25% in methanol, 438 mg, 0.51 mL, 1.2 mmol, 3.0 equiv.), and the solvent was removed under reduced pressure. Thianthrenium salt TT-1 (189 mg, 0.400 mmol, 1.00 equiv.), [Cu(MeCN)$_4$]BF$_4$ (126 mg, 0.401 mmol, 1.00 equiv.), [Ru(bipy)$_3$](PF$_6$)$_2$ (17 mg, 20 μmol, 4.9 mol %), acetonitrile (1.0 mL) and dimethylsulfoxide (1.0 mL, $c_{total}$=0.20 M) were added, and the suspension was degassed by bubbling through argon with a cannula for 5 min. While stirring, the suspension was irradiated for 8 h at 15° C. using a blue LED (60 W). The suspension was added to water (30 mL), and the aqueous phase was extracted with DCM (3×20 mL). The organic phase was washed with saturated NaCl solution (30 mL), dried over MgSO$_4$, and the solvent was removed under reduced pressure. The residue was purified by chromatography on silica gel eluting with hexanes/EtOAc (10:0-4:1 (v/v)) to afford 70 mg (51%) of 1r as white solid.

Rf=0.12 (hexanes/EtOAc, 85:15 (v/v)).

NMR Spectroscopy:

$^1$H NMR (500 MHz, CDCl$_3$, 25° C., δ): 7.80 (apt dd, J=7.2, 1.9 Hz, 1H), 7.39-7.35 (m, 3H), 7.33-7.30 (m, 2H), 7.18-7.14 (m, 1H), 7.08-7.06 (m, 4H), 6.14 (apt t, J=7.0 Hz, 1H).

$^{13}$C NMR {$^1$H} (126 MHz, CDCl$_3$, 25° C., δ): 158.9, 157.9, 156.4, 142.0, 137.7, 135.6, 130.1, 127.9, 124.2, 119.7, 118.9, 117.6, 106.0.

HRMS-ESI (m/z) calc'd. for C$_{17}$H$_{12}$BrNO$_2$Na$^+$ [M+Na]$^+$, 363.994373; found, 363.994320; deviation: +0.15 ppm.

Azide 1s

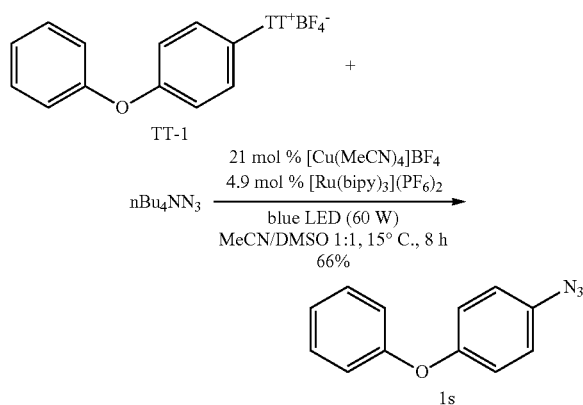

Under ambient atmosphere, a 4 mL glass-vial was charged with thianthrenium salt TT-1 (189 mg, 0.400 mmol, 1.00 equiv.), [Cu(MeCN)$_4$]BF$_4$ (26 mg, 83 μmol, 21 mol %), [Ru(bipy)$_3$](PF$_6$)$_2$ (17 mg, 20 μmol, 4.9 mol %), nBuNN$_3$ (341 mg, 1.20 mmol, 3.00 equiv.), acetonitrile (2.0 mL, c=0.20 M), and the suspension was degassed by bubbling through argon with a cannula for 5 min. While stirring, the suspension was irradiated for 8 h at 15° C. using a blue LED (60 W). The solvent was removed under reduced pressure. The residue was purified by chromatography on silica gel eluting with hexanes/EtOAc (1:0-98:2 (v/v)) to afford 56 mg (66%) of 1s as yellow oil.

Rf=0.58 (hexanes/EtOAc, 95:5 (v/v)).

NMR Spectroscopy:

$^1$H NMR (500 MHz, CD$_2$Cl$_2$, 25° C., δ): 7.36-7.33 (m, 2H), 7.13-7.10 (m, 1H), 7.02-6.98 (m, 6H).

$^{13}$C NMR {$^1$H} (126 MHz, CD$_2$Cl$_2$, 25° C., δ): 157.9, 154.9, 135.6, 130.4, 123.9, 120.9, 120.8, 119.1.

HRMS-CI (m/z) calc'd. for C$_{12}$H$_{10}$N$_3$O$^+$ [M+H]$^+$, 212.081836; found, 212.082080; deviation: −1.15 ppm.

Thianthrenium Salt TT-3

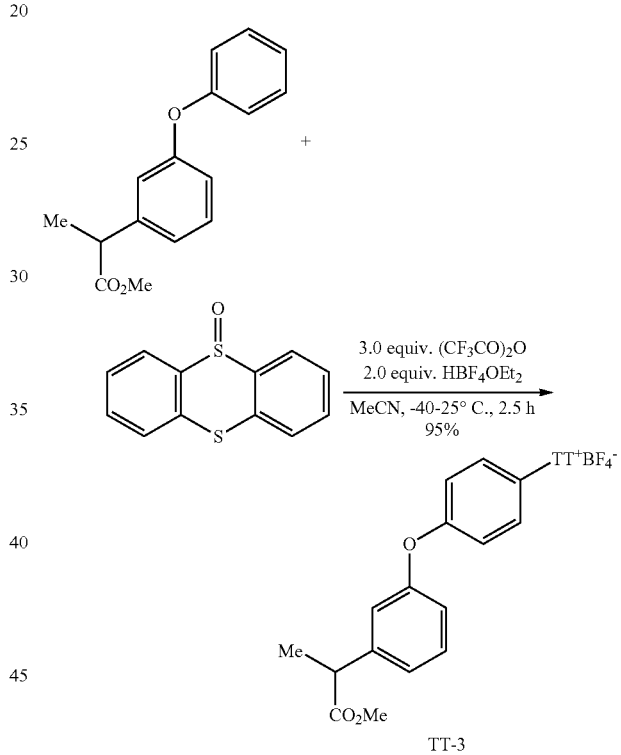

TT-3

Under ambient atmosphere, a 50 mL Schlenk-tube equipped with a magnetic stir bar was charged with fenoprofen methyl ester (260 mg, 1.01 mmol, 1.00 equiv.), thianthrene S-oxide (236 mg, 1.02 mmol, 1.00 equiv.), and MeCN (5.1 mL, c=0.20 M). After cooling to −40° C., trifluoroacetic anhydride (0.42 mL, 0.63 g, 3.0 mmol, 3.0 equiv.) was added while stirring. HBF$_4$.OEt$_2$ (0.28 ml, 0.33 g, 2.1 mmol, 2.0 equiv.) was added dropwise. The mixture was stirred at −40° C. for 30 min, then at ambient temperature for 2 h. The reaction mixture was added to a saturated aqueous NaHCO$_3$ solution (50 mL), and the aqueous phase was extracted with DCM (3×20 mL). The organic phase was washed with aqueous NaBF$_4$ solution (30 mL, 10%), dried over MgSO$_4$, and the solvent was removed under reduced pressure. The residue was purified by chromatography on silica gel eluting with DCM/MeOH (1:0-9:1 (v/v)) to afford 536 mg (95%) of TT-3 as white foam.

Rf=0.39 (DCM/MeOH, 94:6 (v/v)).

NMR Spectroscopy:

$^1$H NMR (500 MHz, CDCl$_3$, 25° C., δ): 8.47 (d, J=6.8 Hz, 2H), 7.86-7.77 (m, 4H), 7.75-7.69 (m, 2H), 7.29 (t, J=7.9 Hz, 1H), 7.24-7.18 (m, 2H), 7.12 (d, J=7.7 Hz, 1H), 6.96-6.89 (m, 3H), 6.84 (dd, J=8.1, 1.5 Hz, 1H), 3.68 (q, J=7.2 Hz, 1H), 3.62 (s, 3H), 1.44 (d, J=7.2 Hz, 3H).

$^{13}$C NMR {$^1$H} (126 MHz, CDCl$_3$, 25° C., δ): 174.5, 162.3, 154.4, 143.2, 136.3, 135.0, 135.0, 130.5, 130.5, 130.4, 124.8, 119.8, 119.2, 119.1, 119.0, 115.8, 52.3, 45.2, 18.6.

$^{19}$F NMR {$^1$H} (471 MHz, CDCl$_3$, 25° C., δ): −151.1, −151.1.

HRMS-ESI (m/z) calc'd. for C$_{28}$H$_{23}$O$_3$S$_2^+$ [M-BF$_4$]$^+$, 471.108315; found, 471.108290; deviation: +0.05 ppm.

Aniline 3

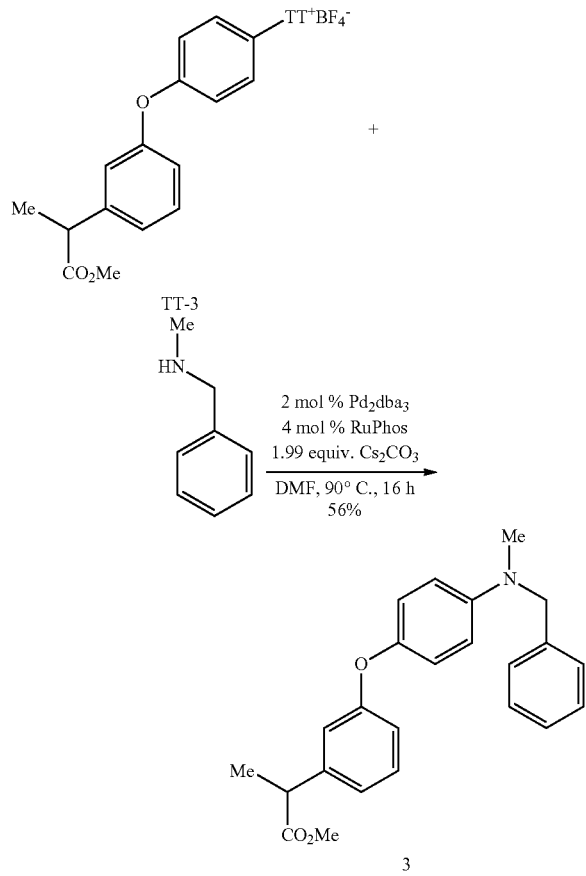

In an argon-filled glovebox, a 4 mL glass-vial equipped with a magnetic stir bar was charged with TT-3 (168 mg, 0.301 mmol, 1.00 equiv.), Pd$_2$dba$_3$ (5 mg, 5 μmol, 2 mol %), RuPhos (6 mg, 0.01 mmol, 4 mol %), Cs$_2$CO$_3$ (195 mg, 0.598 mmol, 1.99 equiv.), and DMF (1.5 mL, c=0.20 M). N-Methylbenzylamine (59 μL, 55 mg, 0.46 mmol, 1.5 equiv.) was added, and the sealed vial was taken out from the glovebox. The suspension was stirred at 90° C. for 16 h. The suspension was added to a aqueous saturated NaHCO$_3$ solution (20 mL), and the aqueous phase was extracted with DCM (3×20 mL). The organic phase was dried over MgSO$_4$, and the solvent was removed under reduced pressure. The residue was purified by chromatography on silica gel eluting with hexanes/EtOAc (1:0-7:3 (v/v)) to afford 63 mg (56%) of 3 as yellowish oil.

R$_f$=0.53 (hexanes/EtOAc, 8:2 (v/v)).

NMR Spectroscopy:

$^1$H NMR (500 MHz, CDCl$_3$, 25° C., δ): 7.37-7.31 (m, 2H), 7.27 (d, J=6.6 Hz, 3H), 7.21 (t, J=7.9 Hz, 1H), 6.97-6.90 (m, 4H), 6.79 (d, J=8.2 Hz, 1H), 6.74 (d, J=9.0 Hz, 2H), 4.51 (s, 2H), 3.72-3.64 (m, 4H), 3.01 (s, 3H), 1.48 (d, J=7.2 Hz, 3H).

$^{13}$C NMR {$^1$H} (126 MHz, CDCl$_3$, 25° C., δ): 174.9, 159.3, 147.1, 146.9, 142.3, 139.1, 129.7, 128.7, 127.1, 127.0, 121.1, 121.1, 116.7, 115.7, 113.8, 57.5, 52.2, 45.5, 39.0, 18.7.

HRMS-ESI (m/z) calc'd. for C$_{24}$H$_{26}$NO$_3^+$ [M+H]$^+$, 376.190719; found, 376.191210; deviation: −1.31 ppm.

Thianthrenium Salt TT-7

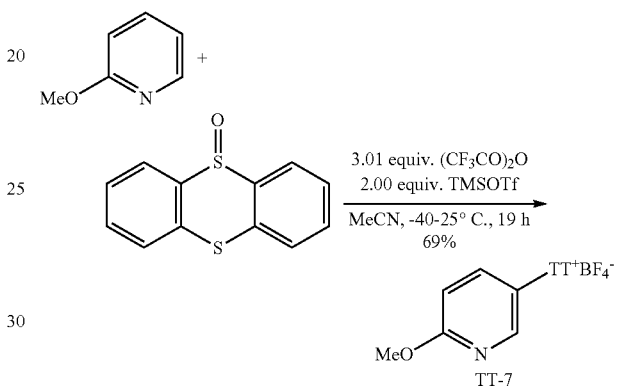

Aflame-dried, 100 mL argon-filled Schlenk-tube equipped with a magnetic stir bar was charged with 2-methoxypyridine (525 μL, 546 mg, 5.00 mmol, 1.00 equiv.), thianthrene S-oxide (1.16 g, 4.99 mmol, 0.998 equiv.), and dry MeCN (20 mL, c=0.25 M). After cooling to −40° C., trifluoroacetic anhydride (2.09 mL, 3.16 g, 15.0 mmol, 3.01 equiv.) was added while stirring. A solution of trimethylsilyl trifluoromethanesulfonate (1.81 mL, 2.22 g, 10.0 mmol, 2.00 equiv.) in 5 mL of dry MeCN was added dropwise over 5 min. The mixture was stirred at −40° C. for 1 h, then at ambient temperature for 18 h. The reaction mixture was concentrated under reduced pressure, and subsequently diluted with DCM (100 mL). The solution was washed with aqueous NaBF$_4$ solution (3×100 mL, 10%), and with water (100 mL). The organic phase was dried over MgSO$_4$, and the solvent was removed under reduced pressure. The residue was purified by chromatography on silica gel eluting with DCM/MeOH (1:0-20:1 (v/v)) to afford 1.42 g (69%) of TT-7 as yellow foam.

R$_f$=0.18 (DCM/MeOH, 10:1 (v/v)).

NMR Spectroscopy:

$^1$H NMR (500 MHz, CDCl$_3$, 25° C., δ): 8.53 (dd, J=7.9, 1.1 Hz, 2H), 7.93 (d, J=2.8 Hz, 1H), 7.88-7.78 (m, 4H), 7.78-7.71 (m, 2H), 7.61 (dd, J=9.1, 2.8 Hz, 1H), 6.79 (d, J=9.1 Hz, 1H), 3.88 (s, 3H).

$^{13}$C NMR {$^1$H} (126 MHz, CDCl$_3$, 25° C., δ): 166.9, 147.6, 138.4, 136.4, 135.1, 135.1, 130.6, 130.4, 118.5, 133.9, 112.8, 54.7.

$^{19}$F NMR {$^1$H} (471 MHz, CDCl$_3$, 25° C., δ): −150.0, −150.0.

HRMS-ESI (m/z) calc'd. for C$_{18}$H$_{14}$NOS$_2^+$ [M-BF$_4$]$^+$, 324.051134; found, 324.050980; deviation: +0.48 ppm.

Oxazolidinone 7

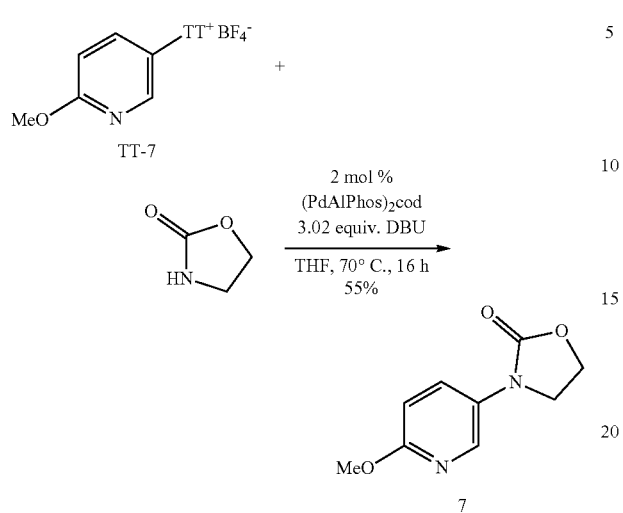

In an argon-filled glovebox, a 4 mL glass-vial equipped with a magnetic stir bar was charged with TT-7 (123 mg, 0.299 mmol, 1.00 equiv.), (PdAlphos)$_2$cod (9 mg, 4 µmol, 2 mol %), and THF (1 mL, c=0.3 M). 2-Oxazolidinone (52 mg, 0.60 mmol, 2.0 equiv.) and DBU (135 µL, 137 mg, 0.903 mmol, 3.02 equiv.) were added, and the sealed vial was taken out from the glovebox. The solution was stirred at 70° C. for 16 h. The solvent was removed under reduced pressure, and the residue was purified by chromatography on silica gel eluting with hexanes/EtOAc (1:0-19:1 (v/v)) to afford 32 mg (55%) of 7 as white solid.

Rf=0.49 (hexanes/EtOAc, 95:5 (v/v)).

NMR Spectroscopy:

$^1$H NMR (500 MHz, CDCl$_3$, 25° C., δ): 8.06-8.03 (m, 2H), 6.76-6.75 (m, 2H), 4.48 (t, J=7.6 Hz, 2H), 4.02 (t, J=7.6 Hz, 2H), 3.90 (s, 3H).

$^{13}$C NMR {$^1$H} (126 MHz, CDCl$_3$, 25° C., δ): 161.0, 155.6, 136.5, 130.6, 129.4, 111.0, 61.7, 53.7, 45.3.

HRMS-ESI (m/z) calc'd. for C$_9$H$_{11}$N$_2$O$_3^+$ [M+H]$^+$, 195.076417; found, 195.076640; deviation: −1.14 ppm.

Thianthrenium Salt TT-15

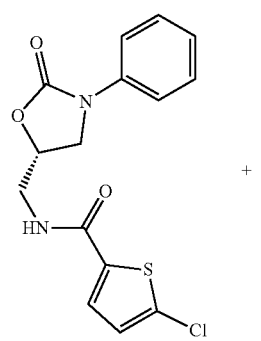

+

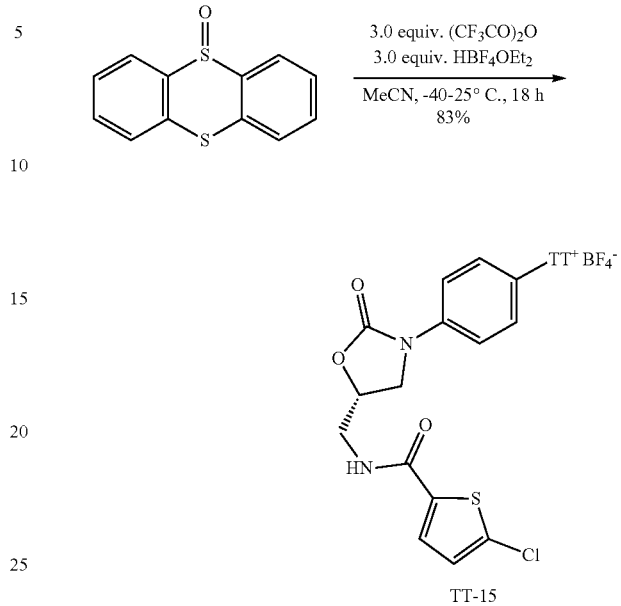

Under ambient atmosphere, a 100 mL Schlenk-tube equipped with a magnetic stir bar was charged with (S)-5-chloro-N-((2-oxo-3-phenyloxazolidin-5-yl)methyl)thiophene-2-carboxamide (800 mg, 2.38 mmol, 1.00 equiv.), thianthrene S-oxide (569 mg, 2.45 mmol, 1.03 equiv.), and MeCN (15 mL, c=0.16 M). After cooling to −40° C., trifluoroacetic anhydride (0.99 mL, 1.5 g, 7.1 mmol, 3.0 equiv.) was added while stirring. HBF$_4$OEt$_2$ (0.97 mL, 1.2 g, 7.1 mmol, 3.0 equiv.) was added dropwise. The mixture was stirred at −40° C. for 1 h, then at ambient temperature for 17 h. The reaction mixture was concentrated under reduced pressure, and subsequently diluted with DCM (100 mL). The solution was poured onto a saturated aqueous NaHCO$_3$ solution (100 mL), and the layers were separated. The organic phase was washed with aqueous NaBF$_4$ solution (2×100 mL, 10%), and with water (100 mL). The organic phase was dried over MgSO$_4$, and the solvent was removed under reduced pressure. The residue was purified by chromatography on silica gel eluting with DCM/MeOH (1:0-19:1 (v/v)) to afford 1.25 g (83%) of TT-15 as white solid.

Rf=0.20 (DCM/MeOH, 95:5 (v/v)).

NMR Spectroscopy:

$^1$H NMR (500 MHz, MeCN-d$_3$, 25° C., δ): 8.34-8.32 (m, 2H), 7.96-7.94 (m, 2H), 7.90-7.86 (m, 2H), 7.82-7.79 (m, 2H), 7.63-7.60 (m, 2H), 7.35 (d, J=4.1 Hz, 1H), 7.33-7.31 (m, 1H), 7.15-7.12 (m, 2H), 6.96 (d, J=4.1 Hz, 1H), 4.83-4.78 (m, 1H), 4.05 (t, J=9.1 Hz, 1H), 3.80 (dd, J=9.3, 6.1 Hz, 1H), 3.71-3.59 (m, 2H).

$^{13}$C NMR {$^1$H} (126 MHz, MeCN-d$_3$, 25° C., δ): 162.3, 155.1, 144.0, 139.1, 137.3, 136.1, 135.8, 135.5, 131.6, 130.9, 130.1, 128.8, 128.7, 120.1, 119.8, 117.3, 73.0, 48.4, 42.9. $^{19}$F NMR {$^1$H} (471 MHz, MeCN-d$_3$, 25° C., δ): −151.5, −151.5.

HRMS-ESI (m/z) calc'd. for C$_{27}$H$_{20}$ClN$_2$O$_3$S$_3^+$ [M-BF$_4$]$^+$, 551.031470; found, 551.031913; deviation: +0.8 ppm.

Triazole 15

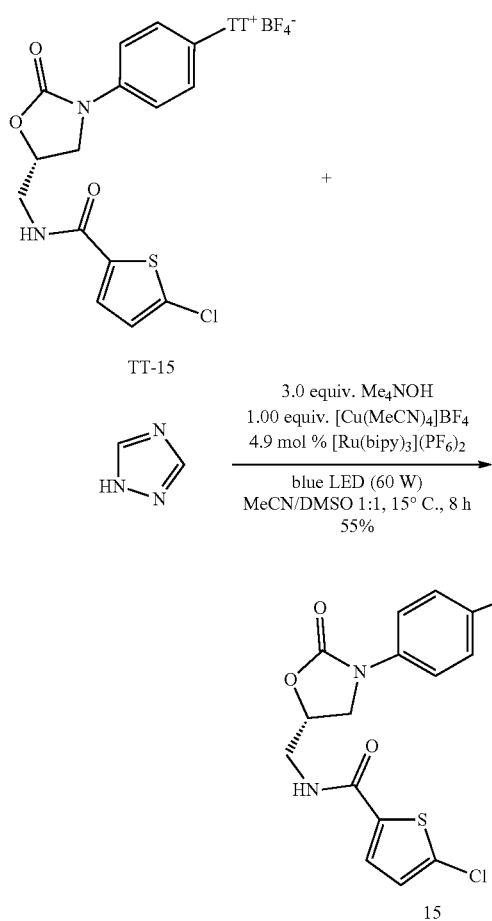

HRMS-ESI (m/z) calc'd. for $C_{17}H_{14}N_5O_3SClNa^+$ [M+Na]$^+$, 426.039808; found, 426.039950; deviation: −0.33 ppm.

Thianthrenium Salt TT-22

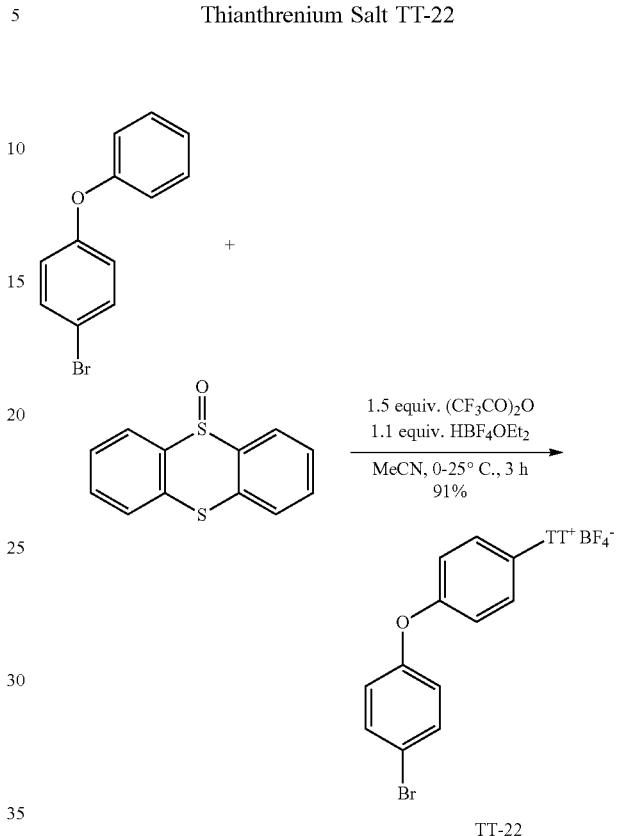

Under ambient atmosphere, a 4 mL glass-vial was charged with 1,2,4-triazole (83 mg, 1.2 mmol, 3.0 equiv.) and tetramethylammonium hydroxide (25% in methanol, 438 mg, 0.51 mL, 1.2 mmol, 3.0 equiv.), and the solvent was removed under reduced pressure. Thianthrenium salt TT-15 (256 mg, 0.401 mmol, 1.00 equiv.), [Cu(MeCN)$_4$]BF$_4$ (126 mg, 0.401 mmol, 1.00 equiv.), [Ru(bipy)$_3$](PF$_6$)$_2$ (17 mg, 20 μmol, 4.9 mol %), acetonitrile (1 mL) and dimethylsulfoxide (1 mL, $c_{total}$=0.2 M) were added, and the suspension was degassed by bubbling through argon with a cannula for 5 min. While stirring, the suspension was irradiated for 8 h at 15° C. using a blue LED (60 W). The suspension was added to water (30 mL), and the aqueous phase was extracted with DCM (3×20 mL). The organic phase was dried over MgSO$_4$, and the solvent was removed under reduced pressure. The residue was purified by chromatography on silica gel eluting with hexanes/EtOAc (1:0-2:1 (v/v)) to afford 89 mg (55%) of 15 as white solid.

Rf=0.13 (hexanes/EtOAc, 2:8 (v/v)).

NMR Spectroscopy:

$^1$H NMR (500 MHz, DMSO-d$_6$, 25° C., δ): 9.25 (s, 1H), 8.99-8.97 (m, 1H), 8.22 (s, 1H), 7.88-7.86 (m, 2H), 7.73-7.71 (m, 2H), 7.69 (d, J=4.1 Hz, 1H), 7.19 (d, J=4.0 Hz, 1H), 4.90-4.84 (m, 1H), 4.23 (t, J=9.0 Hz, 1H), 3.91-3.88 (m, 1H), 3.63 (t, J=5.6 Hz, 2H).

$^{13}$C NMR {$^1$H} (126 MHz, DMSO-d$_6$, 25° C., δ): 160.8, 154.1, 152.3, 142.1, 138.4, 137.8, 133.3, 132.3, 128.4, 128.1, 120.0, 118.8, 71.5, 47.4, 42.2.

Under ambient atmosphere, a 50 mL Schlenk-tube equipped with a magnetic stir bar was charged with bromodiphenylether (2.491 g, 10.00 mmol, 1.000 equiv.), thianthrene S-oxide (2.323 g, 10.00 mmol, 0.9999 equiv.), and MeCN (15 mL, c=0.67 M). HBF$_4$OEt$_2$ (1.5 ml, 1.8 g, 11 mmol, 1.1 equiv.) was added. After cooling to 0° C., trifluoroacetic anhydride (2.1 mL, 3.2 g, mmol, 1.5 equiv.) was added while stirring. The mixture was allowed to warm to ambient temperature, and then was stirred for 3 h. The reaction mixture was concentrated under reduced pressure, and subsequently diluted with DCM (30 mL). The solution was washed with water (40 mL), and with aqueous NaBF$_4$ solution (3×40 mL, 10%). The organic phase was dried over MgSO$_4$, and the solvent was removed under reduced pressure giving a colorless foam. The foam was dissolved in DCM (5 mL), and precipitated by addition of MTBE (100 mL) resulting in a viscous oil. Drying under high vacuum afforded 5.475 g (91%) of TT-22 in a purity of 92% (containing 8% MTBE) as white solid. Further drying afforded an analytically pure sample.

Rf=0.47 (DCM/MeOH, 94:6 (v/v)).

NMR Spectroscopy:

$^1$H NMR (500 MHz, DMSO-d$_6$, 25° C., δ): 8.53 (dd, J=8.1, 1.4 Hz, 2H), 8.07 (dd, J=8.0, 1.3 Hz, 2H), 7.93-7.89 (m, 2H), 7.84 (ddd, J=7.9, 7.5, 1.4 Hz, 2H), 7.62-7.58 (m, 2H), 7.30-7.26 (m, 2H), 7.16-7.12 (m, 2H), 7.06-7.02 (m, 2H).

$^{13}$C NMR {$^1$H} (126 MHz, DMSO-d$_6$, 25° C., δ): 160.4, 153.9, 135.3, 135.2, 134.8, 133.3, 130.8, 130.3, 129.7, 122.3, 119.6, 119.3, 117.8, 117.2.

$^{19}$F NMR {$^{1}$H} (471 MHz, DMSO-d$_6$, 25° C., δ): −148.2, −148.2.

HRMS-ESI (m/z) calc'd. for C$_{24}$H$_{16}$OS$_2$Br$^+$ [M-BF$_4$]$^+$, 462.982061; found, 462.981640; deviation: +0.91 ppm.

Aniline 22

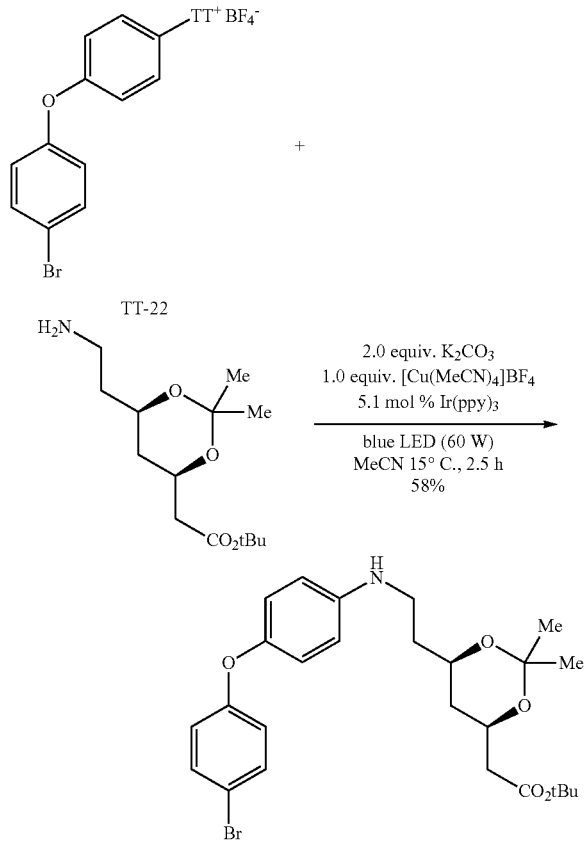

Under ambient atmosphere, a 4 mL glass-vial was charged with thianthrenium salt TT-22 (165 mg, 0.299 mmol, 1.00 equiv.), [Cu(MeCN)$_4$]BF$_4$ (94 mg, 0.30 mmol, 1.0 equiv.), Ir(ppy)$_3$ (10 mg, 15 μmol, 5.1 mol %), K$_2$CO$_3$ (83 mg, 0.60 mmol, 2.0 equiv.), and acetonitrile (1.5 mL, c=0.20 M). Tert-butyl 2-((4R,6R)-6-(2-aminoethyl)-2,2-dimethyl-1,3-dioxan-4-yl)acetate (123 mg, 0.450 mmol, 1.50 equiv.) was added, and the suspension was degassed by bubbling through argon with a cannula for 5 min. While stirring, the suspension was irradiated for 2.5 h at 15° C. using a blue LED (60 W). The suspension was added to an aqueous saturated NaHCO$_3$ solution (20 mL), and the aqueous phase was extracted with DCM (3×20 mL). The organic phase was dried over MgSO$_4$, and the solvent was removed under reduced pressure. The residue was purified by chromatography on silica gel eluting with hexanes/EtOAc (1:0-7:3 (v/v)) to afford 91 mg (58%) of 22 as brown oil.

Rf=0.34 (hexanes/EtOAc, 8:2 (v/v)).

NMR Spectroscopy:

$^{1}$H NMR (500 MHz, CDCl$_3$, 25° C., δ): 7.38-7.32 (m, 2H), 6.90-6.84 (m, 2H), 6.82-6.76 (m, 2H), 6.61-6.54 (m, 2H), 4.31-4.22 (m, 1H), 4.08-3.99 (m, 2H), 3.29-3.14 (m, 2H), 2.44 (dd, J=15.2, 6.9 Hz, 1H), 2.31 (dd, J=15.2, 6.2 Hz, 1H), 1.78 (q, J=6.3 Hz, 2H), 1.60-1.54 (m, 1H), 1.46 (s, 3H), 1.45 (s, 9H), 1.40 (s, 3H), 1.32-1.25 (m, 1H).

$^{13}$C NMR {$^{1}$H} (126 MHz, CDCl$_3$, 25° C., δ): 170.4, 158.6, 147.0, 145.7, 132.5, 121.4, 118.8, 114.2, 113.8, 98.9, 80.8, 68.2, 66.3, 42.8, 41.4, 36.5, 35.7, 30.3, 28.2, 19.9.

HRMS-ESI (m/z) calc'd. for C$_{26}$H$_{35}$NO$_5$Br$^+$ [M+H]$^+$, 520.169324; found, 520.169660; deviation: □0.65 ppm.

Morpholine 23

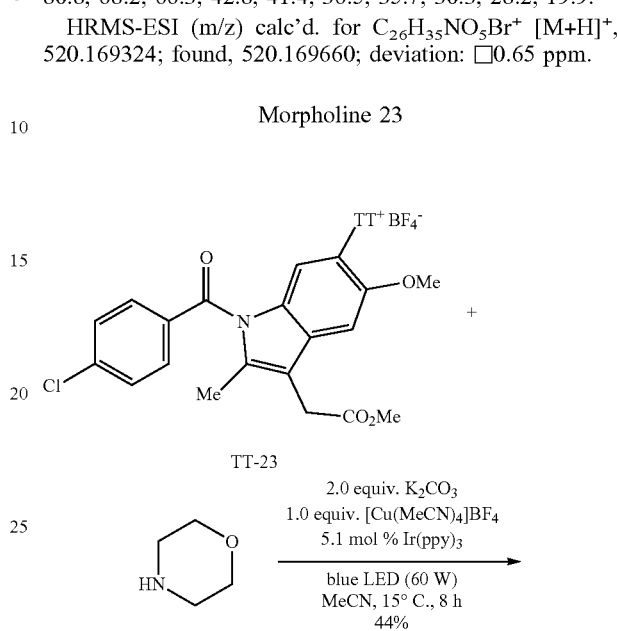

Under ambient atmosphere, a 4 mL glass-vial was charged with thianthrenium salt TT-23 (202 mg, 0.300 mmol, 1.00 equiv.), [Cu(MeCN)$_4$]BF$_4$ (94 mg, 0.30 mmol, 1.0 equiv.), Ir(ppy)$_3$ (10 mg, 15 μmol, 5.1 mol %), K$_2$CO$_3$ (83 mg, 0.60 mmol, 2.0 equiv.), and acetonitrile (2 mL, c=0.1 M). Morpholine (39 mg, 39 μL, 0.45 mmol, 1.5 equiv.) was added, and the suspension was degassed by bubbling through argon with a cannula for 5 min. While stirring, the suspension was irradiated for 8 h at 15° C. using a blue LED (60 W). The solvent was removed under reduced pressure. The residue was purified by chromatography on silica gel eluting with hexanes/EtOAc (1:0-4:6 (v/v)) to afford 60 mg (44%) of 23 as yellow solid.

Rf=0.29 (hexanes/EtOAc, 1:1 (v/v)).

NMR Spectroscopy:

$^{1}$H NMR (500 MHz, CDCl$_3$, 25° C., δ): 7.68-7.63 (m, 2H), 7.51-7.44 (m, 2H), 6.92 (s, 1H), 6.70 (s, 1H), 3.91 (s, 3H), 3.83 (t, J=4.6 Hz, 4H), 3.69 (s, 3H), 3.65 (s, 2H), 2.88-2.80 (m, 4H), 2.30 (s, 3H).

$^{13}$C NMR {$^{1}$H} (126 MHz, CDCl$_3$, 25° C., δ): 171.5, 168.5, 149.9, 139.2, 138.7, 134.3, 133.8, 131.2, 130.8, 129.2, 124.9, 112.6, 105.1, 100.3, 67.3, 55.9, 52.3, 51.6, 30.4, 13.7.

HRMS-ESI (m/z) calc'd. for $C_{24}H_{26}ClN_2O_5^+$ [M+H]$^+$, 457.152475; found, 457.152640; deviation: ☐0.36 ppm.

Thianthrenium Salt TT-25

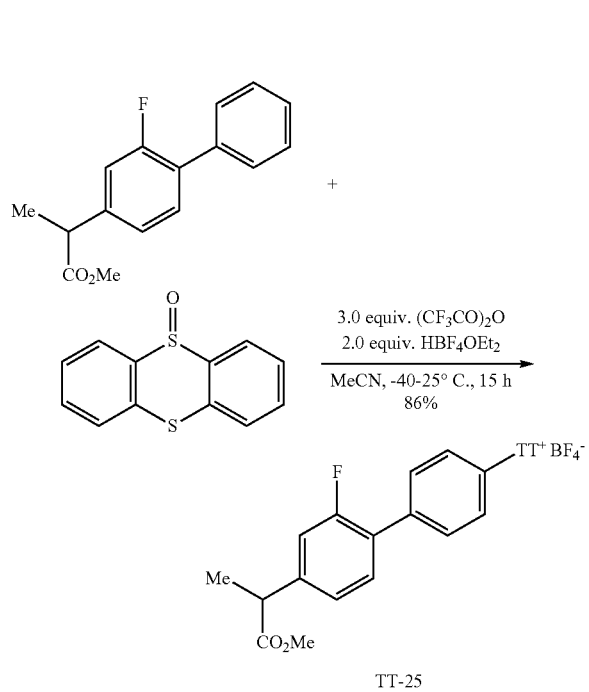

Under ambient atmosphere, a 50 mL Schlenk-tube equipped with a magnetic stir bar was charged with flurbiprofen methyl ester (400 mg, 1.55 mmol, 1.00 equiv.), thianthrene S-oxide (360 mg, 1.55 mmol, 1.00 equiv.), and MeCN (7.7 mL, c=0.20 M). After cooling to −40° C., trifluoroacetic anhydride (0.65 mL, 0.98 g, 4.7 mmol, 3.0 equiv.) was added while stirring. HBF$_4$OEt$_2$ (0.42 ml, 0.50 g, 3.1 mmol, 2.0 equiv.) was added dropwise. The mixture was stirred at −40° C. for 1 h, then at ambient temperature for 14 h. The reaction mixture was added to a saturated aqueous NaHCO$_3$ solution (50 mL), and the aqueous phase was extracted with DCM (3×20 mL). The organic phase was washed with aqueous NaBF$_4$ solution (30 mL, 10%), dried over MgSO$_4$, and the solvent was removed under reduced pressure. The residue was purified by chromatography on silica gel eluting with DCM/MeOH (1:0-9:1 (v/v)) to afford 746 mg (86%) of TT-25 as white solid.

Rf=0.35 (DCM/MeOH, 15:1 (v/v)).

NMR Spectroscopy:

$^1$H NMR (500 MHz, DMSO-d$_6$, 25° C., δ): 8.62 (dd, J=7.9, 1.4 Hz, 2H), 8.09 (d, J=7.1 Hz, 2H), 7.94 (td, J=7.7, 1.5 Hz, 2H), 7.88 (td, J=7.7, 1.4 Hz, 2H), 7.72 (dd, J=8.7, 1.6 Hz, 2H), 7.47 (t, J=8.2 Hz, 1H), 7.35-7.30 (m, 2H), 7.30-7.19 (m, 2H), 3.90 (q, J=7.1 Hz, 1H), 3.60 (s, 3H), 1.41 (d, J=7.2 Hz, 3H).

$^{13}$C NMR {$^1$H} (126 MHz, DMSO-d$_6$, 25° C., δ): 173.6, 158.8 (d, J=247.4 Hz), 144.0 (d, J=7.9 Hz), 139.0, 135.7, 135.4, 134.8, 130.9 (d, J=3.1 Hz), 130.6 (d, J=3.0 Hz), 130.3, 129.6, 128.4, 124.6 (d, J=12.8 Hz), 124.3, 124.2 (d, J=16.0 Hz), 119.1, 115.4 (d, J=23.0 Hz), 52.0, 43.8, 18.3.

$^{19}$F NMR {$^1$H} (471 MHz, DMSO-d$_6$, 25° C., δ): −117.8, −148.2, −148.3.

HRMS-ESI (m/z) calc'd. for $C_{28}H_{22}FO_2S_2^+$ [M−BF$_4$]$^+$, 473.103979; found, 473.103320; deviation: +1.39 ppm.

Aniline 25a

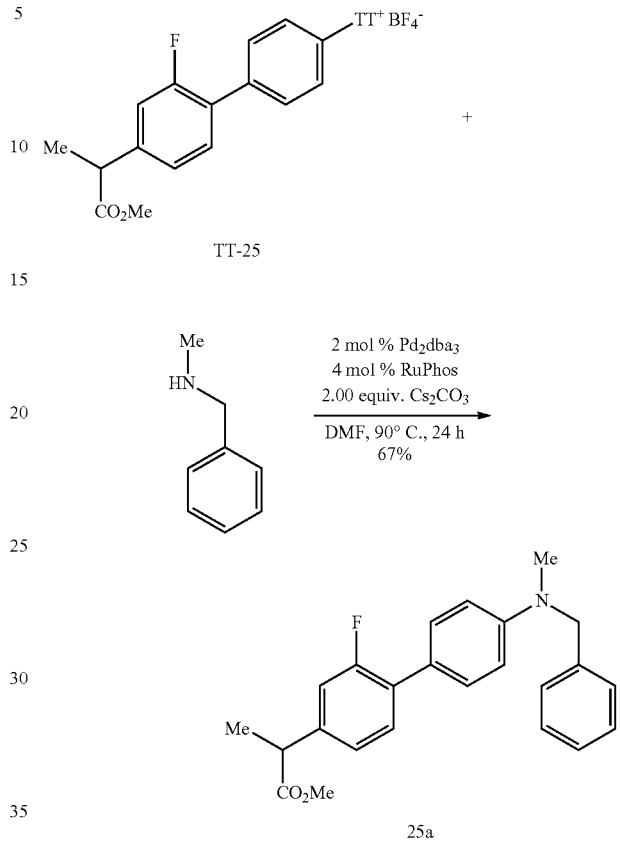

In an argon-filled glovebox, a 4 mL glass-vial equipped with a magnetic stir bar was charged with TT-25 (224 mg, 0.400 mmol, 1.00 equiv.), Pd$_2$dba$_3$ (7 mg, 8 μmol, 2 mol %), RuPhos (7 mg, 0.02 mmol, 4 mol %), Cs$_2$CO$_3$ (261 mg, 0.801 mmol, 2.00 equiv.), and DMF (1 mL, c=0.4 M). N-Methylbenzylamine (77 μL, 72 mg, 0.60 mmol, 1.5 equiv.) was added, and the sealed vial was taken out from the glovebox. The suspension was stirred at 90° C. for 24 h. The solvent was removed under reduced pressure. The residue was purified by chromatography on silica gel eluting with hexanes/EtOAc (1:0-6:4 (v/v)) to afford 101 mg (67%) of 25a as yellowish oil.

Rf=0.35 (hexanes/EtOAc, 9:1 (v/v)).

NMR Spectroscopy:

$^1$H NMR (500 MHz, CDCl$_3$, 25° C., δ): 7.43 (d, J=7.0 Hz, 2H), 7.40-7.31 (m, 3H), 7.30-7.22 (m, 3H), 7.14-7.04 (m, 2H), 6.83 (d, J=8.3 Hz, 2H), 4.59 (s, 2H), 3.74 (q, J=7.2 Hz, 1H), 3.70 (s, 3H), 3.09 (s, 3H), 1.53 (d, J=7.2 Hz, 3H).

$^{13}$C NMR {$^1$H} (126 MHz, CDCl$_3$, 25° C., δ): 174.7, 159.8 (d, J=246.9 Hz), 140.5 (d, J=7.6 Hz), 130.3 (d, J=4.2 Hz), 129.9 (d, J=3.1 Hz), 128.8, 128.0 (d, J=13.4 Hz), 127.1, 126.9, 123.5 (d, J=3.3 Hz), 115.3 (d, J=24.3 Hz), 112.3, 56.7, 52.3, 45.0, 38.8, 18.6.

$^{19}$F NMR {$^1$H} (471 MHz, CDCl$_3$, 25° C., δ): −117.8.

HRMS-ESI (m/z) calc'd. for $C_{24}H_{25}FNO_2^+$ [M+H]$^+$, 378.186382; found, 378.186440; deviation: −0.15 ppm.

Aminoisoxazole 25b

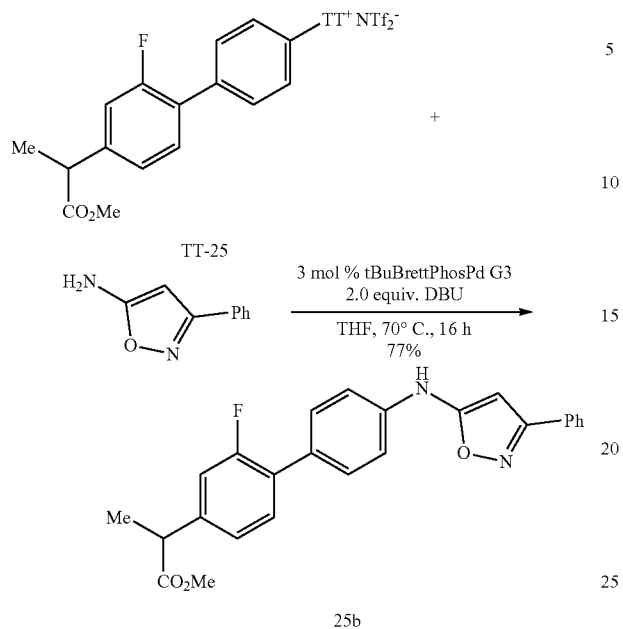

In an argon-filled glovebox, a 4 mL glass-vial equipped with a magnetic stir bar was charged with TT-25 (226 mg, 0.300 mmol, 1.00 equiv.), tBuBrettPhosPd G3 (8 mg, 9 μmol, 3 mol %), and THF (1 mL, c=0.3 M). 5-Amino-3-phenylisoxazole (72 mg, 0.45 mmol, 1.5 equiv.) and DBU (90 μL, 92 mg, 0.60 mmol, 2.0 equiv.) were added, and the sealed vial was taken out from the glovebox. The solution was stirred at 70° C. for 16 h. The solvent was removed under reduced pressure, and the residue was purified by chromatography on silica gel eluting with hexanes/EtOAc (1:0-3:1 (v/v)) to afford 97 mg (77%) of 25b as white solid.

Rf=0.28 (hexanes/EtOAc, 75:25 (v/v)).

NMR Spectroscopy:

$^1$H NMR (500 MHz, DMSO-d$_6$, 25° C., δ): 10.24 (s, 1H), 7.90-7.88 (m, 2H), 7.55-7.47 (m, 6H), 7.37-7.36 (m, 2H), 7.24-7.19 (m, 2H), 6.35 (s, 1H), 3.89 (q, J=7.1 Hz, 1H), 3.62 (s, 3H), 1.43 (d, J=7.1 Hz, 3H).

$^{13}$C NMR {$^1$H} (126 MHz, DMSO-d$_6$, 25° C., δ): 173.8, 165.6, 162.8, 158.9 (d, J=245.9 Hz), 141.8 (d, J=7.7 Hz), 139.5, 130.4 (d, J=3.9 Hz), 130.0, 129.7 (d, J=3.2 Hz), 128.9, 127.7, 126.6, 123.9 (d, J=3.2 Hz), 116.5, 115.2 (d, J=23.4 Hz), 79.4, 52.0, 43.8, 18.3.

$^{19}$F NMR {$^1$H} (471 MHz, DMSO-d$_6$, 25° C., δ): −118.2.

HRMS-ESI (m/z) calc'd. for $C_{25}H_{20}FN_2O_3^-$ [M−H]$^-$, 415.146346; found, 415.146420; deviation: −0.18 ppm.

Triazole 25c

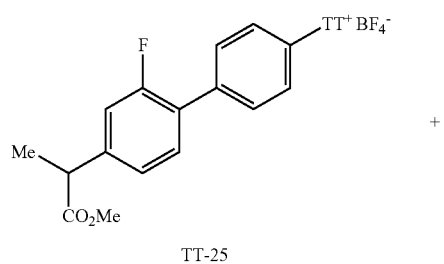

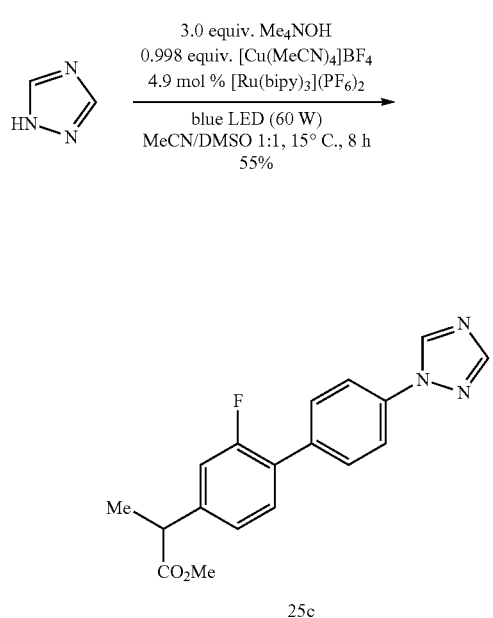

Under ambient atmosphere, a 4 mL glass-vial was charged with 1,2,4-triazole (74 mg, 1.1 mmol, 3.0 equiv.) and tetramethylammonium hydroxide (25% in methanol, 390 mg, 0.45 mL, 1.1 mmol, 3.0 equiv.), and the solvent was removed under reduced pressure. Thianthrenium salt TT-25 (200 mg, 0.357 mmol, 1.00 equiv.), [Cu(MeCN)$_4$]BF$_4$ (112 mg, 0.356 mmol, 0.998 equiv.), [Ru(bipy)$_3$](PF$_6$)$_2$ (15 mg, 17 μmol, 4.9 mol %), acetonitrile (0.89 mL) and dimethylsulfoxide (0.89 mL, $c_{total}$=0.20 M) were added, and the suspension was degassed by bubbling through argon with a cannula for 5 min. While stirring, the suspension was irradiated for 8 h at 15° C. using a blue LED (60 W). The suspension was added to water (30 mL), and the aqueous phase was extracted with DCM (3×20 mL). The organic phase was washed with a saturated aqueous NaCl solution (20 mL), dried over MgSO$_4$, and the solvent was removed under reduced pressure. The residue was purified by chromatography on silica gel eluting with hexanes/EtOAc (9:1-0:1 (v/v)) to afford 69 mg (55%) of 25c as yellowish solid.

Rf=0.46 (hexanes/EtOAc, 2:8 (v/v)).

NMR Spectroscopy:

$^1$H NMR (500 MHz, CDCl$_3$, 25° C., δ): 8.59 (s, 1H), 8.11 (s, 1H), 7.78-7.71 (m, 2H), 7.69-7.62 (m, 2H), 7.40 (t, J=8.0 Hz, 1H), 7.19-7.11 (m, 2H), 3.76 (q, J=7.2 Hz, 1H), 3.69 (s, 3H), 1.53 (d, J=7.0 Hz, 3H).

$^{13}$C NMR {$^1$H} (126 MHz, CDCl$_3$, 25° C., δ): 174.3, 159.7 (d, J=249.0 Hz), 152.7, 142.6 (d, J=7.7 Hz), 140.9, 136.3, 135.5, 130.6 (d, J=3.6 Hz), 130.3 (d, J=3.2 Hz), 126.4 (d, J=13.1 Hz), 123.8 (d, J=3.2 Hz), 120.0, 115.5 (d, J=23.3 Hz), 52.3, 45.0, 18.5.

$^{19}$F NMR {$^1$H} (471 MHz, CDCl$_3$, 25° C., δ): −117.4.

HRMS-ESI (m/z) calc'd. for $C_{18}H_{17}FN_3O_2^+$ [M+H]$^+$, 326.129930; found, 326.129910; deviation: +0.06 ppm.

Aniline 25d

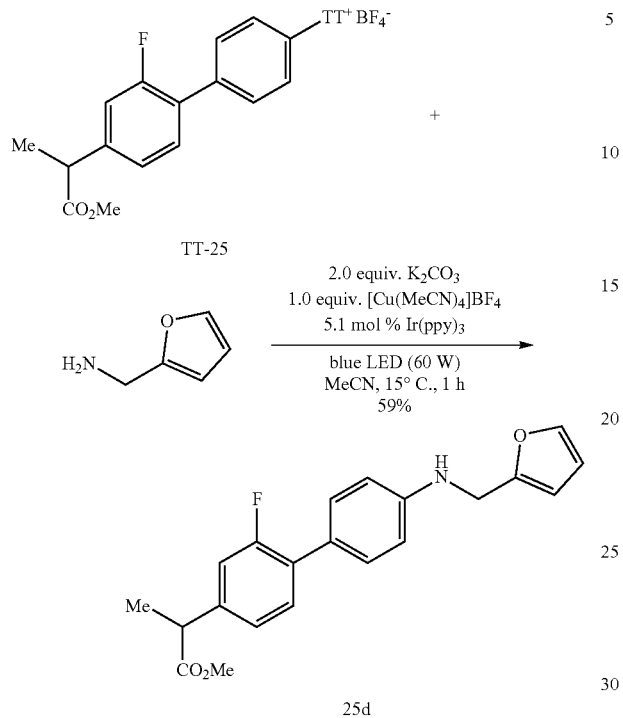

Under ambient atmosphere, a 4 mL glass-vial was charged with thianthrenium salt TT-25 (168 mg, 0.300 mmol, 1.00 equiv.), [Cu(MeCN)$_4$]BF$_4$ (94 mg, 0.30 mmol, 1.0 equiv.), Ir(ppy)$_3$ (10 mg, 15 μmol, 5.1 mol %), K$_2$CO$_3$ (83 mg, 0.60 mmol, 2.0 equiv.), and acetonitrile (1.5 mL, c=0.20 M). Furfurylamine (40 μL, 44 mg, 0.45 mmol, 1.5 equiv.) was added, and the suspension was degassed by bubbling through argon with a cannula for 5 min. While stirring, the suspension was irradiated for 1 h at 15° C. using a blue LED (60 W). The suspension was added to an aqueous saturated NaHCO$_3$ solution (20 mL), and the aqueous phase was extracted with DCM (3×20 mL). The organic phase was dried over MgSO$_4$, and the solvent was removed under reduced pressure. The residue was purified by chromatography on silica gel eluting with hexanes/EtOAc (1:0-2:8 (v/v)) to afford 63 mg (59%) of 25d as yellowish oil.

Rf=0.38 (hexanes/EtOAc, 8:2 (v/v)).

NMR Spectroscopy:

$^1$H NMR (500 MHz, CDCl$_3$, 25° C., δ): 7.42-7.37 (m, 3H), 7.35 (t, J=8.2 Hz, 1H), 7.13-7.05 (m, 2H), 6.76-6.71 (m, 2H), 6.34 (dd, J=3.2, 1.8 Hz, 1H), 6.27 (d, J=3.2 Hz, 1H), 4.36 (d, J=4.7 Hz, 2H), 4.16 (s, 1H), 3.74 (q, J=7.2 Hz, 1H), 3.70 (s, 3H), 1.53 (d, J=7.2 Hz, 3H).

$^{13}$C NMR {$^1$H} (126 MHz, CDCl$_3$, 25° C., δ): 174.7, 159.8 (d, J=247.4 Hz), 152.6, 147.3, 142.1, 140.7 (d, J=7.7 Hz), 130.4 (d, J=4.2 Hz), 130.0 (d, J=3.2 Hz), 128.0 (d, J=13.6 Hz), 125.0, 123.5 (d, J=3.2 Hz), 115.3 (d, J=23.9 Hz), 113.1, 110.5, 107.2, 52.3, 45.0, 41.5, 18.6.

$^{19}$F NMR {$^1$H} (471 MHz, CDCl$_3$, 25° C., δ): −117.8.

HRMS-ESI (m/z) calc'd. for C$_{21}$H$_{20}$NO$_3$FNa$^+$ [M+Na]$^+$, 376.131941; found, 376.131630; deviation: □0.83 ppm.

2-Fluoro-6-(p-fluorophenoxy)benzonitrile (2)

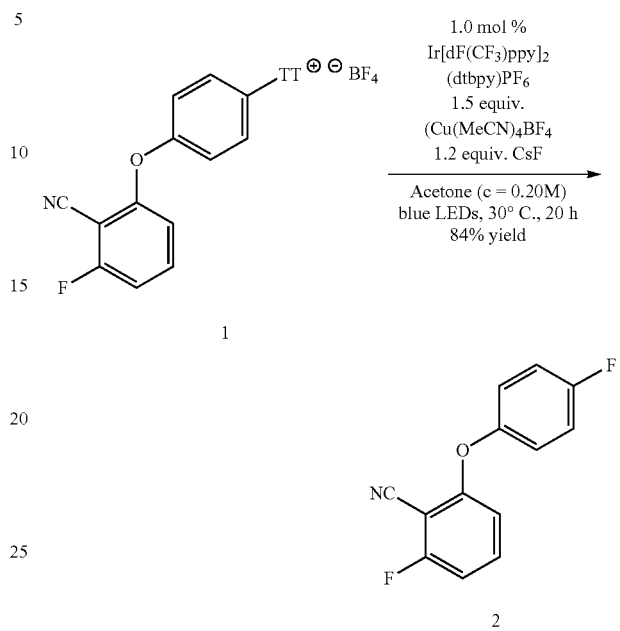

To a 20-mL borosilicate vial equipped with a stir bar was added Ir[dF(CF$_3$)ppy]$_2$(dtbpy)PF$_6$ (22 mg, 20 μmol, 1.0 mol %) and 2-fluoro-6-phenoxybenzonitrile-derived thianthrenium salt 1 (1.03 g, 2.00 mmol, 1.00 equiv.). The vial was transferred into a N$_2$-filled glovebox. After addition of Cu(MeCN)$_4$BF$_4$ (944 mg, 3.00 mmol, 1.50 equiv.), CsF (364 mg, 2.40 mmol, 1.20 equiv.) and acetone (10 mL, c=0.20 M), the vial was capped, transferred out of the glovebox and placed 5 cm away from two 34 W blue LEDs. The temperature was kept at approximately 30° C. through cooling with a fan. After being stirred for 20 h, the reaction mixture was diluted with CH$_2$Cl$_2$ (10 mL), and the resulting mixture was filtered through a short pad of Celite® using CH$_2$Cl$_2$ (15 mL) as eluent. The filtrate was collected and concentrated by rotary evaporation. The residue was purified by chromatography on silica gel eluting with pentane/ethyl acetate (50:1 to 30:1, v/v) to afford 2 (389 mg, 1.68 mmol, 84%) as a colorless solid.

R$_f$=0.32 (hexanes/ethyl acetate 10:1, v/v).

NMR Spectroscopy:

$^1$H NMR (500 MHz, CDCl$_3$, 298 K, δ): 7.47-7.41 (m, 1H), 7.17-7.05 (m, 4H), 6.88 (t, J=8.4 Hz, 1H), 6.56 (d, J=8.6 Hz, 1H) ppm.

$^{13}$C NMR (126 MHz, CDCl$_3$, 298 K, δ): 164.2 (d, J=259.8 Hz), 161.3 (d, J=4.2 Hz), 160.2 (d, J=245.0 Hz), 150.3 (d, J=2.9 Hz), 135.1 (d, J=10.2 Hz), 122.2 (d, J=8.4 Hz), 117.1 (d, J=23.4 Hz), 111.4 (d, J=3.2 Hz), 111.2, 109.9 (d, J=19.7 Hz), 93.6 (d, J=18.3 Hz) ppm.

$^{19}$F NMR (471 MHz, CDCl$_3$, 298 K, δ): −104.52 (t, J=7.4 Hz), −116.49 (m) ppm.

HRMS GC-EI (m/z) calculated for C$_{13}$H$_7$N$_1$O$_1$F$_2^+$ [M]$^+$, 231.049021; found, 231.049340, deviation: −1.38 ppm.

1-Bromo-4-fluoro-2,5-dimethyl-benzene (12)

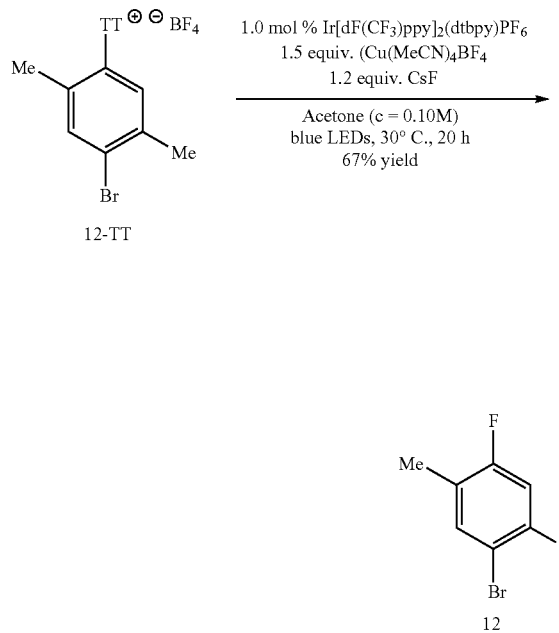

Fluorosalicin Pentaacetate (14)

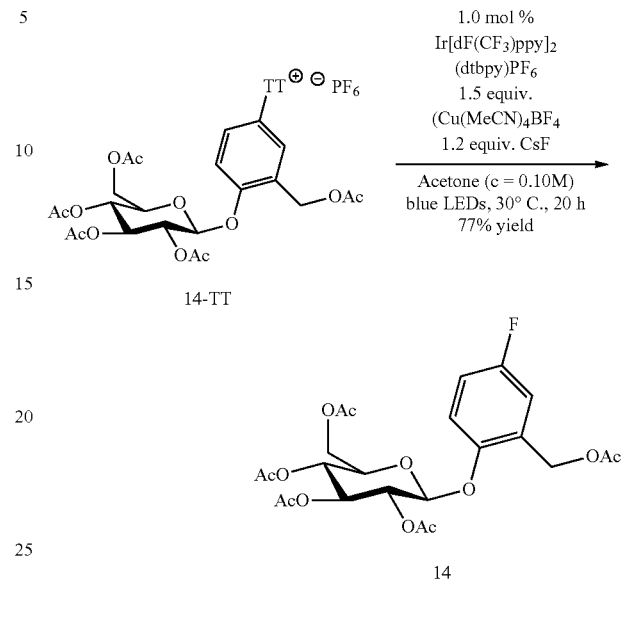

To a 4-mL borosilicate vial equipped with a stir bar was added Ir[dF(CF$_3$)ppy]$_2$(dtbpy)PF$_6$ (3.4 mg, 3.0 µmol, 1.0 mol %) and 4-bromo-m-xylene-derived thianthrenium salt 12-TT (146 mg, 0.300 mmol, 1.00 equiv.). The vial was transferred into a N$_2$-filled glovebox. After addition of Cu(MeCN)$_4$BF$_4$ (142 mg, 0.450 mmol, 1.50 equiv.), CsF (54.7 mg, 0.360 mmol, 1.20 equiv.) and acetone (3.0 mL, c=0.10 M), the vial was capped, transferred out of the glovebox and placed 5 cm away from two 34 W blue LEDs. The temperature was kept at approximately 30° C. through cooling with a fan. After being stirred for 20 h, the reaction mixture was diluted with CH$_2$Cl$_2$ (2 10 mL), and the resulting mixture was filtered through a short pad of Celite® using CH$_2$Cl$_2$ (5 mL) as eluent. The filtrate was collected and concentrated by rotary evaporation at low temperature (approximately 3° C.). The residue was purified by chromatography on silica gel eluting with pentane to afford the mixture of 12 and the corresponding hydro-counterpart 12-H (43.7 mg, 12/12-H=12:1, yield of 12: 67%). Further purification of 12 by chromatography on silica gel eluting with hexanes/CFhCh (200:1, v/v) afforded analytically pure compound 12.

R$_f$=0.70 (pentane).

NMR Spectroscopy:

$^1$H NMR (500 MHz, CDCl$_3$, 298 K, δ): 7.33 (d, J=7.3 Hz, 1H), 6.89 (d, J=10.1 Hz, 1H), 2.33 (s, 3H), 2.21 (s, 3H) ppm.

$^{13}$C NMR (126 MHz, CDCl$_3$, 298 K, δ): 160.4 (d, J=244.4 Hz), 137.0 (d, J=7.8 Hz), 134.6 (d, J=5.4 Hz), 124.2 (d, J=18.5 Hz), 118.5 (d, J=3.2 Hz), 117.3 (d, J=23.3 Hz), 22.7 (d, J=1.2 Hz), 14.0 (d, J=3.0 Hz) ppm.

$^{19}$F NMR (471 MHz, CDCl$_3$, 298 K, δ): −120.19 (m) ppm.

HRMS GC-EI (m/z) calculated for C$_8$H$_8$Br$_1$F$_1$$^+$ [M]$^+$, 201.978804; found, 201.979110, deviation: −1.52 ppm.

To a 4-mL borosilicate vial equipped with a stir bar was added Ir[dF(CF$_3$)ppy]2(dtbpy)PF$_6$ (2.4 mg, 2.1 µmol, 1.0 mol %) and salicin pentaacetate-derived thianthrenium salt 14-TT (171 mg, 0.200 mmol, 1.00 equiv.). The vial was transferred into a N$_2$-filled glovebox. After addition of Cu(MeCN)$_4$BF$_4$ (94.4 mg, 0.300 mmol, 1.50 equiv.), CsF (36.4 mg, 0.240 mmol, 1.20 equiv.) and acetone (2.0 mL, c=0.10 M), the vial was capped, transferred out of the glovebox and placed 5 cm away from two 34 W blue LEDs. The temperature was kept at approximately 30° C. through cooling with a fan. After being stirred for 20 h, the reaction mixture was diluted with CH$_2$Cl$_2$ (2 mL), and the resulting mixture was filtered through a short pad of Celite® using CH$_2$Cl$_2$ (5 mL) as eluent. The filtrate was collected and concentrated by rotary evaporation. The residue was purified by chromatography on silica gel eluting with hexanes/ethyl acetate (40:1, v/v) to afford 14 (79.4 mg, 154 µmol, 77%) as a colorless solid.

R$_f$=0.35 (hexanes/ethyl acetate 3:2, v/v).

NMR Spectroscopy:

$^1$H NMR (500 MHz, CDCl$_3$, 298 K, δ): 7.02 (td, J=8.8, 8.4, 3.8 Hz, 2H), 6.90 (td, J=8.5, 3.2 Hz, 1H), 5.27-5.21 (m, 2H), 5.12 (ddd, J=9.4, 6.3, 3.1 Hz, 1H), 5.06 (d, J=13.5 Hz, 1H), 4.96 (d, J=13.2 Hz, 1H), 4.95 (dd, J=5.4, 2.3 Hz, 1H), 4.23 (dd, J=12.3, 5.3 Hz, 1H), 4.14 (dd, J=12.3, 2.5 Hz, 1H), 3.79 (ddd, J=10.0, 5.3, 2.5 Hz, 1H), 2.08 (s, 3H), 2.07 (s, 3H), 2.03 (s, 3H), 2.00 (s, 3H), 1.99 (s, 3H) ppm.

$^{13}$C NMR (126 MHz, CDCl$_3$, 298 K, δ): 170.5, 170.2, 169.4, 169.3, 158.8 (d, J=242.4 Hz), 150.3 (d, J=2.5 Hz), 128.7 (d, J=7.7 Hz), 118.2 (d, J=8.3 Hz), 115.6 (d, J=24.2 Hz), 115.4 (d, J=23.2 Hz), 100.1, 72.6, 72.1, 71.0, 68.3, 61.9, 60.5, 20.9, 20.7, 20.6 ppm.

$^{19}$F NMR (471 MHz, CDCl$_3$, 298 K, δ): −118.94 (td, J=8.4, 4.4 Hz) ppm.

HRMS-ESI (m/z) calculated for C$_{23}$H$_{27}$F$_1$O$_{12}$Na$^+$ [M+Na]$^+$, 537.137878; found, 537.137930, deviation: −0.10 ppm.

Fluoroflurbiprofen Methylester (19)

Fluorothymol (20)

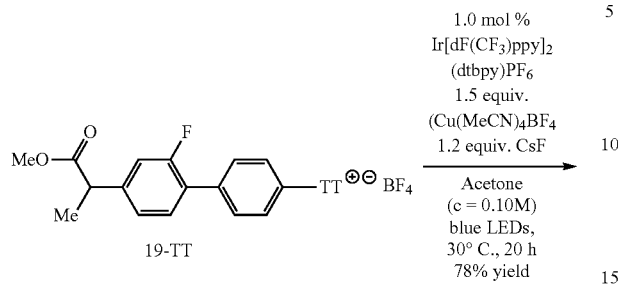

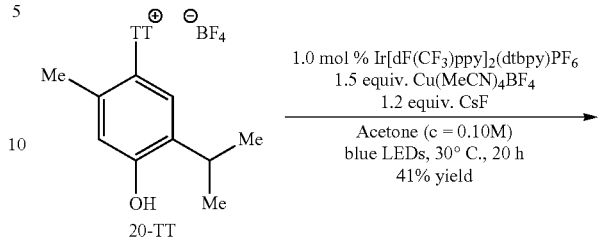

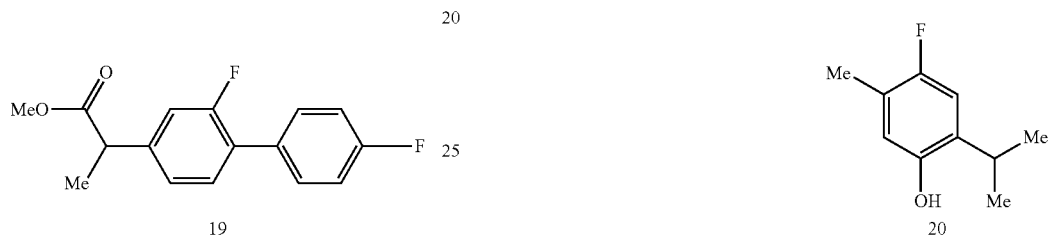

To a 4-mL borosilicate vial equipped with a stir bar was added Ir[dF(CF$_3$)ppy]$_2$(dtbpy)PF$_6$ (2.4 mg, 2.1 μmol, 1.0 mol %) and flurbiprofen methylester-derived thianthrenium salt 19-TT (112 mg, 0.200 mmol, 1.00 equiv.). The vial was transferred into a N$_2$-filled glovebox. After addition of Cu(MeCN)$_4$BF$_4$ (94.4 mg, 0.300 mmol, 1.50 equiv.), CsF (36.4 mg, 0.240 mmol, 1.20 equiv.) and acetone (2.0 mL, c=0.10 M), the vial was capped, transferred out of the glovebox and placed 5 cm away from two 34 W blue LEDs. The temperature was kept at approximately 30° C. through cooling with a fan. After being stirred for 20 h, the reaction mixture was diluted with CH$_2$Cl$_2$ (2 mL), and the resulting mixture was filtered through a short pad of Celite® using CH$_2$Cl$_2$ (5 mL) as eluent. The filtrate was collected and concentrated by rotary evaporation. The residue was purified by chromatography on silica gel eluting with pentane/ethyl acetate (40:1 to 20:1, v/v) to afford 19 (43.0 mg, 156 μmol, 78%) as a colorless liquid.

$R_f$=0.53 (hexanes/ethyl acetate 10:1, v/v).

NMR Spectroscopy:

$^1$H NMR (500 MHz, CDCl$_3$, 298 K, δ): 7.54-7.47 (m, 2H), 7.35 (t, J=8.0 Hz, 1H), 7.19-7.08 (m, 4H), 3.76 (q, J=7.2 Hz, 1H), 3.70 (s, 3H), 1.54 (d, J=7.2 Hz, 3H) ppm.

$^{13}$C NMR (126 MHz, CDCl$_3$, 298 K, δ): 174.5, 162.6 (d, J=246.8 Hz), 159.7 (d, J=248.1 Hz), 142.1 (d, J=7.2 Hz), 131.6 (d, J=3.8 Hz), 130.8 (d, J=3.6 Hz), 130.7 (dd, J=8.2, 2.5 Hz), 127.0 (d, J=14.3 Hz), 123.7 (d, J=3.5 Hz), 115.6 (d, J=21.5 Hz), 115.4 (d, J=23.62 Hz), 52.4, 45.1, 18.6 ppm.

$^{19}$F NMR (471 MHz, CDCl$_3$, 298 K, δ): −114.52 (m), −117.69 (t, J=9.8 Hz) ppm.

HRMS GC-EI (m/z) calculated for C$_{16}$H$_{14}$O$_2$F$_2^+$ [M]$^+$, 276.095637; found, 276.096080, deviation: −1.60 ppm.

To a 4-mL borosilicate vial equipped with a stir bar was added Ir[dF(CF$_3$)ppy]2(dtbpy)PF$_6$ (2.4 mg, 2.1 μmol, 1.0 mol %) and thymol-derived thianthrenium salt 20-TT (90.5 mg, 0.200 mmol, 1.00 equiv.). The vial was transferred into a N$_2$-filled glovebox. After addition of Cu(MeCN)$_4$BF$_4$ (94.4 mg, 0.300 mmol, 1.50 equiv.), CsF (36.4 mg, 0.240 mmol, 1.20 equiv.) and acetone (2.0 mL, c=0.10 M), the vial was capped, transferred out of the glovebox and placed 5 cm away from two 34 W blue LEDs. The temperature was kept at approximately 30° C. through cooling with a fan. After being stirred for 20 h, the reaction mixture was diluted with CH$_2$Cl$_2$ (2 mL), and the resulting mixture was filtered through a short pad of Celite® using CH$_2$Cl$_2$ (5 mL) as eluent. The filtrate was collected and concentrated by rotary evaporation. The residue was purified by chromatography on silica gel eluting with isohexane/ethyl acetate (40:1+2% CH$_2$Cl$_2$, v/v/v) to afford 20 (13.8 mg, 82.0 μmol, 41%) as a slight yellow solid.

$R_f$=0.41 (pentane/ethyl acetate 10:1, v/v).

NMR Spectroscopy:

$^1$H NMR (500 MHz, CDCl$_3$, 298 K, δ): 6.83 (d, J=10.6 Hz, 1H), 6.55 (d, J=6.6 Hz, 1H), 4.48 (br, 1H), 3.13 (hept, J=6.9 Hz, 1H), 2.19 (d, J=1.6 Hz, 3H), 1.22 (d, J=6.9 Hz, 6H) ppm.

$^{13}$C NMR (126 MHz, CDCl$_3$, 298 K, δ): 156.1 (d, J=236.1 Hz), 148.3 (d, J=1.9 Hz), 133.5 (d, J=6.5 Hz), 122.4 (d, J=19.1 Hz), 117.7 (d, J=5.0 Hz), 112.7 (d, J=23.9 Hz), 27.0, 22.7, 14.3 (d, J=3.2 Hz) ppm.

$^{19}$F NMR (471 MHz, CDCl$_3$, 298 K, δ): −127.90 (t, J=8.9 Hz) ppm.

HRMS GC-EI (m/z) calculated for C$_{10}$H$_{13}$O$_1$F$_1^+$ [M]$^+$, 168.094494; found, 168.094710, deviation: −1.29 ppm.

2-Fluoro-9H-xanthen-9-one (23)

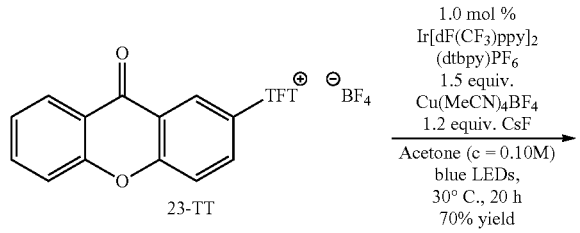

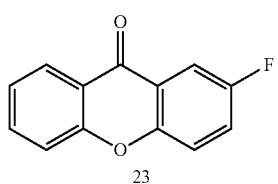

To a 4-mL borosilicate vial equipped with a stir bar was added Ir[dF(CF$_3$)ppy]2(dtbpy)PF$_6$ (2.4 mg, 2.1 μmol, 1.0 mol %) and xanthone-9-one-derived thianthrenium salt 23-TFT (114 mg, 0.200 mmol, 1.00 equiv.). The vial was transferred into a N$_2$-filled glovebox. After addition of Cu(MeCN)$_4$BF$_4$ (94.4 mg, 0.300 mmol, 1.50 equiv.), CsF (36.4 mg, 0.240 mmol, 1.20 equiv.) and acetone (2.0 mL, c=0.10 M), the vial was capped, transferred out of the glovebox and placed 5 cm away from two 34 W blue LEDs. The temperature was kept at approximately 30° C. through cooling with a fan. After being stirred for 20 h, the reaction mixture was diluted with CH$_2$Cl$_2$ (2 mL), and the resulting mixture was filtered through a short pad of Celite® using CH$_2$Cl$_2$ (5 mL) as eluent. The filtrate was collected and concentrated by rotary evaporation. The residue was purified by chromatography on silica gel eluting with pentane/ethyl acetate (30:1, v/v) to afford 23 (29.9 mg, 140 μmol, 70%) as a colorless solid.

R$_f$=0.42 (hexanes/ethyl acetate 10:1, v/v).

NMR Spectroscopy:

$^1$H NMR (500 MHz, CDCl$_3$, 298 K, δ): 8.30 (d, J=7.9 Hz, 1H), 7.94 (dd, J=8.3, 3.0 Hz, 1H), 7.72 (t, J=7.8 Hz, 1H), 7.52-7.40 (m, 3H), 7.37 (t, J=7.5 Hz, 1H) ppm.

$^{13}$C NMR (126 MHz, CDCl$_3$, 298 K, δ): 176.6 (d, J=2.4 Hz), 158.8 (d, J=245.1 Hz), 156.2, 152.5 (d, J=1.5 Hz), 135.2, 126.8, 124.3, 123.0 (d, J=25.5 Hz), 122.8 (d, J=7.1 Hz), 121.1, 120.1 (d, J=7.7 Hz), 118.1, 111.5 (d, J=23.7 Hz) ppm.

$^{19}$F NMR (471 MHz, CDCl$_3$, 298 K, δ): −117.10 (m) ppm.

HRMS-ESI (m/z) calculated for C$_{13}$H$_7$F$_1$O$_2$Na$^+$ [M+Na]$^+$, 237.032228; found, 237.032310, deviation: −0.35 ppm.

Fluoroindomethacin Methylester (24)

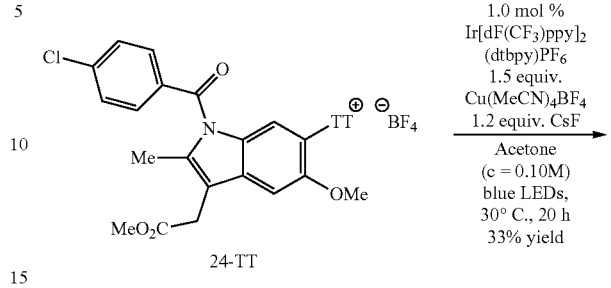

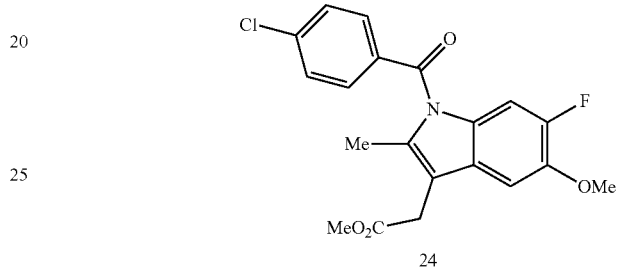

To a 4-mL borosilicate vial equipped with a stir bar was added Ir[dF(CF$_3$)ppy]$_2$(dtbpy)PF$_6$ (2.4 mg, 2.1 μmol, 1.0 mol %) and indomethacin methylester-derived thianthrenium salt 24-TT (135 mg, 0.200 mmol, 1.00 equiv.). The vial was transferred into a N$_2$-filled glovebox. After addition of Cu(MeCN)$_4$BF$_4$ (94.4 mg, 0.300 mmol, 1.50 equiv.), CsF (36.4 mg, 0.240 mmol, 1.20 equiv.) and acetone (2.0 mL, c=0.10 M), the vial was capped, transferred out of the glovebox and placed 5 cm away from two 34 W blue LEDs. The temperature was kept at approximately 30° C. through cooling with a fan. After being stirred for 20 h, the reaction mixture was diluted with CH$_2$Cl$_2$ (2 mL), and the resulting mixture was filtered through a short pad of Celite® using CH$_2$Cl$_2$ (5 mL) as eluent. The filtrate was collected and concentrated by rotary evaporation. The residue was purified by chromatography on silica gel eluting with hexanes/ethyl acetate (10:1 to 6:1, v/v) to afford 24 (25.7 mg, 66.0 μmol, 33%) as a yellow solid.

R$_f$=0.38 (hexanes/ethyl acetate 5:1, v/v).

NMR Spectroscopy:

$^1$H NMR (500 MHz, CDCl$_3$, 298 K, δ): 7.65 (d, J=8.2 Hz, 2H), 7.48 (d, J=7.6 Hz, 2H), 7.01 (d, J=8.0 Hz, 1H), 6.87 (d, J=12.8 Hz, 1H), 3.93 (s, 3H), 3.71 (s, 3H), 3.65 (s, 2H), 2.31 (s, 3H) ppm.

$^{13}$C NMR (126 MHz, CDCl$_3$, 298 K, δ): 171.3, 168.3, 150.5 (d, J=241.5 Hz), 145.1 (d, J=12.5 Hz), 139.7, 135.2 (d, J=4.2 Hz), 133.6, 131.2, 129.4, 129.3, 125.4 (d, J=1.9 Hz), 112.3 (d, J=1.5 Hz), 102.9 (d, J=25.5 Hz), 102.0 (d, J=2.3 Hz), 56.8, 52.3, 30.3, 13.5 ppm.

$^{19}$F NMR (471 MHz, CDCl$_3$, 298 K, δ): −137.96 (dd, J=12.0, 8.3 Hz) ppm.

HRMS-ESI (m/z) calculated for C$_{20}$H$_{17}$Cl$_1$F$_1$N$_1$O$_4$Na$^+$ [M+Na]$^+$, 412.072234; found, 412.072540, deviation: −0.74 ppm.

3-(4-Fluorophenyl)-3-phenylpropan-1-ol (26)

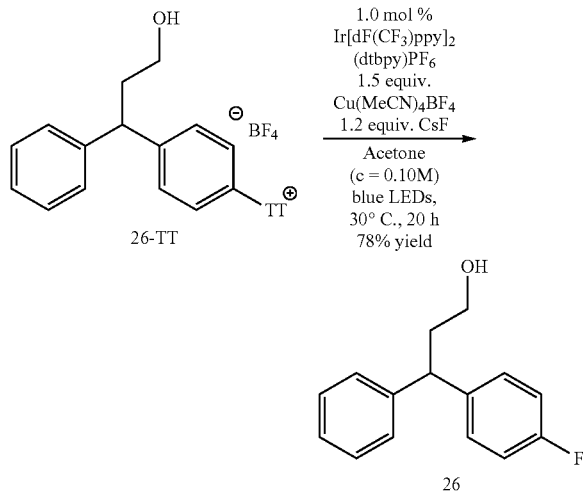

To a 20-mL borosilicate vial equipped with a stir bar was added Ir[dF(CF$_3$)ppy]2(dtbpy)PF$_6$ (5.6 mg, 0.5.0 µmol, 1.0 mol %) and 3,3-diphenylpropan-1-ol-derived thianthrenium salt 26-TT (257 mg, 0.500 mmol, 1.00 equiv.). The vial was transferred into a N$_2$-filled glovebox. After addition of Cu(MeCN)$_4$BF$_4$ (236 mg, 0.750 mmol, 1.50 equiv.), CsF (91.1 mg, 0.600 mmol, 1.20 equiv.) and acetone (5.0 mL, c=0.10 M), the vial was capped, transferred out of the glovebox and placed 5 cm away from two 34 W blue LEDs. The temperature was kept at approximately 30° C. through cooling with a fan. After being stirred for 20 h, the reaction mixture was diluted with CH$_2$Cl$_2$ (4 mL), and the resulting mixture was filtered through a short pad of Celite® using CH$_2$Cl$_2$ (10 mL) as eluent. The filtrate was collected and concentrated by rotary evaporation. The residue was purified by chromatography on silica gel eluting with pentane/ethyl acetate (8:1 to 6:1+2% CH$_2$Cl$_2$, v/v/v) to afford 26 (90.0 mg, 391 µmol, 78%) as a colorless solid.

R$_f$=0.23 (pantane/ethyl acetate 4:1, v/v).

NMR Spectroscopy:

$^1$H NMR (500 MHz, CDCl$_3$, 298 K, δ): 7.37 (t, J=7.5 Hz, 2H), 7.34-7.26 (m, 5H), 7.05 (t, J=8.7 Hz, 2H), 4.21 (t, J=7.9 Hz, 1H), 3.66 (t, J=6.4 Hz, 2H), 2.46-2.29 (m, 2H), 1.66 (br, 1H) ppm.

$^{13}$C NMR (126 MHz, CDCl$_3$, 298 K, δ): 161.5 (d, J=244.4 Hz), 144.4, 140.3 (d, J=3.1 Hz), 129.3 (d, J=7.8 Hz), 128.7, 127.9, 126.5, 115.4 (d, J=21.0 Hz), 60.9, 46.6, 38.4 ppm.

$^{19}$F NMR (471 MHz, CDCl$_3$, 298 K, δ): −116.96 (ddd, J=14.0, 8.7, 5.4 Hz) ppm.

HRMS GC-EI (m/z) calculated for C$_{15}$H$_{15}$O$_1$F$_1$$^+$ [M]$^+$, 230.110143; found, 230.110090, deviation: +0.23 ppm.

Fluoroamiodarone (29)

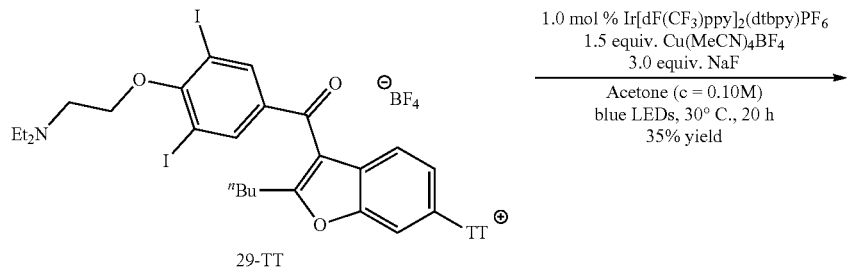

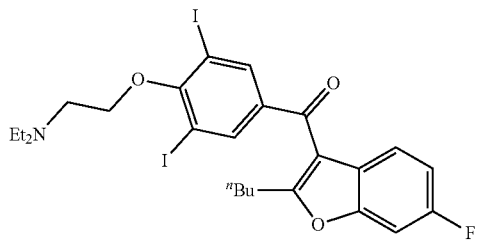

To a 4-mL borosilicate vial equipped with a stir bar was added Ir[dF(CF$_3$)ppy]2(dtbpy)PF$_6$ (1.2 mg, 1.0 μmol, 1.0 mol %) and amiodarone-derived thianthrenium salt 29-TT (102 mg, 0.100 mmol, 1.00 equiv.). The vial was transferred into a N$_2$-filled glovebox. After addition of Cu(MeCN)$_4$BF$_4$ (47.4 mg, 0.150 mmol, 1.50 equiv.), NaF (12.6 mg, 0.300 mmol, 3.00 equiv.) and acetone (1.0 mL, c=0.10 M), the vial was capped, transferred out of the glovebox and placed 5 cm away from two 34 W blue LEDs. The temperature was kept at approximately 30° C. through cooling with a fan. After being stirred for 20 h, the reaction mixture was diluted with CH$_2$Cl$_2$ (2 mL), and the resulting mixture was filtered through a short pad of Celite® using CH$_2$Cl$_2$ (5 mL) as eluent. The filtrate was collected and concentrated by rotary evaporation. The residue was purified by chromatography on silica gel eluting with CH$_2$Cl$_2$/MeOH (100:1 to 20:1+2% Et$_3$N, v/v/v) to afford the title compound 29 with minor impurities. Further purification of 29 by HPLC (YMC-Actus Triart C18 (30×150 mm: 5 μm), MeOH/20 mM NH$_4$HCO$_3$=98:2, flow rate=42.5 mL/min, 25° C., retention time; 10.6 min) provided 29 (23.1 mg, 35.0 μmol, 35% yield; >99% pure by HPLC).

R$_f$=0.29 (CH$_2$Cl$_2$/MeOH 20:1, v/v).

NMR Spectroscopy:

$^1$H NMR (500 MHz, CDCl$_3$, 298 K, δ): 8.19 (s, 2H), 7.39 (dd, J=8.7, 5.3 Hz, 1H), 7.21 (dd, J=8.6, 2.3 Hz, 1H), 7.02 (ddd, J=9.4, 8.6, 2.3 Hz, 1H), 4.18 (t, J=6.5 Hz, 2H), 3.16 (t, J=6.1 Hz, 2H), 2.80 (dd, J=10.3, 5.2 Hz, 6H), 1.85-1.67 (m, 2H), 1.35 (h, J=7.4 Hz, 2H), 1.16 (t, J=7.1 Hz, 6H), 0.91 (t, J=7.3 Hz, 3H) ppm.

$^{13}$C NMR (126 MHz, CDCl$_3$, 298 K, δ): 187.6, 166.7 (d, J=3.6 Hz), 161.6, 161.0 (d, J=243.9 Hz), 153.8 (d, J=13.2 Hz), 140.8, 138.3, 122.9 (d, J=1.8 Hz), 121.7 (d, J=9.7 Hz), 115.8, 112.3 (d, J=23.7 Hz), 99.2 (d, J=26.5 Hz), 91.0, 52.1, 47.9, 30.1, 28.4, 22.7, 13.9, 11.8 ppm.

$^{19}$F NMR (471 MHz, CDCl$_3$, 298 K, δ): −116.32 (m) ppm.

HRMS-ESI (m/z) calculated for C$_{25}$H$_{29}$F$_1$I$_2$N$_1$O$_3^+$ [M+H]$^+$, 664.021542; found, 664.022040, deviation: −0.75 ppm.

Fluoropyriproxyfen (39)

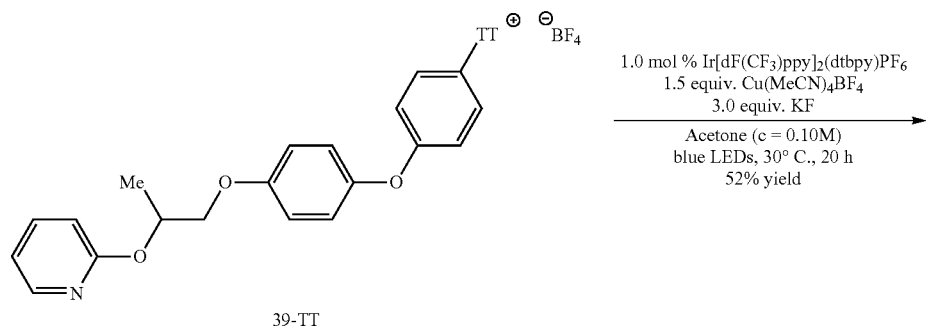

39-TT

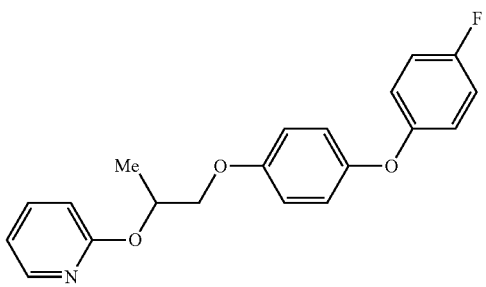

39

To a 4-mL borosilicate vial equipped with a stir bar was added Ir[dF(CF$_3$)ppy]2(dtbpy)PF$_6$ (1.2 mg, 1.0 μmol, 1.0 mol %) and pyriproxyfen-derived thianthrenium salt 39-TT (62.3 mg, 0.100 mmol, 1.00 equiv.). The vial was transferred into a N$_2$-filled glovebox. After addition of Cu(MeCN)$_4$BF$_4$ (47.2 mg, 0.150 mmol, 1.50 equiv.), KF (18.2 mg, 0.300 mmol, 3.00 equiv.) and acetone (1.0 mL, c=0.10 M), the vial was capped, transferred out of the glovebox and placed 5 cm away from two 34 W blue LEDs. The temperature was kept at approximately 30° C. through cooling with a fan. After being stirred for 20 h, the reaction mixture was diluted with CH$_2$Cl$_2$ (2 mL), and the resulting mixture was filtered through a short pad of Celite® using CH$_2$Cl$_2$ (5 mL) as eluent. The filtrate was collected and concentrated by rotary evaporation. The residue was purified by chromatography on silica gel eluting with pentane/ethyl acetate (40:1 to 25:1, v/v) to afford the title compound with minor impurities. Further purification by chromatography on silica gel eluting with toluene/CH$_2$Cl$_2$ (3:1, v/v) provided the title compound 39 (17.6 mg, 52.0 μmol, 52%) as a colorless liquid.

R$_f$=0.30 (pentane/ethyl acetate 20:1, v/v).

NMR Spectroscopy:

$^1$H NMR (500 MHz, CDCl$_3$, 298 K, δ): 8.16-8.14 (m, 1H), 7.63-7.52 (m, 1H), 6.98 (t, J=8.6 Hz, 2H), 6.94-6.88 (s, 6H), 6.88-6.84 (m, 1H), 6.74 (d, J=8.3 Hz, 1H), 5.58 (h, J=6.3, 5.7 Hz, 1H), 4.18 (dd, J=9.8, 5.3 Hz, 1H), 4.07 (dd, J=9.8, 4.8 Hz, 1H), 1.48 (d, J=6.4 Hz, 3H) ppm.

$^{13}$C NMR (126 MHz, CDCl$_3$, 298 K, δ): 163.3, 158.5 (d, J=240.7 Hz), 155.3, 154.4 (d, J=2.7 Hz), 150.9, 146.9, 138.8, 120.3, 119.3 (d, J=8.42 Hz), 116.2 (d, J=23.36 Hz), 116.1, 116.0, 111.8, 71.2, 69.4, 17.2 ppm.

$^{19}$F NMR (471 MHz, CDCl$_3$, 298 K, δ): −121.37 (m) ppm.

HRMS-ESI (m/z) calculated for C$_{20}$H$_{19}$F$_1$N$_1$O$_3$$^+$ [M+H]$^+$, 340.134347; found, 340.134380, deviation: −0.10 ppm.

Salicin Pentaacetate-Derived Thianthrenium Salt 14-TT

Under ambient atmosphere, a 20 mL borosilicate vial was charged with salicin pentaacetat[1] (248 mg, 0.500 mmol, 1.00 equiv.), thianthrene-S-oxide (116 mg, 0.500 mmol, 1.00 equiv.) and dry MeCN (2.0 mL, c=0.25 M). After cooling to 0° C., trifluoroacetic anhydride (0.21 mL, 0.32 g, 1.5 mmol, 3.0 equiv.) addition at 0° C. in one portion, followed by HBF$_4$OEt$_2$ (87 μL, 0.60 mmol, 1.2 equiv.) was added in one portion at 0° C. The vial was sealed with a screw-cap, and the mixture was stirred at 0° C. for 1 h, followed by warming the reaction mixture to 25° C. over a period of 1 h. After stirring at 25° C. for 1 h further, the reaction mixture was concentrated under reduced pressure, and diluted with 10 mL CH$_2$Cl$_2$. The CH$_2$Cl$_2$ phase was poured onto a saturated aqueous NaHCO$_3$ solution (ca. 10 mL). The mixture was poured into a separatory funnel, and the layers were separated. The CH$_2$Cl$_2$ layer was collected, and the aqueous layer was further extracted with CH$_2$Cl$_2$ (2×ca. 10 mL). The combined CH$_2$Cl$_2$ solution was washed with aqueous NaPF$_6$ solution (2×ca. 10 mL, 5% w/w). The organic layer was dried over Na$_2$SO$_4$, filtered, and the solvent was removed under reduced pressure. The residue was purified by chromatography on silica gel eluting with CH$_2$Cl$_2$/i-PrOH (50:1, v/v). The product was collected and dried in vacuo to afford 14-TT (400 mg, 467 μmol, 93%) as a colorless solid.

R$_f$=0.35 (CH$_2$Cl$_2$/MeOH, 15:1, v/v).

NMR Spectroscopy:

$^1$H NMR (500 MHz, CD$_2$Cl$_2$, 298 K, δ): 8.34 (dt, J=7.8, 1.5 Hz, 2H), 7.97 (dt, J=7.9, 1.8 Hz, 2H), 7.91 (tt, J=7.9, 1.4 Hz, 2H), 7.84 (td, J=7.7, 1.5 Hz, 2H), 7.25 (d, J=1.3 Hz, 2H), 7.13 (s, 1H), 5.37-5.28 (m, 2H), 5.24 (d, J=7.2 Hz, 1H), 5.17 (t, J=9.4 Hz, 1H), 4.96 (d, J=2.1 Hz, 2H), 4.28 (dd, J=12.5, 4.9 Hz, 1H), 4.15 (dd, J=12.5, 2.4 Hz, 1H), 3.98 (ddd, J=10.1, 4.9, 2.5 Hz, 1H), 2.06 (s, 3H), 2.05 (s, 3H), 2.03 (s, 3H), 2.02 (s, 3H), 2.01 (s, 3H) ppm.

$^{13}$C NMR (126 MHz, CD$_2$Cl$_2$, 298 K, δ): 170.6, 170.4, 170.1, 169.7, 169.6, 158.0, 137.0 (d, J=2.5 Hz), 135.6, 134.6 (d, J=4.5 Hz), 131.0 (d, J=3.9 Hz), 130.7, 130.3, 129.7, 128.7, 118.8, 117.1, 116.3, 98.4, 72.6, 72.4, 70.9, 68.2, 61.9, 20.8, 20.74, 20.72 ppm.

$^{19}$F NMR (471 MHz, CD$_2$Cl$_2$, 298 K, δ): −72.30 (d, J=711.2 Hz) ppm.

HRMS-ESI (m/z) calculated for C$_{35}$H$_{35}$O$_{12}$S$_2$$^+$ [M-PF$_6$]$^+$, 711.156450; found, 711.157400; deviation: −1.34 ppm.

Thymol-Derived Thianthrenium Salt 20-TT

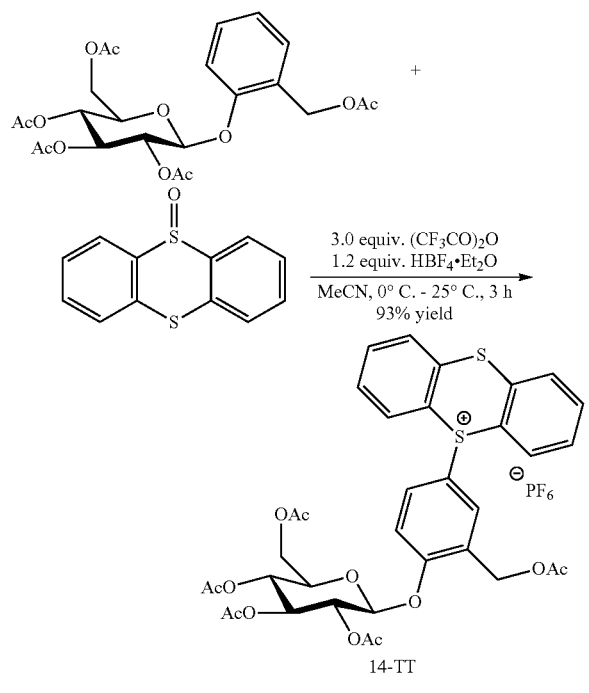

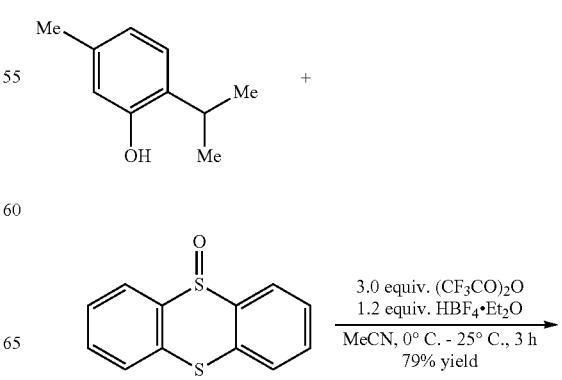

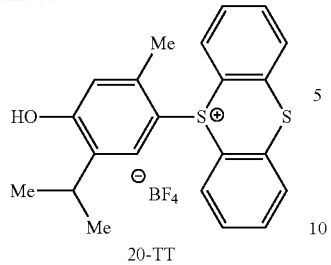

20-TT

Under ambient atmosphere, a 20 mL borosilicate vial was charged with thymol (300 mg, 2.00 mmol, 1.00 equiv.), thianthrene-S-oxide (466 mg, 2.00 mmol, 1.00 equiv.) and dry MeCN (8.0 mL, c=0.25 M). After cooling to 0° C., HBF$_4$OEt$_2$ (348 µL, 2.40 mmol, 1.20 equiv.) was added in one portion at 0° C., followed by trifluoroacetic anhydride (840 µL, 1.27 g, 6.00 mmol, 3.00 equiv.) addition at 0° C. in one portion. The vial was sealed with a screw-cap, and the orange solution was allowed to stand at 0° C. for 1 h, followed by warming the reaction mixture to 25° C. over a period of 1 h. After stirring at 25° C. for 1 h further, the resulting beige solution was concentrated under reduced pressure, and diluted with 10 mL CH$_2$Cl$_2$. The CH$_2$Cl$_2$ solution was poured onto a saturated aqueous NaHCO$_3$ solution (ca. 10 mL). The mixture was poured into a separatory funnel, and the layers were separated. The CH$_2$Cl$_2$ layer was collected, and the aqueous layer was further extracted with CH$_2$Cl$_2$ (2×ca. 10 mL). The combined CH$_2$Cl$_2$ solution was washed with aqueous NaBF$_4$ solution (2×ca. 20 mL, 5% w/w). The CH$_2$Cl$_2$ layer was dried over Na$_2$SO$_4$, filtered, and the solvent was removed under reduced pressure. The residue was purified by chromatography on silica gel eluting with CH$_2$Cl$_2$/i-PrOH (50:1, v/v). The product was dissolved in 2 mL CH$_2$Cl$_2$, and precipitated with 10 mL Et$_2$O. The suspension was decanted, and the solid was dried in vacuo to afford 20-TT (714 mg, 1.58 mmol, 79%) as a colorless solid.

R$_f$=0.35 (CH$_2$Cl$_2$/MeOH, 15:1, v/v).

NMR Spectroscopy:

$^1$H NMR (500 MHz, CD$_2$Cl$_2$, 298 K, δ): 7.92 (d, J=7.9 Hz, 2H), 7.77 (td, J=7.6, 1.5 Hz, 2H), 7.72 (d, J=7.7 Hz, 2H), 7.67 (td, J=7.7, 1.2 Hz, 2H), 7.21 (s, 1H), 6.99 (s, 1H), 3.22 (p, J=6.9 Hz, 1H), 2.54 (s, 3H), 1.05 (d, J=7.0 Hz, 6H) ppm.

$^{13}$C NMR (126 MHz, CD$_2$Cl$_2$, 298 K, δ): 161.5, 142.5, 137.7, 135.2, 134.2, 131.0, 130.9, 130.4, 130.3, 122.8, 120.8, 106.3, 27.2, 22.0, 20.1 ppm.

$^{19}$F NMR (471 MHz, CD$_2$Cl$_2$, 298 K, δ): −150.74 (bs), −150.79 (bs) ppm.

HRMS-ESI (m/z) calculated for C$_{22}$H$_{21}$O$_1$S$_2^+$ [M-BF$_4$]$^+$, 365.102835; found, 365.103090; deviation: −0.70 ppm.

Xanthone-Derived Thianthrenium Salt 23-TFT

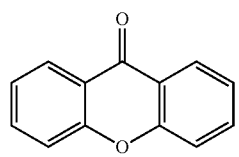
+

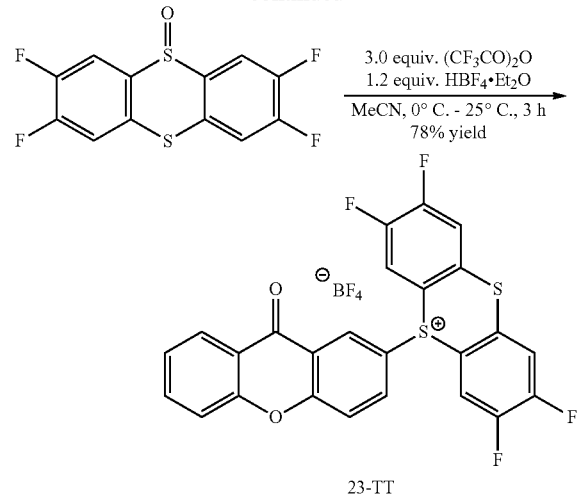

23-TT

Under ambient atmosphere, a 20 mL borosilicate vial was charged with xanthone (392 mg, 2.00 mmol, 1.00 equiv.), tetrafluorothianthrene-S-oxide (628 mg, 2.00 mmol, 1.00 equiv.) and dry MeCN (2.0 mL, c=0.25 M). After cooling to 0° C., trifluoroacetic anhydride (840 µL, 1.27 g, 6.00 mmol, 3.00 equiv.) addition at 0° C. in one portion, followed by HBF$_4$OEt$_2$ (348 µL, 2.40 mmol, 1.20 equiv.) was added in one portion at 0° C. The vial was sealed with a screw-cap, and the mixture was stirred at 0° C. for 1 h, followed by warming the reaction mixture to 25° C. over a period of 1 h. After stirring at 25° C. for 1 h further, the reaction mixture was concentrated under reduced pressure, and diluted with 10 mL CH$_2$Cl$_2$. The CH$_2$Cl$_2$ solution was poured onto a saturated aqueous NaHCO$_3$ solution (ca. 10 mL). The mixture was poured into a separatory funnel, and the layers were separated. The CH$_2$Cl$_2$ layer was collected, and the aqueous layer was further extracted with CH$_2$Cl$_2$ (2×ca. 10 mL). The combined CH$_2$Cl$_2$ solution was washed with aqueous NaBF$_4$ solution (2×ca. 10 mL, 5% w/w). The CH$_2$Cl$_2$ layer was dried over Na$_2$SO$_4$, filtered, and the solvent was removed under reduced pressure. The residue was purified by chromatography on silica gel eluting with CH$_2$Cl$_2$/i-PrOH (50:1, v/v). The product was dissolved in 2 mL CH$_2$Cl$_2$, and precipitated with 10 mL Et$_2$O. The suspension was decanted, and the solid was dried in vacuo to afford 23-TFT (890 mg, 1.56 mmol, 78%) as a colorless solid.

Rf=0.35 (CH$_2$Cl$_2$/MeOH, 15:1, v/v).

NMR Spectroscopy:

$^1$H NMR (500 MHz, DMSO-d$_6$, 298 K, δ): 8.93 (dd, J=9.7, 7.3 Hz, 2H), 8.44 (dd, J=10.2, 7.2 Hz, 2H), 8.20 (d, J=2.7 Hz, 1H), 8.16 (dd, J=8.0, 1.7 Hz, 1H), 7.93 (ddd, J=8.7, 7.1, 1.7 Hz, 1H), 7.83 (d, J=9.2 Hz, 1H), 7.73-7.69 (m, 2H), 7.54 (ddd, J=8.1, 7.1, 1.0 Hz, 1H) ppm.

$^{13}$C NMR (126 MHz, DMSO-d$_6$, 298 K, δ): 174.7, 157.5, 155.4, 152.7 (dd, J=260.2, 13.0 Hz), 149.3 (dd, J=253.3, 13.4 Hz), 136.5, 134.3, 133.3 (dd, J=8.7, 3.4 Hz), 127.8, 126.1, 125.4 (d, J=22.2 Hz), 125.4, 122.0, 121.0, 120.8, 119.9 (d, J=21.8 Hz), 119.7, 118.4, 115.8 (dd, J=7.5, 3.0 Hz) ppm.

$^{19}$F NMR (471 MHz, DMSO-d$_6$, 298 K, δ): −125.40 (dt, J=23.6, 8.7 Hz), −133.87 (dt, J=23.1, 8.6 Hz)), −148.22 (bs), −148.28 (bs) ppm.

HRMS-ESI (m/z) calculated for C$_{25}$H$_{11}$F$_4$O$_2$S2$^+$ [M-BF$_4$]$^+$, 483.013114; found, 483.013440; deviation: −0.67 ppm.

3,3-Diphenylpropan-1-ol-Derived Thianthrenium Salt 26-TT

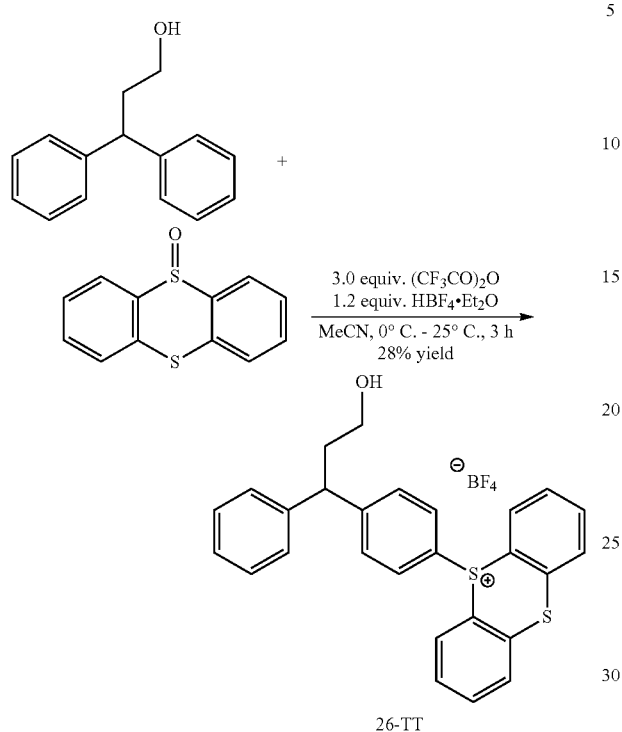

26-TT

Under ambient atmosphere, a 50 mL round-bottom flask was charged with 3,3-diphenylpropan-1-ol (1.15 g, 5.40 mmol, 1.00 equiv.), thianthrene-S-oxide (1.26 g, 5.40 mmol, 1.00 equiv.) and dry MeCN (22 mL, c=0.25 M). After cooling to 0° C., trifluoroacetic anhydride (2.24 mL, 3.44 g, 16.2 mmol, 3.00 equiv.) was added in one portion at 0° C., followed by $HBF_4 \cdot OEt_2$ (886 µL, 6.48 mmol, 1.20 equiv.) addition at 0° C. in one portion. The flask was sealed with a septum, which was equipped with a balloon. The mixture was allowed to stir at 0° C. for 1 h, followed by warming the reaction mixture to 25° C. over a period of 1 h. After stirring at 25° C. for 1 h further, the reaction mixture was concentrated under reduced pressure, and diluted with 20 mL $CH_2Cl_2$. The $CH_2Cl_2$ solution was poured onto a saturated aqueous $NaHCO_3$ solution (ca. 20 mL). After stirring at 25° C. for 2 h, the mixture was poured into a separatory funnel, and the layers were separated. The $CH_2Cl_2$ layer was collected, and the aqueous layer was further extracted with $CH_2Cl_2$ (2×ca. 10 mL). The combined $CH_2Cl_2$ solution was washed with aqueous $NaBF_4$ solution (2×ca. 20 mL, 5% w/w). The $CH_2Cl_2$ layer was dried over $Na_2SO_4$, filtered, and the solvent was removed under reduced pressure. The residue was purified by chromatography on silica gel eluting with $CH_2Cl_2$/i-PrOH (50:1 to 30:1, v/v). The product was collected and dried in vacuo to afford 26-TT (790 mg, 1.54 mmol, 28%) as a colorless foam.

$R_f$=0.28 ($CH_2Cl_2$/MeOH, 15:1, v/v).

NMR Spectroscopy:

$^1$H NMR (500 MHz, $CD_3CN$, 298 K, δ): 8.32 (d, J=7.9 Hz, 2H), 7.94 (d, J=7.9 Hz, 2H), 7.87 (t, J=7.7 Hz, 2H), 7.80 (t, J=7.3 Hz, 2H), 7.41 (d, J=8.7 Hz, 2H), 7.31-7.25 (m, 2H), 7.22 (d, J=6.9 Hz, 2H), 7.18 (t, J=7.1 Hz, 1H), 7.05 (d, J=8.8 Hz, 2H), 4.18 (t, J=7.8 Hz, 1H), 3.33 (t, J=5.8 Hz, 2H), 2.24-2.15 (m, 3H) ppm.

$^{13}$C NMR (126 MHz, $CD_3CN$, 298 K, δ): 152.2, 144.4, 137.5, 136.1, 135.9, 131.7, 131.0, 130.9, 129.7, 129.2, 128.7, 127.7, 122.1, 119.52, 119.50, 60.1, 47.6, 38.3 ppm.

$^{19}$F NMR (471 MHz, $CD_3CN$, 298 K, δ): −151.73 (bs), −151.79 (bs) ppm.

HRMS-ESI (m/z) calculated for $C_{27}H_{23}O_1S_2^+$ [M-BF$_4$]$^+$, 427.118485; found, 427.118620; deviation: −0.32 ppm.

Gemfibrozil Methylester-Derived Thianthrenium Salt 38-TT

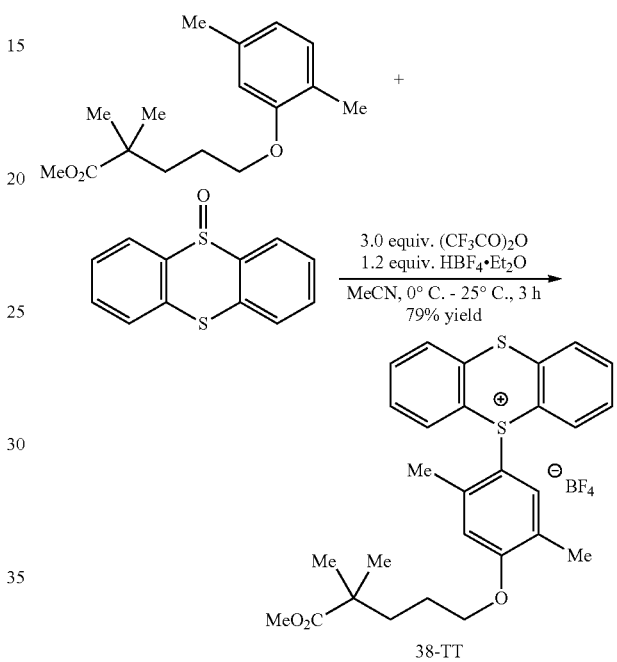

38-TT

Under ambient atmosphere, a 20 mL borosilicate vial was charged with methyl gemfibrozil[3] (528 mg, 2.00 mmol, 1.00 equiv.), thianthrene-S-oxide (464 mg, 2.00 mmol, 1.00 equiv.) and dry MeCN (8.0 mL, c=0.25 M). After cooling to 0° C., trifluoroacetic anhydride (840 µL, 1.27 g, 6.00 mmol, 3.00 equiv.) addition at 0° C. in one portion, followed by $HBF_4OEt_2$ (348 µL, 2.40 mmol, 1.20 equiv.) was added in one portion at 0° C. The vial was sealed with a screw-cap, and the mixture was stirred at 0° C. for 1 h, followed by warming the reaction mixture to 25° C. over a period of 1 h. After stirring at 25° C. for 1 h further, the reaction mixture was concentrated under reduced pressure, and diluted with 10 mL $CH_2Cl_2$. The $CH_2Cl_2$ phase was poured onto a saturated aqueous $NaHCO_3$ solution (ca. 10 mL). The mixture was poured into a separatory funnel, and the layers were separated. The $CH_2Cl_2$ layer was collected, and the aqueous layer was further extracted with $CH_2Cl_2$ (2×ca. 10 mL). The combined $CH_2Cl_2$ solution was washed with aqueous $NaBF_4$ solution (2×ca. 10 mL, 5% w/w). The organic layer was dried over $Na_2SO_4$, filtered, and the solvent was removed under reduced pressure. The residue was purified by chromatography on silica gel eluting with $CH_2Cl_2$/i-PrOH (50:1, v/v). The product was dissolved in 2 mL $CH_2Cl_2$, and precipitated with 10 mL $Et_2O$. The suspension was decanted, and the solid was dried in vacuo to afford 38-TT (900 mg, 1.59 mmol, 79%) as a colorless solid.

Rf=0.35 ($CH_2Cl_2$/MeOH, 15:1, v/v).

NMR Spectroscopy:

$^1$H NMR (500 MHz, CD$_2$Cl$_2$, 298 K, δ): 7.92 (d, J=7.9 Hz, 2H), 7.88 (d, J=8.0 Hz, 2H), 7.79 (t, J=7.6 Hz, 2H), 7.69 (t, J=7.7 Hz, 2H), 6.94 (d, J=9.4 Hz, 2H), 4.03 (t, J=6.0 Hz, 2H), 3.63 (s, 3H), 2.69 (s, 3H), 2.12 (s, 3H), 1.79-1.73 (m, 2H), 1.72-1.65 (m, 2H), 1.19 (s, 6H) ppm.

$^{13}$C NMR (126 MHz, CD$_2$Cl$_2$, 298 K, δ): 178.4, 163.2, 143.1, 136.0, 134.6, 132.5, 132.2, 131.2, 130.7, 129.3, 122.0, 115.8, 108.6, 69.6, 52.1, 42.4, 37.2, 25.4, 25.3, 20.9, 16.3 ppm.

$^{19}$F NMR (471 MHz, CD$_2$Cl$_2$, 298 K, δ): -151.35 (bs), -151.41 (bs) ppm.

HRMS-ESI (m/z) calculated for $C_{28}H_{31}O_3S_2^+$ [M-BF$_4$]$^+$, 479.170915; found, 479.171190; deviation: -0.57 ppm.

Methyl Acetyl-L-Phenylalate Tetrafluorothianthrenium Salt (5-TFT)

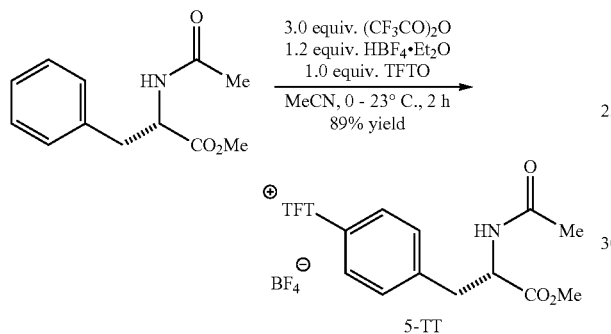

Under ambient atmosphere, a 20 mL round-bottom flask was charged with acetyl-L-phenylalanine methyl ester (664 mg, 3.00 mmol, 1.00 equiv.), and dry MeCN (30 mL, c=0.10 M). After cooling to 0° C., HBF$_4$OEt$_2$ (0.49 mL, 3.6 mmol, 1.2 equiv.) was added to the reaction mixture. Tetrafluorothianthrene-S-oxide (912 mg, 3.00 mmol, 1.00 equiv.) was added at 0° C. in one portion, followed by trifluoroacetic anhydride (1.25 mL, 1.89 g, 9.00 mmol, 3.00 equiv.) addition in one portion at 0° C. The vial was sealed with a screw-cap, and the mixture was allowed to stand at 0° C. for 1 hour and then warmed to 25° C. After stirring the deep purple reaction mixture at 25° C. for 1 hour, the reaction mixture was concentrated under reduced pressure, and diluted with 30 mL CH$_2$Cl$_2$. The CH$_2$Cl$_2$ phase was poured onto a saturated aqueous NaHCO$_3$ solution (ca. 20 mL). The mixture was poured into a separatory funnel, and the layers were separated. The CH$_2$Cl$_2$ layer was washed with aqueous NaBF$_4$ solution (2×ca. 20 mL, 5% w/w), and with water (2×ca. 20 mL). The CH$_2$Cl$_2$ layer was dried over Na$_2$SO$_4$, filtered, and the solvent was removed under reduced pressure. The residue was purified by chromatography on silica gel eluting with CH$_2$Cl$_2$/i-PrOH (30:1, v/v). The product was precipitated by addition of 2 mL CH$_2$Cl$_2$, and 20 mL Et$_2$O. The suspension was decanted, and the solid was dried in vacuo to afford 5-TFT (1.34 g, 89% yield) as a colorless solid.

Rf=0.35 (MeOH/DCM, 1/15, v/v).

NMR Spectroscopy:

$^1$H NMR (500 MHz, CD$_3$CN, 25° C., δ): 8.43-8.39 (m, 2H), 7.96 (dd, J=10.0 Hz, 7.1 Hz, 2H), 7.37-7.35 (m, 2H), 7.15-7.12 (m, 2H), 6.76 (d, J=8.1 Hz, 1H), 4.61-4.57 (m, 1H), 3.60 (s, 3H), 3.17-2.93 (m, 2H), 1.78 (s, 3H).

$^{13}$C {$^1$H} NMR (126 MHz, CD$_3$CN, 25° C., δ): 172.5, 170.7, 154.8 (d, J=261.8 Hz, 13.1 Hz), 151.6 (dd, J=255.4 Hz, 13.6 Hz), 144.9, 135.24 (dd, J=8.5, 3.9 Hz), 132.54, 129.2, 125.6 (dd, J=22.1, 2.3 Hz), 121.6, 121.2 (d, J=21.8 Hz), 115.5-115.4 (m), 54.0, 52.8, 37.7, 22.6.

$^{19}$F NMR (471 MHz, CD$_3$CN, 25° C., δ): -125.3 (m), -133.5 (m), -151.5 (brs), -151.6 (brs).

HRMS-ESI (m/z) calc'd for $C_{24}H_{18}F_4NO_3S_2^+$ [M-BF$_4$]$^+$, 508.0659, found, 508.0659, deviation: 0 ppm.

Methyl Acetyl-L-Tyrosinate (5)

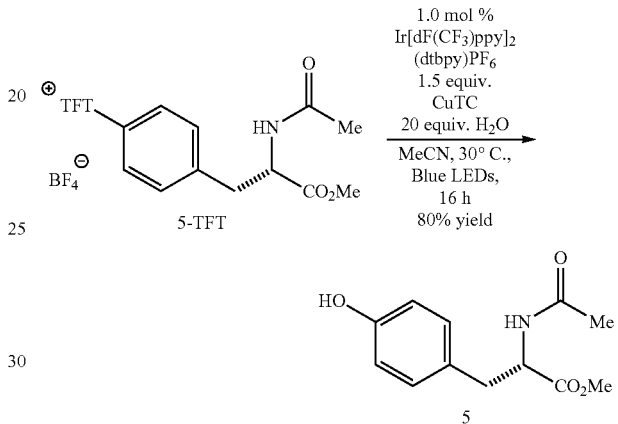

To a 4-mL borosilicate vial, equipped with a magnetic stir bar was added Ir[dF(CF$_3$)ppy]2(dtbpy)PF$_6$ (2.2 mg, 2.0 μmol, 1.0 mol %), copper(I) thiophene-2-carboxylate (57.2 mg, 0.300 mmol, 1.50 equiv.), and methyl acetyl-L-phenylalate tetrafluorothianthrenium salt 5-TFT (119 mg, 0.200 mmol, 1.00 equiv.) at 25° C. The vial was evacuated and then filled with argon; this procedure was repeated three times. MeCN (1 mL, c=0.2 M) was added, followed by H$_2$O (72.1 mg, 721 μL, 4.00 mmol, 20.0 equiv.). The vial was placed in 2 cm distance to two 34 W blue LEDs. The temperature was kept at approximately 30° C. with the use of a cooling fan. The reaction mixture was stirred for 16 hours under blue LED irradiation, and then diluted with ethyl acetate (1 mL). The reaction mixture was filtered through a short pad of silica using ethyl acetate (20 mL) as eluent. The filtrate was collected and concentrated in vacuo, and the residue was then purified by flash column chromatography on silica gel, eluting with ethyl acetate/pentane 1:1 (v/v) to afford 5 (38 mg, 80% yield) as a colorless solid.

Rf=0.30 (ethyl acetate/pentane, 1:2, v/v (UV, cerium molybdate))

NMR Spectroscopy:

$^1$H NMR (500 MHz, CD$_3$CN, 25° C., δ): 7.01 (d, J=8.5 Hz, 2H), 6.72 (d, J=8.6 Hz, 2H), 6.70-6.64 (m, 1H), 4.54 (td, J=7.9 Hz, 5.8 Hz, 1H), 3.63 (s, 3H), 2.98 (dd, J=14.0 Hz, 5.9 Hz, 1H), 2.85 (dd, J=13.9 Hz, 7.9 Hz, 1H), 1.85 (s, 3H).

$^{13}$C {$^1$H} NMR (126 MHz, CD$_3$CN, 25° C., δ): 172.7, 170.6, 156.4, 130.9, 128.4, 115.7, 54.6, 52.2, 36.9, 22.3.

HRMS-ESI (m/z) calc'd for $C_{12}H_{15}NO_4Na^+$ [M+Na]$^+$, 260.0893; found, 260.0896. Deviation: -0.9 ppm.

Hydroxy-Nefiracetam (6)

Hydroxyl Xanthone (9)

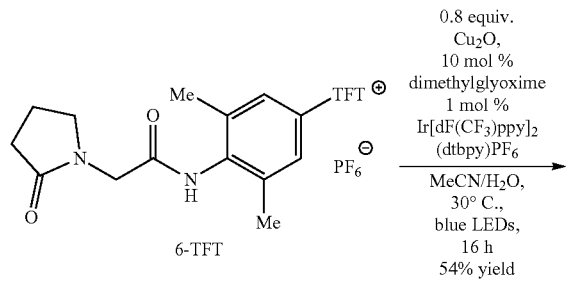

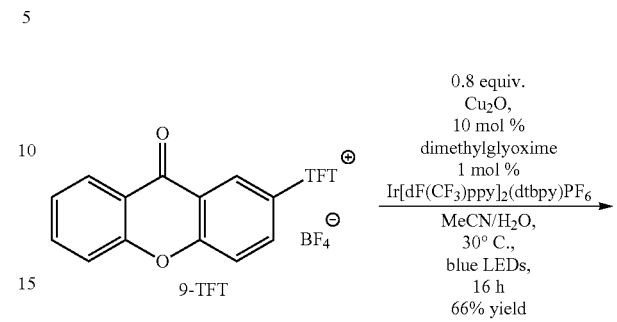

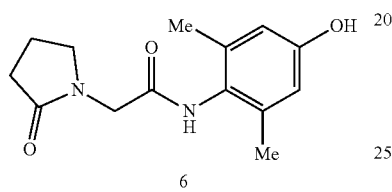

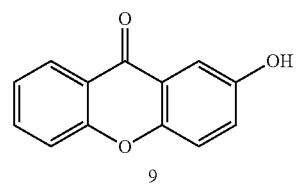

To a 4-mL borosilicate vial, equipped with a magnetic stir bar was added copper(I) oxide (11.5 mg, 80.0 µmol, 0.800 equiv.), dimethylglyoxime (1.2 mg, 10 µmol, 0.10 equiv.), and MeCN/H$_2$O (0.9 mL, v/v=2:1). After stirring for 10 mins at ambient temperature, nefiracetam tetrafluorothianthrenium salt 6-TFT (67.9 mg, 0.100 mmol, 1.00 equiv.), and Ir[dF(CF$_3$)ppy]$_2$(dtbpy)PF$_6$ (1.1 mg, 1.0 µmol, 1.0 mol %) in MeCN (0.40 mL, c=0.25 M) were then added. The vial was evacuated and then filled with argon; this procedure was repeated three times. The vial was placed in 2 cm distance to two 34 W blue LEDs. The temperature was kept at approximately 30° C. with the use of a cooling fan. The reaction mixture was stirred for 16 hours under blue LED irradiation, and then diluted with CH$_2$Cl$_2$ (2 mL). The reaction mixture was filtered through a short pad of Celite using CH$_2$Cl$_2$ (20 mL) as eluent. The filtrate was collected and concentrated in vacuo, and the residue was then purified by flash column chromatography on silica gel, eluting with DCM/MeOH (20:1, v/v) to afford 6 with impurities. Further purification of 6 by HPLC (YMC-Actus Triart C18 (30×150 mm: 5 µM), MeOH/TFA in water (1/1000, v/v)=50:50, flow rate=42.5 mL/min, 25° C., retention time; 2.1 min) provided 6 (14.1 mg, 54%) as a colorless solid.

Rf=0.58 (MeOH/CH$_2$Cl$_2$, 1:10, v/v (UV, cerium molybdate)).

NMR Spectroscopy:

$^1$H NMR (500 MHz, CD$_3$OD, 25° C., δ): 6.51 (s, 2H), 4.15 (s, 2H), 3.62-3.55 (m, 2H), 2.44 (t, J=8.1 Hz, 2H), 2.13 (m, 8H).

$^{13}$C {$^1$H} NMR (101 MHz, CD$_3$OD, 25° C., δ): 177.2, 168.2, 156.0, 136.7, 125.4, 114.2, 48.3, 45.2, 30.0, 17.4, 17.1.

HRMS-ESI (m/z) calc'd for C$_{14}$H$_{17}$N$_2$O$_3$$^+$ [M]$^+$, 261.1245; found, 261.1247; deviation: −0.8 ppm.

To a 4-mL borosilicate vial, equipped with a magnetic stir bar was added copper(I) oxide (22.9 mg, 0.160 mmol, 0.800 equiv.), dimethylglyoxime (2.3 mg, 20 µmol, 0.10 equiv.), and MeCN/H$_2$O (1.6 mL, v/v=5:3). After stirring for 10 mins at ambient temperature, 6-methyl-4-chromanone tetrafluorothianthrenium salt 9-TFT (114 mg, 0.200 mmol, 1.00 equiv.), and Ir[dF(CF$_3$)ppy]$_2$(dtbpy)PF$_6$ (2.2 mg, 2.0 µmol, 1.0 mol %) in MeCN (0.40 mL, c=0.50 M) were then added. The vial was evacuated and then filled with argon; this procedure was repeated three times. The vial was placed in 2 cm distance to two 34 W blue LEDs. The temperature was kept at approximately 30° C. with the use of a cooling fan. The reaction mixture was stirred for 16 hours under blue LED irradiation, and then diluted with CH$_2$Cl$_2$ (2 mL). The reaction mixture was filtered through a short pad of Celite using CH$_2$Cl$_2$ (20 mL) as eluent. The filtrate was collected and concentrated in vacuo, and the residue was then purified by flash column chromatography on silica gel, eluting with ethyl acetate/pentane (1:10, v/v) to afford 9 (27.8 mg, 66% yield) as a colorless solid.

Rf=0.43 (EtOAc/pentane, 1:2, v/v (UV, cerium molybdate))

NMR Spectroscopy:

$^1$H NMR (500 MHz, CD$_3$CN, 25° C., δ): 9.03 (brs, 1H, OH), 8.24 (dd, J=8.0, 1.7 Hz, 1H), 7.82 (td, J=7.9, 7.1, 1.7 Hz, 1H), 7.63 (d, J=3.1 Hz, 1H), 7.57 (d, J=8.5 Hz, 1H), 7.51 (d, J=9.0 Hz, 1H), 7.43 (t, J=7.5 Hz, 1H), 7.37 (dd, J=9.0, 3.1 Hz, 1H).

$^{13}$C {$^1$H} NMR (126 MHz, CO(CD$_3$)$_2$, 25° C., δ): 176.9, 157.0, 154.9, 150.9, 135.7, 127.0, 125.1, 124.6, 123.2, 121.9, 120.3, 118.9, 109.9.

HRMS-ESI (m/z) calc'd for C$_{13}$H$_8$O$_3$$^+$ [M]$^+$, 212.0468; found, 212.0467; deviation: 0.4 ppm.

2-Methoxy-Benzonitrile Thianthrenium Salt (13-TT)

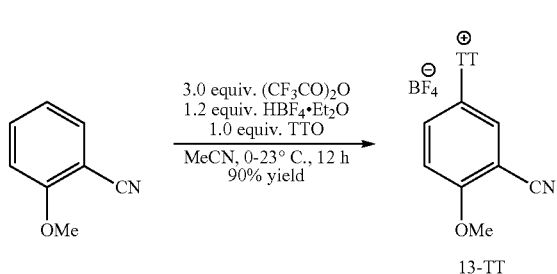

Under an ambient atmosphere, a 20-mL glass vial was charged with 2-methoxy-benzonitrile (266 mg, 2.00 mmol, 1.00 equiv) and MeCN (3.0 mL, c=0.67 M). After cooling to 0° C., HBF$_4$OEt$_2$ (0.34 mL, 0.40 g, 2.4 mmol, 1.2 equiv) and thianthrene-S-oxide (464 mg, 2.00 mmol, 1.00 equiv) was added to the vial while stirring the mixture, leading to a suspension. Subsequently, trifluoroacetic anhydride (0.84 mL, 1.3 g, 6.0 mmol, 3.0 equiv) was added in one portion at 0° C., resulting in a color change to deep purple. Subsequently, the reaction mixture was allowed to reach 23° C. and stirred for 12 hours. The solution was diluted with DCM (5 mL) and poured onto a mixture of DCM (30 mL) and saturated aqueous NaHCO$_3$ solution (20 mL). After stirring for 5 min at 23° C., the mixture was poured into a separating funnel, and the layers were separated. The DCM layer was washed with aqueous NaBF$_4$ solution (10% w/w, 4×ca. 20 mL). The DCM layer was dried over Na$_2$SO$_4$, filtered, and the solvent was removed under reduced pressure. The residue was purified by chromatography on silica gel eluting with DCM/MeOH (30:1 (v/v)), then the solvent was removed in vacuo to afford 13-TT (770 mg, 90% yield) as a colorless solid.

Rf=0.35 (DCM/MeOH, 15:1, v/v).

NMR Spectroscopy:

$^1$H NMR (500 MHz, CD$_3$CN, 25° C., δ): 8.32 (dd, J=8.0, 1.4 Hz, 2H), 7.95 (dd, J=7.9, 1.4 Hz, 2H), 7.87 (td, J=7.7, 1.4 Hz, 2H), 7.79 (td, J=7.7, 1.4 Hz, 2H), 7.40 (d, J=2.7 Hz, 1H), 7.34 (dd, J=9.3, 2.7 Hz, 1H), 7.16 (d, J=9.3 Hz, 1H), 3.92 (s, 3H).

$^{13}$C {$^1$H} NMR (126 MHz, CD$_3$CN, 25° C., δ): 165.4, 137.4, 136.2, 135.9, 135.7, 134.7, 131.8, 131.0, 119.4, 115.5, 115.0, 114.9, 104.5, 58.2.

$^{19}$F NMR (471 MHz, CD$_3$CN, 25° C., δ): −151.5 (brs), −151.6 (brs).

HRMS-ESI (m/z) calc'd for C$_{20}$H$_{14}$NOS$_2^+$ [M]$^+$, 348.0511; found, 348.0508; deviation: 0.9 ppm.

5-Hydroxy-2-methoxybenzonitrile (13)

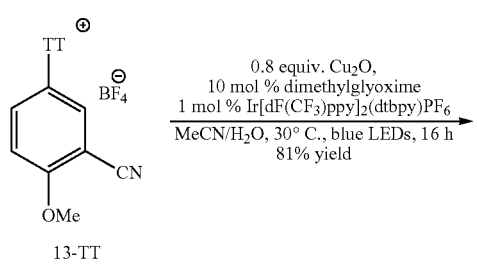

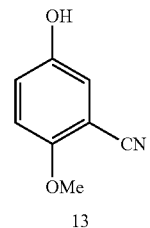

To a 4-mL borosilicate vial, equipped with a magnetic stir bar was added copper(I) oxide (11.5 mg, 80.0 μmol, 0.800 equiv.), dimethylglyoxime (1.2 mg, 10 μmol, 0.10 equiv.), and MeCN/H$_2$O (0.9 mL, v/v=2:1). After stirring for 10 mins at ambient temperature, 2-methoxy-5-methylbenzonitrile thianthrenium salt 13-TT (43.8 mg, 0.100 mmol, 1.00 equiv.), and Ir[dF(CF$_3$)ppy]2(dtbpy)PF$_6$ (1.1 mg, 1.0 μmol, 1.0 mol %) in MeCN (0.40 mL, c=0.25 M) were then added. The vial was evacuated and then filled with argon; this procedure was repeated three times. The vial was placed in 2 cm distance to two 34 W blue LEDs. The temperature was kept at approximately 30° C. with the use of a cooling fan. The reaction mixture was stirred for 16 hours under blue LED irradiation, and then diluted with CH$_2$Cl$_2$ (2 mL). The reaction mixture was filtered through a short pad of Celite using CH$_2$Cl$_2$ (20 mL) as eluent. The filtrate was collected and concentrated in vacuo, and the residue was then purified by flash column chromatography on silica gel, eluting with ethyl acetate/pentane (1:5, v/v) to afford 13 (12.1 mg, 81% yield) as a colorless solid.

Rf=0.35 (EtOAc/pentane, 1:2, v/v, (UV, cerium molybdate)).

NMR Spectroscopy:

$^1$H NMR (500 MHz, CDCl$_3$, 25° C., δ): 7.13-7.03 (m, 2H), 6.85 (d, J=9.9 Hz, 1H), 3.87 (s, 3H).

$^{13}$C {$^1$H} NMR (126 MHz, CDCl$_3$, 25° C., δ): 155.8, 149.6, 122.1, 119.8, 116.4, 112.8, 101.8, 56.6.

HRMS-ESI (m/z) calc'd for C$_8$H$_7$NO$_2^+$ [M]$^+$, 149.0471; found, 149.0473; deviation: −1.1 ppm.

6-Methyl-4-Chromanone Thianthrenium Salt (18-TT)

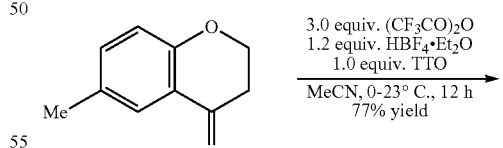

Under an ambient atmosphere, a 20-mL glass vial was charged with 6-methyl-4-chromanone (294 mg, 1.50 mmol, 1.00 equiv) and MeCN (3.0 mL, c=0.50 M). After cooling to 0° C., HBF$_4$.OEt$_2$ (0.26 mL, 0.31 g, 1.8 mmol, 1.2 equiv) and thianthrene-S-oxide (348 mg, 1.50 mmol, 1.00 equiv) was added to the vial while stirring the mixture, leading to a suspension. Subsequently, trifluoroacetic anhydride (0.63 mL, 0.95 g, 4.5 mmol, 3.0 equiv) was added in one portion at 0° C., resulting in a color change to deep purple. Subsequently, the reaction mixture was allowed to reach 23° C. and stirred for 12 hours. The solution was diluted with DCM (5 mL) and poured onto a mixture of DCM (30 mL) and saturated aqueous NaHCO$_3$ solution (20 mL). After stirring for 5 min at 23° C., the mixture was poured into a separating funnel, and the layers were separated. The DCM layer was washed with aqueous NaBF$_4$ solution (10% w/w, 4×ca. 20 mL). The DCM layer was dried over Na$_2$SO$_4$, filtered, and the solvent was removed under reduced pressure. The residue was purified by chromatography on silica gel eluting with DCM/MeOH (30:1 (v/v)), then the solvent was removed in vacuo to afford 18-TT (530 mg, 77% yield) as a light yellow solid.

Rf=0.35 (DCM/MeOH, 15:1, v/v).

NMR Spectroscopy:

$^1$H NMR (500 MHz, CDCl$_3$, 25° C., δ): 8.35 (dd, J=7.9, 1.4 Hz, 2H), 7.84 (dd, J=7.9, 1.5 Hz, 2H), 7.80 (s, 2H), 7.73 (dd, J=7.9, 1.5 Hz, 3H), 6.53 (d, J=2.1 Hz, 1H), 4.71 (t, J=6.5 Hz, 2H), 2.75 (t, J=6.5 Hz, 2H), 2.13 (s, 3H).

$^{13}$C {$^1$H} NMR (126 MHz, CDCl$_3$, 25° C., δ): 189.0, 157.9, 137.1, 135.1, 135.1, 134.3, 133.0, 132.1, 130.5, 130.2, 128.5, 127.7, 123.1, 116.3, 109.4, 69.0, 37.2, 20.6.

$^{19}$F NMR (471 MHz, CDCl$_3$, 25° C., δ): −151.8 (brs), −151.9 (brs).

HRMS-ESI (m/z) calc'd for C$_{22}$H$_{17}$S$_2$O$_2$$^+$ [M-BF$_4$]$^+$, 377.0665; found, 377.0664; deviation: 0.2 ppm.

8-Hydroxy-6-methylchroman-4-one (18)

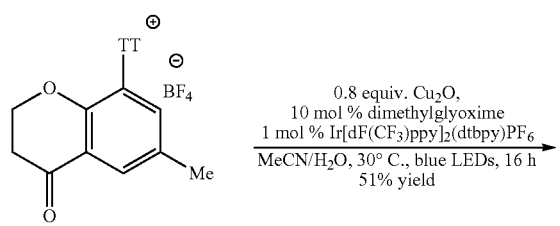

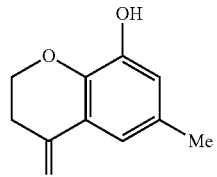

To a 4-mL borosilicate vial, equipped with a magnetic stir bar was added copper(I) oxide (22.9 mg, 0.160 mmol, 0.800 equiv.), dimethylglyoxime (2.3 mg, 20 μmol, 0.10 equiv.), and MeCN/H$_2$O (1.6 mL, v/v=5:3). After stirring for 10 mins at ambient temperature, 6-methyl-4-chromanone thianthrenium salt 18-TT (92.9 mg, 0.200 mmol, 1.00 equiv.), and Ir[dF(CF$_3$)ppy]2(dtbpy)PF$_6$ (2.2 mg, 2.0 μmol, 1.0 mol %) in MeCN (0.40 mL, c=0.50 M) were then added. The vial was evacuated and then filled with argon; this procedure was repeated three times. The vial was placed in 2 cm distance to two 34 W blue LEDs. The temperature was kept at approximately 30° C. with the use of a cooling fan. The reaction mixture was stirred for 16 hours under blue LED irradiation, and then diluted with CH$_2$Cl$_2$ (2 mL). The reaction mixture was filtered through a short pad of Celite using CH$_2$Cl$_2$ (20 mL) as eluent. The filtrate was collected and concentrated in vacuo, and the residue was then purified by flash column chromatography on silica gel, eluting with ethyl acetate/pentane (1:10, v/v) to afford 18 (26.9 mg, 51% yield) as a colorless solid.

Rf=0.28 (EtOAc/pentane, 1:2, v/v (UV, cerium molybdate)).

NMR Spectroscopy:

$^1$H NMR (500 MHz, CD$_3$CN, 25° C., δ): 7.12 (dd, J=2.1, 1.1 Hz, 1H), 6.90 (d, J=2.1 Hz, 1H), 6.70 (brs, 1H, OH), 4.61-4.35 (m, 3H), 2.83-2.68 (m, 2H), 2.16 (s, 3H).

$^{13}$C {$^1$H} NMR (126 MHz, CD$_3$CN, 25° C., δ): 192.6, 149.1, 146.6, 131.7, 122.5, 118.3, 117.5, 68.5, 38.5, 20.7.

HRMS-ESI (m/z) calc'd for C$_{10}$H$_{11}$O$_3$$^+$ [M+H]$^+$, 179.0703; found, 179.0705; deviation: −1.2 ppm.

Hydroxy-Etofenprox (21)

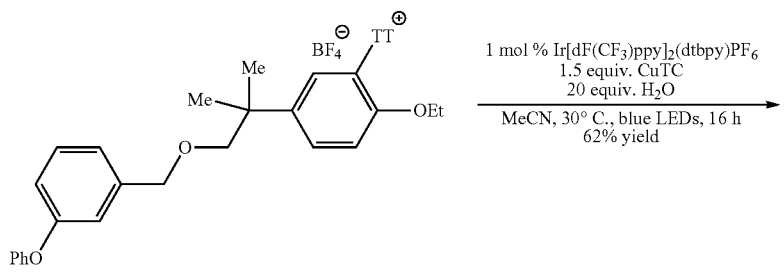

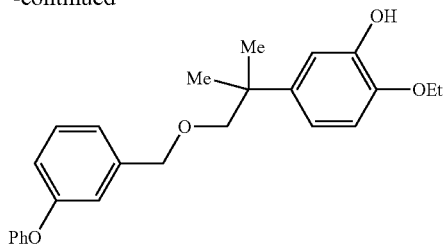

21

To a 4-mL borosilicate vial, equipped with a magnetic stir bar was added copper(I) thiophene-2-carboxylate (28.6 mg, 0.150 mmol, 1.50 equiv.), etofenprox thianthrenium salt 21-TT (67.8 mg, 0.100 mmol, 1.00 equiv.), Ir[dF(CF$_3$)ppy]$_2$(dtbpy)PF$_6$ (1.1 mg, 10 µmol, 1.0 mol %), water (36 µL, 18 mg, 2.0 mmol, 20 equiv.), and MeCN (0.5 mL, c=0.2 M). The vial was evacuated and then filled with argon; this procedure was repeated three times. The vial was placed in 2 cm distance to two 34 W blue LEDs. The temperature was kept at approximately 30° C. with the use of a cooling fan. The reaction mixture was stirred for 16 hours under blue LED irradiation, and then diluted with CH$_2$Cl$_2$ (2 mL). The reaction mixture was filtered through a short pad of Celite using CH$_2$Cl$_2$ (20 mL) as eluent. The filtrate was collected and concentrated in vacuo, and the residue was then purified by flash column chromatography on silica gel, eluting with ethyl acetate/pentane (1:20, v/v) to afford 21 (24.2 mg, 62% yield) as a colorless solid.

R$_f$=0.36 (EtOAc/pentane, 1:20, v/v (UV, cerium molybdate)).

NMR Spectroscopy:

$^1$H NMR (500 MHz, CDCl$_3$, 25° C., δ): 7.40-7.23 (m, 3H), 7.11 (ddt, J=7.7, 6.9, 1.1 Hz, 1H), 7.07-6.87 (m, 6H), 6.84-6.69 (m, 2H), 5.61 (brs, 1H, OH), 4.45 (s, 2H), 4.08 (q, J=7.0 Hz, 2H), 3.40 (s, 2H), 1.42 (t, J=7.0 Hz, 3H), 1.29 (s, 6H).

$^{13}$C {$^1$H} NMR (126 MHz, CDCl$_3$, 25° C., δ): 157.3, 157.2, 145.2, 143.9, 141.0, 140.9, 129.7, 129.5, 123.2, 122.0, 120.0, 117.7, 117.6, 117.5, 112.7, 111.1, 80.2, 72.8, 64.5, 38.7, 26.1, 15.0.

HRMS-ESI (m/z) calc'd for C$_{25}$H$_{28}$O$_4$Na$^+$ [M+Na]$^+$, 415.1880; found, 415.1877; deviation: 0.8 ppm.

1-Ethyl-4-phenoxybenzene (28)

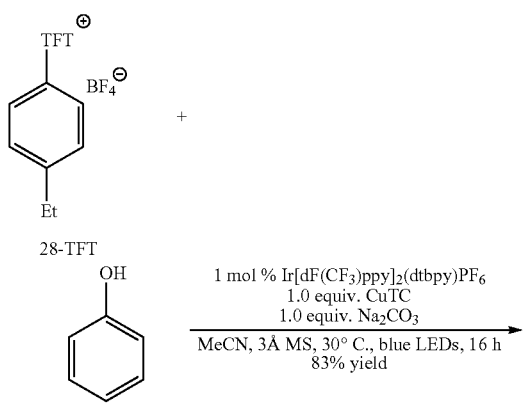

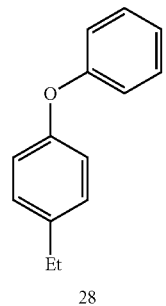

28

In an anhydrous, N$_2$-filled glovebox, a 4-mL borosilicate vial equipped with a magnetic stir bar was charged with copper(I) thiophene-2-carboxylate (38.1 mg, 0.200 mmol, 1.00 equiv.), phenol (37.6 mg, 0.400 mmol, 2.00 equiv.), Na$_2$CO$_3$ (10.6 mg, 0.100 mmol, 1.00 equiv.), and 3 Å molecular sieves (120 mg). Dry MeCN (1 mL, c=0.2 M) was then added into the vial. The vial was sealed with a Teflon cap. The reaction mixture was stirred at 23° C.: After 2 hours, the vial was opened and ethyl benzene-derived tetrafluorothianthrenium salt 28-TFT (48.0 mg, 0.100 mmol, 1.00 equiv.) and Ir[dF(CF$_3$)ppy]$_2$(dtbpy)PF$_6$ (1.1 mg, 1.0 µmol, 1.0 mol %) were added into the reaction mixture. The vial was sealed with the same Teflon cap and transferred out of glovebox. The vial was placed in 2 cm distance to two 34 W blue LEDs. The temperature was kept at approximately 30° C. with the use of a cooling fan. The reaction mixture was stirred for 16 hours under blue LED irradiation, and then diluted with CH$_2$Cl$_2$ (2 mL). The reaction mixture was filtered through a short pad of silica using CH$_2$Cl$_2$ (25 mL) as eluent. The filtrate was collected and concentrated in vacuo, and the residue was then purified by flash column chromatography on silica gel, eluting with pentane to afford 28 (32.8 mg, 83% yield) as a colorless solid.

R$_f$=0.30 (pentane (UV))

NMR Spectroscopy:

$^1$H NMR (500 MHz, CDCl$_3$, 25° C., δ): 7.37-7.30 (m, 2H), 7.18 (d, J=8.6 Hz, 2H), 7.09 (tt, J=7.4 Hz, 1.2 Hz, 1H), 7.01 (dd, J=8.7 Hz, 1.1 Hz, 2H), 6.98-6.94 (m, 2H), 2.66 (q, J=7.6 Hz, 2H), 1.26 (t, J=7.6 Hz, 3H).

$^{13}$C {$^1$H} NMR (126 MHz, CDCl$_3$, 25° C., δ): 157.8, 154.9, 139.3, 129.7, 129.0, 122.8, 119.1, 118.5, 28.2, 15.8.

HRMS-ESI (m/z) calc'd for calc'd for C$_{14}$H$_{14}$O$^+$ [M]$^+$, 198.1039; found, 198.1040. Deviation: −0.2 ppm.

3-(4-Ethylphenoxy)oxetane (33)

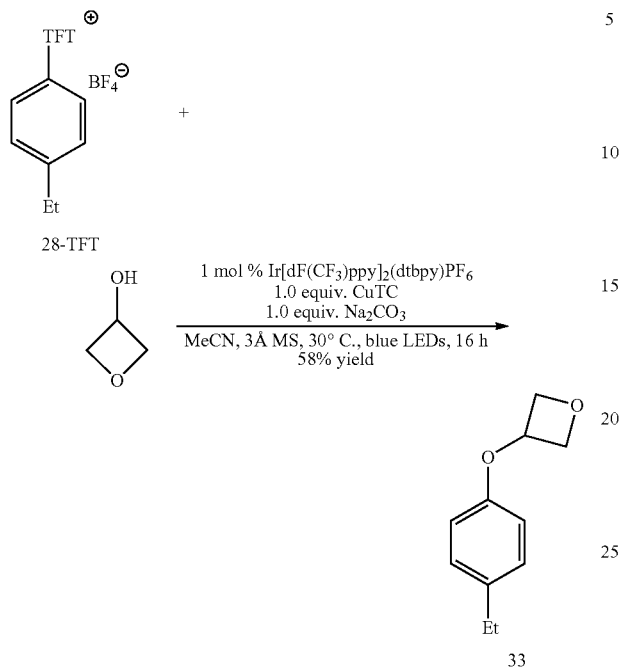

In an anhydrous, N$_2$-filled glovebox, a 4-mL borosilicate vial equipped with a magnetic stir bar was charged with copper(I) thiophene-2-carboxylate (38.1 mg, 0.200 mmol, 1.00 equiv.), 3-hydroxyoxetan (37.0 mg, 31.7 μL, 0.500 mmol, 2.50 equiv.), Na$_2$CO$_3$ (10.6 mg, 0.100 mmol, 1.00 equiv.), and 3 Å molecular sieves (120 mg). Dry MeCN (1 mL, c=0.2 M) was then added into the vial. The vial was sealed with a Teflon cap. The reaction mixture was stirred at 23° C.: After 2 hours, the vial was opened and ethyl benzene-derived tetrafluorothianthrenium salt 28-TFT (48.0 mg, 0.100 mmol, 1.00 equiv.) and Ir[dF(CF$_3$)ppy]2(dtbpy)PF$_6$ (1.1 mg, 1.0 μmol, 1.0 mol %) were added into the reaction mixture. The vial was sealed with the same Teflon cap and transferred out of glovebox. The vial was placed in 2 cm distance to two 34 W blue LEDs. The temperature was kept at approximately 30° C. with the use of a cooling fan. The reaction mixture was stirred for 16 hours under blue LED irradiation, and then diluted with CH$_2$Cl$_2$ (2 mL). The reaction mixture was filtered through a short pad of silica using CH$_2$Cl$_2$ (25 mL) as eluent. The filtrate was collected and concentrated in vacuo, and the residue was then purified by flash column chromatography on silica gel, eluting with EtOAc/pentane (1:100 v/v) to afford 33 (20.6 mg, 58% yield) as a colorless oil.

R$_f$=0.30 (EtOAc/pentane, 1:50, v/v (UV, cerium molybdate))

NMR Spectroscopy:

$^1$H NMR (300 MHz, CDCl$_3$, 25° C., δ): 7.03 (d, J=8.8 Hz, 2H), 6.55 (d, J=8.6 Hz, 2H), 5.15-5.07 (m, 1H), 4.92-4.83 (m, 2H), 4.75-4.61 (m, 2H), 2.51 (q, J=7.6 Hz, 2H), 1.13 (t, J=7.6 Hz, 3H).

$^{13}$C {$^1$H} NMR (126 MHz, CDCl$_3$, 25° C., δ): 154.6, 137.4, 129.0, 114.3, 78.2, 70.1, 28.0, 15.8.

HRMS-ESI (m/z) calc'd for C$_{11}$H$_{15}$O$_2$ [M+H]$^+$, 179.1067; found, 179.1067. Deviation: 0 ppm.

Methoxy-PEG(4) Ethylbenzene (35)

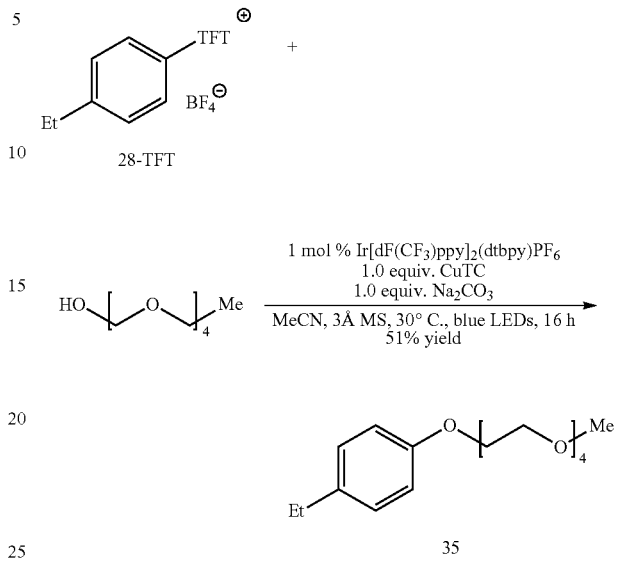

In an anhydrous, N$_2$-filled glovebox, a 4-mL borosilicate vial equipped with a magnetic stir bar was charged with copper(I) thiophene-2-carboxylate (38.1 mg, 0.200 mmol, 1.00 equiv.), 2,5,8,11-tetraoxatridecan-13-ol (208 mg, 200 μL, 1.00 mmol, 5.00 equiv.), Na$_2$CO$_3$ (10.6 mg, 0.100 mmol, 1.00 equiv.), and 3 Å molecular sieves (120 mg). Dry MeCN (1 mL, c=0.2 M) was then added into the vial. The vial was sealed with a Teflon cap. The reaction mixture was stirred at 23° C.: After 2 hours, the vial was opened and ethyl benzene-derived tetrafluorothianthrenium salt 28-TFT (48.0 mg, 0.100 mmol, 1.00 equiv.) and Ir[dF(CF$_3$)ppy]2(dtbpy)PF$_6$ (1.1 mg, 1.0 μmol, 1.0 mol %) were added into the reaction mixture. The vial was sealed with the same Teflon cap and transferred out of glovebox. The vial was placed in 2 cm distance to two 34 W blue LEDs. The temperature was kept at approximately 30° C. with the use of a cooling fan. The reaction mixture was stirred for 16 hours under blue LED irradiation, and then diluted with CH$_2$Cl$_2$ (2 mL). The reaction mixture was filtered through a short pad of silica using CH$_2$Cl$_2$ (25 mL) as eluent. The filtrate was collected and concentrated in vacuo, and the residue was then purified by flash column chromatography on silica gel, eluting with EtOAc/pentane (1:1 v/v) to afford 35 (32.4 mg, 51% yield) as a pale yellow oil.

R$_f$=0.30 (EtOAc/pentane, 2:1, v/v (UV, cerium molybdate))

NMR Spectroscopy:

$^1$H NMR (500 MHz, CDCl$_3$, 25° C., δ): 7.09 (d, J=8.6 Hz, 2H), 6.83 (d, J=8.6 Hz, 2H), 4.10 (dd, J=5.8 Hz, 4.1 Hz, 2H), 3.84 (dd, J=5.8 Hz, 4.1 Hz, 2H), 3.72 (dd, J=5.9 Hz, 3.5 Hz, 2H), 3.68-3.62 (m, 8H), 3.54 (dd, J=5.8 Hz, 3.5 Hz, 1H), 3.37 (s, 3H), 2.58 (q, J=7.6 Hz, 2H), 1.20 (t, J=7.6 Hz, 3H).

$^{13}$C {$^1$H} NMR (126 MHz, CDCl$_3$, 25° C., δ): 156.8, 136.6, 128.7, 114.5, 71.9, 70.8, 70.6, 70.6, 70.5, 69.8, 67.5, 59.0, 28.0, 15.9.

HRMS-ESI (m/z) calc'd for C$_{17}$H$_{28}$O$_5$Na [M+Na]$^+$, 335.1829; found, 335.1827. Deviation: 0.6 ppm.

137
Phenylthio-etofenprox (51)

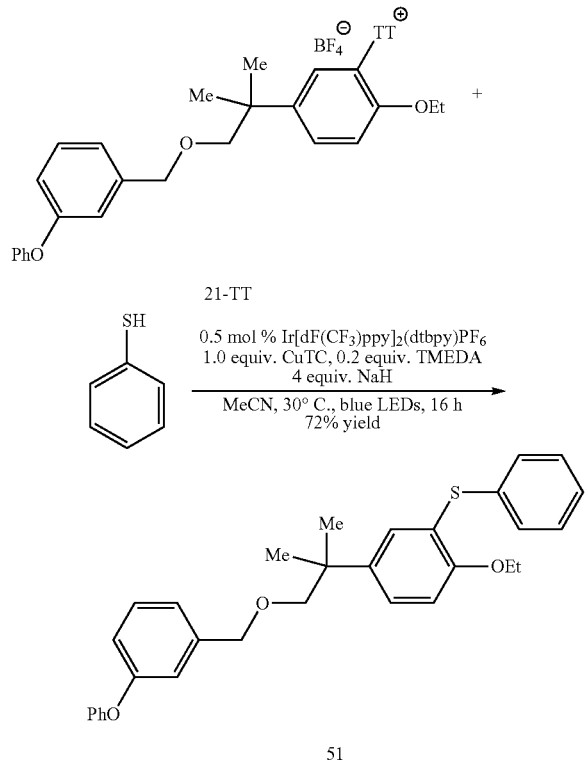

51

To a 4-mL borosilicate vial, equipped with a magnetic stir bar was added Ir[dF(CF$_3$)ppy]2(dtbpy)PF$_6$ (1.1 mg, 1.0 μmol, 0.50 mol %), copper(I) thiophene-2-carboxylate (38 mg, 0.20 mmol, 1.0 equiv.), NaH (c=60% dispersion in mineral oil; 36 mg, 0.80 mmol, 4.0 equiv.), and entofenprox thianthrenium salt 21-TT (135 mg, 0.200 mmol, 1.00 equiv.) at 25° C. The vial was evacuated and then filled with argon; this procedure was repeated three times. MeCN (1 mL, c=0.2 M) was added, followed by 1,2-bis(dimethylamino) ethane (5 mg, 6 μL, 0.04 mmol, 0.2 equiv.) and thiophenol (44.1 mg, 41.0 μL, 0.400 mmol, 2.00 equiv.). The vial was placed in 2 cm distance to two 34 W blue LEDs. The temperature was kept at approximately 30° C. with the use of a cooling fan. The reaction mixture was stirred for 16 hours under blue LED irradiation, then diluted with ethyl acetate (1 mL), and filtered through a short pad of silica using ethyl acetate (20 mL) as eluent. The filtrate was collected and concentrated in vacuo and then purified by flash column chromatography on silica gel, eluting with EtOAc/pentane (1:20 v/v) to afford 51 (69.6 mg, 72% yield) as a colorless solid.

Rf=0.70 (EtOAc/pentane, 1:10 v/v (UV))

NMR Spectroscopy:

$^1$H NMR (500 MHz, CD$_3$CN, 25° C., δ): 7.41-7.32 (m, 2H), 7.32-7.20 (m, 7H), 7.18 (d, J=2.5 Hz, 1H), 7.13 (tt, J=7.4 Hz, 1.1 Hz, 1H), 6.98 (dd, J=8.7 Hz, 1.1 Hz, 2H), 6.97-6.94 (m, 1H), 6.92-6.85 (m, 2H), 6.84 (t, J=2.0 Hz, 1H), 4.34 (s, 2H), 4.01 (q, J=7.0 Hz, 2H), 3.36 (s, 2H), 1.23 (t, J=7.0 Hz, 3H), 1.17 (s, 6H).

$^{13}$C {$^1$H} NMR (126 MHz, CD$_3$CN, 25° C., δ): 157.9, 157.7, 155.9, 141.8, 141.0, 136.0, 135.2, 131.0, 130.9, 130.5, 130.3, 129.7, 127.3, 127.3, 124.0, 122.8, 122.7, 119.4, 118.1, 112.6, 80.3, 72.7, 64.8, 38.9, 26.0, 14.6.

138

HRMS-ESI (m/z) calc'd for C$_{31}$H$_{32}$O$_3$SNa$^+$ [M+Na]$^+$, 507.1964; found, 507.1965. Deviation: −0.1 ppm.

Benzylbromide-Derived Tetrafluorothianthrenium Salt (S2)

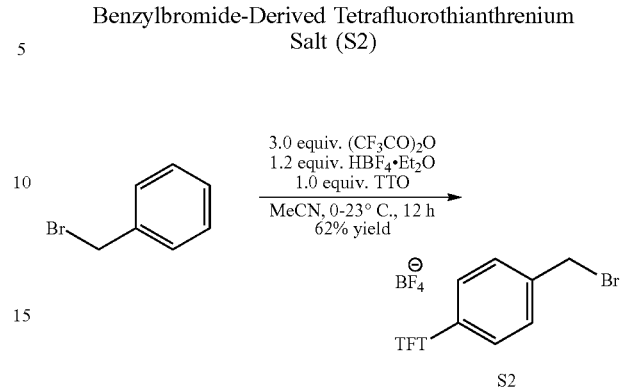

S2

Under an ambient atmosphere, a 20-ml glass vial was charged with benzyl bromide (510 mg, 3.00 mmol, 1.00 equiv) and MeCN (6.0 ml, c=0.50 M). After cooling to 0° C., HBF$_4$OEt$_2$ (0.49 mL, 0.58 g, 3.6 mmol, 1.2 equiv) and tetrafluorothianthrene-S-oxide (912 mg, 3.00 mmol, 1.00 equiv) was added to the vial while stirring the mixture, leading to a suspension. Subsequently, trifluoroacetic anhydride (1.26 mL, 1.86 g, 9.0 mmol, 3.0 equiv) was added in one portion at 0° C., resulting in a color change to deep purple. Subsequently, the reaction mixture was allowed to reach 23° C. and stirred for 12 h. The solution was diluted with DCM (5 mL) and poured onto a mixture of DCM (30 mL) and saturated aqueous NaHCO$_3$ solution (20 mL). After stirring for 5 min at 23° C., the mixture was poured into a separating funnel, and the layers were separated. The DCM layer was washed with aqueous NaBF$_4$ solution (10% w/w, 4×ca. 20 mL). The DCM layer was dried over Na$_2$SO$_4$, filtered, and the solvent was removed under reduced pressure. The residue was purified by chromatography on silica gel eluting with DCM/MeOH (30:1 (v/v)), then the solvent was removed in vacuo to afford S2 (1.01 g, 62%) as a light yellow powder.

Rf=0.35 (DCM/MeOH, 15:1, v/v).

NMR Spectroscopy:

$^1$H NMR (500 MHz, CDCl$_3$, 23° C., δ): 8.47 (dd, J=9.2, 7.2 Hz, 2H), 7.96 (dd, J=9.9, 7.0 Hz, 2H), 7.55 (d, J=8.8 Hz, 2H), 7.22 (d, J=8.7 Hz, 2H), 4.55 (s, 2H) ppm.

$^{13}$C NMR (125 MHz, CDCl$_3$, 23° C., δ): 154.8 (dd, J=262.0, 13.2 Hz), 151.6 (dd, J=255.6, 13.6 Hz), 145.3, 135.3 (dd, J=8.6, 4.1 Hz), 132.0, 129.8, 125.8 (dd, J=22.3, 2.5 Hz), 123.3, 121.2 (d, J=21.7 Hz), 115.2 (dd, J=7.3, 3.6 Hz), 32.1 ppm.

$^{19}$F NMR (471 MHz, CDCl$_3$, 23° C., δ): −125.2 (ddd, J=20.8, 10.1, 7.3 Hz), −133.7 (ddd, J=20.7, 9.4, 7.0 Hz), −150.5 (brs), −150.6 (brs) ppm.

HRMS-ESI (m/z) calc'd for C$_{19}$H$_{10}$Br$_1$F$_4$S$_2$ [M-BF$_4$]$^+$, 456.93381; found, 456.93335; deviation: 1.0 ppm.

1-(Bromomethyl)-4-(trifluoromethyl)benzene (4)

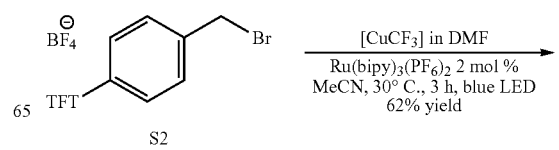

S2

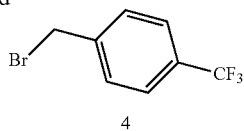

4

In an anhydrous, N$_2$-filled glovebox, a 4-mL borosilicate vial equipped with a magnetic stir bar was charged with CuSCN (54.7 mg, 0.450 mmol, 1.50 equiv), CsF (91.1 mg, 0.600 mmol, 2.00 equiv). DMF (1.5 mL, c=0.30 M) and TMSCF$_3$ (66.5 μL, 64.0 mg, 0.450 mmol, 1.50 equiv) was then added into the vial at 23° C., leading to a yellow suspension. The vial was sealed with a Teflon cap. The reaction mixture was stirred at 23° C. After 30 mins, a mixture of Ru(bipy)$_3$(PF$_6$)$_2$ (5.2 mg, 6.0 μmol, 2.0 mol %) and benzylbromide-derived tetrafluorothianthrenium salts S2 (164 mg, 0.300 mmol, 1.00 equiv) in MeCN (1.5 mL, c=0.20 M) was then added into the reaction with a 2 mL syringe. The vial was sealed with the same Teflon cap again, and was placed 5 cm away from a 34 W blue LED. The reaction was irradiated with the blue LED for 3 hours at approximately 30° C. with the use of a cooling fan. Then the reaction mixture was diluted with DCM (1.0 mL). The resulting solution was filtered through a short pad of silica using DCM (10 mL) as eluent. The filtrate was collected and concentrated in vacuo, and the residue was then purified by flash column chromatography on silica gel, eluting with hexanes to afford 4 (44.2 mg, 62%) as a colorless liquid.

Rf=0.55 (hexanes).

NMR Spectroscopy:

$^1$H NMR (500 MHz, CDCl$_3$, 23° C., δ): 7.64 (d, J=8.1 Hz, 2H), 7.54 (d, J=8.0 Hz, 2H), 4.53 (s, 2H) ppm.

$^{13}$C NMR (126 MHz, CDCl$_3$, 23° C., δ): 141.8, 130.62 (q, J=32.7 Hz), 129.5, 125.9 (q, J=4.0 Hz), 124.1 (q, J=272.5 Hz), 31.9 ppm.

$^{19}$F NMR (471 MHz, CDCl$_3$, 23° C., δ): −62.7 ppm.

HRMS-EI (m/z) calc'd for C$_8$H$_6$Br$_1$F$_3$ [M]$^+$, 237.95996; found, 237.95999; deviation: −0.1 ppm.

Clofibrate Ethyl Ester-Derived Thianthrenium Salt (S4)

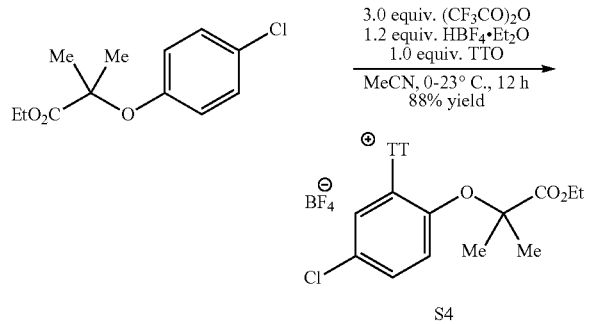

Under an ambient atmosphere, a 20-ml glass vial was charged with methyl gemfibrozil (1.21 g, 5.00 mmol, 1.00 equiv.) and MeCN (5.0 ml, c=1.0 M). After cooling to 0° C., HBF$_4$OEt$_2$ (0.82 mL, 0.97 g, 6.0 mmol, 1.2 equiv) and thianthrene-S-oxide (1.15 g, 5.00 mmol, 1.00 equiv) was added to the vial while stirring the mixture, leading to a suspension. Subsequently, trifluoroacetic anhydride (2.1 mL, 3.2 g, 15 mmol, 3.0 equiv) was added in one portion at 0° C., resulting in a color change to deep purple. Subsequently, the reaction mixture was allowed to reach 23° C. and stirred for 2 h. The solution was diluted with DCM (5 mL) and poured onto a mixture of DCM (30 mL) and saturated NaHCO$_3$ solution. After stirring for 5 min at 23° C., the mixture was poured into a separating funnel, and the layers were separated. The DCM layer was washed with aqueous NaBF$_4$ solution (10% w/w, 4×ca. 20 mL). The DCM layer was dried over Na$_2$SO$_4$, filtered, and the solvent was removed under reduced pressure. The residue was purified by chromatography on silica gel eluting with DCM/MeOH (30:1 (v/v)), then the solvent was removed in vacuo to afford S4 (2.38 g, 88%) as a white powder.

Rf=0.35 (DCM/MeOH, 1/15, v/v).

NMR Spectroscopy:

$^1$H NMR (500 MHz, DMSO-d$_6$, 23° C., δ) δ 8.40 (dd, J=7.8, 1.5 Hz, 2H), 8.10 (dd, J=7.8, 1.5 Hz, 2H), 7.89 (dtd, J=23.2, 7.5, 1.5 Hz, 4H), 7.68 (dd, J=9.0, 2.6 Hz, 1H), 6.92 (d, J=9.0 Hz, 1H), 6.64 (d, J=2.6 Hz, 1H), 4.10 (q, J=7.1 Hz, 2H), 1.63 (s, 6H), 1.05 (t, J=7.1 Hz, 3H) ppm.

$^{13}$C NMR (126 MHz, DMSO-d$_6$, 23° C., δ): 171.8, 152.9, 136.6, 136.3, 135.4, 135.1, 131.0, 130.0, 129.5, 125.8, 119.3, 118.3, 112.4, 82.5, 62.3, 25.2, 14.2 ppm.

$^{19}$F NMR (471 MHz, DMSO-d$_6$, 23° C., δ): −148.2 (brs), −148.3 (brs) ppm.

HRMS-ESI (m/z) calculated for C$_{24}$H$_{22}$O$_3$S$_2$Cl$_1^+$ [M-BF$_4$]$^+$, 457.06934; found, 457.06917; deviation: 0.4 ppm.

CF$_3$-Clofibrate Ethyl Ester (6)

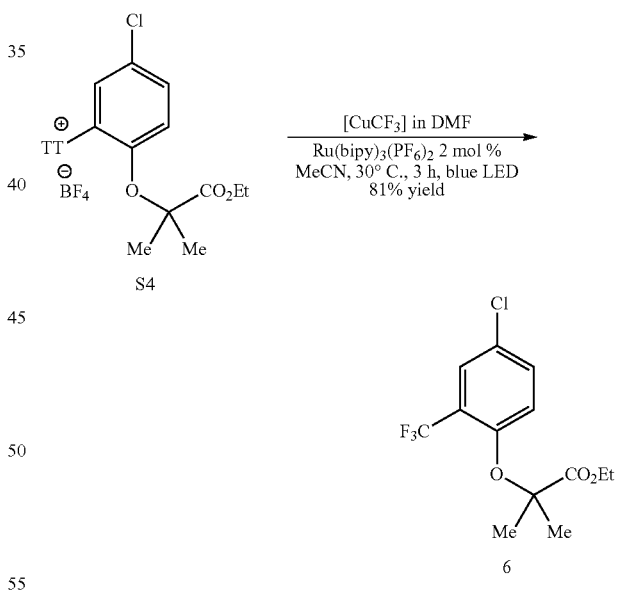

In an anhydrous, N$_2$-filled glovebox, a 4-mL borosilicate vial equipped with a magnetic stir bar was charged with CuSCN (54.7 mg, 0.450 mmol, 1.50 equiv), CsF (91.1 mg, 0.600 mmol, 2.00 equiv). DMF (1.5 mL, c=0.30 M) and TMSCF$_3$ (66.5 μL, 64.0 mg, 0.450 mmol, 1.50 equiv) was then added into the vial at 23° C., leading to a yellow suspension. The vial was sealed with a Teflon cap. The reaction mixture was stirred at 23° C. After 30 mins, a mixture of Ru(bipy)$_3$(PF$_6$)$_2$ (5.2 mg, 6.0 μmol, 2.0 mol %) and clofibrate ethyl ester-derived thianthrenium salt S4 (163 mg, 0.300 mmol, 1.00 equiv) in MeCN (1.5 mL, c=0.20 M)

was then added into the reaction with a 2 mL syringe. The vial was sealed with the same Teflon cap again, and was placed 5 cm away from a 34 W blue LED. The reaction was irradiated with the blue LED for 3 hours at approximately 30° C. with the use of a cooling fan. Then the reaction mixture was diluted with DCM (1.0 mL). The resulting solution was filtered through a short pad of silica using DCM (10 mL) as eluent. The filtrate was collected and concentrated in vacuo, and the residue was then purified by flash column chromatography on silica gel, eluting with ethyl acetate/hexane (1:100 (v/v)) to afford 6 (75.3 mg, 81%) as a colorless solid.

Rf=0.40 (EtOAc/hexanes, 1/14, v/v).

NMR Spectroscopy:

$^1$H NMR (500 MHz, CDCl$_3$, 23° C., δ): 7.53 (d, J=2.7 Hz, 1H), 7.33 (dd, J=8.9, 2.7 Hz, 1H), 6.78 (d, J=8.8 Hz, 1H), 4.23 (q, J=7.1 Hz, 2H), 1.60 (s, 6H), 1.24 (t, J=7.1 Hz, 3H) ppm.

$^{13}$C NMR (126 MHz, CDCl$_3$, 23° C., δ): 173.8, 152.7, 132.4, 127.5 (q, J=5.4 Hz), 126.5, 123.1 (q, J=31.0 Hz), 122.8 (d, J=272.9 Hz, CF$_3$), 119.1, 80.7, 61.8, 25.1, 14.1 ppm.

$^{19}$F NMR (471 MHz, CDCl$_3$, 23° C., δ): −62.5 ppm.

HRMS-ESI (m/z) calc'd for C$_{13}$H$_{15}$O$_3$Cl$_1$F$_3$ [M+H]$^+$, 311.06563; found, 311.06561; deviation: 0.1 ppm.

p-(1-Adamantyl)Toluene-Derived Thianthrenium Salt (S7)

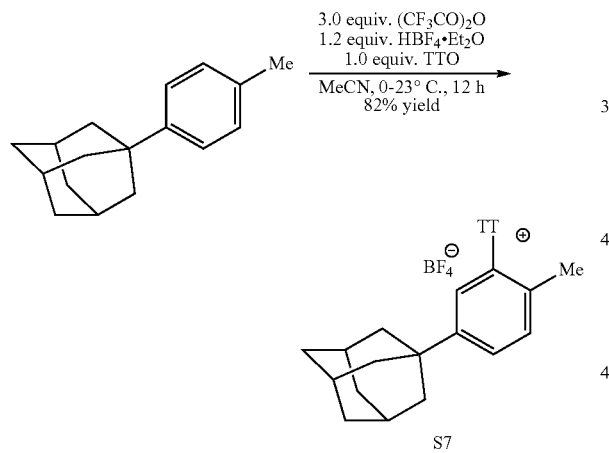

Under an ambient atmosphere, a 20-ml glass vial was charged with p-(1-adamantyl)toluene (339 mg, 1.50 mmol, 1.00 equiv) and MeCN (3.0 ml, c=0.50 M). After cooling to 0° C., HBF$_4$OEt$_2$ (0.25 mL, 0.29 g, 1.8 mmol, 1.2 equiv) and thianthrene-S-oxide (348 mg, 1.50 mmol, 1.00 equiv) was added to the vial while stirring the mixture, leading to a suspension. Subsequently, trifluoroacetic anhydride (0.63 mL, 0.93 g, 4.5 mmol, 3.0 equiv) was added in one portion at 0° C., resulting in a color change to deep purple. Subsequently, the reaction mixture was allowed to reach 23° C. and stirred for 12 h. The solution was diluted with DCM (5 mL) and poured onto a mixture of DCM (30 mL) and saturated aqueous NaHCO$_3$ solution (20 mL). After stirring for 5 min at 23° C., the mixture was poured into a separating funnel, and the layers were separated. The DCM layer was washed with aqueous NaBF$_4$ solution (10% w/w, 4×ca. 20 mL). The DCM layer was dried over Na$_2$SO$_4$, filtered, and the solvent was removed under reduced pressure. The residue was purified by chromatography on silica gel eluting with DCM/MeOH (30:1 (v/v)), then the solvent was removed in vacuo to afford S7 (650 mg, 82%) as a colorless powder.

Rf=0.35 (DCM/MeOH, 15:1, v/v).

NMR Spectroscopy:

$^1$H NMR (500 MHz, CDCl$_3$, 23° C., δ): 8.38 (d, J=7.9 Hz, 2H), 7.86 (d, J=7.9 Hz, 2H), 7.80 (t, J=7.7 Hz, 2H), 7.69 (t, J=7.6 Hz, 2H), 7.44 (d, J=8.0 Hz, 1H), 7.30 (d, J=8.1 Hz, 1H), 6.71 (s, 1H), 2.63 (s, 3H), 1.97 (s, 3H), 1.69-1.67 (m, 3H), 1.60-1.53 (m, 9H) ppm.

$^{13}$C NMR (125 MHz, CDCl$_3$, 23° C., δ): 151.0, 137.2, 134.9, 134.8, 133.8, 130.9, 130.3, 130.2, 125.4, 120.7, 118.0, 77.4, 42.6, 36.3, 36.1, 28.5, 19.8 ppm.

$^{19}$F NMR (471 MHz, CDCl$_3$, 23° C., δ): −151.5 (brs), −151.6 (brs) ppm.

HRMS-ESI (m/z) calc'd for C$_{29}$H$_{29}$S$_2$ [M-BF$_4$]$^+$, 441.17052; found, 441.17061; deviation: −0.2 ppm.

(3r,5r,7r)-1-(4-Methyl-3-(trifluoromethyl)phenyl) adamantane (9)

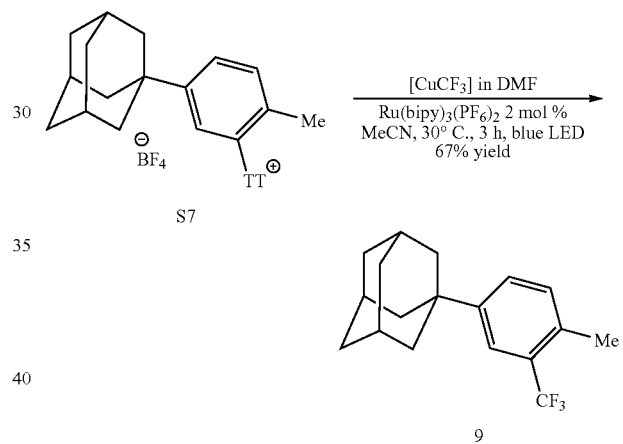

In an anhydrous, N$_2$-filled glovebox, a 4-mL borosilicate vial equipped with a magnetic stir bar was charged with CuSCN (54.7 mg, 0.450 mmol, 1.50 equiv), CsF (91.1 mg, 0.600 mmol, 2.00 equiv). DMF (1.5 mL, c=0.30 M) and TMSCF$_3$ (66.5 μL, 64.0 mg, 0.450 mmol, 1.50 equiv) was then added into the vial at 23° C., leading to a yellow suspension. The vial was sealed with a Teflon cap. The reaction mixture was stirred at 23° C. After 30 mins, a mixture of Ru(bipy)$_3$(PF$_6$)$_2$ (5.2 mg, 6.0 μmol, 2.0 mol %) and 4-adamantyl-toluene-derived thianthrenium salts S7 (159 mg, 0.300 mmol, 1.00 equiv) in MeCN (1.5 mL, c=0.20 M) was then added into the reaction with a 2 mL syringe. The vial was sealed with the same Teflon cap again, and was placed 5 cm away from a 34 W blue LED. The reaction was irradiated with the blue LED for 3 hours at approximately 30° C. with the use of a cooling fan. Then the reaction mixture was diluted with DCM (1.0 mL). The resulting solution was filtered through a short pad of silica using DCM (10 mL) as eluent. The filtrate was collected and concentrated in vacuo, and the residue was then purified by flash column chromatography on silica gel, eluting with hexanes to afford 9 (59.1 mg, 67%) as a colorless solid.

Rf=0.65 (hexanes).

NMR Spectroscopy:

$^1$H NMR (500 MHz, CDCl$_3$, 23° C., δ): 7.62 (s, 1H), 7.44 (d, J=8.1 Hz, 1H), 7.30-7.23 (m, 1H), 2.49 (s, 3H), 2.15 (s, 3H), 1.94 (s, 6H), 1.82 (q, J=12.5 Hz, 6H) ppm.

$^{13}$C NMR (126 MHz, CDCl$_3$, 23° C., δ): 149.1, 133.5, 131.7, 128.4 (q, J=29.2 Hz), 128.1, 124.9 (q, J=273.7 Hz, CF$_3$), 122.3 (q, J=5.7 Hz), 43.1, 36.7, 36.0, 28.9, 18.8 (q, J=2.4 Hz) ppm.

$^{19}$F NMR (471 MHz, CDCl$_3$, 23° C., δ): −61.3 ppm.

HRMS-CI (m/z) calc'd for C$_{18}$H$_{21}$F$_3$ [M]$^+$, 294.15899; found, 294.15921; deviation: −0.8 ppm.

Fenofibrate-Derived Thianthrenium Salt (S9)

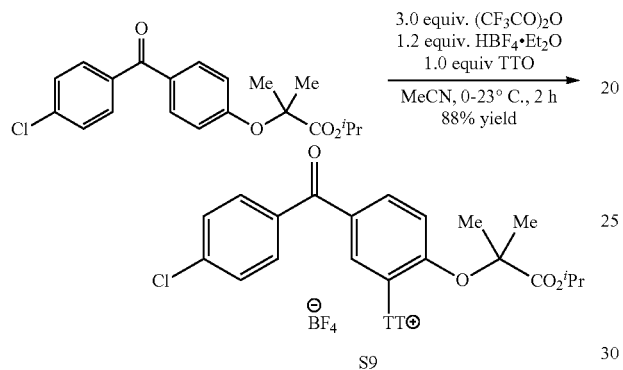

Under an ambient atmosphere, a 20-ml glass vial was charged with fenofibrate (721 mg, 2.00 mmol, 1.00 equiv) and MeCN (5.0 ml, c=0.40 M). After cooling to 0° C., HBF$_4$OEt$_2$ (0.33 mL, 0.39 g, 2.4 mmol, 1.2 equiv) and thianthrene-S-oxide (464 mg, 2.00 mmol, 1.00 equiv) was added to the vial while stirring the mixture, leading to a suspension. Subsequently, trifluoroacetic anhydride (0.84 mL, 1.3 g, 6.0 mmol, 3.0 equiv) was added in one portion at 0° C., resulting in a color change to deep purple. Subsequently, the reaction mixture was allowed to reach 23° C. and stirred for 2 h. The solution was diluted with DCM (5 mL) and poured onto a mixture of DCM (30 mL) and aqueous K$_2$CO$_3$ solution (10% w/w, 10 mL). After stirring for 5 min at 23° C., the mixture was poured into a separating funnel, and the layers were separated. The DCM layer was washed with aqueous NaBF$_4$ solution (10% w/w, 4×ca. 20 mL). The DCM layer was dried over Na$_2$SO$_4$, filtered, and the solvent was removed under reduced pressure. The residue was purified by chromatography on silica gel eluting with DCM/MeOH (30:1 (v/v)), then the solvent was removed in vacuo to afford S9 (1.17 g, 88%) as a colorless powder.

Rf=0.35 (DCM/MeOH, 15:1, v/v).

NMR Spectroscopy:

$^1$H NMR (500 MHz, CD$_3$CN, 23° C., δ): 8.26 (dd, J=7.9, 1.4 Hz, 2H), 7.99 (dd, J=8.8, 2.1 Hz, 1H), 7.94 (dd, J=8.5, 2.0 Hz, 2H), 7.84 (td, J=7.7, 1.4 Hz, 2H), 7.78 (td, J=7.7, 1.4 Hz, 2H), 7.65-7.42 (m, 4H), 6.99 (d, J=8.8 Hz, 1H), 6.95 (d, J=2.0 Hz, 1H), 5.06-4.83 (m, 1H), 1.74 (s, 6H), 1.03 (d, J=6.2 Hz, 6H) ppm.

$^{13}$C NMR (126 MHz, CD$_3$CN, 23° C., δ): 193.3, 172.4, 159.3, 140.0, 138.7, 138.2, 136.9, 136.7, 136.5, 133.9, 132.5, 132.2, 131.7, 131.5, 130.3, 118.5, 111.2, 85.0, 71.6, 26.2, 22.2 ppm. one carbon missing because of overlap.

$^{19}$F NMR (471 MHz, CD$_3$CN, 23° C., δ): −151.7 (brs), −151.8 (brs) ppm.

HRMS-ESI (m/z) calc'd for C$_{32}$H$_{28}$Cl$_1$O$_4$S$_2$$^+$ [M−BF$_4$]$^+$, 575.11120; found, 575.11205; deviation: −1.5 ppm.

C$_2$F$_5$-Fenofibrate (11)

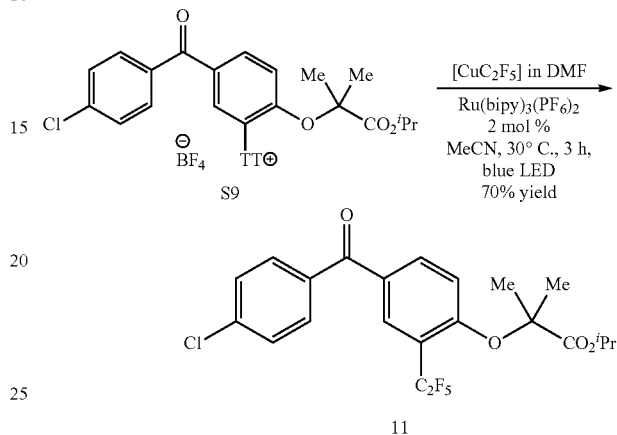

In an anhydrous, N$_2$-filled glovebox, a 4-mL borosilicate vial equipped with a magnetic stir bar was charged with CuSCN (54.7 mg, 0.450 mmol, 1.50 equiv), CsF (91.1 mg, 0.600 mmol, 2.00 equiv). DMF (1.5 mL, c=0.30 M) and TMSC$_2$F$_5$ (78.6 μL, 86.5 mg, 0.450 mmol, 1.50 equiv) was then added into the vial at 23° C., leading to a yellow suspension. The vial was sealed with a Teflon cap. The reaction mixture was stirred at 23° C. After 30 mins, a mixture of Ru(bipy)$_3$(PF$_6$)$_2$ (5.2 mg, 6.0 μmol, 2.0 mol %) and fenofibrate-derived thianthrenium salt S9 (199 mg, 0.300 mmol, 1.00 equiv) in MeCN (1.5 mL, c=0.20 M) was then added into the reaction with a 2 mL syringe. The vial was sealed with the same Teflon cap again, and was placed 5 cm away from a 34 W blue LED. The reaction was irradiated with the blue LED for 3 hours at approximately 30° C. with the use of a cooling fan. Then the reaction mixture was diluted with DCM (1.0 mL). The resulting solution was filtered through a short pad of silica using DCM (10 mL) as eluent. The filtrate was collected and concentrated in vacuo, and the residue was then purified by flash column chromatography on silica gel, eluting with ethyl acetate/hexane (1:60 (v/v)) to afford 11 (100 mg, 70%) as a colorless solid.

Rf=0.40 (EtOAc/hexanes, 1/10, v/v).

NMR Spectroscopy:

$^1$H NMR (500 MHz, CDCl$_3$, 23° C., δ): 8.01 (d, J=2.3 Hz, 1H), 7.87 (dd, J=8.7, 2.3 Hz, 1H), 7.67 (d, J=8.5 Hz, 2H), 7.45 (d, J=8.5 Hz, 2H), 6.82 (d, J=8.8 Hz, 1H), 5.04 (hept, J=6.2 Hz, 1H), 1.67 (s, 6H), 1.16 (s, 3H), 1.15 (s, 3H) ppm.

$^{13}$C NMR (126 MHz, CDCl$_3$, 23° C., δ): 193.0, 172.5, 158.3 (t, J=2.5 Hz), 139.0, 135.7, 134.8, 131.8 (t, J=8.7 Hz), 131.2, 129.6, 128.9, 119.3 (tq, J=38.7, 287.2 Hz, CF$_2$), 118.4 (t, J=22.7 Hz), 115.8, 113.3 (qt, J=256.0, 40.0 Hz, CF$_3$), 80.8, 69.7, 25.2, 21.5 ppm.

$^{19}$F NMR (471 MHz, CDCl$_3$, 23° C., δ): 83.2, 111.8 ppm.

HRMS-ESI (m/z) calc'd for C$_{22}$H$_{21}$O$_4$F$_5$Cl$_1$ [M+H]$^+$, 479.10430; found, 479.10358; deviation: 1.5 ppm.

145
Methyl-O-Methylpodocarpat-Derived Thianthrenium Salt (S10)

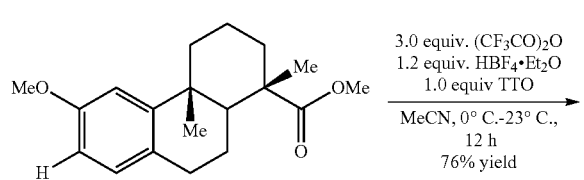

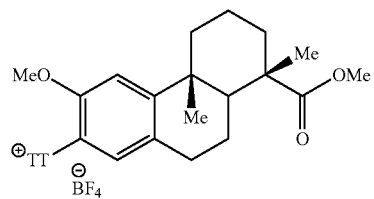

Under an ambient atmosphere, a 20-ml glass vial was charged with methyl-O-methylpodocarpat (453 mg, 1.50 mmol, 1.00 equiv) and MeCN (3.0 ml, c=0.5 M). After cooling to 0° C., HBF$_4$OEt$_2$ (0.25 mL, 0.29 g, 1.8 mmol, 1.2 equiv) and thianthrene-S-oxide (348 g, 1.50 mmol, 1.00 equiv) was added to the vial while stirring the mixture, leading to a suspension. Subsequently, trifluoroacetic anhydride (0.63 mL, 0.96 g, 4.5 mmol, 3.0 equiv) was added in one portion at 0° C., resulting in a color change to deep purple. Subsequently, the reaction mixture was allowed to reach 23° C. and stirred for 12 h. The solution was diluted with DCM (5 mL) and poured onto a mixture of DCM (30 mL) and saturated aqueous NaHCO$_3$ solution (20 mL). After stirring for 5 min at 23° C., the mixture was poured into a separating funnel, and the layers were separated. The DCM layer was washed with aqueous NaBF$_4$ solution (10% w/w, 4×ca. 20 mL). The DCM layer was dried over Na$_2$SO$_4$, filtered, and the solvent was removed under reduced pressure. The residue was purified by chromatography on silica gel eluting with DCM/MeOH (30:1 (v/v)), then the solvent was removed in vacuo to afford S10 (680 mg, 76%) as a colorless powder.

Rf=0.35 (MeOH/DCM, 1/15, v/v).

NMR Spectroscopy:

$^1$H NMR (500 MHz, CDCl$_3$, 23° C., δ): 8.25-8.22 (m, 2H), 7.85-7.81 (m, 2H), 7.80-7.75 (m, 2H), 7.73-7.70 (m, 2H), 6.91 (s, 1H), 6.21 (s, 1H), 3.90 (s, 3H), 3.60 (s, 3H), 2.63-2.54 (m, 2H), 2.21-2.15 (m, 1H), 2.14-2.05 (m, 2H), 1.93-1.80 (m, 2H), 1.59-1.55 (m, 1H), 1.38-1.36 (m, 1H), 1.33-1.26 (m, 1H), 1.21-1.18 (m, 3H), 1.02-0.94 (m, 4H) ppm.

$^{13}$C NMR (126 MHz, CDCl$_3$, 23° C., δ): 177.3, 157.1, 155.9, 137.1, 137.0, 134.7, 134.64, 134.61, 134.57, 130.4, 130.3, 130.1, 130.0, 129.9, 129.1, 117.2, 116.9, 110.8, 105.4, 56.7, 51.6, 51.3, 43.8, 39.3, 39.0, 37.1, 31.2, 28.3, 22.7, 20.3, 19.6 ppm.

$^{19}$F NMR (471 MHz, CDCl$_3$, 23° C., δ): −152.6 (brs), −152.7 (brs) ppm.

HRMS-ESI (m/z) calc'd for C$_{31}$H$_{33}$O$_3$S$_2$ [M-BF$_4$]$^+$, 517.18656; found, 517.18660; deviation: −0.1 ppm.

146
CF$_3$-Methyl-O-Methylpodocarpat (12)

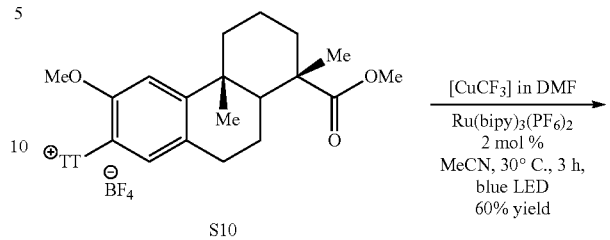

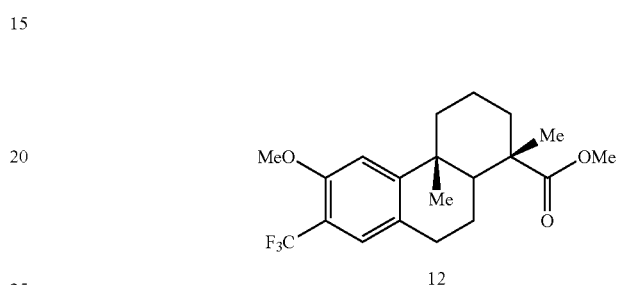

In an anhydrous, N$_2$-filled glovebox, a 4-mL borosilicate vial equipped with a magnetic stir bar was charged with CuSCN (36.5 mg, 0.300 mmol, 1.50 equiv), CsF (61.1 mg, 0.400 mmol, 2.00 equiv). DMF (1.0 mL, c=0.30 M) and TMSCF$_3$ (44.3 μL, 44.8 mg, 0.300 mmol, 1.50 equiv) was then added into the vial at 23° C., leading to a yellow suspension. The vial was sealed with a Teflon cap. The reaction mixture was stirred at 23° C. After 30 mins, a mixture of Ru(bipy)$_3$(PF$_6$)$_2$ (3.4 mg, 4.0 μmol, 2.0 mol %) and methyl-O-methylpodocarpat-derived thianthrenium salt S10 (121 mg, 0.200 mmol, 1.00 equiv) in MeCN (1.0 mL, c=0.20 M) was then added into the reaction with a 2 mL syringe. The vial was sealed with the same Teflon cap again, and was placed 5 cm away from a 34 W blue LED. The reaction was irradiated with the blue LED for 3 hours at approximately 30° C. with the use of a cooling fan. Then the reaction mixture was diluted with DCM (1.0 mL). The resulting solution was filtered through a short pad of silica using DCM (10 mL) as eluent. The filtrate was collected and concentrated in vacuo, and the residue was then purified by flash column chromatography on silica gel, eluting with ethyl acetate/hexane (1:60 (v/v)) to afford 12 (44.2 mg, 60%) as a colorless solid.

Rf=0.45 (EtOAc/hexanes, 1/20, v/v).

NMR Spectroscopy:

$^1$H NMR (500 MHz, CDCl$_3$, 23° C., δ): 7.22 (s, 1H), 6.86 (s, 1H), 3.85 (s, 1H), 3.67 (s, 1H), 2.88-2.84 (m, 1H), 2.76-2.71 (m, 1H), 2.31-2.18 (m, 3H), 2.04-1.93 (m, 2H), 1.68-1.63 (m, 1H), 1.53-1.50 (m, 1H), 1.44-1.38 (m, 1H), 1.28 (s, 3H), 1.12-1.04 (m, 4H) ppm.

$^{13}$C NMR (126 MHz, CDCl$_3$, 23° C., δ): 177.8, 155.5, 153.4, 127.8 (q, J=5.2 Hz), 127.3, 123.9 (q, J=271.8 Hz, CF$_3$), 116.5 (q, J=30.6 Hz), 109.3, 56.0, 52.6, 51.5, 44.1, 39.5, 39.1, 37.6, 31.2, 28.6, 22.9, 21.0, 20.0 ppm.

$^{19}$F NMR (471 MHz, CDCl$_3$, 23° C., δ): −62.0 ppm.

HRMS-ESI (m/z) calc'd for C$_{20}$H$_{25}$O$_3$F$_3$Na$_1$ [M+Na]$^+$, 393.16480; found, 393.16443; deviation: 1.0 ppm.

6-Methoxy-Quinoline-2-Carbonitrile-Derived Thianthrenium Salt (S13)

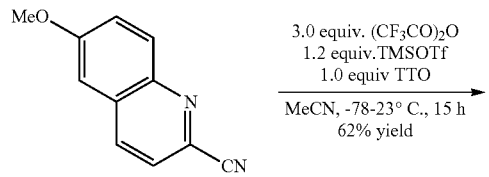

6-Methoxy-5-(trifluoromethyl)quinoline-2-carbonitrile (15)

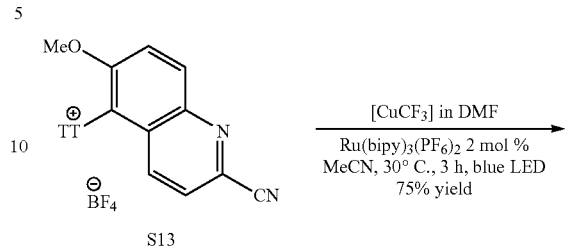

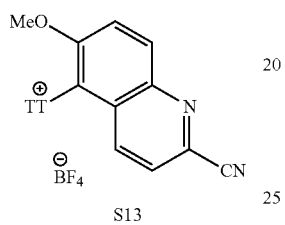

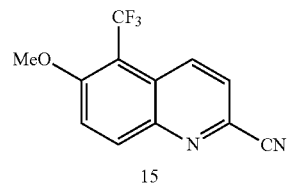

Under Ar atmosphere, a 20-ml glass vial was charged with 6-methoxyquinoline-2-carbonitrile (368 mg, 2.00 mmol, 1.00 equiv) and MeCN (5.0 ml, c=1.0 M). After cooling to −78° C., TMSOTf (0.72 mL, 0.89 g, 4.0 mmol, 2.0 equiv) and thianthrene-S-oxide (464 mg, 2.00 mmol, 1.00 equiv) was added to the vial while stirring the mixture, leading to a suspension. Subsequently, trifluoroacetic anhydride (0.85 mL, 1.3 g, 6.0 mmol, 3.0 equiv) was added in one portion at −78° C., resulting in a color change to deep purple. Subsequently, the reaction mixture was allowed to reach 23° C. and stirred for 15 h. The solution was diluted with DCM (5 mL) and poured onto a mixture of DCM (30 mL) and saturated aqueous NaHCO$_3$ solution (20 mL). After stirring for 5 min at 23° C., the mixture was poured into a separating funnel, and the layers were separated. The DCM layer was washed with aqueous NaBF$_4$ solution (10% w/w, 4×ca. 20 mL). The DCM layer was dried over MgSO$_4$, filtered, and the solvent was removed under reduced pressure. The residue was purified by chromatography on silica gel eluting with DCM/MeOH (30:1 (v/v)), then the solvent was removed in vacuo to afford S13 (598 mg, 62%) as a colorless powder.

Rf=0.35 (MeOH in DCM=7%).

NMR Spectroscopy:

$^1$H NMR (500 MHz, DMSO-d$_6$, 23° C., δ): 9.39 (dd, J=9.6, 0.9 Hz, 1H), 9.22 (dd, J=8.9, 0.9 Hz, 1H), 8.69 (d, J=9.7 Hz, 1H), 8.60-8.49 (m, 3H), 8.31 (td, J=7.7, 1.2 Hz, 2H), 8.06 (ddd, J=8.6, 7.4, 1.3 Hz, 2H), 7.84 (dd, J=8.2, 1.2 Hz, 2H), 4.47 (s, 3H) ppm.

$^{13}$C NMR (126 MHz, DMSO-d$_6$, 23° C., δ): 163.8, 144.1, 141.6, 134.9, 133.3, 132.5, 131.5, 131.3, 130.26, 130.1, 128.8, 126.7, 123.6, 121.4, 117.6, 96.9, 58.8 ppm.

$^{19}$F NMR (471 MHz, DMSO-d$_6$, 23° C., δ): −151.2 (brs), −151.3 (brs) ppm.

HRMS-ESI (m/z) calc'd for C$_{23}$H$_{15}$N$_2$O$_1$S$_2$$^+$ [M-BF$_4$]$^+$, 399.06203; found, 399.06226; deviation: −0.6 ppm.

In an anhydrous, N$_2$-filled glovebox, a 4-mL borosilicate vial equipped with a magnetic stir bar was charged with CuSCN (54.7 mg, 0.450 mmol, 1.50 equiv), CsF (91.1 mg, 0.600 mmol, 2.00 equiv). DMF (1.5 mL, c=0.30 M) and TMSCF$_3$ (66.5 μL, 64.0 mg, 0.450 mmol, 1.50 equiv) was then added into the vial at 23° C., leading to a yellow suspension. The vial was sealed with a Teflon cap. The reaction mixture was stirred at 23° C. After 30 mins, a mixture of Ru(bipy)$_3$(PF$_6$)$_2$ (5.2 mg, 6.0 μmol, 2.0 mol %) and 6-methoxy-quinoline-2-carbonitrile-derived thianthrenium salt S13 (146 mg, 0.300 mmol, 1.00 equiv) in MeCN (1.5 mL, c=0.20 M) was then added into the reaction with a 2 mL syringe. The vial was sealed with the same Teflon cap again, and was placed 5 cm away from a 34 W blue LED. The reaction was irradiated with the blue LED for 3 hours at approximately 30° C. with the use of a cooling fan. Then the reaction mixture was diluted with DCM (1.0 mL). The resulting solution was filtered through a short pad of silica using DCM (10 mL) as eluent. The filtrate was collected and concentrated in vacuo, and the residue was then purified by flash column chromatography on silica gel, eluting with ethyl acetate/hexane (1:100 (v/v)) to afford 15 (48.4 mg, 75%) as a yellow solid.

Rf=0.25 (EtOAc/hexanes, 1/20, v/v).

NMR Spectroscopy:

$^1$H NMR (500 MHz, CDCl$_3$, 23° C., δ): 8.65 (d, J=9.0 Hz, 1H), 8.32 (d, J=9.5 Hz, 1H), 7.70 (dd, J=18.6, 9.3 Hz, 2H), 4.10 (s, 3H) ppm.

$^{13}$C NMR (126 MHz, CDCl$_3$, 23° C., δ): 159.1, 143.5, 136.5, 133.6 (q, J=6.3 Hz), 131.8, 127.3, 124.8, 124.5 (q, J=277.2 Hz, CF$_3$), 118.7, 117.3, 110.4 (q, J=30.2 Hz), 57.3 ppm.

$^{19}$F NMR (471 MHz, CDCl$_3$, 23° C., δ): −52.9 ppm.

HRMS-EI (m/z) calc'd for C$_{12}$H$_7$N$_2$O$_1$F$_3$ [M]$^+$, 252.05050; found, 252.05062; deviation: −0.5 ppm.

CF₃-Boscalid (17)

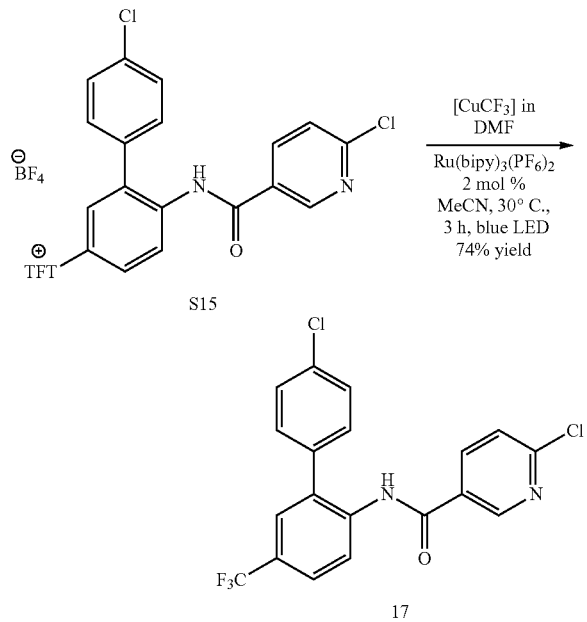

1,3,5-Trimethyl-2-(trifluoromethyl)benzene (19)

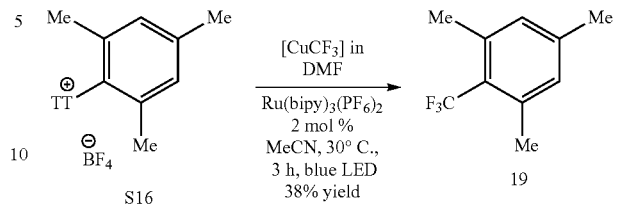

In an anhydrous, N₂-filled glovebox, a 4-mL borosilicate vial equipped with a magnetic stir bar was charged with CuSCN (46.0 mg, 0.375 mmol, 1.50 equiv), CsF (76.1 mg, 0.500 mmol, 2.00 equiv). DMF (1.25 mL, c=0.300 M) and TMSCF₃ (57.2 µL, 53.3 mg, 0.375 mmol, 1.50 equiv) was then added into the vial at 23° C., leading to a yellow suspension. The vial was sealed with a Teflon cap. The reaction mixture was stirred at 23° C. After 30 mins, a mixture of Ru(bipy)₃(PF₆)₂ (4.3 mg, 5.0 µmol, 2.0 mol %) and boscalid-derived tetrafluorothianthrenium salts S15 (179 mg, 0.250 mmol, 1.00 equiv) in MeCN (1.25 mL, c=0.200 M) was then added into the reaction with a 2 mL syringe. The vial was sealed with the same Teflon cap again, and was placed 5 cm away from a 34 W blue LED. The reaction was irradiated with the blue LED for 3 hours at approximately 30° C. with the use of a cooling fan. Then the reaction mixture was diluted with DCM (1.0 mL). The resulting solution was filtered through a short pad of silica using DCM (10 mL) as eluent. The filtrate was collected and concentrated in vacuo, and the residue was then purified by flash column chromatography on silica gel, eluting with ethyl acetate/hexane (1:5 (v/v)) to afford 17 (61.1 mg, 74%) as an off-white solid.

Rf=0.25 (EtOAc/hexanes, 1/3, v/v).

NMR Spectroscopy:

¹H NMR (500 MHz, CDCl₃, 23° C., δ): 8.67 (d, J=8.7 Hz, 1H), 8.45 (dd, J=4.7, 2.0 Hz, 1H), 8.40 (s, 1H), 8.18 (dd, J=7.7, 2.0 Hz, 1H), 7.74-7.67 (m, 1H), 7.52 (s, 1H), 7.48 (d, J=8.2 Hz, 2H), 7.42-7.32 (m, 3H) ppm.

¹³C NMR (126 MHz, CDCl₃, 23° C., δ): 162.6, 151.8, 146.6, 140.6, 137.7, 135.4, 134.8, 132.0, 130.9, 130.6, 129.8, 127.3 (q, J=4.3 Hz), 126.9 (q, J=33.0 Hz), 126.1 (q, J=2.6 Hz), 123.9 (q, J=272.1 Hz, CF₃), 123.1, 121.6 ppm.

¹⁹F NMR (471 MHz, CDCl₃, 23° C., δ): −62.2 ppm.

HRMS-ESI (m/z) calc'd for C₁₉H₁₀Cl₂F₃N₂O₁ [M−H]⁺, 409.01278; found, 409.01280; deviation <0.1 ppm.

In an anhydrous, N₂-filled glovebox, a 4-mL borosilicate vial equipped with a magnetic stir bar was charged with CuSCN (54.7 mg, 0.450 mmol, 1.50 equiv), CsF (91.1 mg, 0.600 mmol, 2.00 equiv). DMF (1.5 mL, c=0.30 M) and TMSCF₃ (66.5 µL, 64.0 mg, 0.450 mmol, 1.50 equiv) was then added into the vial at 23° C., leading to a yellow suspension. The vial was sealed with a Teflon cap. The reaction mixture was stirred at 23° C. After 30 mins, a mixture of Ru(bipy)₃(PF₆)₂ (5.2 mg, 6.0 µmol, 2.0 mol %) and mesitylene-derived thianthrenium salts S16 (96.8 mg, 0.300 mmol, 1.00 equiv) in MeCN (1.5 mL, c=0.20 M) was then added into the reaction with a 2 mL syringe. The vial was sealed with the same Teflon cap again, and was placed 5 cm away from a 34 W blue LED. The reaction was irradiated with the blue LED for 3 hours at approximately 30° C. with the use of a cooling fan. Then the reaction mixture was diluted with DCM (1.0 mL). The resulting solution was filtered through a short pad of silica using DCM (10 mL) as eluent. The filtrate was collected and concentrated in vacuo, and the residue was then purified by flash column chromatography on silica gel, eluting with hexanes to afford 19 (21.4 mg, 38%) as a colorless liquid.

Rf=0.65 (hexanes).

NMR Spectroscopy:

¹H NMR (500 MHz, CDCl₃, 23° C., δ): 6.89 (s, 2H), 2.44 (s, 6H), 2.29 (s, 3H) ppm.

¹³C NMR (126 MHz, CDCl₃, 23° C., δ): 141.0, 137.4, 131.0, 126.3 (q, J=276.0 Hz, CF₃), 124.9 (q, J=27.7 Hz), 21.5 (q, J=3.8 Hz), 21.0 ppm.

¹⁹F NMR (471 MHz, CDCl₃, 23° C., δ): −53.7 ppm.

HRMS-EI (m/z) calc'd for C₁₀H₁₁F₃ [M]⁺, 188.08074; found, 188.08093; deviation: −1.0 ppm.

CF₃-Etofenprox (22)

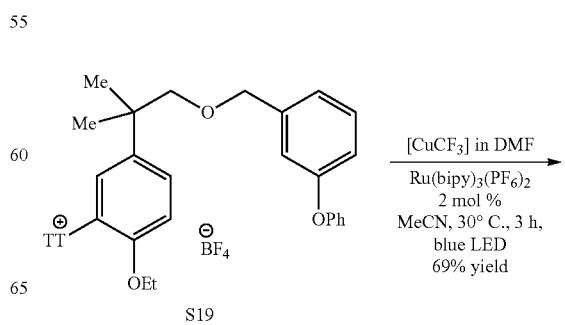

-continued

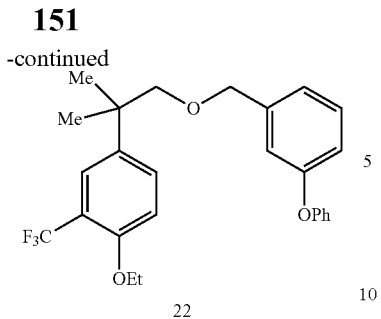

22

In an anhydrous, N$_2$-filled glovebox, a 4-mL borosilicate vial equipped with a magnetic stir bar was charged with CuSCN (54.7 mg, 0.450 mmol, 1.50 equiv), CsF (91.1 mg, 0.600 mmol, 2.00 equiv). DMF (1.5 mL, c=0.30 M) and TMSCF$_3$ (66.5 µL, 64.0 mg, 0.450 mmol, 1.50 equiv) was then added into the vial at 23° C., leading to a yellow suspension. The vial was sealed with a Teflon cap. The reaction mixture was stirred at 23° C. After 30 mins, a mixture of Ru(bipy)$_3$(PF$_6$)$_2$ (5.2 mg, 6.0 µmol, 2.0 mol %) and etofenprox-derived thianthrenium salt S19 (204 mg, 0.300 mmol, 1.00 equiv) in MeCN (1.5 mL, c=0.20 M) was then added into the reaction with a 2 mL syringe. The vial was sealed with the same Teflon cap again, and was placed 5 cm away from a 34 W blue LED. The reaction was irradiated with the blue LED for 3 hours at approximately 30° C. with the use of a cooling fan. Then the reaction mixture was diluted with DCM (1.0 mL). The resulting solution was filtered through a short pad of silica using DCM (10 mL) as eluent. The filtrate was collected and concentrated in vacuo, and the residue was then purified by flash column chromatography on silica gel, eluting with ethyl acetate/hexane (1:200 (v/v)) to afford 22 (91.9 mg, 69%) as a colorless solid.

Rf=0.25 (EtOAc/hexanes, 1/100, v/v).

NMR Spectroscopy:

$^1$H NMR (500 MHz, CDCl$_3$, 23° C., δ): 7.59 (s, 1H), 7.48 (d, J=8.5 Hz, 1H), 7.36 (t, J=7.6 Hz, 2H), 7.30 (t, J=7.7 Hz, 1H), 7.14 (t, J=7.0 Hz, 1H), 7.05 (d, J=8.3 Hz, 2H), 7.01 (d, J=7.5 Hz, 1H), 6.97-6.90 (m, 3H), 4.48 (s, 2H), 4.11 (q, J=7.0 Hz, 2H), 3.45 (s, 2H), 1.45 (t, J=7.0 Hz, 3H), 1.35 (s, 6H) ppm.

$^{13}$C NMR (126 MHz, CDCl$_3$, 23° C., δ): 157.5, 157.3, 155.1, 140.9, 139.2, 131.0, 129.9, 124.8 (q, J=5.3 Hz), 124.1 (q, J=272.4 Hz, CF$_3$), 123.4, 122.1, 119.1, 118.5 (q, J=30.1 Hz), 117.9, 117.7, 112.8, 80.0, 72.9, 64.6, 38.7, 26.2, 14.8 ppm.

$^{19}$F NMR (471 MHz, CDCl$_3$, 23° C., δ): −62.0 ppm.

HRMS-ESI (m/z) calc'd for C$_{26}$H$_{27}$F$_3$O$_3$Na$_1$ [M+Na]$^+$, 467.18045; found, 467.18011; deviation: 0.7 ppm.

Methyl 1-phenylcyclopropane-1-carboxylate-Derived Thianthrenium Salt (S20)

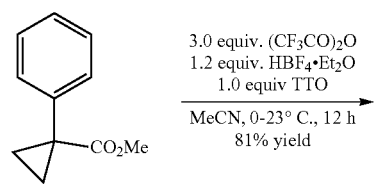

3.0 equiv. (CF$_3$CO)$_2$O
1.2 equiv. HBF$_4$·Et$_2$O
1.0 equiv TTO
⟶
MeCN, 0-23° C., 12 h
81% yield -continued

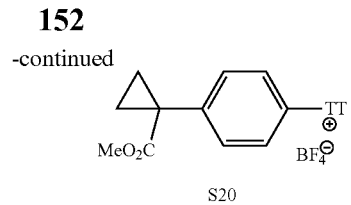

S20

Under an ambient atmosphere, a 20-ml glass vial was charged with methyl 1-phenylcyclopropane-1-carboxylate (352 mg, 2.00 mmol, 1.00 equiv) and MeCN (10 ml, c=0.20 M). After cooling to 0° C., HBF$_4$OEt$_2$ (0.33 mL, 388 mg, 2.40 mmol, 1.20 equiv) and thianthrene-S-oxide (464 mg, 2.00 mmol, 1.00 equiv) was added to the vial while stirring the mixture, leading to a suspension. Subsequently, trifluoroacetic anhydride (0.84 mL, 1.24 g, 6.00 mmol, 3.00 equiv) was added in one portion at 0° C., resulting in a color change to deep purple. Subsequently, the reaction mixture was allowed to reach 23° C. and stirred for 12 h. The solution was diluted with DCM (5 mL) and poured onto a mixture of DCM (30 mL) and saturated aqueous NaHCO$_3$ solution (20 mL). After stirring for 5 min at 23° C., the mixture was poured into a separating funnel, and the layers were separated. The DCM layer was washed with aqueous NaBF$_4$ solution (10% w/w, 4×ca. 20 mL). The DCM layer was dried over Na$_2$SO$_4$, filtered, and the solvent was removed under reduced pressure. The residue was purified by chromatography on silica gel eluting with DCM/MeOH (30:1 (v/v)), then the solvent was removed in vacuo to afford S20 (774 mg, 81%) as a colorless powder.

Rf=0.50 (DCM/MeOH, 15:1, v/v).

NMR Spectroscopy:

$^1$H NMR (500 MHz, CD$_3$CN, 23° C., δ): 8.38 (dd, J=7.9, 1.4 Hz, 2H), 7.96 (dd, J=7.9, 1.5 Hz, 2H), 7.89 (td, J=7.7, 1.4 Hz, 2H), 7.82 (td, J=7.7, 1.4 Hz, 2H), 7.55-7.42 (m, 2H), 7.19-7.04 (m, 2H), 3.52 (s, 3H), 1.54 (q, J=4.2 Hz, 2H), 1.14 (q, J=4.2 Hz, 2H) ppm.

$^{13}$C NMR (125 MHz, CD$_3$CN, 23° C., δ): 174.2, 146.4, 137.5, 136.1, 136.0, 133.6, 131.6, 130.9, 128.6, 123.2, 119.3, 52.9, 29.2, 17.1 ppm.

$^{19}$F NMR (471 MHz, CD$_3$CN, 23° C., δ): −151.4 (brs), −151.5 (brs) ppm.

HRMS-ESI (m/z) calc'd for C$_{23}$H$_{19}$O$_2$S$_2$ [M-BF$_4$]$^+$, 391.08210; found, 391.08214; deviation: −0.1 ppm.

Methyl 1-(4-(perfluoroethyl)phenyl)cyclopropane-1-carboxylate (24)

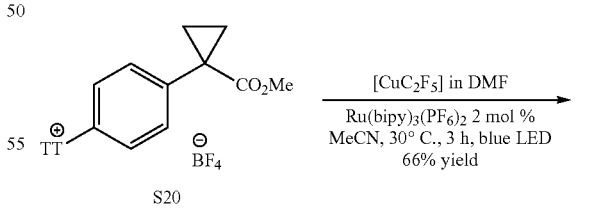

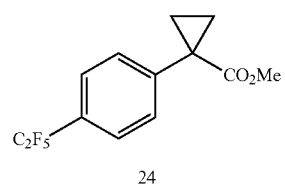

24

In an anhydrous, N$_2$-filled glovebox, a 4-mL borosilicate vial equipped with a magnetic stir bar was charged with CuSCN (54.7 mg, 0.450 mmol, 1.50 equiv), CsF (91.1 mg, 0.600 mmol, 2.00 equiv). DMF (1.5 mL, c=0.30 M) and TMSC$_2$F$_5$ (78.6 μL, 86.5 mg, 0.450 mmol, 1.50 equiv) was then added into the vial at 23° C., leading to a yellow suspension. The vial was sealed with a Teflon cap. The reaction mixture was stirred at 23° C. After 30 mins, a mixture of Ru(bipy)$_3$(PF$_6$)$_2$ (5.2 mg, 6.0 μmol, 2.0 mol %) and methyl 1-phenylcyclopropane-1-carboxylate-derived thianthrenium salts S20 (143 mg, 0.300 mmol, 1.00 equiv) in MeCN (1.5 mL, c=0.20 M) was then added into the reaction with a 2 mL syringe. The vial was sealed with the same Teflon cap again, and was placed 5 cm away from a 34 W blue LED. The reaction was irradiated with the blue LED for 3 hours at approximately 30° C. with the use of a cooling fan. Then the reaction mixture was diluted with DCM (1.0 mL). The resulting solution was filtered through a short pad of silica using DCM (10 mL) as eluent. The filtrate was collected and concentrated in vacuo, and the residue was then purified by flash column chromatography on silica gel, eluting with ethyl acetate/hexane (1:100 (v/v)) to afford 24 (58.2 mg, 66%) as a colorless liquid.

Rf=0.45 (EtOAc/hexanes, 1/30, v/v).

NMR Spectroscopy:

$^1$H NMR (500 MHz, CDCl$_3$, 23° C., δ): 7.53 (d, J=8.2 Hz, 2H), 7.40 (d, J=8.3 Hz, 2H), 3.65 (s, 3H), 1.64 (q, J=4.0 Hz, 2H), 1.23 (q, J=4.0 Hz, 2H) ppm.

$^{13}$C NMR (126 MHz, CDCl$_3$, 23° C., δ): 174.4, 143.8, 131.0, 127.7 (t, J=24.0 Hz), 126.5 (t, J=6.3 Hz), 119.3 (tq, J=285.8, 39.4 Hz, CF$_2$), 113.5 (qt, J=250.7, 39.1 Hz, CF$_3$), 52.6, 29.0, 16.8 ppm.

$^{19}$F NMR (471 MHz, CDCl$_3$, 23° C., δ): −84.7, −114.6 ppm.

HRMS-ESI (m/z) calc'd for C$_{13}$H$_{11}$O$_2$F$_5$Na$_1$ [M+Na]$^+$, 317.05714; found, 317.06710; deviation: 0.1 ppm.

CF$_3$-Bifonazole (26)

0.400 mmol, 2.00 equiv). DMF (1.0 mL, c=0.30 M) and TMSCF$_3$ (44.2 μL, 42.6 mg, 0.300 mmol, 1.50 equiv) was then added into the vial at 23° C., leading to a yellow suspension. The vial was sealed with a Teflon cap. The reaction mixture was stirred at 23° C. After 30 mins, a mixture of Ru(bipy)$_3$(PF$_6$)$_2$ (3.4 mg, 4.0 μmol, 2.0 mol %) and bifonazole-derived tetrafluorothianthrenium salts S22 (136 mg, 0.200 mmol, 1.00 equiv) in MeCN (1.0 mL, c=0.20 M) was then added into the reaction with a 2 mL syringe. The vial was sealed with the same Teflon cap again, and was placed 5 cm away from a 34 W blue LED. The reaction was irradiated with the blue LED for 3 hours at approximately 30° C. with the use of a cooling fan. Then the reaction mixture was diluted with DCM (1.0 mL). The resulting solution was filtered through a short pad of silica using DCM (10 mL) as eluent. The filtrate was collected and concentrated in vacuo, and the residue was then purified by flash column chromatography on silica gel, eluting with ethyl acetate/hexane (1:4 (v/v)) to afford 26 with impurities. Further purification of 26 by HPLC (YMC-Actus Triart C18 (30×150 mm: 5 μm), MeOH/TFA in water (1/1000, v/v)=65: 35, flow rate=42.5 mL/min, 25° C., retention time; 5.5 min) provided 26 as a pale yellow solid. (51.6 mg, 68%, with little CF$_3$-bifonazole-TFA salt) as a colorless solid.

Rf=0.35 (EtOAc/hexanes, 1/2, v/v).

NMR Spectroscopy:

$^1$H NMR (500 MHz, CD$_3$OD, 23° C., δ): 7.75 (d, J=8.2 Hz, 2H), 7.68 (d, J=8.1 Hz, 2H), 7.66 (d, J=8.3 Hz, 2H), 7.38-7.32 (m, 3H), 7.24-7.17 (m, 6H), 6.91 (s, 1H), 3.32-3.25 (m, 1H) ppm.

$^{13}$C NMR (126 MHz, CD$_3$OD, 23° C., δ): 145.2, 141.0, 140.2, 139.9, 130.6 (q, J=32.3 Hz), 130.1, 129.9, 129.8, 129.3, 128.8, 128.6, 126.8 (q, J=3.9 Hz), 125.7 (q, J=271.5 Hz, CF$_3$), 66.3 ppm.

$^{19}$F NMR (471 MHz, CD$_3$OD, 23° C., δ): −63.8, −76.8.

HRMS-ESI (m/z) calc'd for C$_{23}$H$_{18}$N$_2$F$_3$ [M+H]$^+$, 379.14166; found, 379.14148; deviation: 0.5 ppm.

CF$_3$-Indometacin Methyl Ester (27)

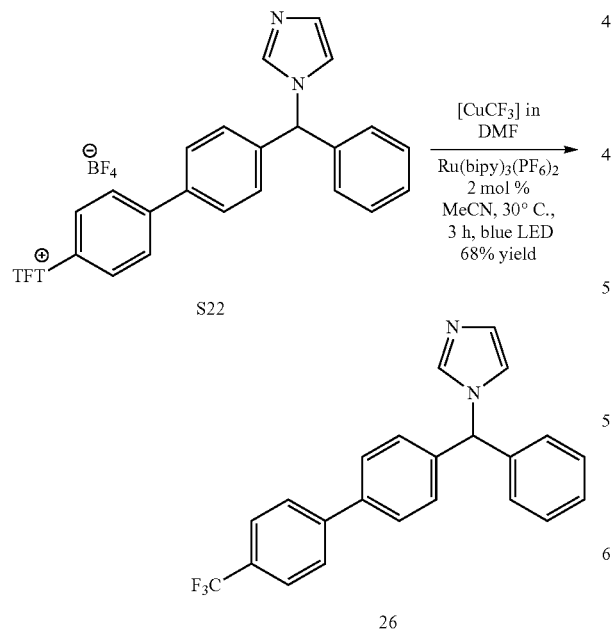

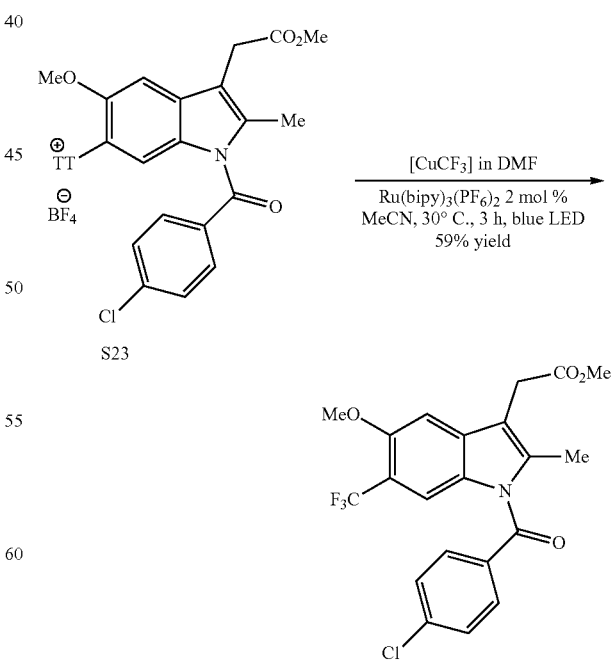

In an anhydrous, N$_2$-filled glovebox, a 4-mL borosilicate vial equipped with a magnetic stir bar was charged with CuSCN (36.4 mg, 0.300 mmol, 1.50 equiv), CsF (61.1 mg, In an anhydrous, N$_2$-filled glovebox, a 4-mL borosilicate vial equipped with a magnetic stir bar was charged with CuSCN (46.0 mg, 0.375 mmol, 1.50 equiv), CsF (76.1 mg, 0.500 mmol, 2.00 equiv). DMF (1.25 mL, c=0.300 M) and TMSCF$_3$ (57.2 μL, 53.3 mg, 0.375 mmol, 1.50 equiv) was then added into the vial at 23° C., leading to a yellow suspension. The vial was sealed with a Teflon cap. The reaction mixture was stirred at 23° C. After 30 mins, a mixture of Ru(bipy)$_3$(PF$_6$)$_2$ (4.3 mg, 5.0 μmol, 2.0 mol %) and indometacin methyl ester-derived thianthrenium salts S23 (170 mg, 0.250 mmol, 1.00 equiv) in MeCN (1.25 mL, c=0.20 M) was then added into the reaction with a 2 mL syringe. The vial was sealed with the same Teflon cap again, and was placed 5 cm away from a 34 W blue LED. The reaction was irradiated with the blue LED for 3 hours at approximately 30° C. with the use of a cooling fan. Then the reaction mixture was diluted with DCM (1.0 mL). The resulting solution was filtered through a short pad of silica using DCM (10 mL) as eluent. The filtrate was collected and concentrated in vacuo, and the residue was then purified by flash column chromatography on silica gel, eluting with ethyl acetate/hexane (1:5 (v/v)) to afford 27 (65.0 mg, 59%) as an off-white solid.

Rf=0.20 (EtOAc/hexanes, 1/10, v/v).

NMR Spectroscopy:

$^1$H NMR (500 MHz, CDCl$_3$, 23° C., δ): 7.64 (d, J=8.5 Hz, 2H), 7.49 (d, J=8.5 Hz, 2H), 7.36 (s, 1H), 7.05 (s, 1H), 3.94 (s, 3H), 3.71 (s, 3H), 3.68 (s, 2H), 2.34 (s, 3H) ppm.

$^{13}$C NMR (126 MHz, CDCl$_3$, 23° C., δ): 171.0, 168.0, 154.0, 139.8, 138.1, 133.3, 133.0, 131.1, 129.3, 129.2, 123.9 (q, J=272.0 Hz, CF$_3$), 114.7 (q, J=30.8 Hz), 113.2 (q, J=6.2 Hz), 112.2, 100.8, 56.3, 52.3, 30.1, 13.6 ppm.

$^{19}$F NMR (471 MHz, CDCl$_3$, 23° C., δ): −61.6 ppm.

HRMS-ESI (m/z) calc'd for C$_{21}$H$_{17}$Cl$_1$F$_3$N$_1$O$_4$Na$_1$ [M+Na]$^+$, 462.06904; found, 462.06836; deviation: 1.5 ppm.

CF$_3$-salicin Pentaacetate (31)

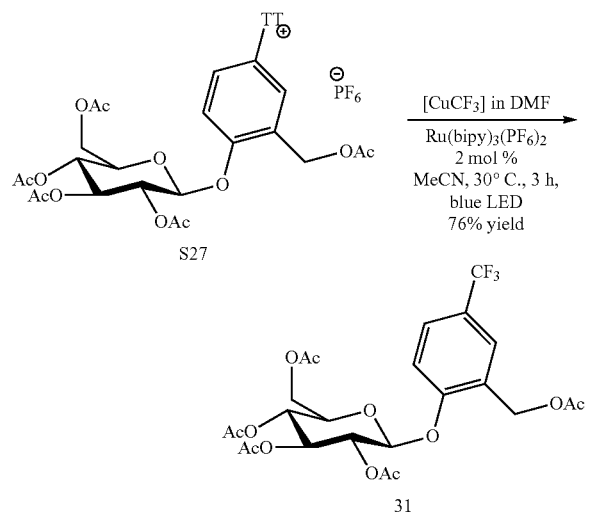

In an anhydrous, N$_2$-filled glovebox, a 4-mL borosilicate vial equipped with a magnetic stir bar was charged with CuSCN (54.7 mg, 0.450 mmol, 1.50 equiv), CsF (91.1 mg, 0.600 mmol, 2.00 equiv). DMF (1.5 mL, c=0.30 M) and TMSCF$_3$ (66.5 μL, 64.0 mg, 0.450 mmol, 1.50 equiv) was then added into the vial at 23° C., leading to a yellow suspension. The vial was sealed with a Teflon cap. The reaction mixture was stirred at 23° C. After 30 mins, a mixture of Ru(bipy)$_3$(PF$_6$)$_2$ (5.2 mg, 6.0 μmol, 2.0 mol %) and salicin pentaacetate-derived thianthrenium salt S27 (257 mg, 0.300 mmol, 1.00 equiv) in MeCN (1.5 mL, c=0.20 M) was then added into the reaction with a 2 mL syringe. The vial was sealed with the same Teflon cap again, and was placed 5 cm away from a 34 W blue LED. The reaction was irradiated with the blue LED for 3 hours at approximately 30° C. with the use of a cooling fan. Then the reaction mixture was diluted with DCM (1.0 mL). The resulting solution was filtered through a short pad of silica using DCM (10 mL) as eluent. The filtrate was collected and concentrated in vacuo, and the residue was then purified by flash column chromatography on silica gel, eluting with ethyl acetate/hexane (1:3 (v/v)) to afford 31 (128 mg, 76%) as a colorless solid.

Rf=0.45 (EtOAc/hexanes, 1/3, v/v).

NMR Spectroscopy:

$^1$H NMR (500 MHz, CDCl$_3$, 23° C., δ): 7.60 (s, 1H), 7.54 (d, J=7.6 Hz, 1H), 7.14 (d, J=8.6 Hz, 1H), 5.35-5.28 (m, 2H), 5.21-5.12 (m, 3H), 5.04 (d, J=13.5 Hz, 1H), 4.27 (dd, J=12.3, 5.3 Hz, 1H), 4.19 (dd, J=12.3, 2.2 Hz, 1H), 3.92-3.88 (m, 1H), 2.12 (s, 3H), 2.09 (s, 3H), 2.06 (s, 3H), 2.05 (s, 3H), 2.04 (s, 3H) ppm.

$^{13}$C NMR (126 MHz, CDCl$_3$, 23° C., δ): 170.6, 170.6, 170.3, 169.5, 169.4, 156.6, 127.1, 126.6 (q, J=3.8 Hz), 126.4 (q, J=3.8 Hz), 125.8 (q, J=33.2 Hz), 124.0 (q, J=271.7 Hz, CF$_3$), 115.3, 98.9, 72.5, 72.4, 71.0, 68.3, 61.9, 60.4, 21.0, 20.8, 20.7 ppm.

$^{19}$F NMR (471 MHz, CDCl$_3$, 23° C., δ): −62.0 ppm.

HRMS-ESI (m/z) calc'd for C$_{24}$H$_{27}$F$_3$O$_{12}$Na$_1$ [M+Na]$^+$, 587.13468; found, 587.13464; deviation: 0.1 ppm.

The invention claimed is:

1. Thianthrene derivative of the Formula (I):

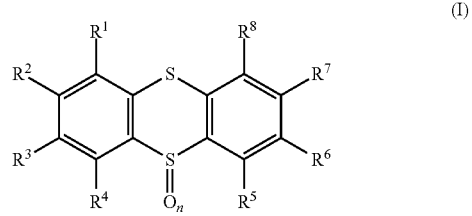

wherein at least four of R$^1$ to R$^8$ are F or CF$_3$, and the others of R$_1$ to R$_8$ are hydrogen, and n is 1.

2. Thianthrene derivative of the Formula (I) according to claim 1 wherein R$_2$, R$_3$, R$_6$ and R$_7$ are F or CF$_3$ and the others of R$^1$ to R$^8$ are hydrogen and wherein n is 1.

3. Process for preparing an aromatic or heteroaromatic thianthrenium salt, comprising reacting a monocyclic or polycyclic, aromatic or heteroaromatic hydrocarbon Ar, which may be substituted or unsubstituted, with an activated thianthrene derivative of the Formula (I) according to claim 1 or mixtures thereof in an organic solvent whereby a thianthrenium salt of the Formula (III) is obtained:

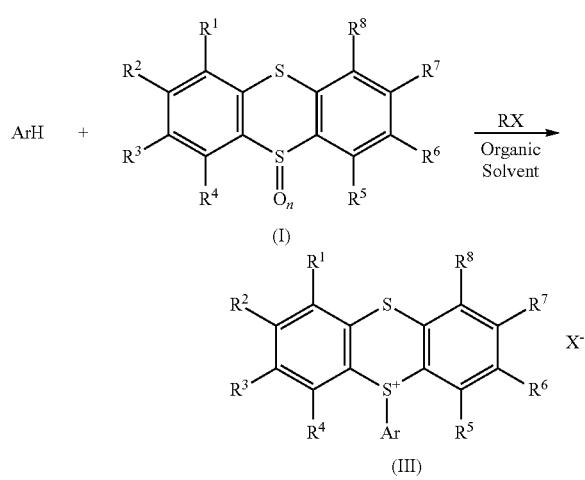

wherein at least four of $R^1$ to $R^8$ are F or $CF_3$, and the others of $R_1$ to $R_8$ are hydrogen, and n is 1, RX is selected from $HBF_4$; $HBF_4$ $OEt_2$, $BF_3$ $OEt_2$, trifluoro methane sulfonic acid (triflic acid), triflic acid anhydride, trifluoro acetic acid, trifluoro acetic acid anhydride, trimethylsilyltriflate and $X^-$ is an anion derived from RX.

4. Process for preparing a thianthrenium salt compound of the Formula (III) according to claim 3, wherein the thianthrene derivative of the Formula (I) is activated by adding a carboxylic acid anhydride if n=1 in formula (I).

5. Process for preparing a thianthrenium salt of the Formula (III) according to claim 4, wherein the reaction is carried out in the presence of a Bronstedt acid or Lewis acid.

6. Process for preparing a thianthrenium salt of the Formula (III) according to claim 3, wherein the thianthrene derivative of the Formula (I) is activated by oxidation if n=0 in formula (I).

7. Process for preparing a thianthrenium salt of the Formula (III) according to claim 6, wherein the thianthrene derivative of the Formula (I) is activated by oxidation with 1-Chloromethyl-4-fluoro-1,4-diazonia bicyclo[2.2.2]octane bis(tetrafluoroborate).

8. Process for preparing a thianthrenium salt of the Formula (III) according to claim 6, wherein the thianthrene derivative of the Formula (I) is activated by electrochemical oxidation.

9. Process for preparing a thianthrenium salt of the Formula (III) according to claim 3 which comprises reacting an electron-poor Ar and a thianthrene derivative of the Formula (I) or a mixture of different thianthrene derivatives of the Formula (I), wherein $R_2$, $R_3$, $R_6$ and $R_7$ are F or $CF_3$ and the others of $R^1$ to $R^8$ are hydrogen and wherein n is 1.

10. Process for preparing an aromatic or heteroaromatic thianthrenium salt according to claim 3, which comprises reacting an electron-rich Ar and a thianthrene derivative of the Formula (I) or a mixture of different thianthrene derivatives of the Formula (I), wherein at least four of $R^1$ to $R^8$ are F or $CF_3$, and the others of $R_1$ to $R_8$ are hydrogen, and n is 1.

* * * * *